(12) United States Patent
Ohno et al.

(10) Patent No.: US 9,040,693 B2
(45) Date of Patent: May 26, 2015

(54) FUSED HETEROCYCLIC DERIVATIVE, MEDICINAL COMPOSITION CONTAINING THE SAME, AND MEDICINAL USE THEREOF

(75) Inventors: Kohsuke Ohno, Azumino (JP); Takashi Miyagi, Azumino (JP); Tomonaga Ozawa, Azumino (JP); Nobuhiko Fushimi, Azumino (JP)

(73) Assignee: KISSEI PHARMACEUTICAL CO., LTD., Nagano (JP)

( * ) Notice: Subject to any disclaimer, the term of this patent is extended or adjusted under 35 U.S.C. 154(b) by 1285 days.

(21) Appl. No.: 12/089,674

(22) PCT Filed: Oct. 17, 2006

(86) PCT No.: PCT/JP2006/320681
§ 371 (c)(1),
(2), (4) Date: Apr. 9, 2008

(87) PCT Pub. No.: WO2007/046392
PCT Pub. Date: Apr. 26, 2007

(65) Prior Publication Data
US 2009/0325900 A1    Dec. 31, 2009

(30) Foreign Application Priority Data

| Oct. 19, 2005 | (JP) | ................. | 2005-304395 |
| May 26, 2006 | (JP) | ................. | 2006-147019 |

(51) Int. Cl.
C07D 495/04 (2006.01)
(52) U.S. Cl.
CPC .................. C07D 495/04 (2013.01)
(58) Field of Classification Search
CPC .................................................. C07D 495/04
USPC ...................................... 544/278; 514/260.1
See application file for complete search history.

(56) References Cited

U.S. PATENT DOCUMENTS

| 6,015,789 A | 1/2000 | Suzuki et al. | |
| 2009/0062258 A1* | 3/2009 | Hamamura et al. | .......... 514/215 |

FOREIGN PATENT DOCUMENTS

| EP | 0 781 774 A2 | 7/1997 |
| EP | 1 847 541 A1 | 10/2007 |
| WO | 97/40846 A1 | 11/1997 |
| WO | 97/44339 A1 | 11/1997 |
| WO | 03/033480 A1 | 4/2003 |
| WO | 2005/049613 A1 | 6/2005 |
| WO | 2005/061518 A1 | 7/2005 |
| WO | 2006/083005 A1 | 8/2006 |
| WO | WO 2006083005 A1 * | 8/2006 |

OTHER PUBLICATIONS

Testa; "Prodrug research: futile or fertile?"; 2004; Biochemical Pharmacology; 68: 2097-2106.*
Vippagunta et al.; "Crystalline solids"; 2001; Advanced Drug Delivery Reviews; 48: 3-26.*
"Represent"; Oxford Advanced American Dictionary; http://oaadonline.oxfordlearnersdictionaries.com/dictionary/represent; accessed Apr. 9, 2014.*
Alexandre Ivachtchenko, et al., "Synthesis of Substituted Thienopyrimidine-4-ones", J. Comb. Chem., 2004, vol. 6, pp. 573-583.
Natale Alfredo Santagati, et al., "Synthesis and spasmolytic action of 2-substituted thienopyrimidin-4-one derivatives", Journal of Pharmacy and Pharmacology, 2002, vol. 54, pp. 717-728.
Rombouts, Frederik J. R., et al. "Deazapurine Solid-Phase Synthesis: Construction of 3-Substituted Pyrrolo [3,2-d]pyrimidine-6-carboxylates on Cross-Linked Polystyrene Bearing a Cysteamine Linker" Journal of Combinatorial Chemistry, vol. 7, No. 4, Jun. 1, 2005, pp. 589-598, XP002541915.
Extended European Search Report dated Jul. 29, 2010 for App. No. 06811925.

* cited by examiner

*Primary Examiner* — Timothy Thomas
(74) *Attorney, Agent, or Firm* — Sughrue Mion, PLLC

(57) ABSTRACT

The present invention provides a compound useful as an agent for the prevention or treatment of a sex hormone-dependent disease or the like. That is, the present invention provides a fused heterocyclic derivative represented by the following general formula (I), a pharmaceutical composition containing the same, a medicinal use thereof and the like. In the formula (I), ring A represents 5-membered cyclic unsaturated hydrocarbon or 5-membered heteroaryl; $R^A$ represents halogen, alkyl, alkenyl, alkynyl, carboxy, alkoxy, carbamoyl, alkylcarbamoyl or the like ; ring B represents aryl or heteroaryl; $R^B$ represents halogen, alkyl, carboxy, alkoxy, carbamoyl, alkylcarbamoyl or the like; $E^1$ and $E^2$ represent an oxygen atom or the like; U represents a single bond or alkylene; X represents a group represented by Y, —$SO_2$—Y, —O—(alkylene)—Y, —O—Z in which Y represents Z, amino or the like; Z represents cycloalkyl, heterocycloalkyl, aryl, heteroaryl or the like; or the like.

(I)

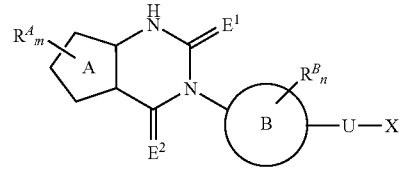

32 Claims, No Drawings

SEQUENCE LISTING

```
<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Glu His Trp Ser Tyr Gly Leu Arg Pro Gly
1               5                   10
```

FUSED HETEROCYCLIC DERIVATIVE, MEDICINAL COMPOSITION CONTAINING THE SAME, AND MEDICINAL USE THEREOF

This application is a 371 of PCT/JP2006/320681 filed Oct. 17, 2006, corresponding to WO2007/046392, published Apr. 26, 2007 and claiming the benefit of Japanese Patent Application No. 304395/2005 filed Oct. 19, 2005 and Japanese Patent Application No. 147019/2006, filed May 26, 2006, the disclosures of which are all incorporated hereby by reference.

TECHNICAL FIELD

The present invention relates to fused heterocyclic derivatives.

More particularly, the present invention relates to fused heterocyclic derivatives which have an antagonistic activity against gonadotropin releasing hormone and can be used for the prevention or treatment of a sex hormone-dependent disease such as benign prostatic hypertrophy, hysteromyoma, endometriosis, metrofibroma, precocious puberty, amenorrhea, premenstrual syndrome, dysmenorrhea or the like, or prodrugs thereof, or pharmaceutically acceptable salts thereof, or hydrates or solvates thereof, and pharmaceutical compositions containing the same and the like.

BACKGROUND ART

Gonadotropin Releasing Hormone (GnRH, GnRH is also called Luteinizing Hormone Releasing Hormone: LHRH, hereinafter referred to as "GnRH") is a peptide consisting of 10 amino acids: pGlu-His-Trp-Ser-Tyr-Gly-Leu-Arg-Pro-Gly-NH2 (SEQ ID NO: 1), which is secreted from the hypothalamus. GnRH secreted into hypophyseal portal vein promotes the production and secretion of gonadotropin of anterior pituitary hormones, Luteinizing Hormone: LH and Follicle Stimulating Hormone: FSH, via the receptors which are considered to exist in the anterior lobe of the pituitary, GnRH receptor. These gonadotropins affect gonad, ovary and testis, to promote the folliclar growth, ovulation and luteinization and spermatogenesis and also promote the production and secretion of sex hormones such as estrogen, progesterone and androgen (see Non-patent reference 1). Accordingly, antagonists specifically and selectively acting on the GnRH receptors should control the activities of GnRH and control the production and secretion of gonadotropin and sex hormones, and therefore, are expected to be useful as an agent for the prevention or treatment of sex hormone-dependent diseases.

As an agent inhibiting the function of GnRH receptor, GnRH receptor superagonists have been used as agents for the treatment of sex hormone-dependent diseases such as prostatic cancer, breast cancer and endometriosis and the like. The GnRH receptor superagonists bind GnRH receptors and exert an initial temporary gonadotropin secretion-stimulating effect so-called "flare-up phenomenon", and then suppress the function by causing gonadotropin depletion and GnRH receptor down-regulation to suppress. Therefore, the GnRH receptor superagonists have a problem that the disease becomes exacerbated transiently by the initially promoted secretion of gonadotropin. On the other hand, the suppression mechanism of GnRH receptor antagonists (hereinafter referred to as "GnRH antagonist") is an inhibition of the binding to GnRH receptors, and therefore, are expected to exert promptly suppressive effects without secretion of gonadotropin. In these years, as GnRH antagonists, peptidic GnRH antagonists such as abarelix and cetrorelix have been developed and used for the treatment of prostatic cancer, infertility and the like. However, since these peptidic GnRH antagonists have bad oral absorbability, they have to be subcutaneously or intramuscularly administered. Thus, development of a non-peptidic GnRH antagonist which can be orally administered wherein local reactivity at injected sites can be reduced and the dosages can be flexibly adjusted is desired (see Non-patent reference 2).

As fused pyrimidine derivatives having a non-peptidic GnRH antagonistic activity, compounds described in Patent references 1 and 2 are known. However, either of the compounds described in Patent reference 1 has a 5-membered hetero ring fused with a pyrimidine ring and an aryl substituent on the 5-membered hetero ring. In addition, the compounds described in Patent reference 2 are pyrimidine derivatives fused with an aromatic 6-membered ring and do not always have enough high oral absorbability. In Patent reference 3 which has been recently published, pyrimidine derivatives fused with a 5-membered hetero ring having a non-peptidic GnRH antagonistic activity are described. However, there is no specific description about compounds except for compounds having a sulfonamide or amide group, and no concrete description about blood kinetics in oral administration.

As compounds having a pyrimidine ring fused with a 5-membered hetero ring, in addition, various compounds are illustrated as a serine protease inhibitor in Patent reference 4, as a blood coagulation factor Xa inhibitor in Patent reference 5, as a herbicide in Patent reference 6 and the like. However, these references do not describe or suggest that a compound having a pyrimidine ring fused with a 5-membered hetero ring of the present invention has a GnRH antagonistic activity.

Non-patent reference 1: *Hyojun Seirigaku* (Standard Physiology), Edition 5, Igakusyoin, pp. 882-891.

Non-patent reference 2: *Sanka to Fujinka* (Obstetrics and Gynecology), 2004, Vol. 71, No. 3, pp. 280-285 and 301-307.

Patent reference 1: International publication No. WO96/24597 pamphlet.

Patent reference 2: International publication No. WO2005/019188 pamphlet.

Patent reference 3: International publication No. WO2006/083005 pamphlet.

Patent reference 4: U.S. Patent publication No. 2003/0004167 description.

Patent reference 5: International publication No. WO00/39131 pamphlet.

Patent reference 6: Japanese patent publication (Tokuhyo) No. H6-510992 gazette.

DISCLOSURE OF THE INVENTION

Objects to be Solved by the Invention

The present invention aims to provide a compound which has a GnRH antagonistic activity.

Means for Solving the Problems

The present inventors have studied earnestly to solve the above problems. As a result, it was newly found that a pyrimidine derivative fused with a 5-membered hetero ring represented by the following general formula (I) has an excellent GnRH antagonistic activity and exerts more excellent blood kinetics in oral administration compared with a pyrimidine derivative fused with an aromatic 6-membered ring, thereby forming the basis of the present invention.

That is, the present invention relates to:

[1] a fused heterocyclic derivative represented by the general formula (I):

[Chem. 1]

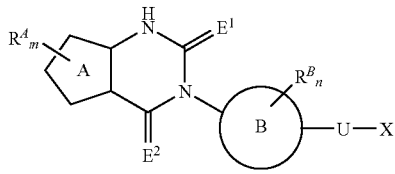

(I)

wherein ring A represents 5-membered cyclic unsaturated hydrocarbon or 5-membered heteroaryl;

$R^A$ represents a halogen atom, a cyano group, a nitro group, an optionally substituted lower alkyl group, an optionally substituted lower alkenyl group, an optionally substituted lower alkynyl group, a hydroxyiminomethyl group, an optionally substituted (lower alkyl)sulfonyl group, an optionally substituted (lower alkyl)sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$ or $SO_2NW^2W^3$ in which $W^1$ to $W^3$ independently represents a hydrogen atom or an optionally substituted lower alkyl group, or $W^2$ and $W^3$ may bind together with the neighboring nitrogen atom to form an optionally substituted cyclic amino group;

m represents an integer number 0 to 3;

ring B represents aryl or heteroaryl;

$R^B$ represents a halogen atom, a cyano group, an optionally substituted lower alkyl group, $OW^4$, $COW^4$, $COOW^4$ or $CONW^5W^6$ in which $W^4$ to $W^6$ may bind together with the neighboring nitrogen atom to form an optionally substituted cyclic amino group;

n represents an integer number 0 to 2;

$E^1$ represents an oxygen atom, a sulfur atom or N—CN;

$E^2$ represents an oxygen atom or NH;

U represents a single bond or an optionally substituted lower alkylene group;

X represents a group represented by Y, —CO—Y, —S$_2$—Y, —S—L—Y, —O—L—Y, —CO—L—Y, —COO—L—Y, —SO—L—Y, —S$_2$—L—Y, —S—Z, —O—Z or —COO—Z in which L represents an optionally substituted lower alkylene group;

Y represents a group represented by Z or —NW$^7$W$^8$ wherein W$^7$ and W$^8$ independently represent a hydrogen atom, an optionally substituted lower alkyl group or Z with the proviso that W$^7$ and W$^8$ are not hydrogen atoms at the same time, or W$^7$ and W$^8$ may bind together with the neighboring nitrogen atom to form an optionally substituted cyclic amino group;

Z represents an optionally fused and optionally substituted cycloalkyl group, an optionally fused and optionally substituted heterocycloalkyl group, an optionally fused and optionally substituted aryl group or an optionally fused and optionally substituted heteroaryl group;

or a prodrug thereof, or a pharmaceutically acceptable salt thereof, or a hydrate or solvate thereof;

[2] a fused heterocyclic derivative as described in the above [1], wherein ring A represents a 5-membered heteroaryl ring, or a prodrug thereof, or a pharmaceutically acceptable salt thereof, or a hydrate or solvate thereof;

[3] a fused heterocyclic derivative as described in the above [2], wherein the 5-membered heteroaryl ring of ring A is any of thiophene rings represented by the formula:

[Chem. 2]

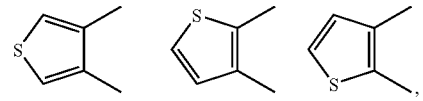

or a prodrug thereof, or a pharmaceutically acceptable salt thereof, or a hydrate or solvate thereof;

[4] a fused heterocyclic derivative as described in the above [3], wherein the 5-membered heteroaryl ring of ring A is a thiophene ring represented by the formula:

[Chem. 3]

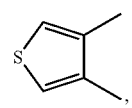

or a prodrug thereof, or a pharmaceutically acceptable salt thereof, or a hydrate or solvate thereof;

[5] a fused heterocyclic derivative as described in any of the above [1] to [4], wherein $R^A$ represents a halogen atom, an optionally substituted lower alkyl group, $COOW^1$ or $CONW^2W^3$ in which $W^1$ to $W^3$ independently represent a hydrogen atom or an optionally substituted lower alkyl group, or $W^2$ and $W^3$ may bind together with the neighboring nitrogen atom to form an optionally substituted cyclic amino group, or a prodrug thereof, or a pharmaceutically acceptable salt thereof, or a hydrate or solvate thereof;

[6] a fused heterocyclic derivative as described in the above [5], wherein $R^A$ represents a lower alkyl group substituted by any group selected from the group consisting of a hydroxyl group, a carboxy group and a carbamoyl group; a carboxy group; or a carbamoyl group, or a prodrug thereof, or a pharmaceutically acceptable salt thereof, or a hydrate or solvate thereof;

[7] a fused heterocyclic derivative as described in any of the above [1] to [6], wherein m represents 0 or 1, or a prodrug thereof, or a pharmaceutically acceptable salt thereof, or a hydrate or solvate thereof;

[8] a fused heterocyclic derivative as described in the above [7], wherein m represents 1 and ring A is a thiophene ring in which $R^A$ binds to the position of ring A at the position shown by the following general formula:

[Chem. 4]

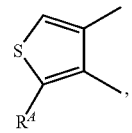

or a prodrug thereof, or a pharmaceutically acceptable salt thereof, or a hydrate or solvate thereof;

[9] a fused heterocyclic derivative as described in any of the above [1] to [8], wherein $E^1$ represents an oxygen atom, or a prodrug thereof, or a pharmaceutically acceptable salt thereof, or a hydrate or solvate thereof;

[10] a fused heterocyclic derivative as described in any of the above [1] to [9], wherein $E^2$ represents an oxygen atom, or a prodrug thereof, or a pharmaceutically acceptable salt thereof, or a hydrate or solvate thereof;

[11] a fused heterocyclic derivative as described in any of the above [1] to [10], wherein ring B represents a benzene ring, a thiophene ring or a pyridine ring, or a prodrug thereof, or a pharmaceutically acceptable salt thereof, or a hydrate or solvate thereof;

[12] a fused heterocyclic derivative as described in the above [11], wherein ring B is any of rings represented by the formula:

[Chem. 5]

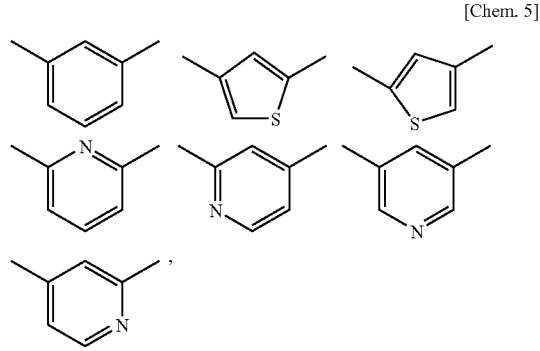

or a prodrug thereof, or a pharmaceutically acceptable salt thereof, or a hydrate or solvate thereof;

[13] a fused heterocyclic derivative as described in the above [12], wherein n is 1 or 2 and ring B is any of rings in which $R^B$ binds to the position of ring B at the position shown by any of the following formulae:

[Chem. 6]

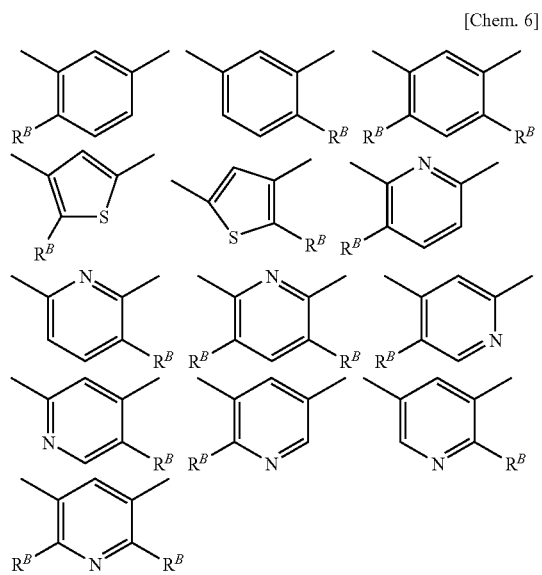

in the formula, $R^B$ has the same meaning as defined above, and when two $R^B$ groups exist, they can be the same or different from each other, or a prodrug thereof, or a pharmaceutically acceptable salt thereof, or a hydrate or solvate thereof;

[14] a fused heterocyclic derivative as described in the above [12] or [13], wherein ring B is any of rings represented by the formula:

[Chem. 7]

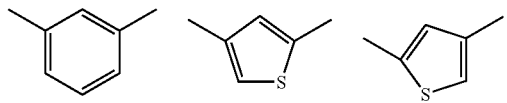

or a prodrug thereof, or a pharmaceutically acceptable salt thereof, or a hydrate or solvate thereof; [15] a fused heterocyclic derivative as described in any of the above [1] to [14], wherein $R^B$ represents a halogen atom, an optionally substituted lower alkyl group, $OW^4$ in which $W^4$ represents a hydrogen atom or an optionally substituted lower alkyl group, or a cyano group, or a prodrug thereof, or a pharmaceutically acceptable salt thereof, or a hydrate or solvate thereof;

[16] a fused heterocyclic derivative as described in the above [15], wherein $R^B$ represents a halogen atom, or a lower alkyl group which may be substituted by a halogen atom, or $OW^4$ in which $W^4$ represents a hydrogen atom or an optionally substituted lower alkyl group, or a prodrug thereof, or a pharmaceutically acceptable salt thereof, or a hydrate or solvate thereof;

[17] a fused heterocyclic derivative as described in the above [16], wherein $R^B$ represents a fluorine atom, a chlorine atom or $OW^4$ in which $W^4$ represents a lower alkyl group, or a prodrug thereof, or a pharmaceutically acceptable salt thereof, or a hydrate or solvate thereof;

[18] a fused heterocyclic derivative as described in any of the above [1] to [17], wherein U represents a single bond, a methylene group or an ethylene group, or a prodrug thereof, or a pharmaceutically acceptable salt thereof, or a hydrate or solvate thereof;

[19] a fused heterocyclic derivative as described in any of the above [1] to [18], wherein X represents a group represented by Y, —S—L—Y, —O—L—Y, —CO—L—Y, —SO$_2$—L—Y, —S—Z or —O—Z in which L, Y and Z have the same meanings as defined above, or a prodrug thereof, or a pharmaceutically acceptable salt thereof, or a hydrate or solvate thereof;

[20] a fused heterocyclic derivative as described in the above [19], wherein U represents a single bond and X represents a group represented by —S—L—Y, —O—L—Y, —CO—L—Y or —SO$_2$—L—Y in which L and Y have the same meanings as defined above, or a prodrug thereof, or a pharmaceutically acceptable salt thereof, or a hydrate or solvate thereof;

[21] a fused heterocyclic derivative as described in the above [19], wherein U represents a methylene group and X represents a group represented by Y in which Y represents —NW$^7$W$^8$ wherein W$^7$ and W$^8$ independently represent a hydrogen atom, an optionally substituted lower alkyl group or Z with the proviso that W$^7$ and W$^8$ are not hydrogen atoms at the same time, or W$^7$ and W$^8$ may bind together with the neighboring nitrogen atom to form an optionally substituted cyclic amino group, —S—Z or —O—Z in which Z has the same meaning as defined above, or a prodrug thereof, or a pharmaceutically acceptable salt thereof, or a hydrate or solvate thereof;

[22] a fused heterocyclic derivative as described in the above [19], wherein U represents an ethylene group and X represents Y with the proviso that Y represents Z and Z has the same meaning as defined above, or a prodrug thereof, or a pharmaceutically acceptable salt thereof, or a hydrate or solvate thereof;

[23] a fused heterocyclic derivative as described in any of the above [1] to [20], wherein L represents a C$_{1-3}$ alkylene group, or a prodrug thereof, or a pharmaceutically acceptable salt thereof, or a hydrate or solvate thereof;

[24] a fused heterocyclic derivative as described in any of the above [1] to [23], wherein Z represents an optionally fused and optionally substituted aryl group, or a prodrug thereof, or a pharmaceutically acceptable salt thereof, or a hydrate or solvate thereof;

[25] a pharmaceutical composition comprising as an active ingredient a fused heterocyclic derivative as described in any of the above [1] to [24], or a prodrug thereof, or a pharmaceutically acceptable salt thereof, or a hydrate or solvate thereof;

[26] a pharmaceutical composition as described in the above [25], which is a gonadotropin releasing hormone antagonist;

[27] a pharmaceutical composition as described in the above [25], which is an agent for the prevention or treatment of a sex hormone-dependent disease, a reproduction regulator, a contraceptive, an ovulation inducing agent or an agent for the prevention of post-operative recurrence of sex hormone-dependent cancers;

[28] a pharmaceutical composition as described in the above [27], wherein the sex hormone-dependent disease is selected from the group consisting of benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer and pituitary tumor;

[29] a pharmaceutical composition as described in the above [25], wherein the composition is an oral formulation; and a method for the prevention or treatment of a sex hormone-dependent disease, a method for the reproduction regulation, contraception, ovulation induction or prevention of post-operative recurrence of sex hormone-dependent cancers, which comprises administering an effective amount of the same; a use of the same for the manufacture of a pharmaceutical composition; a pharmaceutical composition which comprises a combination with at least one drug selected from the group consisting of a gonadotropin releasing hormone agonist, a chemotherapeutic agent, a peptidic gonadotropin releasing hormone antagonist, a 5α-reductase inhibitor, an α-adrenoceptor inhibitor, an aromatase inhibitor, an adrenal androgen production inhibitor and a hormonotherapeutic agent; and the like.

Effects of the Invention

Since a fused heterocyclic derivative (I) of the present invention or a prodrug thereof, or a pharmaceutically acceptable salt thereof, or a hydrate or solvate thereof has an excellent GnRH antagonistic activity, it can control the effect of gonadotropin releasing hormone and control the production and secretion of gonadotropin and sex hormones, and as a result, it can be used as an agent for the prevention or treatment of sex hormone-dependent diseases.

BEST MODE TO PUT THE INVENTION TO PRACTICE

Meanings of terms used in this description are as follows.
The term "5-membered cyclic unsaturated hydrocarbon" means a 5-membered hydrocarbon ring having one or two double bonds.

The term "heteroaryl" means monocyclic heteroaryl having 1 or more hetero atoms selected from the group consisting of a nitrogen atom, an oxygen atom and a sulfur atom such as thiazole, oxazole, isothiazole, isoxazole, pyridine, pyrimidine, pyrazine, pyridazine, pyrrole, furan, thiophene, imidazole, pyrazole, oxadiazole, thiadiazole, triazole, tetrazole, furazan or the like.

The term "optionally substituted" means which may have a substituent.

The term "5-membered heteroaryl" means 5-membered monocyclic heteroaryl as mentioned above, and for example, thiazole, oxazole, isothiazole, isoxazole, pyrrole, furan, thiophene, imidazole, pyrazole, oxadiazole, thiadiazole, triazole and furazan rings and the like can be illustrated.

The term "aryl" means phenyl.

The term "halogen atom" means a fluorine atom, a chlorine atom, a bromine atom or a iodine atom.

The term "lower alkyl" means optionally branched alkyl having 1 to 6 carbon atoms such as methyl, ethyl, propyl, isopropyl, butyl, isobutyl, sec-butyl, tert-butyl, pentyl, isopentyl, neopentyl, tert-pentyl, hexyl or the like.

The term "lower alkenyl" means optionally branched alkenyl having 2 to 6 carbon atoms such as vinyl, allyl, 1-propenyl, isopropenyl, 1-butenyl, 2-butenyl, 2-methylallyl or the like.

The term "lower alkynyl" means optionallybranched alkynyl having 2 to 6 carbon atoms such as ethynyl, 2-propynyl or the like.

The term "(lower alkyl)sulfonyl" means sulfonyl substituted by the above lower alkyl.

The term "(lower alkyl)sulfinyl" means sulfinyl substituted by the above lower alkyl.

The term "lower alkylene" means optionally branched alkylene having 1 to 6 carbon atoms such as methylene, ethylene, methylmethylene, trimethylene, dimetylmethylene, ethylmethylene, methylethylene, propylmethylene, isopropylmethylene, dimethylethylene, butylmethylene, ethylmethylmethylene, pentamethylene, diethylmethylene, dimethyltrimethylene, hexamethylene, diethylethylene or the like.

The term "$C_{1-3}$ alkylene" means the above lower alkylene having 1 to 3 carbon atoms.

The term "lower alkoxy" means optionally branched alkoxy having 1 to 6 carbon atoms such as methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy or the like.

The term "(lower alkoxy)carbonyl" means optionally branched alkoxycarbonyl having 2 to 7 carbon atoms.

The term "(lower alkyl)thio" means optionally branched alkylthio having 1 to 6 carbon atoms.

The term "cycloalkyl" means monocyclic cycloalkyl having 3 to 8 carbon atoms, for example, monocyclic cycloalkyl such as cyclopropyl, cyclobutyl, cyclopentyl, cyclohexyl, cycloheptyl, cyclooctyl and the like can be illustrated.

The term "heterocycloalkyl" means 3 to 8-membered heterocycloalkyl having 1 or more hetero atoms selected from the group consisting of a nitrogen atom, an oxygen atom and a sulfur atom and optionally having 1 or 2 oxo groups such as pyrrolidinyl, piperidinyl, oxopiperidinyl, morpholinyl, piperazinyl, oxopiperazinyl, thiomorpholinyl, azepanyl, diazepanyl, oxazepanyl, thiazepanyl, dioxothiazepanyl, azokanyl, tetrahydrofuranyl, tetrahydropyranyl or the like. In case of having a sulfur atom in the ring, the sulfur atom may be oxidized.

The term "optionally fused" means which may be fused with a ring selected from the group consisting of the above cycloalkyl, the above heterocycloalkyl, the above aryl and the above heteroaryl. As "fused cycloalkyl", "fused heterocycloalkyl", "fused aryl" and "fused heteroaryl", for example, indolyl, isoindolyl, benzofuranyl, isobenzofuranyl, benzothiophenyl, benzoxazolyl, benzothiazolyl, benzoisoxazolyl, benzoisothiazolyl, indazolyl, benzimidazolyl, quinolinyl, isoquinolinyl, phthalazinyl, quinoxalinyl, quinazolinyl, cinnolinyl, indolizinyl, naphthyridinyl, pteridinyl, indanyl, naphtyl, 1,2,3,4-tetrahydronaphthyl, indolinyl, isoindolinyl, 2,3,4,5-tetrahydrobenzo[b]oxepinyl, 6,7,8,9-tetrahydro-5H-benzocycloheptenyl, chromanyl and the like can be illustrated, and the free valency may be on either ring.

The term "cyclic amino" means a group having at least a nitrogen atom which has a binding site in the ring among the above optionally fused heterocycloalkyl. For example, 1-pyrrolidinyl, 1-piperidinyl, 1-piperazinyl, 4-morpholinyl, 4-thiomorpholinyl, 2,3,4,5,6,7-hexahydro-1H-azepin-1-yl, 1-indolinyl, 2-isoindolinyl, 3,4-dihydro-1,5-naphthyridin - 1(2H)-yl, 1,2,3,4-tetrahydroquinolin-1-yl, 3,4-dihydro - quinolin-1(2H)-yl, 3,4-dihydroisoquinolin-2(1H)-yl, octahydroquinolin-1(2H)-yl, octahydroisoquinolin-2(1H)-yl, perhydroquinolin-1-yl, 2,3-dihydro-4H-1,4-benzoxazin-4-yl, 2,3-dihydro-4H-1,4-benzothiazin-4-yl, 3,4-dihydro - quinoxalin-1(2H)-yl, 2,3-dihydro-4H-pyrid[3,2-b][1,4]-oxazin-4-yl, 2,3,4,5-tetrahydro-1H-1-benzoazepin-1-yl, 1,3,4,5-tetrahydro-2H-2-benzoazepin-2-yl, 3,4-dihydro-1,5-benzoxazepin-5(2H)-yl, 2,3-dihydro-4,1-benzothiazepin - 1(5H)-yl, 3,4-dihydro-1,5-benzothiazepin-5(2H)-yl, 2,3-dihydro-4,1-benzoxazepin-1(5H)-yl, 2,3,4,5-tetrahydro -1H-1,5-benzodiazepin-1-yl, 2,3,4,5-tetrahydro-1H-1,4-benzodiazepin-l-yl, 5,6,7,8-tetrahydro-4H-thieno[3,2-b]-azepin-4-yl, 3,4,5,6-tetrahydro-1-benzazocin-1(2H)-yl and the like can be illustrated.

The term "(di) (lower alkyl)amino" means amino mono- or di-substituted by the above lower alkyl. Two lower alkyl groups in di-substituted amino maybe different and the two lower alkyl groups may bind together with the neighboring nitrogen atom to form a cyclic amino group.

The term "(di) (lower alkyl)carbamoyl" means carbamoyl mono- or di-substituted by the above lower alkyl. Two lower alkyl groups in di-substituted amino may be different and the two lower alkyl groups may bind together with the neighboring nitrogen atom to form a cyclic amino group.

The term "acyl" means optionally branched aliphatic carboxylic acyl having 2 to 7 carbon atoms, cycloalkylcarboxylic acyl, heterocycloalkylcarboxylic acyl, arylcarboxylic acyl, or heteroarylcarboxylic acyl.

The term "acylamino" means amino substituted by the above acyl.

In the general formula (I), as ring A, 5-membered heteroaryl is preferable, a thiophene ring is more preferable, and a thiophene ring represented by the following formula:

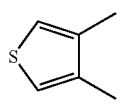

[Chem. 8]

is particularly preferable. As $R^A$, a halogen atom, an optionally substituted lower alkyl group, $COOW^1$, $CONW^2W^3$ in which $W^1$ to $W^3$ independently represent a hydrogen atom or an optionally substituted lower alkyl group, or $W^2$ and $W^3$ may bind together with the neighboring nitrogen atom to form an optionally substituted cyclic amino group, or the like is preferable, a lower alkyl group substituted by a group selected from the group consisting of a hydroxyl group, a carboxy group and a carbamoyl group; a carboxy group or a carbamoyl group is more preferable, and a carboxy group is most preferable. In case that m is 2 or more, $R^A$s maybe the same or different. As m, 0 or 1 is preferable, and when m is 1, as ring A having $R^A$ on the ring, a thiophene ring represented by the following formula:

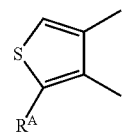

[Chem. 9]

is particularly preferable. In this case, as $R^A$, an optionally substituted lower alkyl group, $COOW^1$ or $CONW^2W^3$ in which $W^1$ to $W^3$ independently represent a hydrogen atom or an optionally substituted lower alkyl group, or $W^2$ and $W^3$ may bind together with the neighboring nitrogen atom to form an optionally substituted cyclic amino group is more preferable.

In the general formula (I), as $E^1$, an oxygen atom is preferable. As $E^2$, an oxygen atom is preferable.

In the general formula (I), as ring B, a benzene ring, a thiophene ring or a pyridine ring is preferable, and a benzene ring or a thiophene ring is more preferable. In this case, binding sites of ring B are preferably as represented by the following formula:

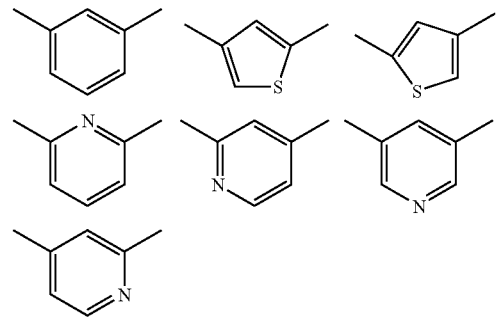

[Chem. 10]

and are more preferably as represented by the following formula:

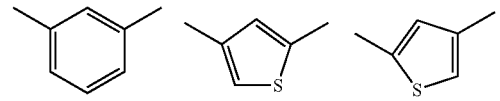

[Chem. 11]

wherein the left bond represents a bond with the nitrogen atom of the fused pyrimidine ring and the right bond represents a bond with U.

In case that n is 1 or 2, as ring B having $R^B$ on the ring, a benzene ring, a thiophene ring or a pyridine ring represented by the following formula:

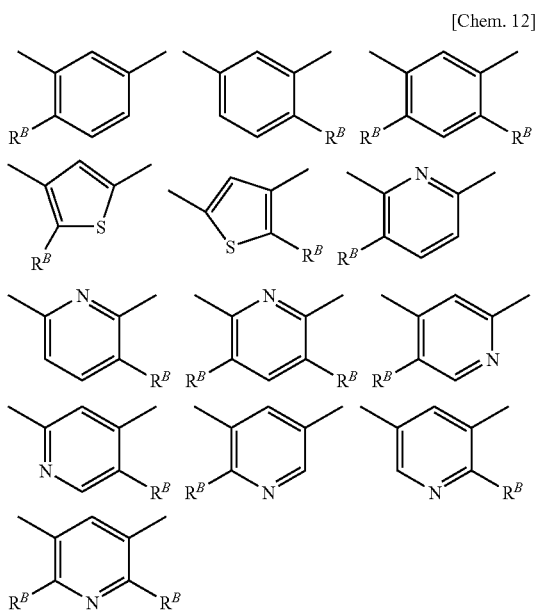

wherein the left bond of the bonds not bound to $R^B$ represents a bond with the nitrogen atom of the fused pyrimidine ring and the right bond represents a bond with U. As $R^B$, a halogen atom, an optionally substituted lower alkyl group, $OW^4$ in which $W^4$ represents a hydrogen atom or an optionally substituted lower alkyl group, a cyano group or the like is preferable, a halogen atom, a lower alkyl group which may be substituted by a halogen atom or $OW^4$ is more preferable, and a fluorine atom, a chlorine atom or $OW^4$ in which $W^4$ is a lower alkyl group is particularly preferable. In case that n is 2, two $R^B$ maybe the same or different. In addition, in case that ring B having $R^B$ on the ring is a benzene ring, a thiophene ring or a pyridine ring represented by the following formula:

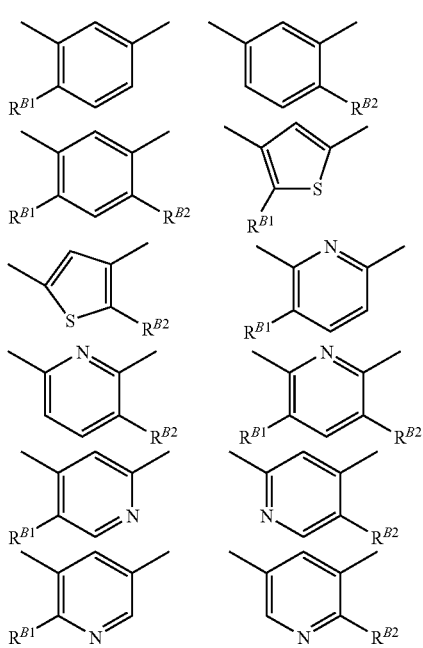

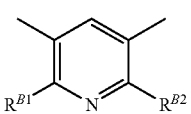

wherein the left bond of the bonds not bound to any of $R^{B1}$ and $R^{B2}$ represents a bond with the nitrogen atom of the fused pyrimidine ring and the right bond represents a bond with U, as $R^{B1}$, a fluorine atom or a chlorine atom is preferable, and as $R^{B2}$, a fluorine atom, a methoxy group or an ethoxy group is preferable and a methoxy group is more preferable.

In the general formula (I), U is preferably a single bond, a methylene group or an ethylene group.

Especially, (i) when U is a single bond, as X, a group represented by —S—L—Y, —O—L—Y, —CO—L—Y or —SO$_2$—L—Y wherein L represents an optionally substituted lower alkylene group; Y represents Z or —NW$^7$W$^8$ in which W$^7$ and W$^8$ independently represent a hydrogen atom, an optionally substituted lower alkyl group or Z with the proviso that both are not a hydrogen atom at the same time, or W$^7$ and W$^8$ may bind together with the neighboring nitrogen atom to form an optionally substituted cyclic amino group; Z represents an optionally fused and optionally substituted cycloalkyl group, an optionally fused and optionally substituted heterocycloalkyl group, an optionally fused and optionally substituted aryl group or an optionally fused and optionally substituted heteroaryl group is preferable, (ii) when U is a methylene group, as X, a group represented by Y with the proviso that Y represents —NW$^7$W$^8$ in which W$^7$ and W$^8$ independently represent a hydrogen atom, an optionally substituted lower alkyl group or Z with the proviso that both are not a hydrogen atom at the same time and W$^7$ is preferably Z, or W$^7$ and W$^8$ may bind together with the neighboring nitrogen atom to form an optionally substituted cyclic amino group, —S—Z or —O—Z is preferable, (iii) when U is an ethylene group, as X, Y with the proviso that Y is Z and Z has the same meaning as defined above, is preferable, since they exert good blood kinetics.

As L, a C$_{1-3}$ lower alkylene group is preferable.

As Z, an optionally fused and optionally substituted heteroaryl group or an optionally fused and optionally substituted aryl group is preferable, and an optionally fused and optionally substituted aryl group is more preferable. In Z, as a substituent which an optionally substituted heteroaryl group or an optionally substituted aryl group may have, a halogen atom, an optionally substituted lower alkyl group or an optionally substituted lower alkoxy group is preferable, and a halogen atom; a lower alkyl group which may be substituted by a halogen atom, a lower alkoxy group or a hydroxyl group; or a lower alkoxy group which may be substituted by a halogen atom, a lower alkoxy group or a hydroxyl group is more preferable.

As a substituent which an optionally substituted cyclic amino group, an optionally substituted cycloalkyl group or an optionally substituted heterocycloalkyl group may have, for example, an oxo group, a halogen atom, a cyano group, a hydroxyl group, an optionally substituted lower alkyl group, a cycloalkyl group, an optionally substituted lower alkoxy group, an optionally substituted (lower alkyl) thio group, a carboxy group, an optionally substituted (lower alkoxy) carbonyl group, a carbamoyl group, a (di) (lower alkyl) carbamoyl group, an optionally substituted aryl group, an aryloxy group, a heteroaryl group, a heteroaryloxy group, an acylamino group and the like can be illustrated, and the same or different two or more groups selected from these groups may exist, and with the proviso that as a substituent which an optionally substituted cyclic amino group $NW^2W^3$ forms in $R^A$ may have, a group containing an aryl group is excluded from the above.

As a substituent which an optionally substituted aryl group or an optionally substituted heteroaryl group may have, for example, a halogen atom, a nitro group, a cyano group, a hydroxyl group, an optionally substituted lower alkyl group, a cycloalkyl group, an optionally substituted lower alkoxy group, an optionally substituted (lower alkyl) thio group, a carboxy group, an optionally substituted (lower alkoxy)carbonyl group, a carbamoyl group, a (di) (lower alkyl)carbamoyl group, an aryl group, an aryloxy group, a heteroaryl group, a heteroaryloxy group, an acylamino group and the like can be illustrated, and the same or different two or more groups selected from these groups may exist.

In an optionally fused and optionally substituted cycloalkyl group, an optionally fused and optionally substituted heterocycloalkyl group, an optionally fused and optionally substituted aryl group and an optionally fused and optionally substituted heteroaryl group, the above substituents may exist on the same or different rings in the fused ring.

In case that Z is an optionally fused and optionally substituted cycloalkyl group or an optionally fused and optionally substituted heterocycloalkyl group, as a substituent which the group may have, an optionally substituted aryl group or a heteroaryl group is preferable.

As a substituent which an optionally substituted lower alkyl, an optionally substituted lower alkylene, an optionally substituted lower alkenyl, an optionally substituted lower alkynyl, an optionally substituted (lower alkyl) sulfonyl, an optionally substituted (lower alkyl) sulfinyl, an optionally substituted lower alkoxy, an optionally substituted (lower alkyl) thio or an optionally substituted (lower alkoxy) carbonyl group may have, a halogen atom, a cyano group, a hydroxyl group, a lower alkoxy group, a (lower alkyl) thio group, an amino group, a (di) (lower alkylamino group, a carboxy group, a (lower alkoxy) carbonyl group, a carbamoyl group, a (di) (lower alkyl) carbamoyl group, an aryl group, a heteroaryl group and the like can be illustrated, and the same or different two or more groups selected from these groups may exist, and with the proviso that in $R^A$, a group containing an aryl group or an heteroaryl group is excluded from the above.

An example of the methods for preparing a fused heterocyclic derivative represented by the general formula (I) of the present invention is shown below.

[Method 1]

Among the fused heterocyclic derivatives represented by the general formula (I) of the present invention, a compound wherein $E^1$ is an oxygen atom can be prepared, for example, by Method 1.

[Chem. 14]

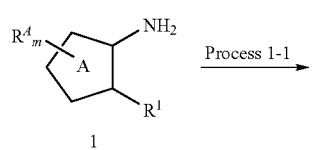

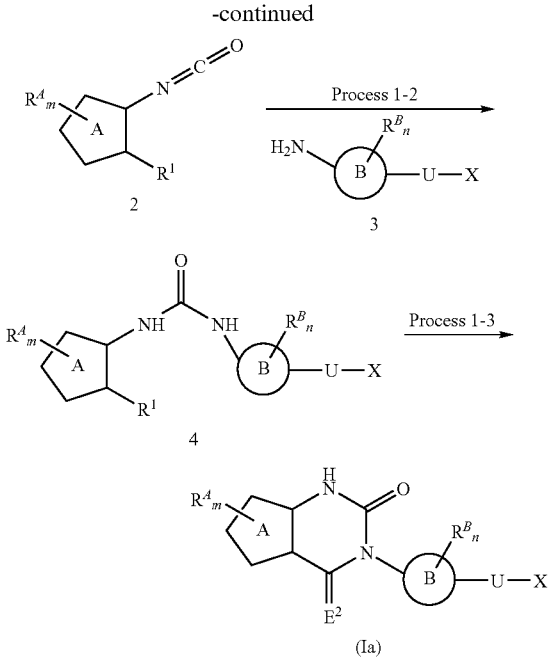

(Ia)

In the formula, $R^1$ represents a nitrile group or a (lower alkoxy) carbonyl group, and ring A, ring B, $R^A$, $R^B$, m, n, $E^2$, U and X have the same meanings as defined above.

Process 1-1

Amine compound (1) can be converted by treating in an inert solvent (for example, tetrahydrofuran, dichloromethane, a mixed solvent thereof or the like) using a reagent such as phosgene, diphosgene, triphosgene or the like in the presence of a base (for example, triethylamine, N,N-diisopropylethylamine, pyridine or the like) usually under ice-cooling to at reflux temperature for 30 minutes to 1 day into Isocyanato compound (2).

Process 1-2

Urea compound (4) or a fused heterocyclic derivative (Ia) of the present invention can be prepared by allowing Isocyanato compound (2) to react with Amine compound (3) in an inert solvent (for example, tetrahydrofuran, dichloromethane or the like) in the presence or absence of a base (for example, triethylamine, N,N-diisopropylethylamine, pyridine, 4-dimethylaminopyridine or the like) usually under ice-cooling to at reflux temperature for 1 hour to 3 days.

Process 1-3

A fused heterocyclic derivative (Ia) of the present invention can be prepared by allowing Urea compound (4) in an inert solvent (for example, tetrahydrofuran, dichloromethane, methanol, ethanol, N,N-dimethylformamide, water or the like) in the presence or absence of a base (for example, triethylamine, N,N-diisopropylethylamine, pyridine, 4-dimethylaminopyridine, sodium methoxide, sodium ethoxide, sodium hydride, sodium hydroxide or the like) usually under ice-cooling to at reflux temperature for 5 minutes to 3 days.

[Method 2]

Among the fused heterocyclic derivatives represented by the general formula (I) of the present invention, a compound wherein $E^2$ is an oxygen atom can be prepared, for example, by Method 2.

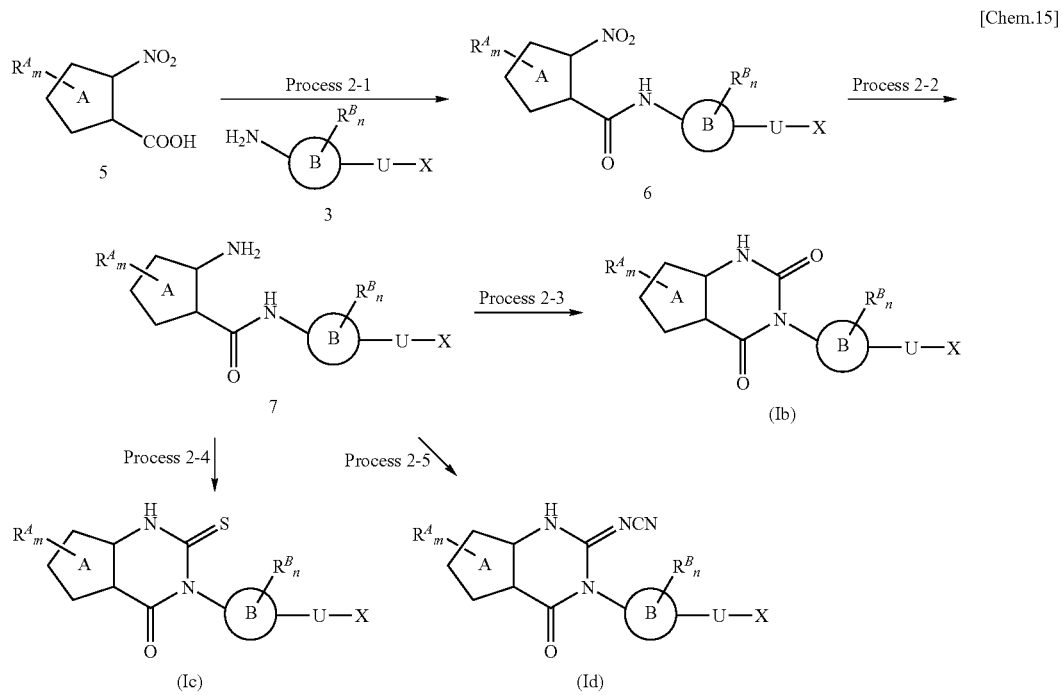

[Chem.15]

In the formula, ring A, ring B, $R^A$, $R^B$, m, n, U and X have the same meanings as defined above.

Process 2-1

Amide compound (6) can be prepared by subjecting Carboxylic acid compound (5) and Amine compound (3) to condensation by an acid chloride method or a condensing agent method generally used. An acid chloride method can be conducted, for example, by treating Carboxylic acid compound (5) in an inert solvent (dichloromethane, 1,2-dichloroethane or toluene) using a reagent such as thionyl chloride, oxalyl chloride or the like in the presence or absence of an additive (for example, N,N-dimethylformamide or the like) usually under ice-cooling to at reflux temperature for 30 minutes to 1 day to convert into an acid chloride, and by allowing the acid chloride to react with Amine compound (3) in an inert solvent (pyridine, dichloromethane, tetrahydrofuran, water or the like) in the presence or absence of a base (triethylamine, N,N-diisopropylethylamine, pyridine, 4-dimethylaminopyridine, potassium carbonate, sodium hydrogen carbonate or the like) usually under ice-cooling to at reflux temperature for 1 hour to 3 days. A condensing agent method can be conducted, for example, by allowing Carboxylic acid compound (5) to react with Amine compound (3) in an inert solvent (N,N-dimethylformamide, dichloromethane or tetrahydrofuran) using a condensing agent (1-ethyl-3-(3-dimethylaminopropyl)carbodiimide hydrochloride, dicyclohexylcarbodiimide or the like) in the presence of an additive (1-hydroxybenzotriazole or the like) in the presence or absence of a base (triethylamine, N,N-diisopropylethylamine, pyridine, 4-dimethylaminopyridine or the like) usually at room temperature to reflux temperature for 1 hour to 3 days.

Process 2-2

Amine compound (7) can be prepared by reducing the nitro group of Amide compound (6) by a catalytic reduction method or a metal hydrogen complex compound reduction method generally used or the like. A catalytic reduction method can be conducted, for example, by treating Amide compound (6) in an inert solvent (methanol, ethanol, ethyl acetate, tetrahydrofuran, acetic acid or the like) using a catalyst (palladium-carbon powder or the like) usually at room temperature to reflux temperature for 1 hour to 3 days. A metal hydrogen complex compound reduction method can be conducted, for example, by treating Amide compound (6) in an inert solvent (methanol, ethanol, tetrahydrofuran or the like) using a reducing agent (sodium borohydride or the like) in the presence of an additive (nickel (II) bromide or the like) usually under ice-cooling to at room temperature for 30 minutes to 1 day.

Process 2-3

A fused heterocyclic derivative (Ib) of the present invention can be prepared by treating Amine compound (7) in an inert solvent (tetrahydrofuran, dichloromethane, N,N-dimethylformamide or the like) using a reagent such as phosgene, diphosgene, triphosgene, 1,1'-carbonylbis-1H-imidazole or the like in the presence or absence of a base (triethylamine, N,N-diisopropylethylamine, pyridine, 4-dimethylaminopyridine, sodium hydride or the like) usually under ice-cooling to at reflux temperature for 30 minutes to 1 day.

Process 2-4

A fused heterocyclic derivative (Ic) of the present invention can be prepared by treating Amine compound (7) in an inert solvent (tetrahydrofuran, N,N-dimethylformamide, methanol or ethanol) using a reagent such as carbon disulfide or the like in the presence of a base (triethylamine, N,N-diisopropylethylamine, sodium hydride, sodium hydroxide, potassium hydroxide or the like) usually under ice-cooling to at reflux temperature for 1 hour to 3 days.

Process 2-5

A fused heterocyclic derivative (Id) of the present invention can be prepared by treating Amine compound (7) in an inert solvent (tetrahydrofuran, N,N-dimethylformamide, methanol, ethanol or the like) using a reagent such as diphenylcyanocarbonimidate or the like in the presence of a base (triethylamine, N,N-diisopropylethylamine, sodium hydride, sodium hydroxide, potassium hydroxide or the like) usually under ice-cooling to at reflux temperature for 1 hour to 3 days.
[Method 3]

Amine compound (3) used as a starting material in the above Method 1 or 2 can be also obtained by reducing Nitro compound (8), which is available commercially or synthesized by a method described in literatures or combining general synthetic methods or the like, by a general reduction method or the like. For example, it can be prepared by the following Method 3.

[Chem. 16]

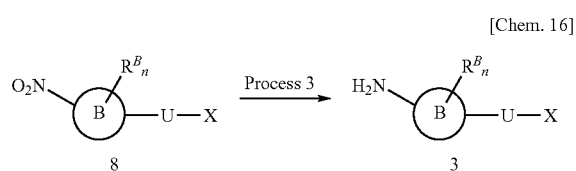

In the formula, ring B, $R^B$, n, U and X have the same meanings as defined above.
Process 3

Amine compound (3) can be prepared by reducing Nitro compound (8) by a catalytic reduction method or a metal hydrogen complex compound reduction method generally used or the like. A catalytic reduction method can be conducted, for example, by treating Nitro compound (8) in an inert solvent (methanol, ethanol, ethyl acetate, tetrahydrofuran, acetic acid or the like) using a catalyst (palladium-carbon powder, rhodium-carbon powder, platinum-carbon powder or the like) usually at room temperature to reflux temperature for 1 hour to 3 days. A metal hydrogen complex compound reduction method can be conducted, for example, by treating Nitro compound (8) in an inert solvent (methanol, ethanol, tetrahydrofuran or the like) using a reducing agent (sodium borohydride or the like) in the presence of an additive (nickel (II) bromide or the like) usually under ice-cooling to at room temperature for 30 minutes to 1 day.

In addition, when a compound used or prepared in the above Methods has a functional group which changes under the reaction conditions or inhibits the reaction progression, needless to say, the group may be protected by an appropriate protective group commonly used by a skilled person in the art and the protective group may be removed in an appropriate step.

A fused heterocyclic derivative represented by the general formula (I) of the present invention can be converted into a prodrug wherein its carboxyl group, hydroxy group and/or amino group is converted, by allowing to react with a reagent to produce a prodrug. In addition, a prodrug of a fused heterocyclic derivative represented by the general formula (I) of the present invention may be a compound to be converted into a compound (I) of the present invention under physiological conditions described in "*Iyakuhin no Kaihatsu*" (Development of medicines), Vol. 7, Molecular design, pp. 163-198, issued by Hirokawa syoten (Hirokawa Book Store).

A fused heterocyclic derivative represented by the general formula (I) or a prodrug thereof can be converted into a pharmaceutically acceptable salt thereof in the usual way. As such a salt, for example, a salt with an inorganic acid such as hydrochloric acid, nitric acid or the like; a salt with an organic acid such as acetic acid, methanesulfonic acid or the like; and a sodium salt and potassium salt; an additive salt with an organic base such as N,N'-dibenzylethylenediamine, 2-aminoethanol or the like can be illustrated.

A fused heterocyclic derivative represented by the general formula (I) or a prodrug thereof sometimes can be obtained as a hydrate or solvate in the course of purification or preparing salts thereof. For a pharmaceutical composition of the present invention, either of a fused heterocyclic derivative or a prodrug thereof, or a pharmaceutically acceptable salt thereof, or a hydrate or solvate thereof can be employed.

Furthermore, a fused heterocyclic derivative represented by the general formula (I) or a prodrug thereof sometimes has tautomers, geometrical isomers and/or optical isomers. For a pharmaceutical composition of the present invention, any of the isomers and a mixture thereof can be employed.

A fused heterocyclic derivative (I) of the present invention has an excellent GnRH antagonistic activity and can control the effect of gonadotropin releasing hormone and control the production and secretion of gonadotropin and sex hormones. As a result, a fused heterocyclic derivative (I) of the present invention or a prodrug thereof, or a pharmaceutically acceptable salt thereof, or a hydrate or solvate thereof is extremely useful as an agent for the prevention or treatment of sex hormone-dependent diseases such as benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer and pituitary tumor; a reproduction regulator, a contraceptive, an ovulation inducing agent or an agent for the prevention of post-operative recurrence of sex hormone-dependent cancers or the like.

A Pharmaceutical composition may be prepared by mixing a fused heterocyclic derivative (I) of the present invention or a prodrug thereof, or a pharmaceutically acceptable salt thereof, or a hydrate or solvate thereof and a conventional pharmaceutical carrier.

The pharmaceutical carrier may be used optionally in combination according to a dosage form as described below. As the pharmaceutical carrier, for example, excipients such as lactose or the like; lubricants such as magnesium stearate or the like; disintegrators such as carboxymethylcellulose or the like; binders such as hydroxypropylmethylcellulose or the like; surfactants such as macrogol or the like; foamings such as sodium hydrogen carbonate or the like; dissolving aids such as cyclodextrin or the like; acidities such as citric acid or the like; stabilizers such as sodium edetate or the like; pH adjusters such as phosphoric acid salt or the like can be illustrated.

As the dosage form of the pharmaceutical composition of the present invention, for example, formulations for oral administration such as powders, granules, fine granules, dry syrups, tablets, capsules and the like; formulations for parenteral administration such as injections, poultices, suppositories and the like are illustrated, and a formulation for oral administration is preferable.

It is preferable to manufacture the above formulations in such a way that the dosage of the compound represented by the general formula (I) of the present invention or a pharmaceutically acceptable salt thereof, or a hydrate or solvate thereof is appropriately within the range of from 0.1 to 1,000 mg per day per adult human in case of oral administration and approximately within the range of from 0.01 to 100 mg per day per adult human in the case of parenteral injection in the formulation.

Furthermore, a pharmaceutical composition of the present invention can include other drug(s). Examples of such other drugs include a GnRH agonist (for example, leuprorelin acetate, gonadorelin, buserelin, triptorelin, goserelin, nafarelin, histrelin, deslorelin, meterelin, lecirelin and the like), a chemotherapeutic agent (for example, ifosfamide, adriamycin, peplomycin, cisplatin, cyclophosphamide, 5-FU, UFT, methotrexate, mitomycin C, mitoxantrone, paclitaxel, dotaxel and the like), a peptidic GnRH antagonist (for example, cetrorelix, ganirelix, abarelix, ozarelix, iturelix, degarelix, teverelix and the like), a 5α-reductase inhibitor (for example, finasteride, dutasteride and the like), an α-adrenoceptor inhibitor (for example, tamsulosin, silodosin, urapidil and the like), an aromatase inhibitor (for example, fadrozole, letrozole, anastrozole, formestane and the like), an adrenal androgen production inhibitor (for example, liarozole and the like), a hormonotherapeutic agent (for example, an antiestrogenic agent such as tamoxifen, fulvestrant and the like, a progestational agent such as medroxyprogesterone and the like, an androgenic agent, an estrogeninc agent and an antiandrogenic agent such as oxendolone, flutamide, nilutamide, bicalutamide and the like) and the like can be illustrated.

EXAMPLES

The present invention is further illustrated in more detail by way of the following Examples and Test Examples. However, the present invention is not limited thereto.

Reference Example 1

2-Chloro-5-(3,4-dihydroquinolin-1(2H)-ylsulfonyl)aniline

To a suspension of 1,2,3,4-tetrahydroquinoline (3.12 g) and sodium hydrogen carbonate (2.66 g) in tetrahydrofuran (60 mL) were added water (6 mL) and a solution of 4-chloro-3-nitro-benzenesulfonyl chloride (5.4 g) in tetrahydrofuran (30 mL) successively, and the mixture was stirred at room temperature overnight. The reaction mixture was diluted with ethyl acetate, and the resulting mixture was washed with water, 1 mol/L hydrochloric acid, water and brine successively, and dried over anhydrous magnesium sulfate. The solvent was removed under reduced pressure to give 1-[(4-chloro-3-nitrophenyl)sulfonyl]-1,2,3,4-tetrahydroquinoline (5.0 g). This material was dissolved in tetrahydrofuran (45 mL). To the solution were added methanol (45 mL), nickel(II) bromide (0.15 g) and sodium borohydride (1.61 g) under ice-cooling, and the mixture was stirred at the same temperature for 30 minutes. Then the mixture was stirred at room temperature for 30 minutes. The reaction mixture was diluted with ethyl acetate, and the resulting mixture was washed with a saturated aqueous sodium hydrogen carbonate solution, water and brine successively, and dried over anhydrous magnesium sulfate. The solvent was removed under reduced pressure, and the residue was purified by column chromatography on silica gel (eluent: n-hexane/ethyl acetate=3/1) to give the title compound (4.33 g).

Reference Examples 2 to 11

The compounds of Reference Examples 2 to 11 described in Tables 1 to 2 were obtained in a similar manner to that described in Reference Example 1 using the corresponding starting materials.

Reference Example 12

2-Chloro-5-(3,4-dihydroquinolin-1(2H)-ylmethyl)aniline

To a solution of 4-chloro-3-nitrobenzyl alcohol (1 g) in methylene chloride (10 mL) were added triethylamine (1.12 mL) and methanesulfonyl chloride (0.5 mL) under ice-cooling, and the mixture was stirred at room temperature for 10 hours. The reaction mixture was diluted with ethyl acetate, and the resulting mixture was washed with water and brine successively, and dried over anhydrous magnesium sulfate. The solvent was removed under reduced pressure to give (4-chloro-3-nitrobenzyl) mesylate (1.08 g). This material was dissolved in acetonitrile (4 mL)-ethanol (4 mL). To the solution were added 1,2,3,4-tetrahydroquinoline (1.62 g) and a catalytic amount of sodium iodide, and the mixture was stirred at 60° C. overnight. The reaction mixture was diluted with ethyl acetate, and the resulting mixture was washed with water and brine successively, and dried over anhydrous magnesium sulfate. The solvent was removed under reduced pressure, and the residue was purified by column chromatography on silica gel (eluent: n-hexane/ethyl acetate=3/1) to give 1-(4-chloro-3-nitrobenzyl)-1,2,3,4-tetrahydroquinoline (1.22 g). This material was dissolved in tetrahydrofuran (12 mL). To the solution were added methanol (12 mL), nickel (II) bromide (44 mg) and sodium borohydride (0.46 g) under ice-cooling, and the mixture was stirred at the same temperature for 30 minutes. Then the mixture was stirred at room temperature for 30 minutes. The reaction mixture was diluted with ethyl acetate, and the resulting mixture was washed with a saturated aqueous sodium hydrogen carbonate solution, water and brine successively, and dried over anhydrous magnesium sulfate. The solvent was removed under reduced pressure, and the residue was purified by column chromatography on silica gel (eluent: n-hexane/ethyl acetate=3/1) to give the title compound (0.79 g).

Reference Example 13

3-Benzyloxy-6-chloroaniline

4-Chloro-3-nitrophenol (0.13 g) was dissolved in N,N-dimethylformamide (3 mL). To the solution were added potassium carbonate (0.31 g) and benzyl bromide (0.14 mL), and the mixture was stirred at room temperature for 2 hours. The reaction mixture was diluted with diethyl ether, and the resulting mixture was washed with water and brine successively, and dried over anhydrous magnesium sulfate. The solvent was removed under reduced pressure, and the residue was dissolved in tetrahydrofuran (3 mL). To the solution were added methanol (3 mL), nickel(II) bromide (8 mg) and sodium borohydride (85 mg) under ice-cooling, and the mixture was stirred at the same temperature for 30 minutes. Then the mixture was stirred at room temperature for 30 minutes. The reaction mixture was diluted with ethyl acetate, and the resulting mixture was washed with a saturated aqueous sodium hydrogen carbonate solution, water and brine successively, and dried over anhydrous magnesium sulfate. The solvent was removed under reduced pressure to give the title compound (0.15 g).

Reference Examples 14 to 17

The compounds of Reference Examples 14 to 17 described in Table 2 were obtained in a similar manner to that described in Reference Example 13 using the corresponding starting materials.

Reference Example 18

3-(2-Phenylethyl)aniline

A mixture of 3-bromonitrobenzene (1 g), styrene (1.7 mL), palladium(II) acetate (95 mg), tris(2-methylphenyl)phosphine (0.3 g) and N,N-diisopropylamine (5 mL) was heated for reflux for 24 hours. The reaction mixture was diluted with diethyl ether, and the resulting mixture was washed with 1 mol/L hydrochloric acid, water and brine successively, and dried over anhydrous magnesium sulfate. The solvent was removed under reduced pressure, and the residue was purified by column chromatography on silica gel (eluent: n-hexane/ ethyl acetate =10/1) to give 3-((E)-2-phenylvinyl)nitrobenzene (0.76 g). To the solution of the obtained 3-((E)-2-phenylvinyl)nitrobenzene (0.26 g) in methanol (10 mL) was added 10% palladium-carbon powder (50 mg), and the mixture was stirred at room temperature under a hydrogen atmosphere for 2 hours. The insoluble material was removed by filtration, and the filtrate was concentrated under reduced pressure to give the title compound (0.22 g).

Reference Example 19

Diethyl 2-aminothiophene-3,4-dicarboxylate

To a mixture of sulfur (6.9 g), ethyl pyruvate (25 g) and ethyl cyanoacetate (24.4 g) in N,N-dimethylformamide (130 mL) was added triethylamine (21.8 g) for 30 minutes at room temperature, and the reaction mixture was stirred at 50° C. for 2 hours. To the reaction mixture were added water (1 L) and brine (50 mL), and the resulting mixture was extracted with diethyl ether (250 mL) three times. The extracts were dried over anhydrous magnesium sulfate and purified by column chromatography on silica gel (eluent: diethyl ether) to give the title compound (28.2 g).

Reference Example 20

1-(2-Fluoro-6-methoxyphenyl)ethanol

To a solution of 2-fluoro-6-methoxybenzaldehyde (0.5 g) in tetrahydrofuran (10 mL) was added methyllithium (1.15 mol/L diethyl ether solution, 3.4 mL) at −78° C., and the mixture was stirred at the same temperature for 1 hour. Then the mixture was stirred at room temperature for 30minutes. To the reaction mixture was added a saturated aqueous ammonium chloride solution, and the resulting mixture was extracted with diethyl ether. The extract was washed with water and brine successively, and dried over anhydrous magnesium sulfate. The solvent was removed under reduced pressure to give the title compound (0.45 g).

Reference Example 21

2-Fluoro-5-[1-(2-fluoro-6-methoxyphenyl)ethoxy] aniline

To a solution of 4-fluoro-3-nitrophenol (this compound was synthesized according to the procedure described in the International publication WO97/39064) (0.2 g), 1-(2-fluoro-6-methoxyphenyl)ethanol (0.22 g) and triphenylphosphine (0.4 g) in tetrahydrofuran (1.5 mL) was added diisopropyl azodicarboxylate (40% toluene solution, 0.84 mL) at room temperature, and the mixture was stirred at room temperature for 2 hours. The reaction mixture was concentrated under reduced pressure, and the residue was purified by column chromatography on silica gel (eluent: n-hexane–n-hexane/ ethyl acetate=8/1) to give 2-fluoro-5-[1-(2-fluoro-6-methoxy-phenyl)ethoxy]-1-nitrobenzene (0.15 g). This material was dissolved in tetrahydrofuran (3 mL). To the solution were added methanol (3 mL), nickel (II) bromide (5 mg) and sodium borohydride (55 mg) under ice-cooling, and the mixture was stirred at the same temperature for 30 minutes. Then the mixture was stirred at room temperature for 30 minutes. The reaction mixture was diluted with ethyl acetate, and the resulting mixture was washed with a saturated aqueous sodium hydrogen carbonate solution, water and brine successively, and dried over anhydrous magnesium sulfate. The solvent was removed under reduced pressure, and the residue was purified by column chromatography on silica gel (eluent: n-hexane/ethyl acetate=3/1) to give the title compound (0.11 g).

Reference Examples 22 to 29

The compounds of Reference Examples 22 to 29 described in Tables 3 to 4 were obtained in a similar manner to that described in Reference Example 13 or Reference Example 21 using the corresponding starting materials.

Reference Example 30

1-[4-Fluoro-3-(tert-butoxycarbonylamino)phenyl]-2-methyl-1-propanone

To concentrated sulfuric acid (10 mL) was added 1-(4-fluorophenyl)-2-methyl-1-propanone (2.92 g) at −20° C., and the mixture was stirred at the same temperature for 15 minutes. To the mixture was added a mixture of fuming nitric acid (1.4 mL) and concentrated sulfuric acid (4.2 mL) at −20° C., and the mixture was stirred at the same temperature for 20 minutes. To the reaction mixture was added ice (100 g), and the mixture was warmed to room temperature with stirring. The mixture was extracted with ethyl acetate, and the extract was washed with water three times, a saturated aqueous sodium hydrogen carbonate solution twice and brine successively, and dried over anhydrous sodium sulfate. The solvent was removed under reduced pressure, and the residue was purified by column chromatography on silica gel (eluent: n-hexane/ethyl acetate=95/5–85/15) to give 1-(4-fluoro-3-nitrophenyl)-2-methyl-1-propanone (1.8 g). This material was dissolved in ethanol (5 mL). To the solution was added 10% palladium-carbon powder (0.36 g), and the mixture was stirred at room temperature under a hydrogen atmosphere for 2 hours. The insoluble material was removed by filtration, and the filtrate was concentrated under reduced pressure. The residue was purified by column chromatography on silica gel (eluent: n-hexane/ethyl acetate=90/10–83/17) to give 1-(3-amino-4-fluorophenyl)-2-methyl-1-propanone (1.45 g). This material was dissolved in tetrahydrofuran (33 mL). To the solution were added 4-dimethylaminopyridine (0.29 g) and di (tert-butyl) dicarbonate (3.49 g), and the mixture was heated for reflux for 1.5 hours. The reaction mixture was poured into 0.5 mol/L hydrochloric acid, and the resulting mixture was extracted with ethyl acetate. The extract was washed with water and brine successively, and dried over anhydrous sodium sulfate. The solvent was removed under reduced pressure, and the residue was purified by column chromatography on silica gel (eluent: n-hexane–n-hexane/ethyl acetate=95/5) to give 1-{4-fluoro-3-[N,N-di(tert-butoxycarbonyl)amino] phenyl}-2-methyl-1-propanone (1.8 g). This material was dissolved in methanol (15 mL). To the solution was added potassium carbonate (1.96 g), and the mixture was stirred at 60° C. for 30 minutes. The reaction mixture was cooled to room temperature. To the mixture were added water and brine, and the resulting mixture was extracted with ethyl acetate. The extract was washed with brine, and dried over anhydrous sodium sulfate. The solvent was removed under reduced pressure, and the residue was purified by column

Reference Example 31

1-(3-Amino-4-fluorophenyl)-2-(5-fluoro-2-methoxyphenyl)-2-methyl-1-propanone

A mixture of 1-[4-fluoro-3-(tert-butoxycarbonyl -amino) phenyl]-2-methyl-1-propanone (0.11 g), 2-bromo-4-fluoroanisole (0.057 mL), palladium(II) acetate (4.5 mg), tri(tert-butyl)phosphine tetrafluoroborate (5.8 mg) and sodium tert-butoxide (96 mg) in tetrahydrofuran (1 mL) was stirred at 70° C. under an argon atmosphere for 3 days. To the reaction mixture was added water, and the mixture was stirred for 10 minutes. The mixture was poured into 1 mol/L hydrochloric acid, and the resulting mixture was extracted with ethyl acetate. The extract was washed with water and brine successively, and dried over anhydrous sodium sulfate. The solvent was removed under reduced pressure, and the residue was purified by column chromatography on silica gel (eluent: n-hexane/ethyl acetate=10/1) to give 1-[4-fluoro-3-(tert-butoxycarbonylamino)phenyl]-2-(5-fluoro -2-methoxyphenyl)-2-methyl-1-propanone (45 mg). This material was dissolved in hydrochloric acid (4 mol/L ethyl acetate solution, 3 mL), and the mixture was stirred at room temperature overnight. The reaction mixture was poured into a saturated aqueous sodium hydrogen carbonate solution, and the resulting mixture was extracted with ethyl acetate. The extract was washed with brine, and dried over anhydrous sodium sulfate. The solvent was removed under reduced pressure, and the residue was purified by column chromatography on aminopropylated silica gel (eluent: n-hexane/ethyl acetate=4/1 -3/1) to give the title compound (25 mg).

Reference Examples 32 to 35

The compounds of Reference Examples 32 to 35 described in Tables 4 to 5 were obtained in a similar manner to that described in Reference Example 31 using the corresponding starting materials.

Reference Example 36

3-(1-Phenylethylthio)aniline

To a mixture of 3-mercaptoaniline (1 g) and potassium carbonate (1.21 g) in N,N-dimethylformamide (20 mL) was added 1-phenylethyl bromide (1.2 mL), and the mixture was stirred at room temperature for 2 hours. To the reaction mixture was added water, and the resulting mixture was extracted with ethyl acetate. The extract was washed with water and brine successively, and dried over anhydrous magnesium sulfate. The solvent was removed under reduced pressure, and the residue was purified by column chromatography on silica gel (eluent: n-hexane–n-hexane/ethyl acetate=1/1) to give the title compound (1.78 g).

Reference Example 37

The compound of Reference Example 37 described in Table 5 was obtained in a similar manner to that described in Reference Example 36 using the corresponding starting material.

Reference Example 38

3-(1-Methyl-1-phenylethylthio)aniline

To a mixed solution of water (1.6 mL)-concentrated sulfuric acid (1.6 mL) was added 3-nitrothiophenol (0.5 g), and the mixture was stirred at room temperature for 1 hour. To the mixture was added a solution of α-methylstyrene (0.38 g) in tetrahydrofuran (1.6 mL), and the mixture was stirred at room temperature for 30 minutes. The reaction mixture was poured into ice water, and the resulting mixture was extracted with ethyl acetate. The extract was washed with water, a saturated aqueous sodium hydrogen carbonate solution and brine successively, and dried over anhydrous magnesium sulfate. The solvent was removed under reduced pressure, and the residue was purified by column chromatography on silica gel (eluent: n-hexane–n-hexane/ethyl acetate=3/2) to give 3-(1-methyl-1-phenylethylthio)nitrobenzene (0.88 g). This material was dissolved in tetrahydrofuran (10 mL). To the solution were added methanol (10 mL), nickel (II) bromide (35 mg) and sodium borohydride (0.37 g) under ice-cooling, and the mixture was stirred at the same temperature for 30 minutes. Then the mixture was stirred at room temperature for 1 hour. The reaction mixture was diluted with ethyl acetate, and the resulting mixture was washed with a saturated aqueous sodium hydrogen carbonate solution, water and brine successively, and dried over anhydrous magnesium sulfate. The solvent was removed under reduced pressure, and the residue was purified by column chromatography on silica gel (eluent: n-hexane–n-hexane/ethyl acetate=3/2) to give the title compound (0.69 g).

Reference Example 39

3-Amino-4-fluoro-N-methyl-N-phenylbenzamide

To a solution of 4-fluoro-3-nitrobenzoic acid (2 g) in methylene chloride (50 mL) were added N,N-dimethylformamide (0.01 mL) and oxalyl chloride (6.86 g), and the mixture was stirred at room temperature for 1 hour. The reaction mixture was concentrated under reduced pressure. A solution of the residue in tetrahydrofuran (10 mL) was added to a mixture of N-methylaniline (1.22 g) and sodium hydrogen carbonate (2.72 g) in tetrahydrofuran (20 mL), and the mixture was stirred at room temperature overnight. The reaction mixture was poured into water, and the resulting mixture was extracted with ethyl acetate. The extract was washed with 1 mol/L hydrochloric acid, water and brine successively, and dried over anhydrous magnesium sulfate. The solvent was removed under reduced pressure to give 4-fluoro-3-nitro-N-methyl-N-phenylbenzamide (2.95 g). This material was dissolved in tetrahydrofuran (50 mL). To the solution were added methanol (50 mL), nickel (II) bromide (0.12 g) and sodium borohydride (1.26 g) under ice-cooling, and the mixture was stirred at the same temperature for 30 minutes. Then the mixture was stirred at room temperature for 30 minutes. The reaction mixture was poured into a saturated aqueous sodium hydrogen carbonate solution, and the resulting mixture was extracted with ethyl acetate. The extract was washed with water and brine successively, and dried over anhydrous magnesium sulfate. The solvent was removed under reduced pressure, and the residue was purified by column chromatography on silica gel (eluent: n-hexane/ethyl acetate=1/1) to give the title compound (2.33 g).

Reference Example 40

The compound of Reference Example 40 described in Table 5 was obtained in a similar manner to that described in Reference Example 39 using the corresponding starting material.

Reference Examples 41 to 42

The compounds of Reference Examples 41 to 42 described in Table 5 were obtained in a similar manner to that described in Reference Example 21 using the corresponding starting materials.

Reference Example 43

4-Fluoro-2-methoxy-5-nitrobenzenesulfonyl chloride

A mixture of 3-fluoro-4-nitrophenol (2.56 g), potassium carbonate (4.5 g) and iodomethane (4.63 g) in N,N-dimethylformamide (15 mL) was stirred at room temperature overnight. The reaction mixture was poured into water, and the resulting mixture was washed with diethyl ether. The extract was washed with water twice, and dried over anhydrous magnesium sulfate. The solvent was removed under reduced pressure to give 3-fluoro-4-nitroanisole (2.56 g). This material was dissolved in 1,2-dichloroethane (13 mL). To the solution was added chlorosulfonic acid (1.3 mL), and the mixture was heated for reflux for 4 hours. The reaction mixture was diluted with methylene chloride, and the resulting mixture was washed with water and brine successively, and dried over anhydrous magnesium sulfate. The solvent was removed under reduced pressure, and the residue was purified by column chromatography on silica gel (eluent: n-hexane/ethyl acetate=2/1) to give the title compound (0.51 g).

Reference Examples 44 to 69

The compounds of Reference Examples 44 to 69 described in Tables 6 to 9 were obtained in a similar manner to that described in Reference Example 1 using the corresponding starting materials.

Reference Example 70

Dimethyl 4-amino-5-methylthiophene-2,3-dicarboxylate hydrochloride

To methanol (15 mL) was added sodium (0.38 g) under ice-cooling, and the mixture was stirred at the same temperature until sodium was dissolved. To the reaction mixture were added ethyl 2-mercaptopropionate (1.81 g) and dimethyl fumarate (2.17 g), and the mixture was heated for reflux for 3 hours. The reaction mixture was cooled to room temperature. To the mixture was added water (100 mL), and the resulting mixture was washed with diethyl ether. The aqueous layer was cooled in ice, and acidified by addition of 2 mol/L hydrochloric acid, and the resulting mixture was extracted with ethyl acetate twice. The extracts were combined and washed with brine, and dried over anhydrous magnesium sulfate. The solvent was removed under reduced pressure, and the residue was purified by column chromatography on silica gel (eluent: n-hexane/ethyl acetate =4/1–3/1) to give 5-methyl-4-oxo-2,3-bismethoxy-carbonyltetrahydrothiophene (2.68 g). This material was dissolved in methanol (8 mL). To the solution was added hydroxylamine hydrochloride (0.92 g), and the mixture was heated for reflux for 2 hours. The reaction mixture was cooled to room temperature. To the mixture was added ethyl acetate (24 mL), and the resulting mixture was stirred for 10 minutes. The precipitates were collected by filtration and washed with ethyl acetate, and dried under reduced pressure to give the title compound (0.77 g).

Reference Examples 71 to 72

The compounds of Reference Examples 71 to 72 described in Table 9 were obtained in a similar manner to that described in Reference Example 30 using the corresponding starting materials.

Reference Examples 73 to 77

The compounds of Reference Examples 73 to 77 described in Tables 9 to 10 were obtained in a similar manner to that described in Reference Example 31 using the corresponding starting materials.

Reference Example 78

4-Bromo-2-(tert-butoxycarbonylamino)-1-fluorobenzene

To a mixture of 1-bromo-4-fluoro-3-nitrobenzene (1.56 g), nickel(II) bromide (78 mg), methanol (28 mL) and tetrahydrofuran (28 mL) was added sodium borohydride (805 mg) under ice-cooling, and the mixture was stirred at the same temperature for 30 minutes. The mixture was stirred at room temperature for 30 minutes, and the reaction mixture was poured into a saturated aqueous sodium hydrogen carbonate solution. The resulting mixture was extracted with ethyl acetate. The extract was washed with water and brine successively, and dried over anhydrous sodium sulfate. The solvent was removed under reduced pressure to give 5-bromo-2-fluoroaniline (1.3 g). This material was dissolved in tetrahydrofuran (30 mL). To the solution were added 4-dimethylaminopyridine(0.26 g)and di(tert-butyl)dicarbonate (3.1 g), and the mixture was heated for reflux for 1.5 hours. The reaction mixture was poured into 0.5 mol/L hydrochloric acid, and the resulting mixture was extracted with ethyl acetate. The extract was washed with water and brine successively, and dried over anhydrous sodium sulfate. The solvent was removed under reduced pressure. To the residue were added methanol (21 mL) and potassium carbonate (2.94 g), and the mixture was heated for reflux for 2 hours. To the reaction mixture was added water, and the mixture was poured into brine. The resulting mixture was extracted with ethyl acetate, and the extract was dried over anhydrous sodium sulfate. The solvent was removed under reduced pressure, and the residue was purified by column chromatography on silica gel (eluent: n-hexane/ethyl acetate=95/5) to give the title compound (1.72 g).

Reference Example 79

2-(3-Amino-4-fluorophenyl)-1-(2-methoxyphenyl)-2-methyl-1-propanone

A mixture of 1-(2-methoxyphenyl)-2-methyl-1-propanone (0.58 g), 4-bromo-2-(tert-butoxycarbonylamino)-1-fluoro-benzene (0.94 g), palladium(II) acetate (37 mg), tri(tert-butyl)phosphine tetrafluoroborate (47 mg) and sodium tert-butoxide (0.78 g) in tetrahydrofuran (10 mL) was stirred at 60° C. under an argon atmosphere overnight. To the reaction mixture was added water, and the mixture was stirred for 10 minutes. The mixture was poured into 1 mol/L hydrochloric acid, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=95/5–85/15) to give 2-[3-(tert-butoxycarbonylamino)-4-fluorophenyl]-1-(2-methoxyphenyl)-2-methyl-1-propanone (0.91 g). To the obtained 2-[3-(tert-butoxycarbonylamino)-4-fluorophenyl]-1-(2-methoxyphenyl)-2-methyl-1-propanone (0.34 g) was added hydrochloric acid (4 mol/L ethyl acetate solution, 3 mL), and the mixture was stirred at room temperature for 3 hours. The reaction mixture was poured into a saturated aqueous sodium hydrogen carbonate solution, and the resulting mixture was extracted with ethyl acetate. The extract was dried over anhydrous sodium sulfate, and the solvent was removed under reduced pressure to give the title compound (0.22 g).

Reference Examples 80 to 81

The compounds of Reference Examples 80 to 81 described in Table 10 were obtained in a similar manner to that described in Reference Example 79 using the corresponding starting materials.

Reference Example 82

The compound of Reference Example 82 described in Table 11 was obtained in a similar manner to that described in Reference Example 21 using phenol and 4-chloro-3-nitrobenzyl alcohol instead of 4-fluoro-3-nitrophenol and 1-(2-fluoro-6-methoxy-phenyl)ethanol, respectively.

Reference Example 83

2-Chloro-5-(2-phenylethyl) aniline

To a suspension of 4-chloro-3-nitrobenzaldehyde (1 g) and benzyltriphenylphosphonium bromide (2.34 g) in toluene (35 mL) was added sodium hydride (55%, 0.28 g), and the mixture was stirred at room temperature overnight. To the reaction mixture was added 1 mol/L hydrochloric acid, and the resulting mixture was extracted with methylene chloride. The extract was washed with brine and dried over anhydrous magnesium sulfate, and the solvent was removed under reduced pressure. The residue was purified by column chromatography on silica gel (eluent: n-hexane/ethyl acetate=10/1) to give 2-chloro-5-((Z)-2-phenylvinyl)-1-nitrobenzene (0.79 g). The obtained 2-chloro-5-((Z)-2-phenyl-vinyl)-1-nitrobenzene (0.16 g) was dissolved in ethanol (6 mL)-methanol (2 mL). To the solution was added 5% rhodium-carbon powder (20 mg) and morpholine (5 mg), and the mixture was stirred at room temperature under a hydrogen atmosphere overnight. The insoluble material was removed by filtration, and the filtrate was concentrated under reduced pressure. The residue was purified by column chromatography on silica gel (eluent: n-hexane/ethyl acetate=5/1) to give the title compound (87 mg).

Reference Example 84

1-(tert-Butoxycarbonylamino)-5-ethynyl-2-fluorobenzene

A mixture of 4-bromo-2-(tert-butoxycarbonylamino)-1-fluorobenzene (0.57 g), trimethylsilylacetylene (0.55 mL), tetrakis(triphenylphosphine)palladium(0) (23 mg) and copper (I) iodide (7 mg) in N,N-diisopropylamine (5.7 mL) was stirred at 80° C. overnight. The reaction mixture was cooled to room temperature, and the mixture was diluted with diethyl ether. The insoluble material was removed by filtration, and the filtrate was concentrated under reduced pressure. The residue was purified by column chromatography on silica gel (eluent: n-hexane/ethyl acetate=15/1) to give 1-(tert-butoxycarbonylamino)-2-fluoro-5-trimethylsilylethynylbenzene (0.6 g). This material was dissolved in tetrahydrofuran (10 mL). To the solution was added tetra(n-butyl)ammonium fluoride (1 mol/L tetrahydrofuran solution, 2.4 mL), and the mixture was stirred at room temperature for 1 hour. The reaction mixture was concentrated under reduced pressure, and the residue was purified by column chromatography on silica gel (eluent: n-hexane/ethyl acetate=20/1 -10/1) to give the title compound (0.34 g).

Reference Example 85

2-Bromo-3,4-difluoroanisole

To a solution of 3,4-difluoroanisole (2 mL) in tetrahydrofuran (50 mL) was added n-butyllithium (2.67 mol/L n-hexane solution, 6.95 mL) at −78° C., and the mixture was stirred at the same temperature for 30 minutes. To the reaction mixture was added bromine (1.04 mL), and the mixture was stirred at −78° C. for 15 minutes. The mixture was stirred under ice-cooling for 1 hour. To the reaction mixture was added a saturated aqueous ammonium chloride solution, and the resulting mixture was extracted with diethyl ether. The extract was washed with a saturated aqueous sodium hydrogen carbonate solution and brine successively, and dried over anhydrous sodium sulfate. The solvent was removed under reduced pressure, and the residue was purified by column chromatography on silica gel (eluent: n-hexane –n-hexane/ethyl acetate=9/1) to give the title compound (0.91 g)

Reference Example 86

2-Fluoro-5-(2-phenylethyl) aniline

A mixture of 1-(tert-butoxycarbonylamino)-5-ethynyl-2-fluorobenzene (0.11 g), iodobenzene (0.1 g), tetrakis-(triphenylphosphine)palladium(0) (16 mg) and copper (I) iodide (5 mg) in N,N-diisopropylamine (2 mL) was stirred at room temperature overnight. The reaction mixture was diluted with ethyl acetate. The insoluble material was removed by filtration, and the filtrate was concentrated under reduced pressure. The residue was purified by column chromatography on silica gel (eluent: n-hexane/ethyl acetate=10/1) to give 1-(tert-butoxycarbonylamino)-2-fluoro-5-phenylethynylbenzene (0.14 g). This material was dissolved in ethyl acetate (3 mL). To the solution was added 10% palladium-carbon powder (50 mg), and the mixture was stirred at room temperature under a hydrogen atmosphere for 2 hours. The insoluble material was removed by filtration, and the filtrate was concentrated under reduced pressure to give 1-(tert-butoxycarbonylamino)-2-fluoro -5-(2-phenylethyl)benzene (0.11 g). To this material was added hydrochloric acid (4 mol/L ethyl acetate solution, 3 mL), and the mixture was stirred at room temperature for 1 hour. The reaction mixture was poured into a saturated aqueous sodium hydrogen carbonate solution, and the resulting mixture was extracted with ethyl acetate. The extract was dried over anhydrous sodium sulfate, and the solvent was removed under reduced pressure.

The residue was purified by column chromatography on silica gel (eluent: n-hexane/ethyl acetate =8/1 -5/1) to give the title compound (53 mg).

Reference Examples 87 to 99

The compounds of Reference Examples 87 to 99 described in Tables 11 to 13 were obtained in a similar manner to that described in Reference Example 86 using the corresponding starting materials.

Reference Example 100

2-Fluoro-4-methoxy-5-(2-phenylethyl)aniline

A mixture of 2-bromo-5-fluoro-4-nitroanisole (0.46 g), phenylacetylene (67 mg), tetrakis(triphenylphosphine) -palladium(0) (38 mg) and copper (I) iodide (13 mg) in N,N-diisopropylamine (5 mL) was stirred at room temperature overnight. The reaction mixture was diluted with ethyl acetate. The insoluble material was removed by filtration, and the filtrate was concentrated under reduced pressure. The residue was purified by column chromatography on silica gel (eluent: n-hexane/ethyl acetate=10/1–5/1) to give 5-fluoro-4-nitro-2-phenylethynylanisole (0.18 g). This material was dissolved in ethyl acetate (5 mL). To the solution was added 10% palladium-carbon powder (0.45 g), and the mixture was stirred at room temperature under a hydrogen atmosphere for 3 hours. The insoluble material was removed by filtration, and the filtrate was concentrated under reduced pressure. The residue was purified by column chromatography on silica gel (eluent: n-hexane/ethyl acetate=10/1–4/1) to give the title compound (87 mg).

Reference Example 101

2-Fluoro-5-[2-(2-methoxyphenyl)-1,1-dimethylethyl]aniline

To a mixture of 2-[3-(tert-butoxycarbonylamino)-4-fluorophenyl]-1-(2-methoxyphenyl)-2-methyl-1-propanone (0.59 g) in tetrahydrofuran (7.5 mL)-water (0.75 mL) was added sodium borohydride (0.17 g), and the mixture was stirred at room temperature for 1 hour. The reaction mixture was diluted with water, and the resulting mixture was extracted with ethyl acetate. The extract was washed with brine and dried over anhydrous sodium sulfate. The solvent was removed under reduced pressure, and the residue was purified by column chromatography on silica gel (eluent: n-hexane/ethyl acetate=4/1) to give 2-[3-(tert -butoxycarbonylamino)-4-fluorophenyl]-1-(2-methoxyphenyl)-2-methyl-1-propanol (0.54 g). This material was dissolved in ethanol (8 mL)-tetrahydrofuran (3 mL). To the solution were added 2 mol/L hydrochloric acid (0.2 mL) and 10% palladium-carbon powder (0.27 g), and the mixture was stirred at room temperature under a hydrogen atmosphere for 5 hours. To the reaction mixture was added sodium hydrogen carbonate, and the mixture was stirred for 10 minutes. The insoluble material was removed by filtration, and the filtrate was concentrated under reduced pressure. The residue was purified by column chromatography on silica gel (eluent: n-hexane/ethyl acetate=7/1) to give 2-[3-(tert -butoxycarbonylamino)-4-fluorophenyl]-1-(2-methoxyphenyl)-2-methylpropane (0.15 g). To this material was added hydrochloric acid (4 mol/L ethyl acetate solution, 3 mL), and the mixture was stirred at room temperature for 1 hour. The reaction mixture was poured into a saturated aqueous sodium hydrogen carbonate solution, and the resulting mixture was extracted with ethyl acetate. The extract was dried over anhydrous sodium sulfate, and the solvent was removed under reduced pressure to give the title compound (0.11 g).

Reference Example 102

4-Chloro-3-nitrothiophenol

To concentrated hydrochloric acid (30 mL) was added 4-chloro-3-nitroaniline (5.18 g) under ice-cooling, and the mixture was stirred at the same temperature for 5 minutes. To the mixture was added a solution of sodium nitrite (3.1 g) in water (30 mL). The mixture was heated to 50° C. To the mixture was added a solution of potassium O-ethyl dithiocarbonate (14.4 g) in water (60 mL), and the mixture was stirred at 50° C. for 1 hour. The reaction mixture was cooled to room temperature, and the mixture was extracted with diethyl ether twice. The extracts were combined and washed with 1 mol/L aqueous sodium hydroxide solution, water and brine successively, and dried over anhydrous magnesium sulfate. The solvent was removed under reduced pressure, and the residue was purified by column chromatography on silica gel (eluent: n-hexane–n-hexane/ethyl acetate=7/3) to give O-ethyl S-(4-chloro-3-nitrophenyl) dithiocarbonate (2.96 g). This material was dissolved in tetrahydrofuran (50 mL). The solution was added to a suspension of lithium aluminum hydride (1.62 g) in tetrahydrofuran (50 mL) under ice-cooling, and the mixture was stirred at room temperature for 10 minutes. The reaction mixture was cooled in ice. To the mixture were added water (1.8 mL), 15% aqueous sodium hydroxide solution (1.8 mL) and water (5.4 mL), and the mixture was stirred at room temperature for 30 minutes. The insoluble material was removed by filtration, and the filtrate was diluted with ethyl acetate. The resulting mixture was washed with 1 mol/L hydrochloric acid, water and brine successively, and dried over anhydrous magnesium sulfate. The solvent was removed under reduced pressure, and the residue was purified by column chromatography on silica gel (eluent: n-hexane/ethyl acetate=9/1–1/9) to give the title compound (1.28 g).

Reference Example 103

5-Benzylthio-2-Chloroaniline

To a solution of 4-chloro-3-nitrothiophenol (0.4 g) and benzyl bromide (0.3 mL) in N,N-dimethylformamide (6 mL) was added potassium carbonate (0.44 g), and the mixture was stirred at room temperature for 15 minutes. To the reaction mixture was added water, and the resulting mixture was extracted with ethyl acetate. The extract was washed with water and brine successively, and dried over anhydrous magnesium sulfate. The solvent was removed under reduced pressure, and the residue was purified by column chromatography on silica gel (eluent: n-hexane –n-hexane/ethyl acetate=9/1) to give 1-benzylthio-4-chloro -3-nitrobenzene (0.54 g). This material was dissolved in methanol (5 mL)-tetrahydrofuran (5 mL). To the solution were added nickel (II) bromide (21 mg) and sodium borohydride (0.22 g) under ice-cooling, and the mixture was stirred at the same temperature for 30 minutes. The mixture was stirred at room temperature for 1 hour. The reaction mixture was diluted with ethyl acetate, and the resulting mixture was washed with a saturated aqueous sodium hydrogen carbonate solution, water and brine successively, and dried over anhydrous magnesium sulfate.

Reference Example 104

2-Fluoro-5-mercaptoaniline

To a mixture of 5-bromo-2-fluoroaniline (4.15 g), methyl 3-mercaptopropionate (2.62 g), 4,5-bis (diphenylphosphino) -9,9-dimethylxanthene (0.63 g) and N,N-diisopropylethylamine (5.64 g) in 1,4-dioxane (80 mL) was added tris (dibenzylidene -acetone) dipalladium(0) (0.3 g), and the mixture was heated for reflux under an argon atmosphere overnight. The insoluble material was removed by filtration, and the filtrate was concentrated under reduced pressure. The residue was purified by column chromatography on silica gel (eluent: n-hexane/ethyl acetate=20/1–5/1–2/1) to give 2-fluoro-5-(2-methoxy -carbonylethylthio) aniline (4.62 g). This material was dissolved in tetrahydrofuran (120 mL). To the solution was added potassium tert-butoxide (1 mol/L tetrahydrofuran solution, 80.6 mL) at −78° C., and the mixture was stirred at the same temperature for 15 minutes. To the reaction mixture was added 1 mol/L hydrochloric acid (81 mL), and the mixture was warmed to room temperature and stirred for 5 minutes. The mixture was poured into ethyl acetate, and the organic layer was separated. The organic layer was washed with brine and dried over anhydrous magnesium sulfate. The solvent was removed under reduced pressure, and the residue was purified by column chromatography on silica gel (eluent: n-hexane/ethyl acetate=4/1) to give the title compound (1.85 g).

Reference Example 105

2-Fluoro-6-methoxybenzyl alcohol

To a solution of 2-fluoro-6-methoxybenzaldehyde (0.63 g) in tetrahydrofuran (5 mL) were added water (0.5 mL) and sodium borohydride (0.17 g), and the mixture was stirred at room temperature for 1 hour. The reaction mixture was diluted with water, and the resulting mixture was extracted with diethyl ether. The extract was washed with brine, and the solvent was removed under reduced pressure to give the title compound (0.58 g).

Reference Examples 106 to 107

The compounds of Reference Examples 106 to 107 described in Table 14 were obtained in a similar manner to that described in Reference Example 105 using the corresponding starting materials.

Reference Example 108

2-Fluoro-6-methoxybenzyl bromide

To a solution of 2-fluoro-6-methoxybenzyl alcohol (0.78 g) and triethylamine (0.91 mL) in ethyl acetate (12 mL) was added methanesulfonyl chloride (0.43 mL) under ice-cooling, and the mixture was stirred at the same temperature for 30 minutes. The insoluble material was removed by filtration, and the insoluble material was washed with ethyl acetate (4 mL). The filtrate and washing were combined. To the mixture was added lithium bromide-monohydrate (2.62 g), and the mixture was stirred at 55° C. for 2 hours. The reaction mixture was poured into water, and the resulting mixture was extracted with ethyl acetate. The extract was washed with water and brine successively, and dried over anhydrous magnesium sulfate. The solvent was removed under reduced pressure, and the residue was purified by column chromatography on silica gel (eluent: n-hexane–n-hexane/ethyl acetate=7/3) to give the title compound (0.82 g).

Reference Examples 109 to 110

The compounds of Reference Examples 109 to 110 described in Table 14 were obtained in a similar manner to that described in Reference Example 108 using the corresponding starting materials.

Reference Example 111

2-(5-Fluoro-2-methoxyphenyl)-2-propanol

To a solution of 5-fluoro-2-methoxybenzaldehyde (1 g) in acetone (4 mL) was added a solution of potassium permanganate (1.54 g) in water (16 mL), and the mixture was heated for reflux for 4 hours. The reaction mixture was cooled to room temperature. To the mixture was added 2 mol/L aqueous sodium hydroxide solution (5.2 mL), and the insoluble material was removed by filtration. The filtrate was washed with ethyl acetate. The aqueous layer was acidified by addition of 2 mol/L hydrochloric acid, and the mixture was extracted with ethyl acetate twice. The extracts were combined and washed with brine, and dried over anhydrous magnesium sulfate. The solvent was removed under reduced pressure, and the residue was purified by column chromatography on silica gel (eluent: n-hexane/ethyl acetate=1/1–ethyl acetate) to give 5-fluoro-2-methoxybenzoic acid (0.66 g). This material was dissolved in N,N-dimethylformamide (15 mL). To the solution were added potassium carbonate (0.63 g) and iodomethane (0.26 mL), and the mixture was stirred at room temperature for 2 hours. The reaction mixture was diluted with ethyl acetate, and the resulting mixture was washed with water and brine successively, and dried over anhydrous magnesium sulfate. The solvent was removed under reduced pressure to give methyl 5-fluoro-2-methoxybenzoate (0.7 g). This material was dissolved in tetrahydrofuran (10 mL). To the solution was added methylmagnesium iodide (3.0 mol/L diethyl ether solution, 3.82 mL) under ice-cooling, and the mixture was stirred at room temperature for 2 hours. To the reaction mixture was added a saturated aqueous ammonium chloride solution, and the resulting mixture was extracted with ethyl acetate. The extract was washed with water and brine successively, and dried over anhydrous magnesium sulfate. The solvent was removed under reduced pressure, and the residue was purified by column chromatography on silica gel (eluent: n-hexane–n-hexane/ethyl acetate=1/1) to give the title compound (0.65 g).

Reference Examples 112 to 113

The compounds of Reference Examples 112 to 113 described in Table 14 were obtained in a similar manner to that described in Reference Example 111 using the corresponding starting materials.

Reference Example 114

2-Fluoro-5-(2-fluorobenzylthio)aniline

To a solution of 2-fluoro-5-mercaptoaniline (0.13 g) and 2-fluorobenzyl bromide (0.12 mL) in N,N-dimethylformamide (5 mL) was added potassium carbonate (0.25 g), and the mixture was stirred at room temperature for 30 minutes. The reaction mixture was diluted with diethyl ether, and the resulting mixture was washed with water twice and brine successively, and dried over anhydrous magnesium sulfate. The solvent was removed under reduced pressure, and the residue was purified by column chromatography on silica gel (eluent: n-hexane/ethyl acetate =6/1) to give the title compound (0.17 g).

Reference Examples 115 to 126

The compounds of Reference Examples 115 to 126 described in Tables 15 to 16 were obtained in a similar manner to that described in Reference Example 114 using the corresponding starting materials.

Reference Example 127

2-Fluoro-5-(1-methyl-1-phenylethylthio)aniline

To a mixture of water (10 mL) and concentrated sulfuric acid (10 mL) were added 2-fluoro-5-mercaptoaniline (1.85 g) and a solution of 2-phenyl-2-propanol (1.76 g) in tetrahydrofuran (10 mL) successively at room temperature, and the mixture was stirred at room temperature for 1 hour. The reaction mixture was poured into ice water, and the resulting mixture was extracted with ethyl acetate. The extract was washed with water, a saturated aqueous sodium hydrogen carbonate solution and brine successively, and dried over anhydrous magnesium sulfate. The solvent was removed under reduced pressure, and the residue was purified by column chromatography on silica gel (eluent: n-hexane/ethyl acetate=6/1–3/1) to give the title compound (1.55 g).

Reference Examples 128 to 141

The compounds of Reference Examples 128 to 141 described in Tables 16 to 18 were obtained in a similar manner to that described in Reference Example 127 using the corresponding starting materials.

Reference Example 142

4-Fluoro-2-methoxy-5-nitrophenol

To a solution of 4-fluoro-2-methoxyphenol (1.42 g) and triethylamine (1.67 mL) in methylene chloride (20 mL) was added ethyl chloroformate (1.05 mL), and the mixture was stirred at room temperature for 3 days. The reaction mixture was poured into 0.5 mol/L hydrochloric acid, and the resulting mixture was extracted with diethyl ether. The extract was washed with water and brine successively, and dried over anhydrous sodium sulfate. The solvent was removed under reduced pressure. To the residue was added concentrated sulfuric acid (7 mL) under ice-cooling, and the mixture was stirred at the same temperature for 15 minutes. To the mixture was added a mixture of fuming nitric acid (0.7 mL) and concentrated sulfuric acid (1 mL) in a dropwise manner under ice-cooling, and the mixture was stirred at the same temperature for 30 minutes. The reaction mixture was poured into ice, and the resulting mixture was stirred at room temperature for 30 minutes. The mixture was extracted with ethyl acetate. The extract was washed with water twice and brine successively, and dried over anhydrous magnesium sulfate. The solvent was removed under reduced pressure, and the residue was purified by column chromatography on silica gel (eluent: n-hexane/ethyl acetate=90/10–67/33) to give 2-ethoxycarbonyloxy-5-fluoro-4-nitroanisole (0.48 g). To this material were added methanol (8 mL) and sodium hydrogen carbonate (0.31 g), and the mixture was stirred at room temperature for 42 hours. The reaction mixture was poured into 0.5 mol/L hydrochloric acid, and the resulting mixture was extracted with ethyl acetate. The extract was washed with water and brine successively, and dried over anhydrous sodium sulfate.

The solvent was removed under reduced pressure. The residue was suspended in a mixed solvent (n-hexane/ethyl acetate=4/1) and collected by filtration, and dried under reduced pressure to give the title compound (0.25 g).

Reference Examples 143 to 147

The compounds of Reference Examples 143 to 147 described in Tables 18 to 19 were obtained in a similar manner to that described in Reference Example 142 using the corresponding starting materials.

Reference Example 148

2-Ethoxy-4-fluoro-5-nitrophenol

To a suspension of 4'-fluoro-2'-hydroxyacetophenone (3.08 g), cesium carbonate (13.0 g) and sodium iodide (0.6 g) in N,N-dimethylformamide (20 mL) was added bromoethane (2.24 mL), and the mixture was stirred at room temperature overnight. The reaction mixture was poured into water, and the resulting mixture was extracted with diethyl ether. The extract was washed with water and brine successively, and dried over anhydrous sodium sulfate. The solvent was removed under reduced pressure. To a solution of the residue and 4,4'-thiobis(6-tert-butyl -o-cresol) (39 mg) in methylene chloride (57.6 mL) was added 3-chloroperbenzoic acid (4.97 g) under ice-cooling, and the mixture was heated for reflux overnight. The reaction mixture was cooled in ice. To the mixture was added 10% aqueous sodium sulfite solution, and the resulting mixture was stirred for 20 minutes. The organic layer was separated and washed with water three times, a saturated aqueous sodium hydrogen carbonate solution, water and brine successively, and dried over anhydrous sodium sulfate. The solvent was removed under reduced pressure, and the residue was dissolved in methanol (10 mL) - tetrahydrofuran (20 mL). To the solution was added sodium methoxide (28% methanol solution, 5 mL), and the mixture was stirred at room temperature for 1 hour. The reaction mixture was poured into 0.5 mol/L hydrochloric acid, and the resulting mixture was extracted with ethyl acetate. The extract was washed with brine and dried over anhydrous sodium sulfate. The solvent was removed under reduced pressure to give 2-ethoxy-4-fluorophenol (3.0 g). The title compound was obtained in a similar manner to that described in Reference Example 142 using this material instead of 4-fluoro-2-methoxyphenol.

Reference Example 149

The compound of Reference Example 149 described in Table 19 was obtained in a similar manner to that described in Reference Example 20 using the corresponding starting material.

Reference Example 150

2-[2-(tert-Butyldimethylsilyloxy) ethoxy]benzyl alcohol

To a suspension of 2-hydroxybenzyl alcohol (0.4 g) and potassium carbonate (0.67 g) in N,N-dimethylformamide (6 mL) was added 2-(tert-butyldimethylsilyloxy)ethyl bromide (1.05 mL), and the mixture was stirred at room temperature overnight.

The reaction mixture was diluted with diethyl ether, and the resulting mixture was washed with water, 1 mol/L aqueous sodium hydroxide solution, water and brine successively, and dried over anhydrous magnesium sulfate. The solvent was removed under reduced pressure, and the residue was purified by column chromatography on silica gel (eluent: n-hexane/ethyl acetate =5/1) to give the title compound (0.32 g).

Reference Example 151

The compound of Reference Example 151 described in Table 19 was obtained in a similar manner to that described in Reference Example 150 using the corresponding starting material.

Reference Example 152

2-(tert-Butyldimethylsilyloxymethyl)benzyl alcohol

To a solution of 1,2-benzenedimethanol (2 g) and imidazole (1.13 g) in N,N-dimethylformamide (30 mL) was added tert-butyldimethylchlorosilane (2.08 g), and the mixture was stirred at room temperature for 3 days. The reaction mixture was diluted with ethyl acetate, and the resulting mixture was washed with 1 mol/L hydrochloric acid, water and brine successively, and dried over anhydrous magnesium sulfate. The solvent was removed under reduced pressure, and the residue was purified by column chromatography on silica gel (eluent: n-hexane–n-hexane/ethyl acetate=3/2) to give the title compound (1.46 g).

Reference Examples 153 to 154

The compounds of Reference Examples 153 to 154 described in Table 20 were obtained in a similar manner to that described in Reference Example 152 using the corresponding starting materials.

Reference Example 155

2,3-Difluoro-6-(2-methoxyethoxy)benzyl alcohol

To a suspension of 2,3-difluoro-6-hydroxybenzaldehyde (0.63 g) and potassium carbonate (0.83 g) in N,N-dimethylformamide (4 mL) was added 2-methoxyethyl bromide (0.45 mL), and the mixture was stirred at room temperature for 3 days. The reaction mixture was poured into water, and the resulting mixture was extracted with diethyl ether. The extract was washed with water and brine successively, and dried over anhydrous sodium sulfate. The solvent was removed under reduced pressure, and the residue was purified by column chromatography on silica gel (eluent: n-hexane/ethyl acetate=85/15–60/40) to give 2,3-difluoro-6-(2-methoxyethoxy)benzaldehyde (0.62 g). This material was dissolved in tetrahydrofuran (6 mL). To the solution were added water (0.6 mL) and sodium borohydride (0.12 g), and the mixture was stirred at room temperature for 1 hour. The reaction mixture was diluted with water, and the resulting mixture was extracted with ethyl acetate. The extract was washed with brine, and dried over anhydrous sodium sulfate. The solvent was removed under reduced pressure to give the title compound (0.61 g).

Reference Examples 156 to 159

The compounds of Reference Examples 156 to 159 described in Table 20 were obtained in a similar manner to that described in Reference Example 155 using the corresponding starting materials.

Reference Example 160

1-(2,3-Difluoro-6-methoxyphenyl)-1-cyclobutanol

To a solution of 3,4-difluoroanisole (2.47 g) in tetrahydrofuran (50 mL) was added n-butyllithium (2.64 mol/L n-hexane solution, 6.5 mL) at −78° C., and the mixture was stirred at the same temperature for 30 minutes. To the reaction mixture was added a solution of cyclobutanone (1 g) in tetrahydrofuran (20 mL), and the mixture was stirred at the same temperature for 30 minutes. To the reaction mixture was added a saturated aqueous ammonium chloride solution, and the resulting mixture was extracted with diethyl ether. The extract was washed with water and brine successively, and dried over anhydrous magnesium sulfate. The solvent was removed under reduced pressure, and the residue was purified by column chromatography on silica gel (eluent: n-hexane/ethyl acetate=5/1) to give the title compound (2.69 g).

Reference Example 161

2-Chloro-5-(1-methyl-1-phenylethoxy)aniline

To a solution of 4-chloro-3-nitrophenol (0.5 g), tri(n-butyl)phosphine (0.72 mL) and 2-phenyl-2-propanol (0.26 g) in tetrahydrofuran (5 mL) was added 1, 1'-azobis (N,N-dimethyl-formamide) (0.5 g), and the mixture was stirred at 60° C. for 20 hours. The reaction mixture was diluted with diethyl ether, and the insoluble material was removed by filtration. The filtrate was concentrated under reduced pressure, and the residue was purified by column chromatography on silica gel (eluent: n-hexane–n-hexane/ethyl acetate=10/1) to give 2-chloro-5-(1-methyl-1-phenylethoxy)-1-nitrobenzene (0.19 g). This material was dissolved in tetrahydrofuran (3.5 mL). To the solution were added methanol (3.5 mL), nickel(II) bromide (11 mg) and sodium borohydride (0.12 g) under ice-cooling, and the mixture was stirred at the same temperature for 30 minutes. Then the mixture was stirred at room temperature for 30 minutes. The reaction mixture was diluted with ethyl acetate, and the resulting mixture was washed with a saturated aqueous sodium hydrogen carbonate solution, water and brine successively, and dried over anhydrous magnesium sulfate. The solvent was removed under reduced pressure, and the residue was purified by column chromatography on silica gel (eluent: n-hexane/ethyl acetate=3/1) to give the title compound (0.14 g).

Reference Examples 162 to 166

The compounds of Reference Examples 162 to 166 described in Table 21 were obtained in a similar manner to that described in Reference Example 161 using the corresponding starting materials.

Reference Examples 167 to 308

The compounds of Reference Examples 167 to 308 described in Tables 22 to 41 were obtained in a similar manner to that described in Reference Example 13 or Reference Example 21 using the corresponding starting materials.

Reference Example 309

4-Cyano-2-fluoro-5-(2,3-difluoro-6-methoxybenzyloxy)aniline

4-Bromo-2-fluoro-5-(2,3-difluoro-6-methoxybenzyloxy)-1-(tert-butoxycarbonylamino)benzene was synthesized in a similar manner to that described in Reference Example 78 using 4-bromo-2-fluoro-5-(2,3-difluoro-6-methoxybenzyloxy)aniline instead of 5-bromo-2-fluoroaniline. A mixture of this compound (0.24 g) and copper (I) cyanide (90 mg) in N-methyl-2-pyrroridone (1 mL) was stirred at 220° C. (outside temperature) for 30 minutes. The reaction mixture was poured into water, and the resulting mixture was extracted with ethyl acetate. The extract was washed with water and brine successively, and dried over anhydrous sodium sulfate. The solvent was removed under reduced pressure, and the residue was purified by column chromatography on silica gel (eluent: n-hexane/ethyl acetate=2/1–1/1) to give the title compound (54 mg).

Reference Example 310

4-Fluoro-3-(2,3-difluoro-6-methoxybenzyloxy)aniline

A suspension of 4-fluoro-3-hydroxybenzoic acid (0.19 g), 2,3-difluoro-6-methoxybenzyl bromide (0.6 g) and potassium carbonate (0.5 g) in N,N-dimethylformamide (3 mL) was stirred at room temperature for 8 hours. The reaction mixture was poured into water, and the resulting mixture was extracted with diethyl ether. The extract was washed with water and brine successively, and dried over anhydrous sodium sulfate. The solvent was removed under reduced pressure, and the residue was dissolved in tetrahydrofuran (6 mL). To the solution were added methanol (3 mL), water (3 mL) and lithium hydroxide-monohydrate (0.5 g), and the mixture was stirred at room temperature for 1 hour. To the reaction mixture was added 1 mol/L hydrochloric acid (15 mL), and the resulting mixture was extracted with ethyl acetate. The extract was washed with water and brine successively, and dried over anhydrous sodium sulfate. The solvent was removed under reduced pressure. The residue was suspended in a mixed solvent (n-hexane/ethyl acetate=4/1) and collected by filtration, and dried under reduced pressure to give 4-fluoro-3-(2,3-difluoro-6-methoxybenzyloxy)benzoic acid (0.31 g). This material was dissolved in 1,4-dioxane (4 mL). To the solution were added triethylamine (0.41 mL) and diphenylphosphoryl azide (0.21 mL), and the mixture was stirred at room temperature for 1 hour. Then the mixture was heated for reflux for 4 hours. To the reaction mixture was added 1 mol/L aqueous sodium hydroxide solution (4 mL), and the mixture was stirred at room temperature for 1 hour. The reaction mixture was poured into a saturated aqueous sodium hydrogen carbonate solution, and the resulting mixture was extracted with ethyl acetate. The extract was washed with brine and dried over anhydrous sodium sulfate. The solvent was removed under reduced pressure, and the residue was purified by column chromatography on silica gel (eluent: n-hexane/ethyl acetate=2/1–1/1) to give crude product. To the crude product was added methylene chloride, and the insoluble material was removed by filtration.

The solvent of the filtrate was removed under reduced pressure to give the title compound (70 mg).

Reference Examples 311 to 321

The compounds of Reference Examples 311 to 321 described in Tables 41 to 43 were obtained in a similar manner to that described in Reference Example 13 or Reference Example 21 using the corresponding starting materials.

Reference Example 322

The compound of Reference Example 322 described in Table 43 was obtained in a similar manner to that described in Reference Example 160 using the corresponding starting material.

Reference Examples 323 to 324

The compounds of Reference Examples 323 to 324 described in Table 43 were obtained in a similar manner to that described in Reference Example 161 using the corresponding starting materials.

Reference Example 325

2,3-Difluoro-6-methoxyphenol

To a solution of 2,3-difluoro-6-methoxybenzaldehyde (2.58 g) in methylene chloride (45 mL) was added 3-chloroperbenzoic acid (5.97 g) under ice-cooling, and the mixture was heated for reflux overnight. The reaction mixture was cooled in ice. To the mixture was added 10% aqueous sodium sulfite solution, and the resulting mixture was stirred for 20 minutes. The organic layer was separated and washed with water twice, a saturated aqueous sodium hydrogen carbonate solution, water and brine successively, and dried over anhydrous magnesium sulfate. The solvent was removed under reduced pressure, and the residue was dissolved in tetrahydrofuran (15 mL)-methanol (7.5 mL). To the solution was added sodium methoxide (28% methanol solution, 3.75 mL), and the mixture was stirred at room temperature for 1 hour. The reaction mixture was poured into 1 mol/L hydrochloric acid, and the resulting mixture was extracted with ethyl acetate. The extract was washed with brine and dried over anhydrous magnesium sulfate. The solvent was removed under reduced pressure, and the residue was purified by column chromatography on silica gel (eluent: n-hexane–n-hexane/ethyl acetate=2/3) and column chromatography on aminopropylated silica gel (eluent: ethyl acetate/methanol=9/1–3/2) successively to give the title compound (1.7 g).

Reference Example 326

The compound of Reference Example 326 described in Table 43 was obtained in a similar manner to that described in Reference Example 325 using the corresponding starting material.

Reference Example 327

2,4-Difluoro-5-nitrobenzyl alcohol

To a solution of 2,4-difluorobenzaldehyde (2.27 g) in methylene chloride (6 mL) was added concentrated sulfuric acid (6 mL) under ice-cooling, and the mixture was stirred for 15 minutes. To the mixture was added fuming nitric acid (1 mL)

under ice-cooling, and the mixture was stirred at the same temperature for 30 minutes. Then the mixture was stirred at room temperature for 1 hour. The reaction mixture was diluted with ethyl acetate. To the mixture was added water, and the organic layer was separated. The organic layer was washed with a saturated aqueous sodium hydrogen carbonate solution twice, water and brine successively, and dried over anhydrous magnesium sulfate. The solvent was removed under reduced pressure, and the residue was purified by column chromatography on silica gel (eluent: n-hexane–n-hexane/ethyl acetate=7/3) to give 2,4-difluoro-5-nitrobenzaldehyde (2.63 g). The obtained 2,4-difluoro-5-nitrobenzaldehyde (1 g) was dissolved in tetrahydrofuran (15 mL). To the solution was added sodium borohydride (0.3 g), and the mixture was stirred at room temperature for 5 minutes. To the reaction mixture was added 1 mol/L hydrochloric acid, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane –n-hexane/ethyl acetate=1/1) to give the title compound (0.76 g)

Reference Example 328

The compound of Reference Example 328 described in Table 43 was obtained in a similar manner to that described in Reference Example 327 using the corresponding starting material.

Reference Examples 329 to 331

The compounds of Reference Examples 329 to 331 described in Table 44 were obtained in a similar manner to that described in Reference Example 21 using 2,3-difluoro-6-methoxyphenol or 2,3-difluoro-6-(2-methoxyethoxy) phenol and 4-fluoro-3-nitrobenzyl alcohol or 2,4-difluoro-5-nitrobenzyl alcohol or 4-fluoro-2-methoxy-5-nitrobenzyl alcohol instead of 4-fluoro-3-nitrophenol and 1-(2-fluoro-6-methoxyphenyl) -ethanol, respectively.

Reference Example 332

2,3-Difluoro-6-(2-methoxyethoxy)aniline

To a suspension of 3,4-difluorophenol (1.43 g) and cesium carbonate (4.89 g) in N,N-dimethylformamide (10 mL) was added 2-methoxyethyl bromide (0.94 mL), and the mixture was stirred at room temperature for 4 days. The reaction mixture was poured into water, and the resulting mixture was extracted with diethyl ether. The extract was washed with 1 mol/L aqueous sodium hydroxide solution, water and brine successively, and dried over anhydrous sodium sulfate. The solvent was removed under reduced pressure, and the residue was dissolved in tetrahydrofuran (39 mL). To the solution was added n-butyllithium (2.64 mol/L n-hexane solution, 3.25 mL) at −78° C., and the mixture was stirred at the same temperature for 30 minutes. To the reaction mixture was added dryice (10 g), and the mixture was stirred at room temperature for 30 minutes. The reaction mixture was acidified by addition of 2 mol/L hydrochloric acid, and the resulting mixture was extracted with ethyl acetate. The extract was washed with brine and dried over anhydrous magnesium sulfate. The solvent was removed under reduced pressure to give 2,3-difluoro-6-(2-methoxyethoxy)benzoic acid (1.48 g). The obtained 2,3-difluoro-6-(2-methoxyethoxy)benzoic acid (0.5 g) was dissolved in 1,4-dioxane (10 mL). To the solution were added triethylamine (0.45 mL) and diphenylphosphoryl azide (0.61 mL), and the mixture was stirred at room temperature overnight. To the reaction mixture was added ethanol (0.99 g), and the mixture was heated for reflux for 5 hours. The reaction mixture was diluted with ethyl acetate, and the resulting mixture was washed with 1 mol/L hydrochloric acid, water and brine successively, and dried over anhydrous magnesium sulfate. The solvent was removed under reduced pressure. To a suspension of the residue in ethanol (10 mL) was added 5 mol/L aqueous sodium hydroxide solution (4.3 mL), and the mixture was heated for reflux for 2 hours. The reaction mixture was diluted with ethyl acetate, and the resulting mixture was washed with water twice and brine, and dried over anhydrous magnesium sulfate. The solvent was removed under reduced pressure, and the residue was purified by column chromatography on silica gel (eluent: n-hexane/ethyl acetate=3/1) to give the title compound (75 mg).

Reference Example 333

The compound of Reference Example 333 described in Table 44 was obtained in a similar manner to that described in Reference Example 332 using the corresponding starting material.

Reference Example 334

2-Fluoro-5-[N-(2,6-difluorophenyl)-N-methylamino] methyl-4-methoxyaniline

To a solution of 4-fluoro-2-methoxy-5-nitrobenzyl alcohol (0.3 g) in methylene chloride (5 mL) were added triethylamine (0.31 mL) and methanesulfonyl chloride (0.14 mL) at room temperature, and the mixture was stirred for 3 hours. The reaction mixture was diluted with methylene chloride, and the resulting mixture was washed with water and brine, and dried over anhydrous magnesium sulfate. The solvent was removed under reduced pressure, and the residue was dissolved in acetonitrile (2 mL)-ethanol (2 mL). To the solution were added a catalytic amount of sodium iodide and 2,6-difluoroaniline (0.45 mL), and the mixture was stirred at 60° C. overnight. The reaction mixture was diluted with ethyl acetate, and the resulting mixture was washed with water and brine, and dried over anhydrous magnesium sulfate. The solvent was removed under reduced pressure, and the residue was purified by column chromatography on silica gel (eluent: n-hexane–n-hexane/ethyl acetate=2/3) to give 5-fluoro-2-[N-(2,6-difluorophenyl) amino]methyl-4-nitroanisole (0.41 g). This material was dissolved in N,N-dimethylformamide (3 mL). To the solution was added sodium hydride (55%, 84 mg) under ice-cooling, and the mixture was stirred at the same temperature for 5 minutes. To the reaction mixture was added iodomethane (0.096 mL), and the mixture was stirred at room temperature overnight. To the reaction mixture was added a saturated aqueous ammonium chloride solution, and the resulting mixture was extracted with ethyl acetate. The extract was washed with water and brine, and dried over anhydrous magnesium sulfate. The solvent was removed under reduced pressure, and the residue was purified by column chromatography on silica gel (eluent: n-hexane–n-hexane/ethyl acetate=1/1) to give 5-fluoro-2-[N-(2,6-difluorophenyl)-N-methyl -amino]methyl-4-nitroanisole (0.17 g). This material was dissolved in methanol (3 mL)-tetrahydrofuran (3 mL). To the solution were added nickel (II) bromide (5 mg) and sodium borohydride (52 mg) under ice-cooling, and the mixture was stirred at the same temperature for 15 minutes. The mixture was stirred at room temperature for 15 minutes. The reaction mixture was diluted with ethyl acetate, and the resulting mixture was washed with a saturated aqueous sodium hydrogen carbonate solution, water and brine successively, and dried over anhydrous magnesium sulfate. The solvent was removed under reduced pressure, and the residue was purified by column chromatography on silica gel (eluent: n-hexane–n-hexane/ethyl acetate=3/2) to give the title compound (0.12 g).

Reference Example 335

The compound of Reference Example 335 described in Table 44 was obtained in a similar manner to that described in Reference
Example 334 using the corresponding starting material.

Reference Example 336

2-Fluoro-5-[N-(2-fluoro-6-methoxyphenyl)-N-methylamino]-methylaniline

To a solution of 4-fluoro-3-nitrobenzoic acid (1.57 g) in methylene chloride (25 mL) were added N,N-dimethylformamide (0.005 mL) and oxalyl chloride (4.32 g), and the mixture was stirred at room temperature for 1 hour. The reaction mixture was concentrated under reduced pressure. A solution of the residue in tetrahydrofuran (5 mL) was added to a suspension of 2-fluoro-6-methoxyaniline (1.2 g) and sodium hydrogen carbonate (2.14 g) in tetrahydrofuran (10 mL), and the mixture was stirred at room temperature overnight. The reaction mixture was poured into water, and the resulting mixture was extracted with ethyl acetate. The extract was washed with 1 mol/L hydrochloric acid, water and brine successively, and dried over anhydrous magnesium sulfate. The solvent was removed under reduced pressure. The residue was suspended in methylene chloride and collected by filtration, and dried under reduced pressure to give 4-fluoro-3-nitro-N-(2-fluoro-6-methoxyphenyl)benzamide (1.1 g). This material was dissolved in N,N-dimethylformamide (12 mL). To the solution were added sodium hydride (55%, 172 mg) and iodomethane (0.76 g) under ice-cooling, and the mixture was stirred at room temperature overnight. The reaction mixture was poured into water, and the resulting mixture was extracted with ethyl acetate. The extract was washed with water three times and brine, and dried over anhydrous magnesium sulfate. The solvent was removed under reduced pressure to give 4-fluoro-3-nitro-N-(2-fluoro-6-methoxyphenyl)-N-methyl -benzamide (1.15 g). The obtained 4-fluoro-3-nitro-N-(2-fluoro-6-methoxyphenyl)-N-methylbenzamide (0.3 g) was dissolved in methanol (10 mL)-tetrahydrofuran (10 mL). To the solution were added nickel (II) bromide (10 mg) and sodium borohydride (0.11 g) under ice-cooling, and the mixture was stirred at the same temperature for 30 minutes. The mixture was stirred at room temperature for 30 minutes. The reaction mixture was poured into a saturated aqueous sodium hydrogen carbonate solution, and the resulting mixture was extracted with ethyl acetate. The extract was washed with water and brine, and dried over anhydrous magnesium sulfate. The solvent was removed under reduced pressure to give 3-amino-4-fluoro -N-(2-fluoro-6-methoxyphenyl)-N-methylbenzamide (0.27 g). This material was dissolved in tetrahydrofuran (8 mL). To the solution was added borane-tetrahydrofuran complex (1 mol/L tetrahydrofuran solution, 3.3 mL), and the mixture was heated for reflux for 2 hours. To the reaction mixture was added methanol under ice-cooling, and the mixture was stirred for 10 minutes. The mixture was poured into a saturated aqueous sodium hydrogen carbonate solution, and the resulting mixture was extracted with ethyl acetate. The extract was washed with brine and dried over anhydrous magnesium sulfate. The solvent was removed under reduced pressure, and the residue was purified by column chromatography on silica gel (eluent: n-hexane/ethyl acetate=3/1) to give the title compound (0.11 g).

Reference Examples 337 to 340

The compounds of Reference Examples 337 to 340 described in Table 45 were obtained in a similar manner to that described in Reference Example 336 using the corresponding starting materials.

Reference Examples 341 to 342

The compounds of Reference Examples 341 to 342 described in Table 45 were obtained in a similar manner to that described in Reference Example 325 using the corresponding starting materials.

Reference Examples 343 to 344

The compounds of Reference Examples 343 to 344 described in Table 45 were obtained in a similar manner to that described in Reference Example 21 using 2,3-difluoro-6-(2-ethoxyethoxy) -phenol or 2,3-difluoro-6-[2-(tert-butyldimethylsilyloxy) -ethoxy]phenol and 4-fluoro-3-nitrobenzyl alcohol instead of 4-fluoro-3-nitrophenol and 1-(2-fluoro-6-methoxyphenyl) -ethanol, respectively.

Reference Example 345

4-Fluoro-3-nitro-2-methoxybenzoic acid

To 4-fluoro-2-methoxybenzoic acid (0.96 g) was added concentrated sulfuric acid (6 mL) under ice-cooling, and the mixture was stirred for 15 minutes. To the mixture was added concentrated nitric acid (0.6 mL) under ice-cooling, and the mixture was stirred at the same temperature for 1 hour. To the reaction mixture was added ice, and the resulting mixture was stirred at room temperature for 10 minutes. The mixture was extracted with ethyl acetate. The extract was washed with water twice and brine, and dried over anhydrous magnesium sulfate. The solvent was removed under reduced pressure. To the residue was added a mixed solvent (n-hexane/ethyl acetate=2/1), and the insoluble material was collected by filtration, and dried under reduced pressure to give the title compound (0.78 g).

Reference Example 346

The compound of Reference Example 346 described in Table 46 was obtained in a similar manner to that described in Reference Example 336 using the corresponding starting materials.

Example 1

5-Methoxycarbonyl-3-[2-chloro-5-(3,4-dihydroquinolin -1(2H)-ylsulfonyl)phenyl]thieno[3,4-d]pyrimidine-2,4(1H,3H) -dione To a suspension of dimethyl 4-aminothiophene-2,3-dicarboxylate hydrochloride (0.5 g) and triethylamine (0.84 mL)

in tetrahydrofuran (10 mL) was added a solution of triphosgene (0.41 g) in tetrahydrofuran (5 mL), and the mixture was stirred at 60° C. for 1 hour. The insoluble material was removed by filtration, and the filtrate was concentrated under reduced pressure. The residue was dissolved in tetrahydrofuran (8 mL). The solution was added to a solution of 2-chloro-5-(3,4-dihydroquinolin-1(2H)-ylsulfonyl)aniline (0.64 g) and 4-dimethylaminopyridine (0.49g) in tetrahydrofuran (8 mL), and the mixture was stirred at 60° C. for 2 hours. The reaction mixture was diluted with ethyl acetate, and the resulting mixture was washed with 1 mol/L hydrochloric acid and brine successively, and dried over anhydrous magnesium sulfate. The solvent was removed under reduced pressure, and the residue was dissolved in methanol (15 mL). To the solution was added sodium methoxide (28% methanol solution, 1.15 mL), and the mixture was stirred at room temperature for 10 minutes. The reaction mixture was diluted with ethyl acetate, and the resulting mixture was washed with 1 mol/L hydrochloric acid, water and brine successively, and dried over anhydrous magnesium sulfate. The solvent was removed under reduced pressure, and the residue was purified by column chromatography on silica gel (eluent: n-hexane/ethyl acetate=1/1) to give the title compound (0.65 g).

Examples 2 to 21

The compounds of Examples 2 to 21 described in Tables 47 to 49 were obtained in a similar manner to that described in Example 1 using the corresponding starting materials. However, in case of Example 6, ethanol and sodium ethoxide were used instead of methanol and sodium methoxide, respectively.

Example 22

5-Carboxy-3-[2-chloro-5-(3,4-dihydroquinolin-1 (2H)-yl -sulfonyl)phenyl]thieno[3,4-d]pyrimidine-2, 4(1H,3H)-dione To a solution of 5-methoxycarbonyl-3-[2-chloro-5-(3,4-dihydroquinolin-1(2H)-ylsulfonyl)phenyl]thieno[3,4-d]-pyrimidine-2,4(1H,3H)-dione (0.2 g) in methanol (12 mL) -tetrahydrofuran (4 mL) was added lithium hydroxide-monohydrate (0.16 g), and the mixture was stirred at 60° C. overnight. To the reaction mixture was added 1 mol/L hydrochloric acid, and the precipitated crystals were collected by filtration. The crystals were washed with water and dried under reduced pressure to give the title compound (0.18 g).

Examples 23 to 29

The compounds of Examples 23 to 29 described in Tables 50 to 51 were obtained in a similar manner to that described in Example 1 and Example 22 using the corresponding starting materials.

Example 30

5-Carbamoyl-3-[2-chloro-5-(3,4-dihydroquinolin-1 (2H)-yl -sulfonyl)phenyl]thieno[3,4-d]pyrimidine-2, 4(1H,3H)-dione To a solution of 5-carboxy-3-[2-chloro-5-(3,4-dihydroquinolin-1(2H)-ylsulfonyl)phenyl]thieno[3,4-d]-pyrimidine-2,4(1H,3H)-dione (14 mg) in tetrahydrofuran (1 mL) was added 1,1'-carbonylbis-1H-imidazole (9 mg), and the mixture was stirred at room temperature for 1 hour. To the reaction mixture was added 28% aqueous ammonia solution (0.5 mL), and the mixture was stirred at room temperature for 1 hour. The reaction mixture was diluted with ethyl acetate, and the resulting mixture was washed with water and brine successively, and dried over anhydrous magnesium sulfate. The solvent was removed under reduced pressure, and the residue was purified by column chromatography on silica gel (eluent: methylene chloride/ methanol=10/1) to give the title compound (13 mg).

Example 31

5-Methylcarbamoyl-3-[2-chloro-5-(3,4-dihydroquinolin-1(2H) -ylsulfonyl)phenyl]thieno[3,4-d]pyrimidine-2,4(1H,3H)-dione The title compound was obtained in a similar manner to that described in Example 30 using the corresponding starting material.

Example 32

5-(1-Hydroxy-1-methylethyl)-3-[2-chloro-5-(3,4-dihydro -quinolin-1(2H)-ylsulfonyl)phenyl]thieno[3, 4-d]pyrimidine -2,4(1H,3H)-dione To a solution of 5-methoxycarbonyl-3-[2-chloro-5-(3,4-dihydroquinolin-1(2H)-ylsulfonyl)phenyl]thieno[3,4-d]-pyrimidine-2,4(1H,3H)-dione (0.1 g) in tetrahydrofuran (10 mL) was added methylmagnesium iodide (3 mol/L diethyl ether solution, 0.19 mL) under ice-cooling, and the mixture was stirred at room temperature overnight. To the reaction mixture was added a saturated aqueous ammonium chloride solution, and the resulting mixture was extracted with ethyl acetate. The extract was washed with water and brine successively, and dried over anhydrous magnesium sulfate. The solvent was removed under reduced pressure, and the residue was purified by column chromatography on silica gel (eluent: n-hexane/ethyl acetate=1/1) to give the title compound (85 mg).

Example 33

5-Hydroxymethyl-3-[2-chloro-5-(3,4-dihydroquinolin-1(2H) -ylsulfonyl)phenyl]thieno[3,4-d]pyrimidine-2,4(1H,3H)-dione To a solution of 5-methoxycarbonyl-3-[2-chloro-5-(3,4-dihydroquinolin-1(2H)-ylsulfonyl)phenyl]thieno[3,4-d]-pyrimidine-2,4(1H,3H)-dione (0.2 g) in tetrahydrofuran (4 mL) was added diisobutylaluminum hydride (1.01 mol/L toluene solution, 1.5 mL) under ice-cooling, and the mixture was stirred for 1 hour. To the reaction mixture was added ethyl acetate, and the mixture was stirred for 10minutes. To the mixture was added 1 mol/L hydrochloric acid, and the resulting mixture was extracted with ethyl acetate. The extract was washed with brine and dried over anhydrous magnesium sulfate. The solvent was removed under reduced pressure, and the residue was purified by column chromatography on silica gel (eluent: n-hexane/ethyl acetate=1/1) to give the title compound (0.11 g).

Example 34

5-Formyl-3-[2-chloro-5-(3,4-dihydroquinolin-1(2H)-yl -sulfonyl)phenyl]thieno[3,4-d]pyrimidine-2,4(1H, 3H)-dione To a solution of 5-hydroxymethyl-3-[2-chloro-5-(3,4-dihydroquinolin-1(2H)-ylsulfonyl)phenyl]thieno[3,4-d]-pyrimidine-2,4(1H,3H)-dione (77 mg) in N,N-dimethylformamide (2.1 mL) was added manganese (IV) dioxide (0.77 g), and the mixture was stirred at room temperature overnight. The reaction mixture was diluted with ethyl acetate, and the insoluble material was removed by filtration. The filtrate was washed with water and brine successively, and dried over anhydrous magnesium sulfate. The solvent was removed under reduced pressure, and the residue was purified by column chromatography on silica gel (eluent: n-hexane/ethyl acetate=1/1) to give the title compound (32 mg).

Example 35

5-Methoxycarbonyl-3-{2-fluoro-5-[1-(2-fluoro-6-methoxy-phenyl) ethoxy]phenyl}thieno[3,4-d]pyrimidine-2,4(1H,3H)-dione To a mixture of dimethyl 4-aminothiophene-2,3-dicarboxylate hydrochloride (90 mg) and triethylamine (0.15 mL) in tetrahydrofuran (3 mL) was added a solution of triphosgene (74 mg) in tetrahydrofuran (3 mL), and the mixture was stirred at 60° C. for 30 minutes. The insoluble material was removed by filtration, and the filtrate was concentrated under reduced pressure. The residue was dissolved in tetrahydrofuran (3 mL). The solution was added to a solution of 2-fluoro-5-[1-(2-fluoro-6-methoxyphenyl)ethoxy]aniline (0.1 g) and 4-dimethylaminopyridine (88 mg) in tetrahydrofuran (3 mL), and the mixture was stirred at 60° C. overnight. To the reaction mixture was added 1 mol/L hydrochloric acid, and the resulting mixture was extracted with ethyl acetate. The extract was washed with water and brine successively, and dried over anhydrous magnesium sulfate. The solvent was removed under reduced pressure, and the residue was dissolved in methanol (5 mL). To the solution was added sodium methoxide (28% methanol solution, 0.21 mL), and the mixture was stirred at room temperature for 15 minutes. To the reaction mixture was added 1 mol/L hydrochloric acid, and the resulting mixture was extracted with ethyl acetate. The extract was washed with water and brine successively, and dried over anhydrous magnesium sulfate. The solvent was removed under reduced pressure, and the residue was purified by column chromatography on silica gel (eluent: n-hexane/ethyl acetate=1/2) to give the title compound (0.14 g)

Examples 36 to 47

The compounds of Examples 36 to 47 described in Tables 52 to 53 were obtained in a similar manner to that described in Example 35 using the corresponding starting materials.

Example 48

5-Carboxy-3-{2-fluoro-5-[1-(2-fluoro-6-methoxyphenyl)-ethoxy]phenyl}[3,4-d]pyrimidine-2,4(1H,3H)-dione To a mixture of 5-methoxycarbonyl-3-{2-fluoro-5-[1-(2-fluoro-6-methoxyphenyl)ethoxy]phenyl}thieno[3,4-d]-pyrimidine-2,4(1H,3H)-dione (0.12 g) and methanol (3 mL) was added lithium hydroxide-monohydrate (99 mg), and the mixture was stirred at 50° C. for 1 hour. The reaction mixture was acidified by addition of 1 mol/L hydrochloric acid, and the precipitated crystals were collected by filtration. The crystals were washed with water and dried under reduced pressure to give the title compound (0.11 g).

Examples 49 to 60

The compounds of Examples 49 to 60 described in Tables 53 to 55 were obtained in a similar manner to that described in Example 48 using the corresponding starting materials.

Examples 61 to 65

The compounds of Examples 61 to 65 described in Table 55 were obtained in a similar manner to that described in Example 35 using the corresponding starting materials.

Examples 66 to 70

The compounds of Examples 66 to 70 described in Tables 55 to 56 were obtained in a similar manner to that described in Example 48 or Example 93 using the corresponding starting materials.

Example 71

The compound of Example 71 described in Table 56 was obtained in a similar manner to that described in Example 35 using the corresponding starting material.

Example 72

5-Methoxycarbonyl-3-[3-(1-phenylethylsulfinyl) phenyl]-thieno[3,4-d]pyrimidine-2,4(1H,3H)-dione To a solution of 5-methoxycarbonyl-3-[3-(1-phenyl-ethylthio)phenyl]thieno[3,4-d]pyrimidine-2,4(1H,3H)-dione (50 mg) in acetone (3 mL)-water (0.6 mL) were added sodium hydrogen carbonate (24 mg) and OXONE (registered trademark) (84 mg), and the mixture was stirred at room temperature for 30 minutes. The reaction mixture was extracted with ethyl acetate, and the extract was washed with 1 mol/L hydrochloric acid, water and brine successively, and dried over anhydrous magnesium sulfate.

The solvent was removed under reduced pressure. The residue was suspended in methanol and collected by filtration, and dried under reduced pressure to give the title compound (45 mg).

Example 73

5-Methoxycarbonyl-3-[3-(1-phenylethylsulfonyl) phenyl]-thieno[3,4-d]pyrimidine-2,4(1H,3H)-dione To a solution of 5-methoxycarbonyl-3-[3-(1-phenyl-ethylthio) phenyl]thieno[3,4-d]pyrimidine-2,4(1H,3H)-dione (50 mg) in acetone (3 mL)-water (0.6 mL) were added sodium hydrogen carbonate (77 mg) and OXONE (registered trademark) (0.28 g), and the mixture was stirred at room temperature for 30 minutes. The reaction mixture was extracted with ethyl acetate, and the extract was washed with 1 mol/L hydrochloric acid, water and brine successively, and dried over anhydrous magnesium sulfate.

The solvent was removed under reduced pressure. The residue was suspended in methanol and collected by filtration, and dried under reduced pressure to give the title compound (48 mg).

Examples 74 to 76

The compounds of Examples 74 to 76 described in Tables 56 to 57 were obtained in a similar manner to that described in Example 35 using the corresponding starting materials.

Example 77

The compound of Example 77 described in Table 57 was obtained in a similar manner to that described in Example 73 using the corresponding starting material.

Example 78

The compound of Example 78 described in Table 57 was obtained in a similar manner to that described in Example 35 using the corresponding starting materials.

Examples 79 to 82

The compounds of Examples 79 to 82 described in Table 57 were obtained in a similar manner to that described in Example 48 using the corresponding starting materials.

Example 83

The compound of Example 83 described in Table 58 was obtained in a similar manner to that described in Example 73 and Example 48 using the corresponding starting materials.

Examples 84 to 87

The compounds of Examples 84 to 87 described in Table 58 were obtained in a similar manner to that described in Example 48 using the corresponding starting materials.

Example 88

The compound of Example 88 described in Table 58 was obtained in a similar manner to that described in Example 73 and Example 48 using the corresponding starting materials.

Examples 89 to 92

The compounds of Examples 89 to 92 described in Tables 58 to 59 were obtained in a similar manner to that described in Example 35 using the corresponding starting materials.

Example 93

5-Carboxy-3-[2-fluoro-5-(N-methyl-N-phenylcarbamoyl)-phenyl]thieno[3,4-d]pyrimidine-2,4(1H,3H)-dione A mixture of 5-methoxycarbonyl-3-[2-fluoro-5-(N-methyl-N-phenylcarbamoyl)phenyl]thieno[3,4-d]pyrimidine-2,4(1H,3H)-dione (0.18 g) and lithium hydroxide-monohydrate (0.17 g) in tetrahydrofuran (6 mL)-methanol (3 mL)-water (3 mL) was stirred at room temperature for 2 hours. The reaction mixture was poured into 1 mol/L hydrochloric acid, and the resulting mixture was extracted with ethyl acetate. The extract was washed with brine and dried over anhydrous sodium sulfate. The solvent was removed under reduced pressure, and the residue was purified by column chromatography on silica gel (eluent: methylene chloride/methanol=8/1) to give the title compound (0.12 g).

Example 94

The compound of Example 94 described in Table 59 was obtained in a similar manner to that described in Example 35 and Example 93 using the corresponding starting materials.

Examples 95 to 97

The compounds of Examples 95 to 97 described in Table 59 were obtained in a similar manner to that described in Example 93 using the corresponding starting materials.

Examples 98 to 100

The compounds of Examples 98 to 100 described in Tables 59 to 60 were obtained in a similar manner to that described in Example 35 using the corresponding starting materials.

Examples 101 to 103

The compounds of Examples 101 to 103 described in Table 60 were obtained in a similar manner to that described in Example 48 using the corresponding starting materials.

Examples 104 to 108

The compounds of Examples 104 to 108 described in Table 61 were obtained in a similar manner to that described in Example 1 using the corresponding starting materials.

Examples 109 to 201

The compounds of Examples 109 to 201 described in Tables 61 to 74 were obtained in a similar manner to that described in Example 1 and Example 48 or Example 93 using the corresponding starting materials.

Example 202

5-Carboxy-3-[2-fluoro-5-(1-methyl-1-phenylethylsulfonyl)-phenyl]thieno[3,4-d]pyrimidine-2,4(1H,3H)-dione 5-Methoxycarbonyl-3-[2-fluoro-5-(1-methyl-1-phenyl-ethylthio)phenyl]thieno[3,4-d]pyrimidine-2,4(1H,3H)-dione was obtained in a similar manner to that described in Example 35 using 2-fluoro-5-(1-methyl-1-phenylethylthio)aniline instead of 2-fluoro-5-[1-(2-fluoro-6-methoxyphenyl)-ethoxy]aniline. This compound (0.1 g) was dissolved in methylene chloride (2 mL). To the solution was added 3-chloroperbenzoic acid (92 mg), and the mixture was stirred at room temperature overnight. The reaction mixture was poured into water. To the mixture was added 1 mol/L aqueous sodium thiosulfate solution, and the resulting mixture was extracted with ethyl acetate. The extract was washed with brine and dried over anhydrous magnesium sulfate. The solvent was removed under reduced pressure, and the residue was purified by column chromatography on silica gel (eluent: n-hexane/ethyl acetate =1/1–1/2) to give 5-methoxycarbonyl-3-[2-fluoro-5-(1-methyl-1-phenylethylsulfonyl)phenyl]thieno[3,4-d]-pyrimidine-2,4(1H,3H)-dione (0.1 g). The title compound was obtained in a similar manner to that described in Example 93 using the obtained 5-methoxycarbonyl-3-[2-fluoro-5-(1-methyl-1-phenylethylsulfonyl)phenyl]thieno[3,4-d]-pyrimidine-2,4(1H,3H)-dione instead of 5-methoxycarbonyl -3-[2-fluoro-5-(N-methyl-N-phenylcarbamoyl) phenyl]thieno -[3,4-d]pyrimidine-2,4(1H,3H)-dione.

Examples 203 to 232

The compounds of Examples 203 to 232 described in Tables 75 to 79 were obtained in a similar manner to that described in Example 202 using the corresponding starting materials.

Example 233

5-Carboxy-3-[2-fluoro-5-(2,3-difluoro-6-methoxybenzyloxy) -4-methoxyphenyl]thieno[3,4-d]pyrimidine-2,4(1H,3H)-dione To a suspension of dimethyl 4-aminothiophene-2,3-dicarboxylate hydrochloride (0.13 g) and triethylamine (0.21 mL) in tetrahydrofuran (5 mL) was added triphosgene (99 mg) under ice-cooling, and the mixture was stirred at 60° C. for 30 minutes. The reaction mixture was diluted with ethyl acetate, and the insoluble material was removed by filtration. The filtrate was concentrated under reduced pressure, and the residue was dissolved in tetrahydrofuran (4 mL). The solution was added to a solution of 2-fluoro-5-(2,3-difluoro-6-methoxy -benzyloxy)-4-methoxyaniline (0.16 g) and 4-dimethylamino -pyridine (0.12 g) in tetrahydrofuran (4 mL), and the mixture was stirred at 60° C. for 3 days. The reaction mixture was passed through IST ISOLUTE SCX and eluted with ethyl acetate. The eluate was concentrated under reduced pressure, and the residue was dissolved in methanol (5 mL). To the solution was added sodium methoxide (28% methanol solution, 0.29 mL), and the mixture was stirred at room temperature for 30 minutes. To the reaction mixture was added 1 mol/L hydrochloric acid, and the resulting mixture was extracted with ethyl acetate. The extract was washed with brine and dried over anhydrous sodium sulfate, and the solvent was removed under reduced pressure. A mixture of the residue and lithium hydroxide-monohydrate (0.21 g) in tetrahydrofuran (4 mL)-methanol (2 mL)-water (2 mL) was stirred at room temperature for 30 minutes. The reaction mixture was poured into 1 mol/L hydrochloric acid, and the resulting mixture was extracted with ethyl acetate. The extract was washed with water and brine successively, and dried over anhydrous sodium sulfate. The solvent was removed under reduced pressure, and the residue was purified by column chromatography on silica gel (eluent: n-hexane/ethyl acetate=1/2–ethyl acetate) to give the title compound (0.13 g).

Examples 234 to 391

The compounds of Examples 234 to 391 described in Tables 79 to 102 were obtained in a similar manner to that described in Example 233 using the corresponding starting materials.

Example 392

The compound of Example 392 described in Table 102 was obtained in a similar manner to that described in Example 35 and Example 33 using the corresponding starting materials.

Examples 393 to 395

The compounds of Examples 393 to 395 described in Table 102 were obtained in a similar manner to that described in Example 30 using the corresponding starting materials.

Example 396

5-Carboxy-3-{2-fluoro-5-[2,3-difluoro-6-(2-hydroxyethoxy) -benzyloxy]phenyl }[3,4-d]pyrimidine-2,4(1H,3H)-dione To a suspension of dimethyl 4-aminothiophene-2,3-dicarboxylate hydrochloride (0.11 g) and triethylamine (0.19 mL) in tetrahydrofuran (5 mL) was added triphosgene (84 mg) under ice-cooling, and the mixture was stirred at 60° C. for 30 minutes. The reaction mixture was diluted with ethyl acetate, and the insoluble material was removed by filtration. The filtrate was concentrated under reduced pressure, and the residue was dissolved in tetrahydrofuran (4 mL). The solution was added to a solution of 2-fluoro-5-{2,3-difluoro-6-[2-(tert -butyldimethylsilyloxy)ethoxy]benzyloxy}aniline (0.17 g) and 4-dimethylaminopyridine (99 mg) in tetrahydrofuran (4 mL), and the mixture was stirred at 60° C. overnight. The reaction mixture was passed through IST ISOLUTE SCX and eluted with ethyl acetate. The eluate was concentrated under reduced pressure, and the residue was dissolved in methanol (4 mL). To the solution was added sodium methoxide (28% methanol solution, 0.23 mL), and the mixture was stirred at room temperature for 30minutes. To the reaction mixture was added 1 mol/L hydrochloric acid, and the resulting mixture was extracted with ethyl acetate. The extract was washed with brine and dried over anhydrous sodium sulfate. The solvent was removed under reduced pressure, and the residue was dissolved in tetrahydrofuran (4 mL). To the solution was added tetra(n-butyl)ammonium fluoride (1 mol/L tetrahydrofuran solution, 1.2 mL), and the mixture was stirred at room temperature for 3 hours. The reaction mixture was poured into 1 mol/L hydrochloric acid, and the resulting mixture was extracted with ethyl acetate. The extract was washed with 1 mol/L hydrochloric acid, water and brine successively, and dried over anhydrous sodium sulfate. The solvent was removed under reduced pressure. A mixture of the residue and lithium hydroxide-monohydrate (0.17 g) in tetrahydrofuran (5 mL) -methanol (2.5 mL)-water (2.5 mL) was stirred at room temperature for 30 minutes. To the reaction mixture was added 1 mol/L hydrochloric acid, and the resulting mixture was extracted with ethyl acetate. The extract was washed with water and brine successively, and dried over anhydrous sodium sulfate. The solvent was removed under reduced pressure, and the residue was purified by column chromatography on silica gel (eluent: ethyl acetate) to give the title compound (0.13 g).

Examples 397 to 410

The compounds of Examples 397 to 410 described in Tables 102 to 104 were obtained in a similar manner to that described in Example 396 using the corresponding starting materials.

Examples 411 to 416

The compounds of Examples 411 to 416 described in Tables 104 to 105 were obtained in a similar manner to that described in Example 233 using the corresponding starting materials.

Example 417

5-Ethoxycarbonyl-3-{2-fluoro-5-[2,3-difluoro-6-(2-hydroxy -ethoxy) benzyloxy]phenyl}[3,4-d]pyrimidine-2, 4(1H,3H) -dione To a suspension of 5-carboxy-3-{2-fluoro-5-[2,3-difluoro-6-(2-hydroxyethoxy)benzyloxy]phenyl}thieno[3,4-d]-pyrimidine-2,4(1H,3H)-dione (0.65 g) in ethanol (10 mL) -tetrahydrofuran (5 mL) was added p-toluenesulfonic acid-monohydrate (24 mg), and the mixture was stirred at 90° C. (outside temperature) overnight. The reaction mixture was concentrated under reduced pressure, and the residue was purified by column chromatography on silica gel (eluent: n-hexane/ethyl acetate=1/2–1/4) to give the title compound (0.39 g).

Example 418

5-Ethoxycarbonyl-3-(5-{6-[2-(ethoxycarbonyloxy)ethoxy]-2,3-difluorobenzyloxy}-2-fluorophenyl)thieno[3,4-d]pyrimidine -2,4(1H,3H)-dione To a suspension of 5-ethoxycarbonyl-3-{2-fluoro-5-[2,3-difluoro-6-(2-hydroxyethoxy)benzyloxy]phenyl}thieno[3,4-d]-pyrimidine-2,4(1H,3H)-dione (80 mg) in ethyl acetate (2 mL) were added pyridine (0.036 mL) and ethyl chloroformate (0.021 mL), and the mixture was stirred at room temperature overnight. The reaction mixture was poured into 1 mol/L hydrochloric acid, and the resulting mixture was extracted with ethyl acetate. The extract was washed with water and brine, and dried over anhydrous sodium sulfate. The solvent was removed under reduced pressure, and the residue was purified by column chromatography on silica gel (eluent: n-hexane/ethyl acetate=1/2) to give the title compound (38 mg).

Example 419

The compound of Example 419 described in Table 106 was obtained in a similar manner to that described in Example 418 using the corresponding starting material.

Examples 420 to 426

The compounds of Examples 420 to 426 described in Tables 106 to 107 were obtained in a similar manner to that described in Example 233 using the corresponding starting materials.

Example 427

The compound of Example 427 described in Table 107 was obtained in a similar manner to that described in Example 396 using the corresponding starting material.

Example 428

The compound of Example 428 described in Table 107 was obtained in a similar manner to that described in Example 233 using the corresponding starting material.

Tables 1 to 46 and Tables 47 to 107 show the chemical structure and $^1$H-NMR data of the above compounds of Reference Examples 1 to 346 and Examples 1 to 428, respectively.

The abbreviations in these Tables: "Ref No.", "Ex No.", "Strc" and "Solv", represent Reference Example number, Example number, chemical structure and measurement solvent of $^1$H-NMR, respectively.

TABLE 1

| Ref No. | Strc | $^1$H-NMR (CDCl$_3$) δ ppm: |
|---|---|---|
| 1 | | 1.6-1.75 (2H, m), 2.49 (2H, t, J = 6.5 Hz), 3.75-3.85 (2H, m), 4.2 (2H, brs), 6.8-6.9 (1H, m), 6.96 (1H, d, J = 1.8 Hz), 7.0-7.3 (4H, m), 7.7-7.8 (1H, m) |
| 2 | | 1.5-1.65 (2H, m), 1.7-1.9 (2H, m), 2.4-2.5 (2H, m), 3.55-3.85 (2H, m), 4.22 (2H, brs), 7.0-7.05 (1H, m), 7.09 (1H, d, J = 2.0 Hz), 7.1-7.3 (4H, m), 7.31 (1H, d, J = 8.4 Hz) |
| 3 | | 3.18 (3H, s), 4.22 (2H, brs), 6.8-6.85 (1H, m), 6.9 (1H, d, J = 2.0 Hz), 7.1-7.15 (2H, m), 7.2-7.35 (4H, m) |
| 4 | | 0.9-1.1 (1H, m), 1.2-1.4 (4H, m), 1.45-1.65 (3H, m), 1.7-1.8 (2H, m), 2.74 (3H, s), 3.65-3.8 (1H, m), 4.28 (2H, brs), 7.05-7.1 (1H, m), 7.2 (1 H, d, J = 2.2 Hz), 7.34 (1 H, d, J = 8.5 Hz) |

TABLE 1-continued

| Ref No. | Strc | ¹H-NMR (CDCl₃) δ ppm: |
|---|---|---|
| 5 | | 3.28 (3H, s), 4.22 (2H, brs), 6.8-6.85 (1H, m), 6.97 (1H, d, J = 2.4 Hz), 7.1-7.15 (1H, m), 7.25-7.3 (1H, m), 7.6-7.75 (2H, m), 8.25-8.35 (1H, m) |
| 6 | | 3.21 (3H, s), 4.26 (2H, brs), 7.05-7.1 (1H, m), 7.14 (1H, d, J = 1.9 Hz), 7.2-7.3 (3H, m), 7.36 (1H, d, J = 8.0 Hz), 7.4-7.45 (1H, m) |
| 7 | | 0.94 (6H, d, J = 6.6 Hz), 1.8-1.9 (1H, m), 2.7 (3H, s), 2.74 (2H, d, J = 7.5 Hz), 4.32 (2H, brs), 7.0-7.1 (1H, m), 7.16 (1H, d, J = 1.7 Hz), 7.37 (1H, d, J = 8.2 Hz) |
| 8 | | 1.6-1.75 (2H, m), 2.48 (2H, t, J = 6.5 Hz), 3.7-3.85 (4H, m), 6.75-6.8 (1H, m), 6.85-7.25 (6H, m), 7.7-7.8 (1H, m) |
| 9 | | 3.16 (3H, s), 4.26 (2H, brs), 6.8-6.85 (1H, m), 6.92 (1H, d, J = 2.4 Hz), 7.0-7.30 (4H, m), 7.32 (1H, d, J = 8.2 Hz) |
| 10 | | 2.32 (3H, s), 3.16 (3H, s), 4.22 (2H, brs), 6.8-6.9 (2H, m), 6.92 (1H, d, J = 2.4 Hz), 6.95-7.25 (3H, m), 7.31 (1H, d, J = 8.4 Hz) |

TABLE 2

| Ref No. | Strc | ¹H-NMR (CDCl₃) δ ppm: |
|---|---|---|
| 11 | | 4.26 (2H, brs), 6.7-6.9 (1H, m), 7.0-7.3 (8H, m) |
| 12 | | 1.95-2.05 (2H, m), 2.81 (2H, t, J = 6.3 Hz), 3.25-3.4 (2H, m), 4.0 (2H, brs), 4.34 (2H, s), 6.4-6.5 (1H, m), 6.55-6.7 (3H, m), 6.9-7.0 (2H, m), 7.1-7.2 (1H, m) |

TABLE 2-continued

| Ref No. | Strc | ¹H-NMR (CDCl₃) δ ppm: |
|---|---|---|
| 13 | | 4.02 (2H, brs), 5.0 (2H, s), 6.3-6.45 (2H, m), 7.12 (1H, d, J = 8.7 Hz), 7.25-7.45 (5H, m) |
| 14 | | 2.36 (3H, s), 4.03 (2H, brs), 4.97 (2H, s), 6.3-6.45 (2H, m), 7.13 (1H, d, J = 8.8 Hz), 7.15-7.3 (3H, m), 7.35-7.4 (1H, m) |
| 15 | | 2.37 (3H, s), 4.02 (2H, brs), 4.96 (2H, s), 6.3-6.45 (2H, m), 7.1-7.3 (5H, m) |
| 16 | | 4.04 (2H, brs), 5.06 (2H, s), 6.3-6.4 (2H, m), 7.13 (1H, d, J = 8.6 Hz), 7.52 (2H, d, J = 8.1 Hz), 7.64 (2H, d, J = 8.1 Hz) |
| 17 | | 1.6 (3H, d, J = 6.2 Hz), 3.93 (2H, brs), 5.15-5.25 (1H, m), 6.15-6.3 (2H, m), 7.01 (1H, d, J = 8.9 Hz), 7.2-7.35 (5H, m) |
| 18 | | 2.75-2.95 (4H, m), 6.5-6.65 (3H, m), 7.05-7.35 (6H, m) |

TABLE 3

| Ref No. | Strc | (Solv) ¹H-NMR δ ppm: |
|---|---|---|
| 19 | | (CDCl₃) 1.25-1.4 (6H, m), 4.2-4.35 (4H, m), 5.95 (2H, s), 6.6 (1H, s) |
| 20 | | (CDCl₃) 1.56 (3H, d, J = 6.9 Hz), 3.32 (1H, d, J = 10.7 Hz), 3.89 (3H, s), 5.2-5.3 (1H, m), 6.65-6.75 (2H, m), 7.1-7.2 (1H, m) |
| 21 | | (CDCl₃) 1.69 (3H, d, J = 6.6 Hz), 3.6 (2H, brs), 3.88 (3H, s), 5.73 (1H, q, J = 6.6 Hz), 6.15-6.25 (1H, m), 6.36 (1H, dd, J = 7.5 Hz, 2.7 Hz), 6.55-6.7 (2H, m), 6.76 (1H, dd, J = 10.7 Hz, 9.0 Hz), 7.1-7.2 (1H, m) |
| 22 | | (CDCl₃) 1.59 (3H, d, J = 6.5 Hz), 3.62 (2H, brs), 5.18 (1H, q, J = 6.5 Hz), 6.1-6.2 (1H, m), 6.3 (1H, dd, J = 7.6 Hz, 2.4 Hz), 6.7-6.8 (1H, m), 7.2-7.4 (5H, m) |
| 23 | | (CDCl₃) 3.69 (2H, brs), 3.86 (3H, s), 4.95-5.05 (2H, m), 6.3-6.4 (1H, m), 6.44 (1H, dd, J = 7.6 Hz, 3.1 Hz), 6.65-6.8 (2H, m), 6.88 (1H, dd, J = 10.7 Hz, 8.9 Hz), 7.25-7.35 (1H, m) |
| 24 | | (CDCl₃) 1.73 (3H, d, J = 6.6 Hz), 3.64 (2H, brs), 5.62 (1H, q, J = 6.6 Hz), 6.15-6.25 (1H, m), 6.36 (1H, dd, J = 7.6 Hz, 2.7 Hz), 6.7-6.9 (3H, m), 7.15-7.25 (1H, m) |
| 25 | | (CDCl₃) 1.74 (3H, d, J = 6.7 Hz), 3.63 (2H, brs), 5.93 (1H, q, J = 6.7 Hz), 6.1-6.2 (1H, m), 6.33 (1H, dd, J = 7.6 Hz, 2.6 Hz), 6.76 (1H, dd, J = 10.5 Hz, 9.1 Hz), 7.05-7.15 (1H, m), 7.2-7.3 (2H, m) |

TABLE 3-continued

| Ref No. | Strc | (Solv) ¹H-NMR δ ppm: |
|---|---|---|
| 26 | (structure: 2-fluoro-5-[1-(2-fluorophenyl)ethoxy]aniline) | (CDCl₃) 1.6 (3H, d, J = 6.5 Hz), 3.64 (2H, brs), 5.52 (1H, q, J = 6.5 Hz), 6.1-6.2 (1H, m), 6.3 (1H, dd, J = 7.6 Hz, 2.9 Hz), 6.78 (1H, dd, J = 10.7 Hz, 9.1 Hz), 7.0-7.15 (2H, m), 7.15-7.3 (1H, m), 7.35-7.45 (1H, m) |

TABLE 4

| Ref No. | Strc | (Solv) ¹H-NMR δ ppm: |
|---|---|---|
| 27 | (structure: 2-fluoro-5-[1-(2-methoxyphenyl)ethoxy]aniline) | (CDCl₃) 1.53 (3H, d, J = 6.3 Hz), 3.6 (2H, brs), 3.88 (3H, s), 5.57 (1H, q, J = 6.3 Hz), 6.05-6.15 (1H, m), 6.29 (1H, dd, J = 7.5 Hz, 3.0 Hz), 6.7-6.95 (3H, m), 7.15-7.25 (1H, m), 7.3-7.4 (1H, m) |
| 28 | (structure: 2-fluoro-5-[1-(2-chlorophenyl)ethoxy]aniline) | (CDCl₃) 1.58 (3H, d, J = 6.4 Hz), 3.63 (2H, brs), 5.57 (1H, q, J = 6.4 Hz), 6.05-6.15 (1H, m), 6.25 (1H, dd, J = 7.5 Hz, 2.7 Hz), 6.76 (1H, dd, J = 10.5 Hz, 9.1 Hz), 7.15-7.25 (2H, m), 7.34 (1H, dd, J = 7.7 Hz, 1.5 Hz), 7.46 (1H, dd, J = 7.5 Hz, 1.6 Hz) |
| 29 | (structure: 2-fluoro-5-[1-(3-chlorophenyl)ethoxy]aniline) | (CDCl₃) 1.57 (3H, d, J = 6.5 Hz), 3.64 (2H, brs), 5.14 (1H, q, J = 6.5 Hz), 6.05-6.15 (1H, m), 6.29 (1H, dd, J = 7.3 Hz, 3.1 Hz), 6.78 (1H, dd, J = 10.8 Hz, 8.8 Hz), 7.15-7.35 (4H, m) |

TABLE 4-continued

| Ref No. | Strc | (Solv) ¹H-NMR δ ppm: |
|---|---|---|
| 30 | (structure: tert-butyl N-[2-fluoro-5-(2-methylpropanoyl)phenyl]carbamate) | (CDCl₃) 1.21 (6H, d, J = 6.8 Hz), 1.55 (9H, s), 3.5-3.6 (1H, m), 6.74 (1H, brs), 7.1-7.2 (1H, m), 7.6-7.7 (1H, m), 8.65-8.8 (1H, m) |
| 31 | (structure: 1-(3-amino-4-fluorophenyl)-2-(5-fluoro-2-methoxyphenyl)-2-methylpropan-1-one) | (CDCl₃) 1.57 (6H, s), 3.38 (3H, s), 3.6-3.7 (2H, m), 6.63 (1H, dd, J = 9.3 Hz, 4.7 Hz), 6.65-6.75 (1H, m), 6.8-6.95 (2H, m), 7.15-7.25 (2H, m) |
| 32 | (structure: 1-(3-amino-4-fluorophenyl)-2-methyl-2-phenylpropan-1-one) | (CDCl₃) 1.58 (6H, s), 3.5-3.8 (2H, m), 6.7-6.8 (2H, m), 7.06 (1H, dd, J = 8.7 Hz, 1.8 Hz), 7.2-7.4 (5H, m) |
| 33 | (structure: 1-(3-amino-4-fluorophenyl)-2-(2-methoxyphenyl)-2-methylpropan-1-one) | (CDCl₃) 1.58 (6H, s), 3.41 (3H, s), 3.5-3.7 (2H, m), 6.65-6.75 (2H, m), 6.8-6.9 (1H, m), 7.0-7.1 (1H, m), 7.15-7.3 (2H, m), 7.46 (1H, dd, J = 7.5 Hz, 1.4 Hz) |
| 34 | (structure: 1-(3-amino-4-fluorophenyl)-2-(2-fluorophenyl)-2-methylpropan-1-one) | (CDCl₃) 1.63 (6H, s), 3.6-3.75 (2H, m), 6.65-6.75 (1H, m), 6.8-6.85 (1H, m), 6.85-6.95 (1H, m), 7.2-7.3 (3H, m), 7.45-7.55 (1H, m) |

TABLE 5

| Ref No. | Strc | (Solv) ¹H-NMR δ ppm: |
|---|---|---|
| 35 | (structure: 1-(3-amino-4-fluorophenyl)-2-(3-fluorophenyl)-2-methylpropan-1-one) | (CDCl₃) 1.57 (6H, s), 3.6-3.75 (2H, m), 6.7-7.35 (7H, m) |

TABLE 5-continued

| Ref No. | Strc | (Solv) ¹H-NMR δ ppm: |
|---|---|---|
| 36 | | (DMSO-d₆) 1.52 (3H, d, J = 7.0 Hz), 4.47 (1H, q, J = 7.0 Hz), 5.11 (2H, s), 6.35-6.5 (2H, m), 6.55-6.6 (1H, m), 6.91 (1H, t, J = 7.7 Hz), 7.15-7.4 (5H, m) |
| 37 | | (DMSO-d₆) 4.33 (2H, s), 5.19 (2H, s), 6.4-6.55 (2H, m), 6.6-6.65 (1H, m), 6.95-7.0 (1H, m), 7.3-7.4 (1H, m), 7.45-7.5 (2H, m) |
| 38 | | (DMSO-d₆) 1.61 (6H, s), 5.07 (2H, s), 6.27 (1H, dd, J = 7.5 Hz, 0.7 Hz), 6.45-6.6 (2H, m), 6.8-6.9 (1H, m), 7.15-7.35 (3H, m), 7.4-7.5 (2H, m) |
| 39 | | (CDCl₃) 3.47 (3H, s), 3.64 (2H, brs), 6.45-6.55 (1H, m), 6.7 (1H, dd, J = 10.7 Hz, 8.6 Hz), 6.87 (1H, dd, J = 8.6 Hz, 2.3 Hz), 7.0-7.05 (2H, m), 7.1-7.2 (1H, m), 7.2-7.3 (2H, m) |
| 40 | | (CDCl₃) 3.47 (3H, s), 3.98 (2H, brs), 6.4-6.5 (1H, m), 6.85 (1H, d, J = 1.8 Hz), 6.96 (1H, d, J = 8.3 Hz), 7.0-7.1 (2H, m), 7.1-7.2 (1H, m), 7.2-7.3 (2H, m) |
| 41 | | (CDCl₃) 4.0 (2H, brs), 5.3 (1H, q, J = 6.3 Hz), 6.15-6.25 (1H, m), 6.34 (1H, d, J = 2.8 Hz), 7.05 (1H, d, J = 8.9 Hz), 7.35-7.55 (5H, m) |
| 42 | | (CDCl₃) 3.92 (3H, s), 3.99 (2H, brs), 5.95 (1H, q, J = 6.2 Hz), 6.15-6.25 (1H, m), 6.33 (1H, d, J = 2.7 Hz), 6.9-7.1 (3H, m), 7.3-7.4 (1H, m), 7.51 (1H, d, J = 7.7 Hz) |

TABLE 6

| Ref No. | Strc | (Solv) ¹H-NMR δ ppm: |
|---|---|---|
| 43 | | (CDCl3) 4.18 (3H, s), 7.0 (1H, d, J = 11.8 Hz), 8.83 (1H, d, J = 7.8 Hz) |
| 44 | | (CDCl3) 3.88 (3H, s), 4.25 (2H, s), 7.0-7.1 (1H, m), 7.1-7.15 (1H, m), 7.23 (1H, d, J = 1.8 Hz), 7.25-7.3 (1H, m), 7.4-7.5 (1H, m), 7.65-7.7 (1H, m), 7.9-7.95 (1H, m), 10.61 (1H, s) |
| 45 | | (CDCl3) 1.07 (3H, t, J = 7.1 Hz), 3.6 (2H, q, J = 7.1 Hz), 4.23 (2H, s), 6.89 (1H, dd, J = 8.3 Hz, 1.8 Hz), 6.96 (1H, d, J = 1.8 Hz), 7.05-7.1 (2H, m), 7.25-7.4 (4H, m) |
| 46 | | (CDCl3) 3.14 (3H, s), 4.29 (2H, s), 6.83 (1H, dd, J = 8.5 Hz, 1.9 Hz), 6.92 (1H, d, J = 1.9 Hz), 7.01 (1H, dd, J = 8.2 Hz, 2.5 Hz), 7.34 (1H, d, J = 8.2 Hz), 7.38 (1H, d, J = 8.5 Hz) |
| 47 | | (CDCl3) 3.15-3.25 (3H, m), 4.29 (2H, s), 6.75-6.9 (2H, m), 6.95 (1H, dd, J = 8.1 Hz, 2.3 Hz), 7.06 (1H, d, J = 2.3 Hz), 7.25-7.4 (2H, m) |
| 48 | | (CDCl3) 3.23 (3H, s), 4.28 (2H, s), 6.84 (1H, dd, J = 8.0 Hz, 2.3 Hz), 6.92 (1H, d, J = 2.3 Hz), 7.15-7.2 (2H, m), 7.31 (1H, d, J = 8.6 Hz), 8.5-8.55 (2H, m) |

TABLE 6-continued

| Ref No. | Strc | (Solv) ¹H-NMR δ ppm: |
|---|---|---|
| 49 | 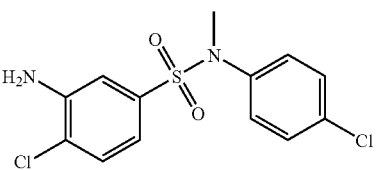 [SMILES: CN(c1ccc(Cl)cc1)S(=O)(=O)c1ccc(Cl)c(N)c1] | (CDCl3) 3.15 (3H, s), 4.25 (2H, s), 6.82 (1H, dd, J = 8.5 Hz, 2.1 Hz), 6.9 (1H, d, J = 2.1 Hz), 7.05-7.1 (2H, m), 7.25-7.35 (3H, m) |
| 50 | 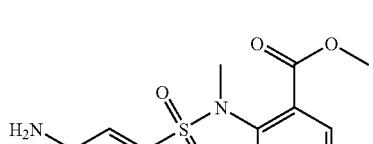 | (CDCl3) 3.28 (3H, s), 3.84 (3H, s), 4.25 (2H, brs), 6.9-7.05 (3H, m), 7.3-7.5 (3H, m), 7.8-7.9 (1H, m) |

TABLE 7

| Ref No. | Strc | (Solv) ¹H-NMR δ ppm: |
|---|---|---|
| 51 | 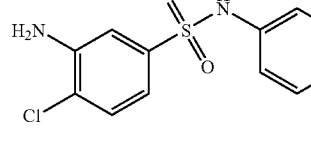 | (CDCl3) 3.15 (3H, s), 3.8 (3H, s), 4.23 (2H, s), 6.8-6.9 (3H, m), 6.92 (1H, d, J = 2.0 Hz), 7.0-7.05 (2H, m), 7.31 (1H, d, J = 8.2 Hz) |
| 52 | 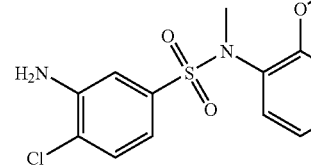 | (CDCl3) 3.75 (3H, s), 4.27 (2H, s), 6.55-6.7 (3H, m), 6.74 (1H, s), 7.0-7.1 (1H, m), 7.1-7.2 (2H, m), 7.28 (1H, d, J = 7.9 Hz) |
| 53 | 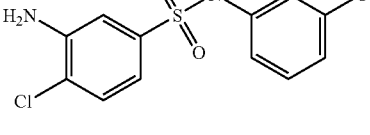 | (CDCl3) 3.67 (3H, s), 4.22 (2H, s), 6.75-6.8 (1H, m), 6.85-6.95 (1H, m), 6.98 (1H, s), 7.0-7.1 (2H, m), 7.14 (1H, d, J = 2.4 Hz), 7.24 (1H, d, J = 8.6 Hz), 7.5 (1H, dd, J = 7.7 Hz, 1.6 Hz) |

TABLE 7-continued

| Ref No. | Strc | (Solv) ¹H-NMR δ ppm: |
|---|---|---|
| 54 | 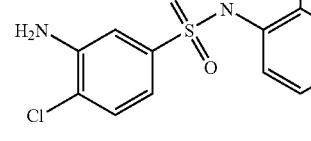 | (CDCl3) 3.77 (3H, s), 4.23 (2H, s), 6.31 (1H, s), 6.75-6.85 (2H, m), 6.9-7.0 (3H, m), 7.07 (1H, d, J = 2.4 Hz), 7.27 (1H, d, J = 8.0 Hz) |
| 55 | 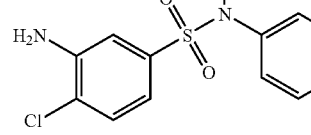 | (CDCl3) 3.2 (3H, s), 3.48 (3H, s), 4.21 (2H, brs), 6.75-6.85 (1H, m), 6.9-6.95 (1H, m), 6.99 (1H, dd, J = 8.3 Hz, 2.0 Hz), 7.04 (1H, d, J = 2.0 Hz), 7.25-7.35 (3H, m) |
| 56 | | (CDCl3) 3.16 (3H, s), 3.77 (3H, s), 4.24 (2H, s), 6.6-6.7 (1H, m), 6.7-6.8 (1H, m), 6.8-6.9 (2H, m), 6.94 (1H, d, J = 2.4 Hz), 7.15-7.25 (1H, m), 7.3 (1H, d, J = 8.1 Hz) |
| 57 | | (CDCl3) 3.2-3.25 (3H, m), 4.26 (2H, brs), 6.9-7.0 (1H, m), 7.0-7.1 (2H, m), 7.1-7.15 (1H, m), 7.25-7.35 (3H, m) |
| 58 | | (CDCl3) 3.17 (3H, s), 4.25 (2H, brs), 6.83 (1H, dd, J = 8.3 Hz, 2.1 Hz), 6.85-7.05 (4H, m), 7.2-7.35 (2H, m) |

TABLE 8

| Ref No. | Strc | (Solv) ¹H-NMR δ ppm: |
|---|---|---|
| 59 | | (CDCl3) 3.15 (3H, s), 4.27 (2H, brs), 6.82 (1H, dd, J = 8.2 Hz, 2.2 Hz), 6.91 (1H, d, J = 2.2 Hz), 6.95-7.05 (2H, m), 7.05-7.15 (2H, m), 7.31 (1H, d, J = 8.2 Hz) |
| 60 | | (CDCl3) 3.15 (3H, s), 4.25 (2H, s), 6.82 (1H, dd, J = 8.5 Hz, 2.1 Hz), 6.9 (1H, d, J = 2.1 Hz), 7.05-7.1 (2H, m), 7.25-7.35 (3H, m) |
| 61 | | (CDCl3) 3.18 (3H, s), 4.25 (2H, s), 7.03 (1H, dd, J = 8.5 Hz, 2.0 Hz), 7.1 (1H, d, J = 2.0 Hz), 7.2-7.4 (5H, m) |
| 62 | | (CDCl3) 3.17 (3H, s), 4.24 (2H, s), 6.82 (1H, dd, J = 8.4 Hz, 1.9 Hz), 6.89 (1H, d, J = 1.9 Hz), 7.1-7.2 (4H, m), 7.3-7.35 (1H, m) |
| 63 | | (CDCl3) 3.19 (3H, s), 4.29 (2H, s), 7.0-7.1 (1H, m), 7.1-7.2 (2H, m), 7.2-7.25 (1H, m), 7.36 (1H, d, J = 8.0 Hz), 7.43 (1H, d, J = 2.2 Hz) |
| 64 | | (DMSO-d6) 3.12 (3H, s), 5.59 (2H, s), 6.5-6.6 (1H, m), 6.7-6.8 (2H, m), 7.05-7.2 (3H, m), 7.2-7.4 (3H, m) |
| 65 | | (CDCl3) 3.2-3.25 (3H, m), 3.91 (2H, brs), 6.95-7.15 (5H, m), 7.2-7.35 (2H, m) |
| 66 | | (CDCl3) 3.2 (3H, s), 3.5 (3H, s), 3.86 (2H, s), 6.8-6.85 (1H, m), 6.9-6.95 (1H, m), 7.0-7.1 (3H, m), 7.25-7.35 (2H, m) |

TABLE 9

| Ref No. | Strc | (Solv) ¹H-NMR δ ppm: |
|---|---|---|
| 67 | (structure) | (CDCl3) 3.33 (3H, s), 3.46 (2H, brs), 3.58 (3H, s), 3.81 (3H, s), 6.73 (1H, d, J = 12.6 Hz), 6.8-6.95 (2H, m), 7.15-7.3 (3H, m) |
| 68 | (structure) | (CDCl3) 3.35 (3H, s), 3.51 (2H, brs), 3.7 (3H, s), 6.67 (1H, d, J = 12.2 Hz), 7.15-7.3 (6H, m) |
| 69 | (structure) | (CDCl3) 3.18 (3H, s), 3.88 (2H, s), 6.85-6.95 (2H, m), 7.0-7.05 (1H, m), 7.1-7.15 (2H, m), 7.2-7.35 (3H, m) |
| 70 | (structure) | (DMSO-d6) 2.27 (3H, s), 3.75 (3H, s), 3.8 (3H, s) |
| 71 | (structure) | (CDCl3) 1.21 (3H, t, J = 7.1 Hz), 3.01 (2H, q, J = 7.1 Hz), 7.0-7.1 (1H, m), 7.42 (1H, d, J = 8.6 Hz), 7.55-7.6 (1H, m), 8.75-8.85 (1H, m) |
| 72 | (structure) | (CDCl3) 1.21 (6H, d, J = 6.8 Hz), 3.5-3.6 (1H, m), 7.05 (1H, brs), 7.43 (1H, d, J = 8.5 Hz), 7.55-7.6 (1H, m), 8.78 (1H, brs) |
| 73 | (structure) | (CDCl3) 4.17 (2H, brs), 4.22 (2H, s), 7.2-7.35 (7H, m), 7.35-7.4 (1H, m) |

TABLE 10

| Ref No. | Strc | (Solv) ¹H-NMR δ ppm: |
|---|---|---|
| 74 | (structure) | (CDCl3) 1.5 (6H, d, J = 7.1 Hz), 4.0-4.2 (3H, m), 7.15-7.4 (8H, m) |
| 75 | (structure) | (CDCl3) 1.57 (6H, s), 3.98 (2H, brs), 6.65 (1H, dd, J = 8.4 Hz, 2.1 Hz), 6.99 (1H, d, J = 2.1 Hz), 7.03 (1H, d, J = 8.4 Hz), 7.2-7.4 (5H, m) |
| 76 | (structure) | (CDCl3) 1.58 (6H, s), 3.42 (3H, s), 3.94 (2H, brs), 6.65-6.75 (1H, m), 6.8 (1H, dd, J = 8.6 Hz, 2.0 Hz), 6.98 (1H, d, J = 8.6 Hz), 7.0-7.1 (1H, m), 7.15 (1H, d, J = 2.0 Hz), 7.2-7.3 (1H, m), 7.4-7.5 (1H, m) |
| 77 | (structure) | (CDCl3) 1.63 (6H, s), 4.0 (2H, brs), 6.76 (1H, dd, J = 8.5 Hz, 1.9 Hz), 6.85-6.95 (1H, m), 7.01 (1H, d, J = 8.5 Hz), 7.15-7.3 (3H, m), 7.45-7.55 (1H, m) |
| 78 | (structure) | (CDCl3) 1.53 (9H, s), 6.7 (1H, brs), 6.93 (1H, dd, J = 11.0 Hz, 8.5 Hz), 7.05-7.1 (1H, m), 8.33 (1H, brs) |
| 79 | (structure) | (CDCl3) 1.51 (6H, s), 3.5-3.9 (5H, m), 6.35-6.45 (1H, m), 6.6-6.75 (2H, m), 6.75-6.9 (2H, m), 6.9-7.0 (1H, m), 7.2-7.3 (1H, m) |
| 80 | (structure) | (CDCl3) 1.54 (6H, s), 3.72 (2H, brs), 6.6-6.75 (2H, m), 6.9-7.0 (1H, m), 7.2-7.3 (2H, m), 7.35-7.45 (1H, m), 7.5-7.55 (2H, m) |
| 81 | (structure) | (CDCl3) 1.57 (6H, s), 3.61 (3H, s), 6.55-6.65 (2H, m), 6.65-6.75 (1H, m), 6.8-6.9 (2H, m), 7.15-7.25 (1H, m) |

TABLE 11

| Ref No. | Strc | (Solv) ¹H-NMR δ ppm: |
|---|---|---|
| 82 | 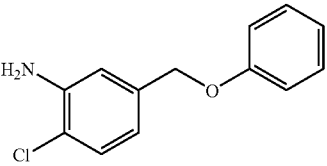 [SMILES: Nc1cc(COc2ccccc2)ccc1Cl] | (CDCl3) 4.07 (2H, s), 4.96 (2H, s), 6.74 (1H, dd, J = 8.0 Hz, 1.9 Hz), 6.85 (1H, d, J = 1.9 Hz), 6.9-7.0 (3H, m), 7.2-7.35 (3H, m) |
| 83 | 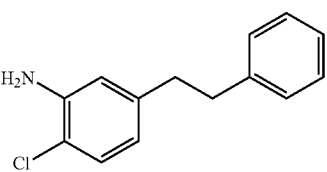 | (CDCl3) 2.75-2.9 (4H, m), 3.95 (2H, brs), 6.5-6.6 (2H, m), 7.1-7.35 (6H, m) |
| 84 | 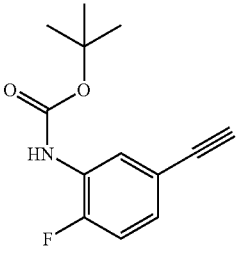 [SMILES: C#Cc1ccc(F)c(NC(=O)OC(C)(C)C)c1] | (CDCl3) 1.53 (9H, s), 2.99 (1H, s), 6.68 (1H, brs), 6.95-7.05 (1H, m) 705-7.15 (1H, m), 8.25-8.35 (1H, m) |
| 85 | 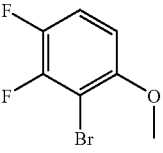 | (CDCl3) 3.88 (3H, s), 6.55-6.65 (1H, m), 7.05-7.15 (1H, m) |
| 86 | 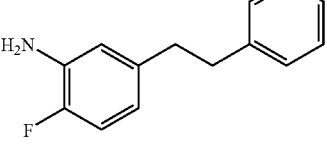 | (CDCl3) 2.75-2.9 (4H, m), 3.64 (2H, brs), 6.45-6.55 (1H, m), 6.55-6.65 (1H, m), 6.8-6.9 (1H, m), 7.1-7.3 (5H, m) |
| 87 | 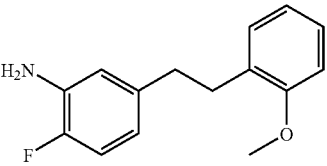 | (CDCl3) 2.7-2.8 (2H, m), 2.8-2.9 (2H, m), 3.63 (2H, brs), 3.83 (3H, s), 6.45-6.55 (1H, m), 6.6-6.65 (1H, m), 6.8-6.9 (3H, m), 7.05-7.1 (1H, m), 7.15-7.25 (1H, m) |
| 88 | 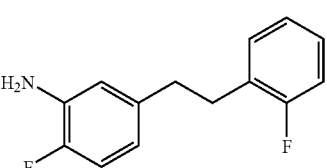 | (CDCl3) 2.75-2.85 (2H, m), 2.85-2.95 (2H, m), 3.64 (2H, brs), 6.45-6.55 (1H, m), 6.55-6.65 (1H, m), 6.8-6.9 (1H, m), 6.95-7.25 (4H, m) |

TABLE 11-continued

| Ref No. | Strc | (Solv) ¹H-NMR δ ppm: |
|---|---|---|
| 89 | 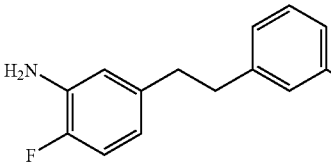 | (CDCl3) 2.7-2.9 (4H, m), 3.65 (2H, brs), 3.79 (3H, s), 6.45-6.55 (1H, m), 6.55-6.65 (1H, m), 6.65-6.8 (3H, m), 6.8-6.95 (1H, m), 7.15-7.25 (1H, m) |

TABLE 12

| Ref No. | Strc | (Solv) ¹H-NMR δ ppm: |
|---|---|---|
| 90 | 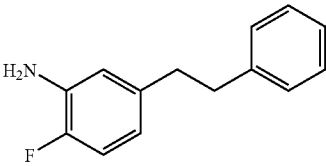 [SMILES: Nc1cc(CCc2ccccc2)ccc1F] | (CDCl3) 2.7-2.85 (4H, m), 3.55-3.75 (2H, br), 3.79 (3H, s), 6.45-6.55 (1H, m), 6.55-6.65 (1H, m), 6.75-6.95 (3H, m), 7.0-7.15 (2H, m) |
| 91 | 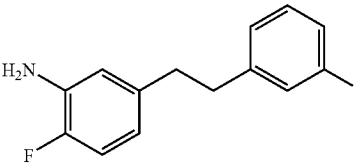 | (CDCl3) 2.75-2.9 (4H, m), 3.65 (2H, brs), 6.4-6.5 (1H, m), 6.55-6.65 (1H, m), 6.8-6.95 (4H, m), 7.15-7.3 (1H, m) |
| 92 | 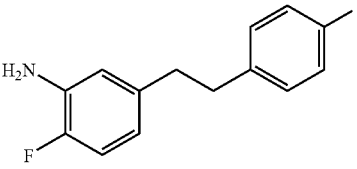 | (CDCl3) 2.7-2.9 (4H, m), 3.65 (2H, brs), 6.4-6.5 (1H, m), 6.5-6.6 (1H, m), 6.8-7.0 (3H, m), 7.05-7.15 (2H, m) |
| 93 | 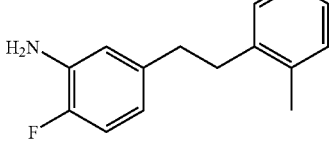 | (CDCl3) 2.3 (3H, s), 2.7-2.8 (2H, m), 2.8-2.9 (2H, m), 6.45-6.55 (1H, m), 6.55-6.65 (1H, m), 6.85-6.95 (1H, m), 7.05-7.2 (4H, m) |

TABLE 12-continued
| Ref No. | Strc | (Solv) ¹H-NMR δ ppm: |
|---|---|---|
| 94 | 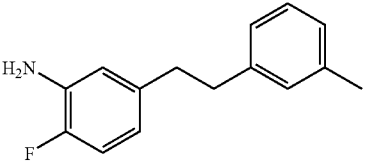 [SMILES: Cc1cccc(CCc2ccc(F)c(N)c2)c1] | (CDCl3) 2.33 (3H, s), 2.7-2.9 (4H, m), 6.45-6.55 (1H, m), 6.55-6.65 (1H, m), 6.85-6.95 (1H, m), 6.95-7.05 (3H, m), 7.1-7.25 (1H, m) |
| 95 | 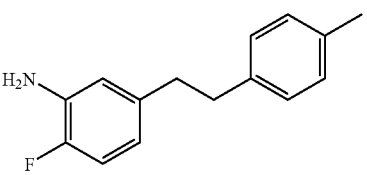 [SMILES: Cc1ccc(CCc2ccc(F)c(N)c2)cc1] | (CDCl3) 2.32 (3H, s), 2.7-2.9 (4H, m), 6.45-6.55 (1H, m), 6.55-6.65 (1H, m), 6.8-6.95 (1H, m), 7.0-7.15 (4H, m) |
| 96 | 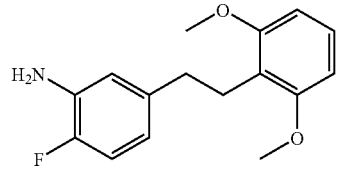 [SMILES: COc1cccc(OC)c1CCc1ccc(F)c(N)c1] | (CDCl3) 2.6-2.7 (2H, m), 2.85-2.95 (2H, m), 3.5-3.75 (2H, br), 3.79 (3H, s), 6.5-6.6 (3H, m), 6.6-6.7 (1H, m), 6.8-6.9 (1H, m), 7.13 (1H, t, J = 8.5 Hz) |
| 97 | 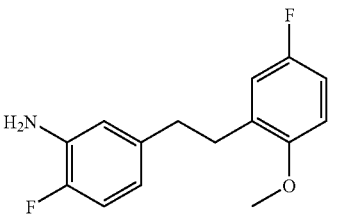 | (CDCl3) 2.7-2.8 (2H, m), 2.8-2.9 (2H, m), 3.5-3.75 (2H, br), 3.79 (3H, s), 6.45-6.55 (1H, m), 6.55-6.65 (1H, m), 6.7-6.9 (4H, m) |
TABLE 13
| Ref No. | Strc | (Solv) ¹H-NMR δ ppm: |
|---|---|---|
| 98 | 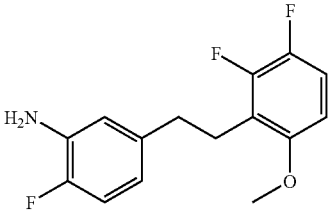 | (CDCl3) 2.7-2.8 (2H, m), 2.8-2.9 (2H, m), 3.5-3.9 (5H, m), 6.45-6.55 (1H, m), 6.55-6.65 (2H, m), 6.65-6.75 (1H, m), 6.85-6.95 (1H, m) |
| 99 | 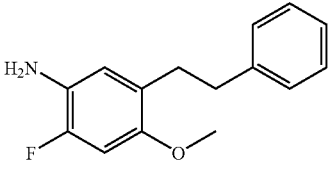 [SMILES: COc1cc(F)c(N)cc1CCc1ccccc1] | (CDCl3) 2.65-2.75 (2H, m), 2.85-2.95 (2H, m), 3.35-3.9 (5H, m), 6.45-6.55 (2H, m), 6.6-6.65 (1H, m), 6.8-6.9 (1H, m), 6.9-7.0 (1H, m) |
| 100 | 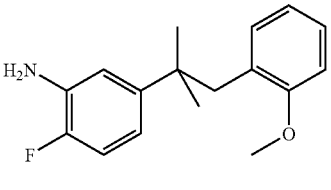 [SMILES: COc1ccccc1CC(C)(C)c1ccc(F)c(N)c1] | (CDCl3) 2.75-2.9 (4H, m), 3.05-3.65 (2H, br), 3.72 (3H, s), 6.5-6.65 (2H, m), 7.15-7.3 (5H, m) |
| 101 | 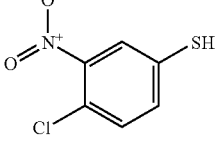 | (CDCl3) 1.25 (6H, s), 2.86 (2H, s), 3.45-3.85 (5H, m), 6.6-6.7 (1H, m), 6.7-6.9 (5H, m), 7.1-7.2 (1H, m) |
| 102 | 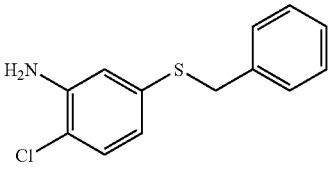 [SMILES: Nc1cc(SCc2ccccc2)ccc1Cl] | (DMSO-d6) 5.8-6.8 (1H, br), 7.64 (2H, brs), 8.06 (1H, brs) |
| 103 | 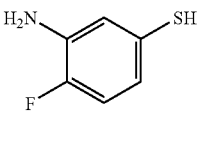 | (DMSO-d6) 4.15 (2H, s), 5.37 (2H, s), 6.5 (1H, dd, J = 8.2 Hz, 2.2 Hz), 6.77 (1H, d, J = 2.2 Hz), 7.08 (1H, d, J = 8.2 Hz), 7.2-7.4 (5H, m) |
| 104 | 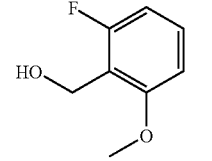 | (CDCl3) 3.34 (1H, s), 3.71 (2H, brs), 6.55-6.65 (1H, m), 6.7-6.75 (1H, m), 6.84 (1H, dd, J = 10.8 Hz, 8.3 Hz) |
| 105 | 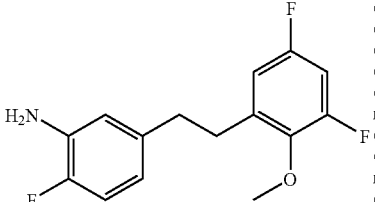 | (CDCl3) 2.3 (1H, t, J = 6.8 Hz), 3.89 (3H, s), 4.7-4.8 (2H, m), 6.65-6.75 (2H, m), 7.15-7.3 (1H, m) |

TABLE 14

| Ref No. | Strc | (Solv) ¹H-NMR δ ppm: |
|---|---|---|
| 106 | | (CDCl3) 2.23 (1H, t, J = 6.4 Hz), 3.84 (3H, s), 4.66 (2H, d, J = 6.4 Hz), 6.75-6.85 (1H, m), 6.9-7.0 (1H, m), 7.0-7.1 (1H, m) |
| 107 | | (CDCl3) 2.35 (1H, t, J = 7.0 Hz), 3.87 (3H, s), 4.75-4.8 (2H, m), 6.55-6.65 (1H, m), 7.0-7.1 (1H, m) |
| 108 | | (CDCl3) 3.91 (3H, s), 4.55-4.65 (2H, m), 6.65-6.75 (2H, m), 7.2-7.3 (1H, m) |
| 109 | | (CDCl3) 3.87 (3H, s), 4.5 (2H, s), 6.75-6.85 (1H, m), 6.95-7.0 (1H, m), 7.0-7.1 (1H, m) |
| 110 | | (CDCl3) 3.89 (3H, s), 4.55-4.6 (2H, m), 6.55-6.6 (1H, m), 7.0-7.15 (1H, m) |
| 111 | | (CDCl3) 1.59 (6H, s), 3.89 (3H, s), 4.05 (1H, s), 6.8-6.95 (2H, m), 7.0-7.1 (1H, m) |
| 112 | | (CDCl3) 1.66 (3H, s), 1.67 (3H, s), 3.93 (3H, s), 5.08 (1H, s), 6.65-6.75 (2H, m), 7.1-7.2 (1H, m) |

TABLE 14-continued

| Ref No. | Strc | (Solv) ¹H-NMR δ ppm: |
|---|---|---|
| 113 | | (CDCl3) 1.67 (3H, s), 1.68 (3H, s), 3.91 (3H, s), 5.04 (1H, s), 6.6-6.7 (1H, m), 6.95-7.05 (1H, m) |

TABLE 15

| Ref No. | Strc | (Solv) ¹H-NMR δ ppm: |
|---|---|---|
| 114 | | (CDCl3) 4.0 (2H, s), 4.33 (2H, s), 6.55-6.7 (2H, m), 6.8-6.9 (1H, m), 6.95-7.35 (4H, m) |
| 115 | | (DMSO-d6) 4.1 (2H, s), 5.2 (2H, s), 6.4-6.5 (1H, m), 6.7-6.8 (1H, m), 6.9 (1H, dd, J = 11.3 Hz, 8.6 Hz), 7.2-7.35 (5H, m) |
| 116 | | (CDCl3) 3.68 (2H, brs), 4.05 (2H, s), 6.65-6.75 (1H, m), 6.75-6.9 (4H, m), 7.1-7.25 (1H, m) |
| 117 | | (DMSO-d6) 2.75-2.85 (2H, m), 3.05-3.15 (2H, m), 5.21 (2H, s), 6.45-6.55 (1H, m), 6.75-6.85 (1H, m), 6.9-7.0 (1H, m), 7.15-7.35 (5H, m) |
| 118 | | (CDCl3) 3.66 (2H, brs), 3.77 (3H, s), 4.05-4.1 (2H, m), 6.6-6.7 (2H, m), 6.7-6.75 (1H, m), 6.75-6.9 (2H, m), 7.1-7.2 (1H, m) |
| 119 | | (CDCl3) 3.5-3.8 (5H, m), 4.05-4.1 (2H, m), 6.45-6.55 (1H, m), 6.65-6.75 (1H, m), 6.8-6.9 (2H, m), 6.95-7.05 (1H, m) |

TABLE 15-continued

| Ref No. | Strc | (Solv) ¹H-NMR δ ppm: |
|---|---|---|
| 120 | H₂N–C₆H₄–S–CH₂–C₆H₅ (3-aminophenyl benzyl sulfide) | (CDCl3) 3.62 (2H, brs), 4.1 (2H, s), 6.45-6.55 (1H, m), 6.6-6.65 (1H, m), 6.7-6.75 (1H, m), 7.0-7.1 (1H, m), 7.2-7.35 (5H, m) |
| 121 | H₂N–(2-F,5-)C₆H₃–S–CH₂–(2-OMe)C₆H₄ | (CDCl3) 3.66 (2H, brs), 3.82 (3H, s), 4.06 (2H, s), 6.65-6.7 (1H, m), 6.75 (1H, dd, J = 8.5 Hz, 2.2 Hz), 6.8-6.9 (3H, m), 7.1-7.15 (1H, m), 7.15-7.25 (1H, m) |

TABLE 16

| Ref No. | Strc | (Solv) ¹H-NMR δ ppm: |
|---|---|---|
| 122 | H₂N–(2-F)C₆H₃–S–CH₂–(2,6-Cl₂)C₆H₃ | (CDCl3) 3.69 (2H, s), 4.32 (2H, s), 6.7-6.8 (1H, m), 6.8-6.9 (2H, m), 7.05-7.15 (1H, m), 7.25-7.3 (2H, m) |
| 123 | H₂N–(2-F)C₆H₃–S–CH₂–(2-Cl)C₆H₄ | (CDCl3) 3.68 (2H, s), 4.12 (2H, s), 6.6-6.7 (1H, m), 6.7-6.8 (1H, m), 6.8-6.9 (1H, m), 7.1-7.2 (3H, m), 7.3-7.4 (1H, m) |
| 124 | H₂N–(2-F)C₆H₃–S–CH₂–(3-Cl)C₆H₄ | (CDCl3) 3.69 (2H, s), 3.96 (2H, s), 6.6-6.65 (1H, m), 6.7-6.75 (1H, m), 6.8-6.9 (1H, m), 7.05-7.1 (1H, m), 7.15-7.25 (3H, m) |

TABLE 16-continued

| Ref No. | Strc | (Solv) ¹H-NMR δ ppm: |
|---|---|---|
| 125 | H₂N–(2-F)C₆H₃–S–CH₂–(3-F)C₆H₄ | (CDCl3) 3.68 (2H, brs), 3.99 (2H, s), 6.6-6.65 (1H, m), 6.7-6.75 (1H, m), 6.8-7.0 (4H, m), 7.15-7.25 (1H, m) |
| 126 | H₂N–(2-F)C₆H₃–S–CH₂–(2-OMe,5-F)C₆H₃ | (CDCl3) 3.68 (2H, brs), 3.79 (3H, s), 4.01 (2H, s), 6.6-6.7 (1H, m), 6.7-6.8 (2H, m), 6.8-6.95 (3H, m) |
| 127 | H₂N–(2-F)C₆H₃–S–C(CH₃)₂–C₆H₅ | (CDCl3) 1.67 (6H, s), 3.55 (2H, brs), 6.45-6.55 (2H, m), 6.75-6.85 (1H, m), 7.15-7.25 (1H, m), 7.25-7.35 (2H, m), 7.35-7.45 (2H, m) |
| 128 | H₂N–C₆H₄–S–C(CH₃)₂–(2-F)C₆H₄ | (DMSO-d6) 1.66 (6H, s), 5.07 (2H, s), 6.1-6.2 (1H, m), 6.4-6.55 (2H, m), 6.75-6.9 (1H, m), 6.95-7.35 (4H, m) |
| 129 | H₂N–C₆H₄–S–C(CH₃)₂–(3-F)C₆H₄ | (DMSO-d6) 1.61 (6H, s), 5.09 (2H, s), 6.2-6.3 (1H, m), 6.45-6.55 (2H, m), 6.85-6.9 (1H, m), 7.0-7.1 (1H, m), 7.15-7.4 (3H, m) |

TABLE 17

| Ref No. | Strc | (Solv) ¹H-NMR δ ppm: |
|---|---|---|
| 130 | | (CDCl3) 1.82 (3H, s), 1.83 (3H, s), 3.55 (2H, brs), 3.81 (3H, s), 6.45-6.65 (3H, m), 6.65-6.8 (2H, m), 7.1-7.2 (1H, m) |
| 131 | | (CDCl3) 1.68 (6H, s), 3.57 (2H, brs), 3.9 (3H, s), 6.4-6.55 (2H, m), 6.7-6.8 (2H, m), 6.8-6.95 (2H, m) |
| 132 | | (CDCl3) 1.8-1.85 (6H, m), 3.58 (2H, brs), 6.45-6.6 (2H, m), 6.75-6.85 (3H, m), 7.1-7.2 (1H, m) |
| 133 | | (CDCl3) 1.82 (3H, s), 1.83 (3H, s), 3.59 (2H, brs), 3.79 (3H, s), 6.4-6.5 (1H, m), 6.55-6.65 (2H, m), 6.75-6.85 (1H, m), 6.95-7.05 (1H, m) |
| 134 | | (CDCl3) 1.71 (6H, s), 3.54 (2H, brs), 3.92 (3H, s), 6.4-6.5 (2H, m), 6.7-6.85 (2H, m), 6.95 (1H, d, J = 8.1 Hz), 7.0-7.05 (1H, m), 7.2-7.3 (1H, m) |
| 135 | | (CDCl3) 1.72 (6H, s), 3.55 (2H, brs), 6.45-6.5 (2H, m), 6.7-6.8 (1H, m), 6.95-7.0 (1H, m), 7.0-7.1 (2H, m), 7.15-7.25 (1H, m) |
| 136 | | (CDCl3) 1.8 (6H, s), 3.52 (2H, s), 6.4-6.5 (2H, m), 6.7-6.8 (1H, m), 7.05-7.2 (3H, m), 7.4-7.45 (1H, m) |
| 137 | | (CDCl3) 1.65 (6H, s), 3.6 (2H, s), 6.45-6.55 (2H, m), 6.75-6.85 (1H, m), 7.15-7.3 (3H, m), 7.35-7.4 (1H, m) |

TABLE 18

| Ref No. | Strc | (Solv) $^1$H-NMR δ ppm: |
|---|---|---|
| 138 | | (CDCl3) 1.65 (6H, s), 3.58 (2H, brs), 6.45-6.55 (2H, m), 6.79 (1H, dd, J = 11.0 Hz, 8.2 Hz), 6.85-6.95 (1H, m), 7.05-7.2 (2H, m), 7.2-7.3 (1H, m) |
| 139 | | (CDCl3) 1.67 (6H, s), 3.58 (2H, brs), 3.9 (3H, s), 6.4-6.55 (2H, m), 6.75-6.85 (1H, m), 6.87 (1H, d, J = 8.5 Hz), 6.99 (1H, d, J = 2.6 Hz), 7.2 (1H, dd, J = 8.5 Hz, 2.6 Hz) |
| 140 | | (CDCl3) 1.8-1.95 (1H, m), 2.3-2.5 (3H, m), 2.55-2.65 (2H, m), 3.56 (2H, s), 6.35-6.5 (2H, m), 3.56 (2H, s), 6.95-7.0 (2H, m), 7.1-7.2 (1H, m), 7.2-7.3 (2H, m) |
| 141 | | (CDCl3) 2.1-2.3 (4H, m), 3.51 (2H, brs), 3.65-3.75 (2H, m), 4.0-4.1 (2H, m), 6.2-6.25 (1H, m), 6.3-6.35 (1H, m), 6.7-6.8 (1H, m), 7.15-7.35 (5H, m) |
| 142 | | (CDCl3) 4.0 (3H, s), 5.55 (1H, s), 6.74 (1H, d, J = 11.7 Hz), 7.67 (1H, d, J = 7.3 Hz) |
| 143 | | (CDCl3) 2.32 (3H, s), 5.26 (1H, s), 7.06 (1H, d, J = 11.0 Hz), 7.48 (1H, d, J = 6.1 Hz) |
| 144 | | (CDCl3) 1.26 (3H, t, J = 7.5 Hz), 2.7 (2H, q, J = 7.5 Hz), 5.99 (1H, s), 7.06 (1H, d, J = 11.3 Hz), 7.48 (1H, d, J = 5.8 Hz) |
| 145 | | (CDCl3) 5.35 (1H, d, J = 3.7 Hz), 7.05-7.15 (1H, m), 7.79 (1H, dd, J = 8.8 Hz, 7.1 Hz) |

TABLE 19

| Ref No. | Strc | (Solv) $^1$H-NMR δ ppm: |
|---|---|---|
| 146 | (2-chloro-4-fluoro-5-nitrophenol) | (CDCl3) 5.7 (1H, s), 7.35 (1H, d, J = 9.7 Hz), 7.75 (1H, d, J = 6.7 Hz) |
| 147 | (2-bromo-4-fluoro-5-nitrophenol) | (CDCl3) 5.73 (1H, s), 7.49 (1H, d, J = 9.7 Hz), 7.72 (1H, d, J = 6.7 Hz) |
| 148 | (2-ethoxy-4-fluoro-5-nitrophenol) | (CDCl3) 1.53 (3H, t, J = 7.0 Hz), 4.21 (2H, q, J = 7.0 Hz), 5.58 (1H, s), 6.71 (1H, d, J = 11.9 Hz), 7.66 (1H, d, J = 7.1 Hz) |
| 149 | (1-(2,3-difluoro-6-methoxyphenyl)ethanol) | (CDCl3) 1.57 (3H, d, J = 6.9 Hz), 3.31 (1H, d, J = 11.2 Hz), 5.15-5.3 (1H, m), 6.55-6.65 (1H, m), 6.95-7.05 (1H, m) |
| 150 | (TBS-protected glycol ether benzyl alcohol) | (CDCl3) 0.1 (6H, s), 0.91 (9H, s), 3.95-4.0 (2H, m), 4.05-4.15 (2H, m), 4.68 (2H, s), 6.85-7.0 (2H, m), 7.2-7.3 (2H, m) |
| 151 | (TBS-protected glycol ether 1-phenylethanol) | (CDCl3) 0.1 (6H, s), 0.91 (9H, s), 1.54 (3H, d, J = 6.4 Hz), 3.14 (1H, d, J = 6.4 Hz), 3.95-4.0 (2H, m), 4.05-4.15 (2H, m), 5.0-5.1 (1H, m), 6.85-7.0 (2H, m), 7.2-7.25 (1H, m), 7.25-7.35 (1H, m) |

TABLE 19-continued

| Ref No. | Strc | (Solv) ¹H-NMR δ ppm: |
|---------|------|----------------------|
| 152 | | (DMSO-d6) 0.08 (6H, s), 0.9 (9H, s), 4.52 (2H, d, J = 5.4 Hz), 4.74 (2H, s), 5.06 (1H, t, J = 5.4 Hz), 7.2-7.3 (2H, m), 7.35-7.45 (2H, m) |

TABLE 20

| Ref No. | Strc | (Solv) ¹H-NMR δ ppm: |
|---------|------|----------------------|
| 153 | | (DMSO-d6) 0.12 (3H, s), 0.14 (3H, s), 0.95 (9H, s), 1.34 (3H, d, J = 6.6 Hz), 4.8 (2H, s), 4.9-5.1 (2H, m), 7.2-7.4 (3H, m), 7.45-7.55 (1H, m) |
| 154 | | (DMSO-d6) 0.08 (6H, s), 0.9 (9H, s), 4.48 (2H, d, J = 5.7 Hz), 4.7 (2H, s), 5.16 (1H, t, J = 5.7 Hz), 7.1-7.35 (4H, m) |
| 155 | | (CDCl3) 3.35-3.5 (4H, m), 3.7-3.75 (2H, m), 4.15-4.2 (2H, m), 4.7-4.8 (2H, m), 6.55-6.65 (1H, m), 6.95-7.1 (1H, m) |
| 156 | | (CDCl3) 1.23 (3H, t, J = 6.9 Hz), 3.58 (2H, q, J = 6.9 Hz), 3.7-3.8 (2H, m), 4.15-4.25 (2H, m), 4.75 (2H, s), 6.55-6.65 (1H, m), 6.95-7.1 (1H, m) |

TABLE 20-continued

| Ref No. | Strc | (Solv) ¹H-NMR δ ppm: |
|---|---|---|
| 157 | | (CDCl3) 2.0-2.15 (2H, m), 3.28 (1H, t, J = 7.1 Hz), 3.35 (3H, s), 3.59 (2H, t, J = 5.6 Hz), 4.11 (2H, t, J = 5.8 Hz), 4.7-4.8 (2H, m), 6.5-6.6 (1H, m), 6.95-7.1 (1H, m) |
| 158 | | (CDCl3) 0.1 (6H, s), 0.91 (9H, s), 3.19 (1H, t, J = 6.9 Hz), 3.9-4.0 (2H, m), 4.05-4.15 (2H, m), 4.7-4.8 (2H, m), 6.55-6.65 (1H, m), 6.95-7.1 (1H, m) |
| 159 | | (CDCl3) 0.05 (6H, s), 0.89 (9H, s), 1.95-2.05 (2H, m), 2.52 (1H, t, J = 7.0 Hz), 3.81 (2H, t, J = 5.8 Hz), 4.12 (2H, t, J = 6.0 Hz), 4.7-4.8 (2H, m), 6.55-6.65 (1H, m), 7.0-7.1 (1H, m) |

TABLE 21

| Ref No. | Strc | (Solv) ¹H-NMR δ ppm: |
|---|---|---|
| 160 | | (CDCl3) 1.8-1.95 (1H, m), 2.25-2.5 (3H, m), 2.65-2.75 (3H, m), 3.82 (3H, s), 6.5-6.6 (1H, m), 6.95-7.05 (1H, m) |
| 161 | | (CDCl3) 1.68 (6H, s), 3.84 (2H, s), 5.98 (1H, dd, J = 8.8 Hz, 2.4 Hz), 6.11 (1H, d, J = 2.4 Hz), 6.92 (1H, d, J = 8.8 Hz), 7.25-7.3 (1H, m), 7.3-7.4 (2H, m), 7.4-7.5 (2H, m) |
| 162 | | (CDCl3) 1.7-1.75 (6H, m), 3.89 (2H, s), 6.1 (1H, dd, J = 8.7 Hz, 2.6 Hz), 6.23 (1H, d, J = 2.6 Hz), 6.95-7.15 (3H, m), 7.2-7.3 (1H, m), 7.45-7.5 (1H, m) |

TABLE 21-continued

| Ref No. | Strc | (Solv) ¹H-NMR δ ppm: |
|---|---|---|
| 163 | | (DMSO-d6) 0.78 (3H, t, J = 7.3 Hz), 1.59 (3H, s), 1.8-2.0 (2H, m), 5.16 (2H, s), 5.76 (1H, dd, J = 8.5 Hz, 2.9 Hz), 6.21 (1H, d, J = 2.9 Hz), 6.86 (1H, d, J = 8.5 Hz), 7.2-7.3 (1H, m), 7.3-7.4 (4H, m) |
| 164 | | (DMSO-d6) 1.76 (6H, s), 5.16 (2H, s), 5.7-5.8 (1H, m), 6.15-6.25 (1H, m), 6.8-6.9 (1H, m), 7.25-7.45 (3H, m), 7.5-7.6 (1H, m) |
| 165 | | (CDCl3) 1.8-2.1 (2H, m), 2.5-2.7 (4H, m), 3.56 (2H, brs), 5.8-5.9 (1H, m), 6.05-6.1 (1H, m), 6.65-6.7 (1H, m), 7.2-7.3 (1H, m), 7.3-7.4 (2H, m), 7.4-7.5 (2H, m) |
| 166 | | (CDCl3) 1.85-1.95 (1H, m), 2.35-2.5 (1H, m), 2.6-2.85 (4H, m), 3.36 (2H, brs), 3.71 (3H, s), 6.05-6.15 (1H, m), 6.5-6.55 (1H, m), 6.65-6.75 (1H, m), 7.0-7.1 (1H, m) |

TABLE 22

| Ref No. | Strc | (Solv) ¹H-NMR δ ppm: |
|---|---|---|
| 167 | | (CDCl3) 1.7-1.85 (1H, m), 1.9-2.2 (3H, m), 2.7-2.95 (2H, m), 4.0 (2H, brs), 5.2-5.3 (1H, m), 6.35-6.45 (2H, m), 7.1-7.4 (5H, m) |
| 168 | | (CDCl3) 4.01 (2H, brs), 5.07 (2H, s), 6.3-6.45 (2H, m), 7.0-7.5 (5H, m) |
| 169 | | (CDCl3) 4.04 (2H, brs), 5.0 (2H, s), 6.32 (1H, dd, J = 8.7 Hz, 2.8 Hz), 6.38 (1H, d, J = 2.8 Hz), 6.95-7.05 (1H, m), 7.1-7.2 (3H, m), 7.3-7.4 (1H, m) |

TABLE 22-continued

| Ref No. | Strc | (Solv) $^1$H-NMR δ ppm: |
|---|---|---|
| 170 | | (CDCl3) 4.03 (2H, brs), 4.95 (2H, s), 6.32 (1H, dd, J = 8.4 Hz, 2.7 Hz), 6.38 (1H, d, J = 2.7 Hz), 7.0-7.1 (2H, m), 7.12 (1H, d, J = 9.0 Hz), 7.35-7.4 (2H, m) |
| 171 | | (CDCl3) 4.04 (2H, brs), 4.98 (2H, s), 6.31 (1H, dd, J = 8.8 Hz, 2.9 Hz), 6.38 (1H, d, J = 2.9 Hz), 7.13 (1H, d, J = 8.8 Hz), 7.2-7.35 (3H, m), 7.41 (1H, s) |
| 172 | | (CDCl3) 3.82 (3H, s), 4.02 (2H, brs), 4.98 (2H, s), 6.34 (1H, dd, J = 9.0 Hz, 2.9 Hz), 6.39 (1H, d, J = 2.9 Hz), 6.8-6.9 (1H, m), 6.9-7.0 (2H, m), 7.12 (1H, d, J = 9.0 Hz), 7.25-7.35 (1H, m) |
| 173 | | (CDCl3) 1.6 (3H, d, J = 6.2 Hz), 3.93 (2H, brs), 5.15-5.25 (1H, m), 6.15-6.3 (2H, m), 7.01 (1H, d, J = 8.9 Hz), 7.2-7.35 (5H, m) |
| 174 | | (CDCl3) 1.6 (3H, d, J = 6.2 Hz), 3.93 (2H, brs), 5.15-5.25 (1H, m), 6.15-6.3 (2H, m), 7.01 (1H, d, J = 8.9 Hz), 7.2-7.35 (5H, m) |

TABLE 23

| Ref No. | Strc | (Solv) $^1$H-NMR δ ppm: |
|---|---|---|
| 175 | | (CDCl3) 3.86 (3H, s), 4.01 (2H, brs), 5.05 (2H, s), 6.37 (1H, dd, J = 8.8 Hz, 2.9 Hz), 6.42 (1H, d, J = 2.9 Hz), 6.85-7.0 (2H, m), 7.11 (1H, d, J = 8.8 Hz), 7.25-7.35 (1H, m), 7.4-7.45 (1H, m) |
| 176 | | (CDCl3) 3.82 (3H, s), 4.02 (2H, brs), 4.92 (2H, s), 6.34 (1H, dd, J = 8.6 Hz, 2.7 Hz), 6.38 (1H, d, J = 2.7 Hz), 6.85-6.95 (2H, m), 7.11 (1H, d, J = 8.6 Hz), 7.3-7.35 (2H, m) |
| 177 | | (CDCl3) 4.03 (2H, brs), 5.1 (2H, s), 6.35 (1H, dd, J = 8.7 Hz, 2.8 Hz), 6.4 (1H, d, J = 2.8 Hz), 7.13 (1H, d, J = 8.7 Hz), 7.2-7.3 (2H, m), 7.35-7.4 (1H, m), 7.45-7.55 (1H, m) |

TABLE 23-continued

| Ref No. | Strc | (Solv) ¹H-NMR δ ppm: |
|---|---|---|
| 178 | | (CDCl3) 4.02 (2H, brs), 4.96 (2H, s), 6.31 (1H, dd, J = 8.9 Hz, 2.9 Hz), 6.36 (1H, d, J = 2.9 Hz), 7.12 (1H, d, J = 8.9 Hz), 7.3-7.4 (4H, m) |
| 179 | | (CDCl3) 4.04 (2H, s), 5.14 (2H, s), 6.34 (1H, dd, J = 8.8 Hz, 2.8 Hz), 6.4 (1H, d, J = 2.8 Hz), 7.11 (1H, d, J = 8.8 Hz), 7.2-7.25 (1H, m), 7.48 (1H, d, J = 7.8 Hz), 7.65-7.75 (1H, m), 8.55-8.6 (1H, m) |
| 180 | | (CDCl3) 2.1-2.2 (1H, m), 2.2-2.3 (1H, m), 4.05 (2H, brs), 4.2-4.35 (2H, m), 5.24 (1H, t, J = 3.6 Hz), 6.39 (1H, dd, J = 8.4 Hz, 2.8 Hz), 6.42 (1H, d, J = 2.8 Hz), 6.85-6.95 (2H, m), 7.16 (1H, d, J = 8.4 Hz), 7.2-7.3 (2H, m) |
| 181 | | (CDCl3) 4.04 (2H, s), 5.14 (2H, s), 6.3-6.45 (2H, m), 7.11 (1H, d, J = 8.6 Hz), 7.2-7.25 (1H, m), 7.48 (1H, d, J = 7.8 Hz), 7.65-7.75 (1H, m), 8.55-8.6 (1H, m) |

TABLE 24

| Ref No. | Strc | (Solv) ¹H-NMR δ ppm: |
|---|---|---|
| 182 | | (DMSO-d6) 1.54 (3H, d, J = 6.3 Hz), 5.26 (2H, s), 5.55 (1H, q, J = 6.3 Hz), 6.1 (1H, dd, J = 8.9 Hz, 2.9 Hz), 6.34 (1H, d, J = 2.9 Hz), 6.99 (1H, d, J = 8.9 Hz), 7.15-7.25 (2H, m), 7.25-7.45 (2H, m) |
| 183 | | (DMSO-d6) 1.5 (3H, d, J = 6.5 Hz), 5.24 (2H, s), 5.36 (1H, q, J = 6.5 Hz), 6.12 (1H, dd, J = 9.0 Hz, 2.8 Hz), 6.34 (1H, d, J = 2.8 Hz), 6.98 (1H, d, J = 9.0 Hz), 7.0-7.1 (1H, m), 7.15-7.25 (2H, m), 7.35-7.45 (1H, m) |
| 184 | | (DMSO-d6) 1.49 (3H, d, J = 6.2 Hz), 5.22 (2H, s), 5.35 (1H, q, J = 6.2 Hz), 6.11 (1H, dd, J = 8.8 Hz, 2.8 Hz), 6.33 (1H, d, J = 2.8 Hz), 6.97 (1H, d, J = 8.8 Hz), 7.1-7.2 (2H, m), 7.35-7.45 (2H, m) |

TABLE 24-continued

| Ref No. | Strc | (Solv) ¹H-NMR δ ppm: |
|---|---|---|
| 185 | | (DMSO-d6) 1.35-1.5 (1H, m), 1.7-1.9 (3H, m), 1.9-2.05 (2H, m), 2.75-2.95 (2H, m), 5.26 (2H, s), 5.36 (1H, d, J = 9.2 Hz), 6.16 (1H, dd, J = 9.0 Hz, 2.8 Hz), 6.38 (1H, d, J = 2.8 Hz), 7.01 (1H, d, J = 9.0 Hz), 7.1-7.2 (3H, m), 7.2-7.3 (1H, m) |
| 186 | | (DMSO-d6) 1.66 (3H, d, J = 6.6 Hz), 5.3 (2H, s), 5.91 (1H, q, J = 6.6 Hz), 6.0 (1H, dd, J = 8.8 Hz, 2.8 Hz), 6.31 (1H, d, J = 2.8 Hz), 6.98 (1H, d, J = 8.8 Hz), 7.25-7.35 (1H, m), 7.4-7.5 (2H, m) |
| 187 | | (DMSO-d6) 1.45 (3H, d, J = 6.3 Hz), 3.86 (3H, s), 5.22 (2H, s), 5.54 (1H, q, J = 6.3 Hz), 6.02 (1H, dd, J = 8.5 Hz, 2.9 Hz), 6.28 (1H, d, J = 2.9 Hz), 6.85-7.05 (3H, m), 7.2-7.3 (2H, m) |
| 188 | | (DMSO-d6) 1.49 (3H, d, J = 6.2 Hz), 3.73 (3H, s), 5.21 (2H, s), 5.29 (1H, q, J = 6.2 Hz), 6.11 (1H, dd, J = 9.0 Hz, 2.9 Hz), 6.34 (1H, dd, J = 2.9 Hz), 6.75-6.85 (1H, m), 6.85-7.0 (3H, m), 7.2-7.3 (1H, m) |

TABLE 25

| Ref No. | Strc | (Solv) ¹H-NMR δ ppm: |
|---|---|---|
| 189 | | (DMSO-d6) 1.47 (3H, d, J = 6.4 Hz), 3.72 (3H, s), 5.19 (2H, s), 5.28 (1H, q, J = 6.4 Hz), 6.1 (1H, dd, J = 8.6 Hz, 2.9 Hz), 6.33 (1H, d, J = 2.9 Hz), 6.85-6.9 (2H, m), 6.95 (1H, d, J = 8.6 Hz), 7.25-7.3 (2H, m) |
| 190 | | (DMSO-d6) 0.85-0.95 (3H, m), 1.85-2.0 (1H, m), 2.05-2.2 (1H, m), 5.28 (2H, s), 5.37 (1H, t, J = 7.2 Hz), 6.1 (1H, dd, J = 8.7 Hz, 2.9 Hz), 6.34 (1H, d, J = 2.9 Hz), 6.95-7.1 (3H, m), 7.3-7.45 (1H, m) |
| 191 | | (DMSO-d6) 1.55 (3H, d, J = 6.2 Hz), 5.28 (2H, s), 5.57 (1H, q, J = 6.2 Hz), 6.03 (1H, dd, J = 9.0 Hz, 2.8 Hz), 6.34 (1H, d, J = 2.8 Hz), 6.98 (1H, d, J = 9.0 Hz), 7.45-7.55 (1H, m), 7.65-7.75 (3H, m) |

TABLE 25-continued

| Ref No. | Strc | (Solv) $^1$H-NMR δ ppm: |
|---|---|---|
| 192 | | (DMSO-d6) 1.52 (3H, d, J = 6.4 Hz), 5.25 (2H, s), 5.48 (1H, q, J = 6.4 Hz), 6.13 (1H, dd, J = 8.9 Hz, 2.8 Hz), 6.36 (1H, d, J = 2.8 Hz), 6.99 (1H, d, J = 8.9 Hz), 7.55-7.75 (4H, m) |
| 193 | | (DMSO-d6) 1.52 (3H, d, J = 6.3 Hz), 5.46 (1H, q, J = 6.3 Hz), 6.11 (1H, dd, J = 8.7 Hz, 2.9 Hz), 6.34 (1H, d, J = 2.9 Hz), 6.98 (1H, d, J = 8.7 Hz), 7.59 (2H, d, J = 8.2 Hz), 7.71 (2H, d, J = 8.2 Hz) |
| 194 | | (CDCl3) 4.02 (2H, s), 5.06 (2H, s), 6.37 (1H, dd, J = 8.7 Hz, 2.9 Hz), 6.41 (1H, d, J = 2.9 Hz), 6.85-7.0 (2H, m), 7.13 (1H, d, J = 8.7 Hz), 7.25-7.4 (1H, m) |
| 195 | | (CDCl3) 4.04 (2H, s), 5.21 (2H, s), 6.35-6.45 (2H, m), 7.15 (1H, d, J = 8.8 Hz), 7.2-7.3 (1H, m), 7.3-7.4 (2H, m) |
| 196 | | (CDCl3) 1.58 (3H, d, J = 6.4 Hz), 3.94 (2H, s), 5.59 (1H, q, J = 6.4 Hz), 6.16 (1H, dd, J = 8.8 Hz, 2.8 Hz), 6.23 (1H, d, J = 2.8 Hz), 7.01 (1H, d, J = 8.8 Hz), 7.15-7.25 (2H, m), 7.3-7.4 (1H, m), 7.4-7.5 (1H, m) |

TABLE 26

| Ref No. | Strc | (Solv) $^1$H-NMR δ ppm: |
|---|---|---|
| 197 | | (CDCl3) 1.58 (3H, d, J = 6.5 Hz), 3.95 (2H, s), 5.17 (1H, q, J = 6.5 Hz), 6.19 (1H, dd, J = 9.0 Hz, 2.9 Hz), 6.27 (1H, d, J = 2.9 Hz), 7.03 (1H, d, J = 9.0 Hz), 7.15-7.3 (3H, m), 7.3-7.35 (1H, m) |
| 198 | | (CDCl3) 1.55-1.6 (3H, m), 3.94 (2H, s), 5.15-5.25 (1H, m), 6.15-6.3 (2H, m), 6.95-7.05 (1H, m), 7.2-7.35 (4H, m) |

TABLE 26-continued

| Ref No. | Strc | (Solv) ¹H-NMR δ ppm: |
|---|---|---|
| 199 | | (CDCl3) 1.85-2.3 (4H, m), 3.65-3.75 (1H, m), 3.98 (2H, s), 4.3-4.4 (1H, m), 5.3-5.4 (1H, m), 6.26 (1H, dd, J = 8.6 Hz, 2.7 Hz), 6.31 (1H, d, J = 2.7 Hz), 7.0-7.1 (3H, m), 7.15-7.25 (1H, m), 7.25-7.3 (1H, m) |
| 200 | | (CDCl3) 0.98 (3H, t, J = 7.4 Hz), 1.75-2.05 (2H, m), 3.91 (2H, s), 4.9-4.95 (1H, m), 6.2 (1H, dd, J = 8.8 Hz, 2.8 Hz), 6.27 (1H, J = 2.8 Hz), 7.0 (1H, d, J = 8.8 Hz), 7.2-7.35 (5H, m) |
| 201 | | (CDCl3) 1.74 (3H, d, J = 6.6 Hz), 3.95 (2H, s), 5.65 (1H, q, J = 6.6 Hz), 6.28 (1H, dd, J = 8.7 Hz, 2.9 Hz), 6.34 (1H, d, J = 2.9 Hz), 6.8-6.9 (2H, m), 7.03 (1H, d, J = 8.7 Hz), 7.15-7.25 (1H, m) |
| 202 | | (CDCl3) 0.89 (3H, d, J = 6.7 Hz), 1.02 (3H, d, J = 6.8 Hz), 2.0-2.15 (1H, m), 4.71 (1H, J = 6.4 Hz), 6.18 (1H, dd, J = 8.7 Hz, 2.8 Hz), 6.26 (1H, d, J = 2.8 Hz), 6.98 (1H, d, J = 8.7 Hz), 7.2-7.35 (5H, m) |
| 203 | | (CDCl3) 0.85-1.05 (3H, m), 1.2-1.3 (2H, m), 1.6-1.9 (2H, m), 4.6-4.65 (1H, m), 6.1-6.25 (2H, m), 6.96 (1H, d, J = 8.9 Hz), 7.2-7.35 (5H, m) |
| 204 | | (CDCl3) 0.97 (3H, t, J = 7.3 Hz), 1.75-2.0 2H, m), 4.85-4.95 (1H, m), 6.18 (1H, dd, J = 8.7 Hz, 2.8 Hz), 6.26 (1H, d, J = 8.7 Hz), 7.02 (1H, d, J = 2.8 Hz), 7.15-7.35 (5H, m) |

TABLE 27

| Ref No. | Strc | (Solv) ¹H-NMR δ ppm: |
|---|---|---|
| 205 | | (CDCl3) 1.2-1.55 (7H, m), 1.7-1.85 (1H, m), 1.9-2.0 (1H, m), 4.95-5.0 (1H, m), 6.19 (1H, dd, J = 8.7 Hz, 2.7 Hz), 6.26 (1H, d, J = 2.7 Hz), 6.99 (1H, d, J = 8.7 Hz), 7.2-7.35 (5H, m) |
| 206 | | (CDCl3) 3.07 (2H, t, J = 7.1 Hz), 4.0 (2H, s), 4.1 (2H, t, J = 7.1 Hz), 6.26 (1H, dd, J = 8.7 Hz, 2.7 Hz), 6.31 (1H, d, J = 2.7 Hz), 7.1 (1H, d, J = 8.7 Hz), 7.2-7.35 (5H, m) |

TABLE 27-continued

| Ref No. | Strc | (Solv) $^1$H-NMR δ ppm: |
|---|---|---|
| 207 | H2N-(2-Cl,5-O-phenyl)-O-CH2CH2-(2-F-phenyl) | (CDCl3) 3.1 (2H, t, J = 7.0 Hz), 4.0 (2H, brs), 4.11 (2H, t, J = 7.0 Hz), 6.26 (1H, dd, J = 8.7 Hz, 2.8 Hz), 6.31 (1H, d, J = 2.8 Hz), 7.0-7.15 (3H, m), 7.15-7.3 (2H, m) |
| 208 | H2N-(2-Cl,5-O-phenyl)-O-CH(CH3)-CH2-phenyl | (CDCl3) 1.27 (3H, d, J = 5.8 Hz), 2.75-2.85 (1H, m), 3.0-3.1 (1H, m), 3.98 (2H, s), 4.4-4.55 (1H, m), 6.2-6.35 (2H, m), 7.09 (1H, d, J = 8.9 Hz), 7.15-7.35 (5H, m) |
| 209 | H2N-(2-Cl,5-O-phenyl)-O-CH(Et)-(2-F-phenyl) | (CDCl3) 0.99 (3H, t, J = 7.4 Hz), 1.8-2.05 (2H, m), 3.94 (2H, s), 5.25-5.35 (1H, m), 6.21 (1H, dd, J = 8.9 Hz, 2.9 Hz), 6.28 (1H, d, J = 2.9 Hz), 7.0-7.15 (3H, m), 7.15-7.3 (1H, m), 7.3-7.4 (1H, m) |
| 210 | H2N-(2-Cl,5-O-phenyl)-O-CH2-CH(CH3)-phenyl | (CDCl3) 1.39 (3H, d, J = 7.0 Hz), 3.15-3.25 (1H, m), 3.85-4.05 (4H, m), 6.2-6.35 (2H, m), 7.09 (1H, d, J = 8.6 Hz), 7.2-7.35 (5H, m) |
| 211 | H2N-(2-Cl,5-O-phenyl)-O-CH2-(3,5-diF-phenyl) | (DMSO-d6) 5.04 (2H, s), 5.35 (2H, s), 6.22 (1H, dd, J = 8.7 Hz, 3.0 Hz), 6.43 (1H, d, J = 3.0 Hz), 7.07 (1H, d, J = 8.7 Hz), 7.1-7.25 (3H, m) |
| 212 | H2N-(2-Cl,5-O-phenyl)-O-CH2-(2,5-diF-phenyl) | (DMSO-d6) 5.03 (2H, s), 5.35 (2H, s), 6.25 (1H, dd, J = 8.5 Hz, 2.8 Hz), 6.45 (1H, d, J = 2.8 Hz), 7.08 (1H, d, J = 8.5 Hz), 7.2-7.4 (3H, m) |

TABLE 28

| Ref No. | Strc | (Solv) $^1$H-NMR δ ppm: |
|---|---|---|
| 213 | H2N-(2-Cl,5-O-phenyl)-O-CH2-C(CH3)2-phenyl | (DMSO-d6) 1.36 (6H, s), 3.88 (2H, s), 5.25 (2H, s), 6.11 (1H, dd, J = 8.8 Hz, 2.8 Hz), 6.34 (1H, d, J = 2.8 Hz), 7.01 (1H, d, J = 8.8 Hz), 7.15-7.25 (1H, m), 7.25-7.35 (2H, m), 7.4-7.45 (2H, m) |
| 214 | H2N-(2-Cl,5-O-phenyl)-O-CH(CH3)-(2,5-diOMe-phenyl) | (CDCl3) 1.53 (3H, d, J = 6.2 Hz), 3.71 (3H, s), 3.85 (3H, s), 3.91 (2H, s), 5.57 (1H, q, J = 6.2 Hz), 6.2 (1H, dd, J = 8.9 Hz, 2.9 Hz), 6.27 (1H, d, J = 2.9 Hz), 6.73 (1H, dd, J = 8.8 Hz, 3.1 Hz), 6.8 (1H, d, J = 8.8 Hz), 6.93 (1H, d, J = 3.1 Hz), 7.0 (1H, d, J = 8.9 Hz) |

TABLE 28-continued

| Ref No. | Strc | (Solv) ¹H-NMR δ ppm: |
|---|---|---|
| 215 | | (CDCl3) 1.58 (3H, d, J = 6.5 Hz), 3.77 (6H, s), 3.94 (2H, brs), 5.11 (1H, q, J = 6.5 Hz), 6.22 (1H, dd, J = 8.5 Hz, 2.7 Hz), 6.28 (1H, d, J = 2.7 Hz), 6.3-6.35 (1H, m), 6.45-6.5 (2H, m), 7.02 (1H, d, J = 8.5 Hz) |
| 216 | | (CDCl3) 1.56 (3H, d, J = 6.4 Hz), 3.86 (3H, s), 3.95 (2H, s), 5.14 (1H, q, J = 6.4 Hz), 6.15-6.3 (2H, m), 6.85-6.95 (1H, m), 7.0-7.1 (3H, m) |
| 217 | | (CDCl3) 1.58 (3H, d, J = 6.4 Hz), 5.48 (1H, q, J = 6.4 Hz), 6.22 (1H, dd, J = 8.7 Hz, 2.8 Hz), 6.28 (1H, d, J = 2.8 Hz), 6.55-6.7 (2H, m), 7.02 (1H, d, J = 8.7 Hz), 7.25-7.3 (1H, m) |
| 218 | | (DMSO-d6) 5.05 (2H, s), 5.37 (2H, s), 6.25 (1H, dd, J = 9.0 Hz, 2.8 Hz), 6.46 (1H, d, J = 2.8 Hz), 7.09 (1H, d, J = 9.0 Hz), 7.47 (1H, dd, J = 8.7 Hz, 2.6 Hz), 7.55 (1H, d, J = 8.7 Hz), 7.6 (1H, d, J = 2.6 Hz) |
| 219 | | (DMSO-d6) 5.03 (2H, s), 5.35 (2H, s), 6.25 (1H, dd, J = 8.7 Hz, 2.8 Hz), 6.45 (1H, d, J = 2.8 Hz), 7.08 (1H, d, J = 8.7 Hz), 7.25-7.35 (1H, m), 7.45-7.5 (1H, m), 7.55-7.6 (1H, m) |

TABLE 29

| Ref No. | Strc | (Solv) ¹H-NMR δ ppm: |
|---|---|---|
| 220 | | (CDCl3) 1.6 (3H, d, J = 6.4 Hz), 3.56 (2H, brs), 5.26 (1H, q, J = 6.4 Hz), 6.15-6.3 (3H, m), 6.9-7.0 (1H, m), 7.2-7.4 (5H, m) |

TABLE 29-continued

| Ref No. | Strc | (Solv) ¹H-NMR δ ppm: |
|---|---|---|
| 221 | | (CDCl3) 1.52 (3H, d, J = 6.3 Hz), 3.87 (3H, s), 3.94 (2H, brs), 5.55 (1H, q, J = 6.3 Hz), 6.18 (1H, dd, J = 8.8 Hz, 2.8 Hz), 6.26 (1H, d, J = 2.8 Hz), 6.75-6.85 (1H, m), 6.85-6.95 (1H, m), 7.01 (1H, d, J = 8.8 Hz), 7.06 (1H, dd, J = 9.2 Hz, 3.1 Hz) |
| 222 | | (CDCl3) 1.51 (3H, d, J = 6.3 Hz), 3.87 (3H, s), 3.93 (2H, brs), 5.54 (1H, q, J = 6.3 Hz), 6.17 (1H, dd, J = 8.8 Hz, 3.0 Hz), 6.25 (1H, d, J = 3.0 Hz), 6.55-6.65 (2H, m), 7.01 (1H, d, J = 8.8 Hz), 7.25-7.35 (1H, m) |
| 223 | | (CDCl3) 1.46 (3H, t, J = 7.0 Hz), 1.55 (3H, d, J = 6.3 Hz), 3.9 (2H, brs), 4.05-4.15 (2H, m), 5.6-5.65 (1H, m), 6.2 (1H, dd, J = 8.9 Hz, 2.9 Hz), 6.28 (1H, d, J = 2.9 Hz), 6.8-6.95 (2H, m), 7.0 (1H, d, J = 8.9 Hz), 7.15-7.25 (1H, m), 7.3-7.4 (1H, m) |
| 224 | | (CDCl3) 1.69 (3H, d, J = 6.6 Hz), 3.85-3.95 (5H, m), 5.7-5.8 (1H, m), 6.28 (1H, dd, J = 8.8 Hz, 2.5 Hz), 6.35 (1H, d, J = 2.5 Hz), 6.6-6.7 (2H, m), 7.0 (1H, d, J = 8.8 Hz), 7.1-7.2 (1H, m) |
| 225 | | (CDCl3) 1.59 (3H, d, J = 6.4 Hz), 5.23 (1H, q, J = 6.4 Hz), 6.15-6.25 (2H, m), 6.83 (1H, d, J = 8.0 Hz), 7.2-7.4 (5H, m) |
| 226 | | (DMSO-d6) 3.84 (3H, s), 4.92 (2H, s), 5.31 (2H, s), 6.2-6.25 (1H, m), 6.43 (1H, d, J = 2.7 Hz), 6.8-6.9 (1H, m), 6.93 (1H, d, J = 8.2 Hz), 7.06 (1H, d, J = 8.6 Hz), 7.35-7.45 (1H, m) |

TABLE 30

| Ref No. | Strc | (Solv) ¹H-NMR δ ppm: |
|---|---|---|
| 227 | | (DMSO-d6) 1.65 (3H, d, J = 6.7 Hz), 5.01 (2H, s), 5.85-6.0 (2H, m), 6.0-6.15 (2H, m), 6.75-6.85 (1H, m), 7.25-7.45 (3H, m) |

TABLE 30-continued

| Ref No. | Strc | (Solv) ¹H-NMR δ ppm: |
|---|---|---|
| 228 | | (CDCl3) 1.58 (3H, d, J = 6.4 Hz), 3.64 (2H, s), 5.16 (1H, q, J = 6.4 Hz), 6.1-6.15 (1H, m), 6.29 (1H, dd, J = 7.6 Hz, 3.0 Hz), 6.75-6.85 (1H, m), 6.9-7.0 (1H, m), 7.0-7.15 (2H, m), 7.2-7.35 (1H, m) |
| 229 | | (CDCl3) 1.51 (3H, d, J = 6.4 Hz), 3.86 (3H, s), 5.45-5.55 (1H, m), 6.05-6.15 (1H, m), 6.25-6.3 (1H, m), 6.7-6.85 (2H, m), 6.85-6.95 (1H, m), 7.05-7.1 (1H, m) |
| 230 | | (CDCl3) 4.06 (2H, s), 5.2 (2H, s), 6.3-6.45 (2H, m), 7.14 (1H, d, J = 9.0 Hz), 7.4-7.45 (1H, m), 7.6-7.75 (3H, m) |
| 231 | | (CDCl3) 3.44 (3H, s), 3.75-3.8 (2H, m), 4.06 (2H, s), 4.15-4.2 (2H, m), 5.09 (2H, s), 6.34 (1H, dd, J = 8.7 Hz, 2.8 Hz), 6.47 (1H, d, J = 2.8 Hz), 6.85-7.0 (2H, m), 7.09 (1H, d, J = 8.7 Hz), 7.2-7.3 (1H, m), 7.4-7.45 (1H, m) |
| 232 | | (CDCl3) 3.71 (2H, s), 3.83 (3H, s), 5.0-5.05 (2H, m), 6.3-6.35 (1H, m), 6.4-6.45 (1H, m), 6.55-6.65 (1H, m), 6.85-6.95 (1H, m), 7.05-7.2 (1H, m) |
| 233 | | (CDCl3) 1.69 (3H, d, J = 6.7 Hz), 3.62 (2H, s), 3.86 (3H, s), 5.71 (1H, q, J = 6.7 Hz), 6.15-6.25 (1H, m), 6.3-6.4 (1H, m), 6.5-6.6 (1H, m), 6.7-6.8 (1H, m), 6.95-7.05 (1H, m) |

TABLE 31

| Ref No. | Strc | (Solv) ¹H-NMR δ ppm: |
|---|---|---|
| 234 | | (CDCl3) 2.49 (3H, s), 4.02 (2H, brs), 5.07 (2H, s), 6.3-6.45 (2H, m), 7.12 (1H, d, J = 8.7 Hz), 7.15-7.25 (1H, m), 7.25-7.35 (2H, m), 7.44 (1H, d, J = 7.4 Hz) |

TABLE 31-continued

| Ref No. | Strc | (Solv) ¹H-NMR δ ppm: |
|---|---|---|
| 235 | | (CDCl3) 3.73 (2H, brs), 5.0-5.1 (2H, m), 6.25-6.35 (1H, m), 6.35-6.45 (1H, m), 6.8-6.95 (2H, m), 7.1-7.2 (1H, m) |
| 236 | | (CDCl3) 3.74 (2H, brs), 4.98 (2H, s), 6.2-6.3 (1H, m), 6.35-6.45 (1H, m), 6.85-7.0 (2H, m), 7.25-7.4 (1H, m) |
| 237 | | (CDCl3) 3.74 (2H, brs), 5.05-5.1 (2H, m), 6.25-6.35 (1H, m), 6.35-6.45 (1H, m), 6.85-6.95 (1H, m), 7.05-7.15 (1H, m) |
| 238 | | (CDCl3) 3.71 (2H, brs), 3.86 (3H, s), 5.03 (2H, s), 6.25-6.35 (1H, m), 6.4-6.45 (1H, m), 6.8-7.0 (3H, m), 7.25-7.35 (1H, m), 7.4-7.45 (1H, m) |
| 239 | | (CDCl3) 1.41 (3H, t, J = 7.0 Hz), 4.08 (2H, q, J = 7.0 Hz), 5.04 (2H, s), 6.25-6.35 (1H, m), 6.4-6.45 (1H, m), 6.8-7.0 (3H, m), 7.2-7.3 (1H, m), 7.4-7.45 (1H, m) |
| 240 | | (CDCl3) 3.71 (2H, s), 5.05 (2H, s), 6.25-6.3 (1H, m), 6.35-6.7 (2H, m), 6.85-6.95 (1H, m), 7.1-7.2 (1H, m), 7.2-7.3 (1H, m), 7.3-7.4 (1H, m), 7.5-7.55 (1H, m) |
| 241 | | (CDCl3) 2.39 (6H, s), 3.71 (2H, brs), 4.95 (2H, s), 6.3-6.35 (1H, m), 6.4-6.45 (1H, m), 6.85-6.95 (1H, m), 7.0-7.1 (2H, m), 7.1-7.2 (1H, m) |

TABLE 32

| Ref No. | Strc | (Solv) ¹H-NMR δ ppm: |
|---|---|---|
| 242 | | (CDCl3) 3.73 (2H, brs), 5.05-5.15 (2H, m), 6.25-6.35 (1H, m), 6.35-6.45 (1H, m), 6.85-6.95 (1H, m), 7.45-7.6 (2H, m) |
| 243 | | (CDCl3) 2.2-2.3 (3H, m), 3.71 (2H, brs), 5.05-5.1 (2H, m), 6.3-6.4 (1H, m), 6.4-6.5 (1H, m), 6.85-6.95 (1H, m), 7.05-7.15 (2H, m) |
| 244 | | (CDCl3) 3.95-4.0 (3H, m), 5.02 (2H, s), 6.25-6.35 (1H, m), 6.35-6.45 (1H, m), 6.85-6.95 (1H, m), 6.95-7.1 (2H, m), 7.15-7.25 (1H, m) |
| 245 | | (CDCl3) 3.74 (2H, brs), 5.09 (2H, s), 6.2-6.3 (1H, m), 6.35-6.45 (1H, m), 6.85-6.95 (1H, m), 7.2-7.25 (1H, m), 7.4-7.5 (2H, m) |
| 246 | | (CDCl3) 3.7 (2H, brs), 3.83 (3H, s), 5.0 (2H, s), 6.25-6.3 (1H, m), 6.35-6.45 (1H, m), 6.75-7.0 (3H, m), 7.15-7.2 (1H, m) |
| 247 | | (CDCl3) 3.4-4.0 (5H, m), 5.02 (2H, s), 6.25-6.35 (1H, m), 6.35-6.45 (1H, m), 6.75-6.85 (1H, m), 6.85-6.95 (1H, m), 6.95-7.05 (2H, m) |
| 248 | | (CDCl3) 3.7 (2H, brs), 5.04 (2H, s), 6.25-6.35 (1H, m), 6.35-6.45 (1H, m), 6.85-6.95 (2H, m), 7.3-7.45 (1H, m) |

TABLE 33

| Ref No. | Strc | (Solv) ¹H-NMR δ ppm: |
|---|---|---|
| 249 | | (CDCl3) 3.2-4.0 (5H, m), 4.98 (2H, s), 6.25-6.35 (1H, m), 6.4-6.45 (1H, m), 6.75-6.9 (2H, m), 7.2-7.25 (1H, m), 7.4-7.45 (1H, m) |
| 250 | | (CDCl3) 3.72 (2H, brs), 5.07 (2H, s), 6.25-6.3 (1H, m), 6.35-6.45 (1H, m), 6.85-6.95 (1H, m), 7.25-7.4 (3H, m), 7.55-7.6 (1H, m) |
| 251 | | (CDCl3) 3.4-4.0 (5H, m), 5.07 (2H, s), 6.3-6.4 (1H, m), 6.4-6.5 (1H, m), 6.85-6.95 (1H, m), 7.17 (1H, d, J = 9.0 Hz), 7.35 (1H, d, J = 9.0 Hz) |
| 252 | | (CDCl3) 5.07 (2H, s), 6.25-6.35 (1H, m), 6.4-6.45 (1H, m), 6.85-6.95 (1H, m), 7.1-7.25 (1H, m), 7.55-7.65 (1H, m), 7.8-7.85 (1H, m) |
| 253 | | (CDCl3) 3.73 (2H, brs), 5.18 (2H, s), 6.2-6.3 (1H, m), 6.35-6.45 (1H, m), 6.85-6.95 (1H, m), 7.0-7.1 (1H, m), 7.4-7.55 (1H, m), 7.6-7.7 (1H, m) |
| 254 | | (CDCl3) 2.2-2.3 (3H, m), 3.71 (2H, brs), 5.02 (2H, s), 6.25-6.35 (1H, m), 6.35-6.45 (1H, m), 6.75-6.95 (2H, m), 7.1-7.2 (1H, m) |
| 255 | | (CDCl3) 2.06 (3H, s), 3.83 (3H, s), 4.95-5.05 (2H, m), 6.5 (1H, d, J = 7.7 Hz), 6.55-6.65 (1H, m), 6.75 (1H, d, J = 11.2 Hz), 7.05-7.15 (1H, m) |

TABLE 34

| Ref No. | Strc | (Solv) ¹H-NMR δ ppm: |
|---|---|---|
| 256 | | (CDCl3) 2.06 (3H, s), 3.86 (3H, s), 4.95-5.05 (2H, m), 6.52 (1H, d, J = 8.0 Hz), 6.65-6.8 (3H, m), 7.25-7.35 (1H, m) |
| 257 | | (CDCl3) 2.37 (3H, s), 3.71 (2H, brs), 5.05-5.15 (2H, m), 6.3-6.4 (1H, m), 6.4-6.5 (1H, m), 6.85-7.0 (2H, m), 7.2-7.3 (1H, m) |
| 258 | | (CDCl3) 3.7 (2H, brs), 3.85 (3H, s), 5.0-5.05 (2H, m), 6.3-6.35 (1H, m), 6.4-6.45 (1H, m), 6.65-6.7 (1H, m), 6.85-6.95 (1H, m), 7.3-7.4 (1H, m) |
| 259 | | (CDCl3) 2.32 (3H, s), 5.0 (2H, s), 6.25-6.35 (1H, m), 6.4-6.45 (1H, m), 6.85-7.0 (2H, m), 7.05-7.1 (1H, m), 7.2-7.3 (1H, m) |
| 260 | | (CDCl3) 3.92 (3H, s), 5.1 (2H, s), 6.25-6.3 (1H, m), 6.35-6.45 (1H, m), 6.85-6.95 (2H, m), 7.1-7.2 (1H, m), 7.2-7.3 (1H, m) |
| 261 | | (CDCl3) 3.9 (3H, s), 5.05-5.1 (2H, m), 6.25-6.3 (1H, m), 6.35 (1H, m), 6.8-7.0 (2H, m), 7.0-7.1 (2H, m) |
| 262 | | (CDCl3) 1.08 (2H, t, J = 7.4 Hz), 2.47 (2H, q, J = 7.4 Hz), 3.85 (3H, s), 4.95-5.05 (2H, m), 6.53 (1H, d, J = 8.0 Hz), 6.65-6.8 (3H, m), 7.25-7.35 (1H, m) |

TABLE 34-continued

| Ref No. | Strc | (Solv) ¹H-NMR δ ppm: |
|---|---|---|
| 263 | | (CDCl3) 1.08 (3H, t, J = 7.6 Hz), 2.47 (2H, q, J = 7.6 Hz), 3.83 (3H, s), 5.0-5.05 (2H, m), 6.51 (1H, d, J = 7.7 Hz), 6.55-6.65 (1H, m), 6.77 (1H, d, J = 11.5 Hz), 7.05-7.15 (1H, m) |

TABLE 35

| Ref No. | Strc | (Solv) ¹H-NMR δ ppm: |
|---|---|---|
| 264 | | (CDCl3) 3.83 (3H, s), 5.1 (2H, s), 6.3-6.4 (1H, m), 6.4-6.45 (1H, m), 6.75-6.85 (1H, m), 6.85-6.95 (1H, m), 7.1-7.15 (1H, m) |
| 265 | | (CDCl3) 3.84 (3H, s), 5.12 (2H, s), 6.3-6.4 (1H, m), 6.4-6.45 (1H, m), 6.81 (1H, d, J = 9.3 Hz), 6.85-6.95 (1H, m), 7.42 (1H, d, J = 9.3 Hz) |
| 266 | | (CDCl3) 2.2-2.25 (3H, m), 3.82 (3H, s), 5.0-5.05 (2H, m), 6.3-6.4 (1H, m), 6.4-6.5 (1H, m), 6.62 (1H, d, J = 8.5 Hz), 6.85-6.95 (1H, m), 7.05-7.15 (1H, m) |
| 267 | | (CDCl3) 3.7 (2H, brs), 4.98 (2H, s), 6.25-6.3 (1H, m), 6.35-6.45 (1H, m), 6.8-6.9 (1H, m), 7.25-7.45 (5H, m) |
| 268 | | (CDCl3) 0.011 (3H, s), 0.016 (3H, s), 0.86 (9H, s), 3.75-3.85 (1H, m), 3.85-4.0 (3H, m), 5.05-5.15 (1H, m), 6.2-6.3 (2H, m), 7.0 (1H, d, J = 9.0 Hz), 7.2-7.4 (5H, m) |

TABLE 35-continued

| Ref No. | Strc | (Solv) $^1$H-NMR δ ppm: |
|---|---|---|
| 269 | | (DMSO-d6) 0.06 (6H, s), 0.89 (9H, s), 4.79 (2H, s), 5.03 (2H, s), 5.32 (2H, s), 6.21 (1H, dd, J = 8.5 Hz, 2.8 Hz), 6.43 (1H, J = 2.8 Hz), 7.06 (1H, d, J = 8.5 Hz), 7.2-7.5 (4H, m) |
| 270 | | (DMSO-d6) 0.07 (6H, s), 0.9 (9H, s), 4.72 (2H, s), 4.99 (2H, s), 5.3 (2H, s), 6.2 (1H, dd, J = 8.6 Hz, 2.8 Hz), 6.43 (1H, d, J = 2.8 Hz), 7.05 (1H, d, J = 8.6 Hz), 7.2-7.4 (4H, m) |

TABLE 36

| Ref No. | Strc | (Solv) $^1$H-NMR δ ppm: |
|---|---|---|
| 271 | | (CDCl3) 0.116 (3H, s), 0.12 (3H, s), 0.92 (9H, s), 1.5-1.6 (3H, m), 3.92 (2H, s), 3.95-4.05 (2H, m), 4.05-4.15 (2H, m), 5.65 (1H, q, J = 6.4 Hz), 6.19 (1H, dd, J = 8.9 Hz, 2.9 Hz), 6.3 (1H, d, J = 2.9 Hz), 6.8-7.0 (3H, m), 7.15-7.25 (1H, m), 7.3-7.4 (1H, m) |
| 272 | | (DMSO-d6) 0.11 (3H, s), 0.12 (3H, s), 0.91 (9H, s), 1.52 (3H, d, J = 6.3 Hz), 4.75-4.9 (2H, m), 5.22 (2H, s), 5.5-5.55 (1H, m), 6.0-6.1 (1H, m), 6.29 (1H, d, J = 2.8 Hz), 6.9 (1H, d, J = 8.6 Hz), 7.2-7.3 (2H, m), 7.3-7.4 (2H, m) |
| 273 | | (CDCl3) 0.09 (6H, s), 0.9 (9H, s), 3.95-4.05 (5H, m), 4.05-4.15 (2H, m), 5.07 (2H, s), 6.3-6.4 (1H, m), 6.42 (1H, d, J = 2.9 Hz), 6.85-7.0 (2H, m), 7.1 (1H, d, J = 8.7 Hz), 7.2-7.3 (1H, m), 7.4-7.45 (1H, m) |

TABLE 36-continued
| Ref No. | Strc | (Solv) $^1$H-NMR δ ppm: |
|---|---|---|
| 274 | 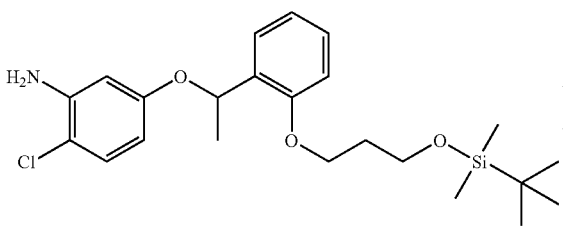 [SMILES: CC(Oc1ccc(Cl)c(N)c1)c1ccccc1OCCCO[Si](C)(C)C(C)(C)C] | (CDCl3) 0.065 (3H, s), 0.067 (3H, s), 0.9 (9H, s), 1.54 (3H, d, J = 6.2 Hz), 2.0-2.1 (2H, m), 3.8-3.95 (5H, m), 4.1-4.2 (2H, m), 5.55-5.65 (1H, m), 6.15-6.2 (1H, m), 6.27 (1H, d, J = 2.8 Hz), 6.85-6.95 (2H, m), 6.99 (1H, d, J = 8.9 Hz), 7.15-7.25 (1H, m), 7.3-7.35 (1H, m) |
| 275 | 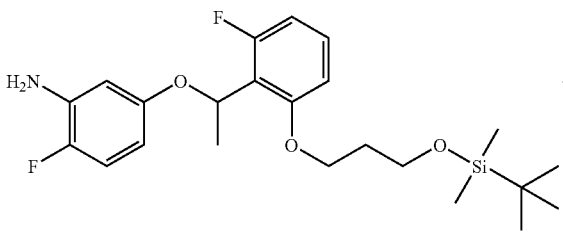 [SMILES: CC(Oc1ccc(F)c(N)c1)c1c(F)cccc1OCCCO[Si](C)(C)C(C)(C)C] | (CDCl3) 0.06 (3H, s), 0.07 (3H, s), 0.9 (9H, s), 1.68 (3H, d, J = 6.6 Hz), 2.0-2.1 (2H, m), 3.61 (2H, s), 3.8-3.9 (2H, m), 4.05-4.15 (2H, m), 5.65-5.8 (1H, m), 6.15-6.25 (1H, m), 6.3-6.4 (1H, m), 6.55-6.7 (2H, m), 6.7-6.8 (1H, m), 7.1-7.2 (1H, m) |
| 276 | 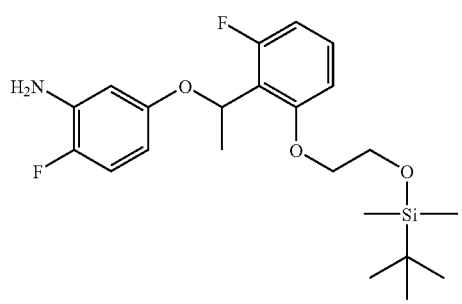 [SMILES: CC(Oc1ccc(F)c(N)c1)c1c(F)cccc1OCCO[Si](C)(C)C(C)(C)C] | (CDCl3) 0.116 (3H, s), 0.123 (3H, s), 0.93 (9H, s), 1.69 (3H, d, J = 6.6 Hz), 3.62 (2H, s), 3.95-4.2 (4H, m), 5.75-5.8 (1H, m), 6.15-6.25 (1H, m), 6.35-6.45 (1H, m), 6.6-6.7 (2H, m), 6.7-6.8 (1H, m), 7.1-7.2 (1H, m) |
TABLE 37
| Ref No. | Strc | (Solv) $^1$H-NMR δ ppm: |
|---|---|---|
| 277 | 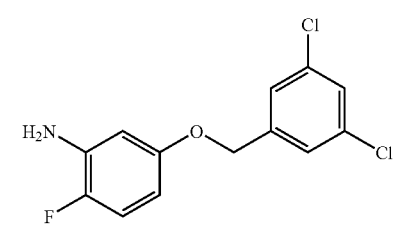 [SMILES: Nc1cc(OCc2cc(Cl)cc(Cl)c2)ccc1F] | (CDCl3) 3.4-4.0 (2H, br), 4.93 (2H, s), 6.2-6.25 (1H, m), 6.35-6.4 (1H, m), 6.85-6.95 (1H, m), 7.25-7.35 (3H, m) |
| 278 | 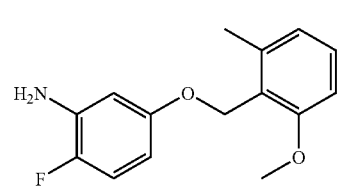 [SMILES: COc1cccc(C)c1COc1ccc(F)c(N)c1] | (CDCl3) 2.37 (3H, s), 3.45-4.0 (5H, m), 5.04 (2H, s), 6.3-6.4 (1H, m), 6.4-6.5 (1H, m), 6.75-6.8 (1H, m), 6.8-6.95 (2H, m), 7.15-7.25 (1H, m) |
| 279 | 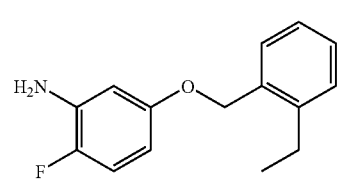 [SMILES: CCc1ccccc1COc1ccc(F)c(N)c1] | (CDCl3) 1.25 (3H, t, J = 7.6 Hz), 2.7 (2H, q, J = 7.6 Hz), 3.5-3.9 (2H, br), 4.97 (2H, s), 6.25-6.35 (1H, m), 6.35-6.45 (1H, m), 6.85-6.95 (1H, m), 7.15-7.35 (3H, m), 7.35-7.45 (1H, m) |

TABLE 37-continued

| Ref No. | Strc | (Solv) $^1$H-NMR δ ppm: |
|---|---|---|
| 280 | | (CDCl3) 3.5-3.85 (2H, br), 3.87 (3H, s), 4.99 (2H, s), 6.2-6.3 (1H, m), 6.35-6.45 (1H, m), 6.85-6.95 (1H, m), 7.3-7.4 (2H, m) |
| 281 | | (CDCl3) 3.6-3.9 (2H, br), 5.08 (2H, s), 6.25-6.35 (1H, m), 6.4-6.45 (1H, m), 6.85-6.95 (1H, m), 7.6-7.75 (2H, m) |
| 282 | | (CDCl3) 1.25 (3H, t, J = 7.7 Hz), 2.67 (2H, q, J = 7.7 Hz), 3.5-3.9 (2H, br), 4.95 (2H, s), 6.25-6.35 (1H, m), 6.35-6.45 (1H, m), 6.85-6.95 (1H, m), 7.1-7.35 (4H, m) |
| 283 | | (CDCl3) 3.38 (3H, s), 3.6-3.85 (2H, br), 4.54 (2H, s), 5.05 (2H, s), 6.25-6.35 (1H, m), 6.35-6.45 (1H, m), 6.85-6.95 (1H, m), 7.3-7.35 (2H, m), 7.35-7.5 (2H, m) |
| 284 | | (CDCl3) 3.4 (3H, s), 3.55-3.85 (2H, br), 4.47 (2H, s), 4.98 (2H, s), 6.25-6.3 (1H, m), 6.35-6.45 (1H, m), 6.8-6.9 (1H, m), 7.25-7.4 (4H, m) |

TABLE 38

| Ref No. | Strc | (Solv) $^1$H-NMR δ ppm: |
|---|---|---|
| 285 | | (CDCl3) 3.74 (2H, brs), 5.15 (2H, s), 6.25-6.35 (1H, m), 6.35-6.45 (1H, m), 6.85-6.95 (1H, m), 7.65 (1H, t, J = 8.0 Hz), 7.97 (2H, d, J = 8.0 Hz) |

TABLE 38-continued
| Ref No. | Strc | (Solv) $^1$H-NMR δ ppm: |
|---|---|---|
| 286 | | (CDCl3) 2.29 (3H, s), 2.45 (3H, s), 3.45-3.95 (5H, m), 4.97 (2H, s), 6.25-6.35 (1H, m), 6.35-6.45 (1H, m), 6.85-6.95 (1H, m), 7.09 (1H, d, J = 2.2 Hz), 7.21 (1H, d, J = 2.2 Hz) |
| 287 | | (CDCl3) 3.55-3.85 (2H, br), 3.87 (3H, s), 5.0-5.1 (2H, m), 6.25-6.35 (1H, m), 6.4-6.45 (1H, m), 6.8-7.0 (3H, m) |
| 288 | | (CDCl3) 3.5-3.85 (2H, br), 3.88 (3H, s), 5.08 (2H, s), 6.3-6.4 (1H, m), 6.4-6.45 (1H, m), 6.85-6.95 (1H, m), 7.1-7.2 (1H, m), 7.3-7.35 (1H, m), 7.4-7.5 (1H, m) |
| 289 | | (CDCl3) 3.55-3.9 (2H, br), 5.05 (2H, s), 6.2-6.3 (1H, m), 6.35-6.45 (1H, m), 6.8-6.95 (2H, m), 6.95-7.1 (1H, m) |
| 290 | | (CDCl3) 3.55-3.9 (2H, br), 5.09 (2H, s), 6.25-6.35 (1H, m), 6.35-6.45 (1H, m), 6.85-6.95 (1H, m), 7.3-7.4 (1H, m), 7.45-7.6 (2H, m) |
| 291 | | (CDCl3) 3.73 (2H, brs), 3.86 (3H, s), 5.01 (2H, s), 6.2-6.3 (1H, m), 6.35-6.45 (1H, m), 6.85-6.95 (1H, m), 7.05-7.15 (2H, m) |
TABLE 39
| Ref No. | Strc | (Solv) $^1$H-NMR δ ppm: |
|---|---|---|
| 292 | 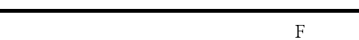 | (CDCl3) 2.3 (3H, s), 3.55-3.9 (5H, m), 4.99 (2H, s), 6.25-6.35 (1H, m), 6.35-6.45 (1H, m), 6.8-6.95 (2H, m), 6.95-7.05 (1H, m) |

TABLE 39-continued

| Ref No. | Strc | (Solv) ¹H-NMR δ ppm: |
|---|---|---|
| 293 | | (CDCl3) 3.5-3.95 (8H, m), 4.98 (2H, s), 6.25-6.35 (1H, m), 6.35-6.45 (1H, m), 6.85-6.95 (2H, m), 7.05 (1H, d, J = 2.4 Hz) |
| 294 | | (CDCl3) 3.5-3.95 (5H, m), 5.0 (2H, s), 6.2-6.3 (1H, m), 6.35-6.45 (1H, m), 6.75-6.85 (1H, m), 6.85-6.95 (1H, m), 6.95-7.05 (1H, m) |
| 295 | | (CDCl3) 3.75 (3H, s), 3.85 (3H, s), 5.05-5.15 (2H, m), 6.5-7.3 (5H, m) |
| 296 | | (CDCl3) 3.2-3.6 (2H, br), 3.75 (3H, s), 3.82 (3H, s), 5.05-5.15 (2H, m), 6.53 (1H, d, J = 9.0 Hz), 6.55-6.7 (2H, m), 7.05-7.15 (1H, m) |
| 297 | | (CDCl3) 3.41 (3H, s), 3.6-4.0 (4H, m), 4.05-4.15 (2H, m), 5.05-5.1 (2H, m), 6.25-6.35 (1H, m), 6.45-6.55 (1H, m), 6.6-6.65 (1H, m), 6.8-6.9 (1H, m), 7.05-7.15 (1H, m) |
| 298 | | (CDCl3) 1.19 (3H, t, J = 7.0 Hz), 3.56 (2H, q, J = 7.0 Hz), 3.7-3.8 (2H, m), 4.05-4.15 (2H, m), 5.05-5.1 (2H, m), 6.25-6.35 (1H, m), 6.45-6.55 (1H, m), 6.6-6.65 (1H, m), 6.8-6.9 (1H, m), 7.05-7.15 (1H, m) |

TABLE 40
| Ref No. | Strc | (Solv) $^1$H-NMR δ ppm: |
|---|---|---|
| 299 | 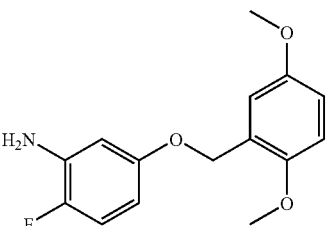 | (CDCl3) 3.5-3.9 (8H, m), 5.0 (2H, s), 6.25-6.35 (1H, m), 6.4-6.45 (1H, m), 6.75-6.9 (3H, m), 7.03 (1H, d, J = 2.3 Hz) |
| 300 | 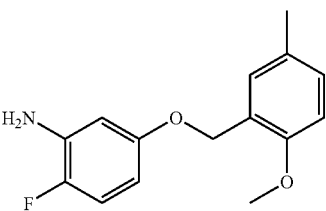 | (CDCl3) 2.29 (3H, s), 3.45-3.95 (5H, m), 4.99 (2H, s), 6.25-6.35 (1H, m), 6.4-6.45 (1H, m), 6.79 (1H, d, J = 8.3 Hz), 6.8-6.9 (1H, m), 7.08 (1H, dd, J = 8.3 Hz, 1.8 Hz), 7.23 (1H, d, J = 1.8 Hz) |
| 301 | 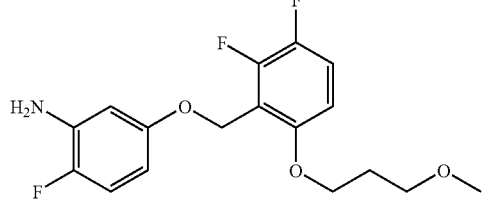 | (CDCl3) 1.95-2.1 (2H, m), 3.29 (3H, s), 3.49 (2H, t, J = 6.1 Hz), 4.06 (2H, t, J = 6.1 Hz), 5.0-5.05 (2H, m), 6.25-6.35 (1H, m), 6.4-6.45 (1H, m), 6.55-6.65 (1H, m), 6.85-6.95 (1H, m), 7.05-7.15 (1H, m) |
| 302 | 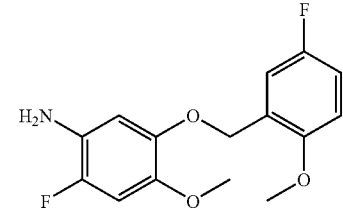 [SMILES: COc1ccc(F)cc1COc1cc(N)c(F)cc1OC] | (CDCl3) 3.1-3.7 (2H, br), 3.81 (3H, s), 3.83 (3H, s), 5.07 (2H, s), 6.39 (1H, d, J = 8.8 Hz), 6.66 (1H, d, J = 12.1 Hz), 6.75-6.85 (1H, m), 6.9-7.0 (1H, m), 7.2-7.25 (1H, m) |
| 303 | 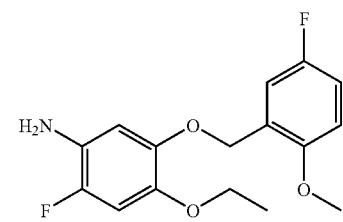 [SMILES: CCOc1cc(F)c(N)cc1OCc1cc(F)ccc1OC] | (CDCl3) 1.41 (3H, t, J = 7.0 Hz), 3.1-3.7 (2H, br), 3.83 (3H, s), 4.01 (2H, q, J = 7.0 Hz), 5.06 (2H, s), 6.42 (1H, d, J = 8.6 Hz), 6.67 (1H, d, J = 12.1 Hz), 6.75-6.85 (1H, m), 6.9-7.0 (1H, m), 7.2-7.3 (1H, m) |
| 304 | 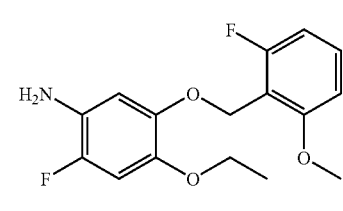 [SMILES: CCOc1cc(F)c(N)cc1OCc1c(F)cccc1OC] | (CDCl3) 1.34 (3H, t, J = 7.0 Hz), 3.1-3.7 (2H, br), 3.84 (3H, s), 3.96 (2H, q, J = 7.0 Hz), 5.05-5.15 (2H, m), 6.53 (1H, d, J = 9.0 Hz), 6.64 (1H, d, J = 11.9 Hz), 6.65-6.75 (2H, m), 7.2-7.3 (1H, m) |
| 305 | 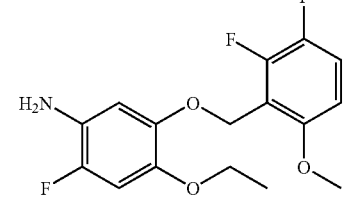 | (CDCl3) 1.35 (3H, t, J = 7.0 Hz), 3.1-3.7 (2H, br), 3.82 (3H, s), 3.96 (2H, q, J = 7.0 Hz), 5.05-5.15 (2H, m), 6.52 (1H, d, J = 9.0 Hz), 6.55-6.7 (2H, m), 7.05-7.15 (1H, m) |

TABLE 41

| Ref No. | Strc | (Solv) ¹H-NMR δ ppm: |
|---|---|---|
| 306 | | (CDCl3) 3.55 (2H, brs), 3.83 (3H s), 5.05-5.15 (2H, m), 6.5-6.65 (2H, m), 6.75-6.85 (1H, m), 7.05-7.2 (1H, m) |
| 307 | | (CDCl3) 3.5-3.8 (2H, br), 3.84 (3H, s), 5.05-5.15 (2H, m), 6.5-6.65 (2H, m), 7.0 (1H, d, J = 10.4 Hz), 7.05-7.2 (1H, m) |
| 308 | | (CDCl3) 3.72 (2H, brs), 3.84 (3H, s), 5.05-5.15 (2H, m), 6.5-6.65 (2H, m), 7.05-7.2 (2H, m) |
| 309 | | (CDCl3) 3.85 (3H, s), 4.23 (2H, brs), 5.1-5.15 (2H, m), 6.47 (1H, d, J = 7.2 Hz), 6.6-6.65 (1H, m), 7.1-7.2 (2H, m) |
| 310 | | (CDCl3) 3.53 (2H, brs), 3.83 (3H, s), 5.1-5.15 (2H, m), 6.15-6.25 (1H, m), 6.45-6.5 (1H, m), 6.55-6.65 (1H, m), 6.8-6.9 (1H, m), 7.05-7.2 (1H, m) |
| 311 | | (CDCl3) 3.1-3.7 (2H, br), 3.76 (3H, s), 5.1 (2H, s), 6.52 (1H, d, J = 8.7 Hz), 6.64 (1H, d, J = 12.0 Hz), 6.85-6.95 (2H, m), 7.25-7.35 (1H, m) |
| 312 | | (CDCl3) 3.77 (3H, s), 5.25 (2H, s), 6.55 (1H, d, J = 8.9 Hz), 6.66 (1H, d, J = 12.0 Hz), 7.15-7.25 (1H, m), 7.3-7.4 (2H, m) |

TABLE 42

| Ref No. | Strc | (Solv) ¹H-NMR δ ppm: |
|---|---|---|
| 313 | | (CDCl3) 3.55 (2H, brs), 5.12 (2H, s), 6.45-6.6 (1H, m), 6.75-6.85 (1H, m), 6.85-7.0 (2H, m), 7.25-7.4 (1H, m) |
| 314 | | (CDCl3) 3.57 (2H, brs), 5.28 (2H, s), 6.5-6.6 (1H, m), 6.75-6.85 (1H, m), 7.2-7.3 (1H, m), 7.3-7.4 (2H, m) |
| 315 | | (CDCl3) 3.1-3.7 (2H, br), 3.76 (3H, s), 3.82 (3H, s), 5.1-5.15 (2H, m), 6.27 (1H, dd, J = 8.3 Hz, 2.6 Hz), 6.48 (1H, d, J = 2.6 Hz), 6.55-6.65 (1H, m), 6.73 (1H, d, J = 8.3 Hz), 7.05-7.15 (1H, m) |
| 316 | | (CDCl3) 3.43 (3H, s), 3.7-3.8 (5H, m), 4.1-4.15 (2H, m), 5.1-5.2 (2H, m), 6.55-6.7 (3H, m), 7.0-7.15 (1H, m) |
| 317 | | (CDCl3) 1.21 (3H, t, J = 6.8 Hz), 3.2-3.85 (9H, m), 4.05-4.2 (2H, m), 5.1-5.2 (2H, m), 6.55-6.7 (3H, m), 7.0-7.15 (1H, m) |
| 318 | | (CDCl3) 3.44 (3H, s), 3.5-3.8 (4H, m), 4.05-4.15 (2H, m), 5.15-5.2 (2H, m), 6.55-6.65 (1H, m), 6.65-6.85 (2H, m), 7.0-7.15 (1H, m) |
| 319 | | (CDCl3) 1.21 (3H, t, J = 7.0 Hz), 3.59 (2H, q, J = 7.0 Hz), 3.75-3.85 (2H, m), 4.1-4.15 (2H, m), 5.15-5.2 (2H, m), 6.55-6.7 (2H, m), 6.7-6.8 (1H, m), 7.05-7.15 (1H, m) |

TABLE 42-continued

| Ref No. | Strc | (Solv) $^1$H-NMR δ ppm: |
|---|---|---|
| 320 | | (CDCl3) 0.04 (6H, s), 0.87 (9H, s), 3.92 (2H, t, J = 5.1 Hz), 4.05 (2H, t, J = 5.1 Hz), 5.0-5.1 (2H, m), 6.25-6.35 (1H, m), 6.4-6.45 (1H, m), 6.6-6.7 (1H, m), 6.8-6.9 (1H, m), 7.0-7.15 (1H, m) |

TABLE 43

| Ref No. | Strc | (Solv) $^1$H-NMR δ ppm: |
|---|---|---|
| 321 | | (CDCl3) 0.01 (6H, s), 0.86 (9H, s), 1.9-2.0 (2H, m), 3.74 (2H, t, J = 6.1 Hz), 4.07 (2H, t, J = 6.0 Hz), 5.0-5.05 (2H, m), 6.25-6.35 (1H, m), 6.35-6.45 (1H, m), 6.55-6.65 (1H, m), 6.8-6.95 (1H, m), 7.05-7.15 (1H, m) |
| 322 | | (CDCl3) 1.85-1.95 (1H, m), 2.21 (1H, s), 2.3-2.5 (3H, m), 2.65-2.8 (2H, m), 6.8-6.9 (2H, m), 7.15-7.25 (1H, m) |
| 323 | | (CDCl3) 1.85-2.0 (1H, m), 2.2-2.35 (1H, m), 2.7-2.85 (4H, m), 3.58 (2H, brs), 6.05-6.15 (1H, m), 6.2-6.3 (1H, m), 6.7-6.85 (3H, m), 7.15-7.25 (1H, m) |
| 324 | | (CDCl3) 1.8-1.85 (6H, m), 3.2-3.9 (2H, br), 6.0-6.05 (1H, m), 6.2-6.25 (1H, m), 6.65-6.75 (1H, m), 6.8-6.9 (2H, m), 7.15-7.3 (1H, m) |
| 325 | | (CDCl3) 3.88 (3H, s), 5.5-5.6 (1H, m), 6.5-6.7 (2H, m) |

TABLE 43-continued

| Ref No. | Strc | (Solv) $^1$H-NMR δ ppm: |
|---|---|---|
| 326 | | (CDCl3) 3.5 (3H, s), 3.65-3.75 (2H, m), 4.1-4.15 (2H, m), 6.5-6.65 (1H, m), 6.65-6.7 (1H, m), 7.38 (1H, s) |
| 327 | | (CDCl3) 4.81 (2H, s), 7.0-7.1 (1H, m), 8.25-8.35 (1H, m) |
| 328 | | (CDCl3) 3.95 (3H, s), 4.69 (2H, s), 6.72 (1H, d, J = 12.5 Hz), 8.17 (1H, d, J = 8.7 Hz) |

TABLE 44

| Ref No. | Strc | (Solv) $^1$H-NMR δ ppm: |
|---|---|---|
| 329 | | (CDCl3) 3.59 (2H, brs), 3.83 (3H, s), 5.08 (2H, s), 6.55-6.6 (1H, m), 6.7-6.9 (2H, m), 6.97 (1H, dd, J = 9.8 Hz, 6.8 Hz) |
| 330 | | (CDCl3) 3.42 (2H, brs), 3.73 (3H, s), 3.82 (3H, s), 5.07 (2H, s), 6.5-6.65 (2H, m), 6.75-6.85 (1H, m), 6.96 (1H, d, J = 9.8 Hz) |
| 331 | | (CDCl3) 3.45 (3H, s), 3.7-3.8 (2H, m), 4.05-4.15 (2H, m), 5.04 (2H, s), 6.55-6.65 (1H, m), 6.7-6.85 (2H, m), 6.85-6.95 (1H, m), 7.0-7.05 (1H, m) |

TABLE 44-continued

| Ref No. | Strc | (Solv) ¹H-NMR δ ppm: |
|---|---|---|
| 332 | (structure) | (CDCl3) 3.44 (3H, s), 3.7-3.75 (2H, m), 3.99 (2H, brs), 4.05-4.15 (2H, m), 6.35-6.55 (2H, m) |
| 333 | (structure) | (CDCl3) 3.8-3.95 (5H, m), 6.4-6.5 (2H, m) |
| 334 | (structure) | (CDCl3) 2.75-2.85 (3H, m), 3.39 (2H, brs), 3.65 (3H, s), 4.17 (2H, s), 6.56 (1H, d, J = 12.9 Hz), 6.75-6.95 (4H, m) |
| 335 | (structure) | (CDCl3) 2.78 (3H, s), 3.41 (2H, brs), 3.67 (3H, s), 4.22 (2H, s), 6.56 (1H, d, J = 12.8 Hz), 6.95-7.0 (1H, m), 7.13 (1H, d, J = 10.4 Hz), 7.25-7.3 (2H, m) |
| 336 | (structure) | (CDCl3) 2.7-2.8 (3H, m), 3.65 (2H, brs), 3.86 (3H, s), 4.05 (2H, s), 6.6-6.7 (3H, m), 6.8-6.9 (2H, m), 6.95-7.05 (1H, m) |

TABLE 45

| Ref No. | Strc | (Solv) ¹H-NMR δ ppm: |
|---|---|---|
| 337 | (structure) | (CDCl3) 2.75-2.8 (3H, m), 3.68 (2H, brs), 4.1 (2H, s), 6.6-6.7 (1H, m), 6.75-7.0 (5H, m) |
| 338 | (structure) | (CDCl3) 2.73 (3H, s), 3.2-4.0 (2H, br), 4.19 (2H, s), 6.75-6.85 (1H, m), 6.85-6.95 (1H, m), 6.95-7.05 (2H, m), 7.25-7.3 (2H, m) |

TABLE 45-continued

| Ref No. | Strc | (Solv) ¹H-NMR δ ppm: |
|---|---|---|
| 339 | | (CDCl3) 2.75-2.8 (3H, m), 3.67 (2H, brs), 3.83 (3H, s), 4.08 (2H, s), 6.45-6.55 (1H, m), 6.6-6.7 (1H, m), 6.75-6.95 (3H, m) |
| 340 | | (CDCl3) 2.75-2.8 (3H, m), 3.42 (3H, s), 3.6-3.85 (4H, m), 4.05-4.15 (4H, m), 6.5-6.55 (1H, m), 6.6-6.7 (1H, m), 6.7-6.85 (1H, m), 6.85-7.0 (2H, m) |
| 341 | | (CDCl3) 1.31 (3H, t, J = 7.0 Hz), 3.67 (2H, q, J = 7.0 Hz), 3.7-3.75 (2H, m), 4.1-4.15 (2H, m), 6.5-6.65 (1H, m), 6.65-6.75 (1H, m), 7.75 (1H, s) |
| 342 | | (CDCl3) 0.15 (6H, s), 0.95 (9H, s), 3.85-3.95 (2H, m), 4.0-4.1 (2H, m), 6.5-6.65 (1H, m), 6.65-6.75 (1H, m), 7.36 (1H, s) |
| 343 | | (CDCl3) 1.24 (3H, t, J = 7.0 Hz), 3.6 (2H, q, J = 7.0 Hz), 3.75-3.85 (2H, m), 4.05-4.15 (2H, m), 5.05 (2H, s), 6.55-6.65 (1H, m), 6.7-6.85 (2H, m), 6.85-6.95 (1H, m), 6.95-7.05 (1H, m) |
| 344 | | (CDCl3) 0.09 (6H, s), 0.9 (9H, s), 3.95-4.0 (2H, m), 4.0-4.1 (2H, m), 5.03 (2H, s), 6.55-6.65 (1H, m), 6.7-6.85 (2H, m), 6.85-7.0 (2H, m) |

TABLE 46

| Ref No. | Strc | (Solv) ¹H-NMR δ ppm: |
|---|---|---|
| 345 | | (DMSO-d6) 3.97 (3H, s), 7.4 (1H, d, J = 13.9 Hz), 8.47 (1H, d, J = 8.8 Hz), 13.0-13.7 (1H, br) |
| 346 | | (CDCl3) 2.75-2.85 (3H, m), 3.39 (2H, brs), 3.65 (3H, s), 3.81 (3H, s), 4.16 (2H, s), 6.45-6.55 (1H, m), 6.56 (1H, d, J = 12.7 Hz), 6.75-6.85 (1H, m), 6.89 (1H, d, J = 10.3 Hz) |

TABLE 47

| Ex No. | Strc | (Solv) ¹H-NMR δ ppm: |
|---|---|---|
| 1 | | (CDCl₃) 1.6-1.75 (2H, m), 2.45-2.6 (2H, m), 3.7-3.85 (2H, m), 3.94 (3H, s), 6.82 (1H, s), 7.0-7.15 (2H, m), 7.15-7.25 (1H, m), 7.49 (1H, dd, J = 8.4 Hz, 2.0 Hz), 7.54 (1H, d, J = 8.4 Hz), 7.6 (1H, d, J = 2.0 Hz), 7.7-7.8 (1H, m), 9.47 (1H, s) |
| 2 | | (CDCl₃) 1.6-1.75 (2H, m), 2.4-2.6 (2H, m), 3.7-3.8 (1H, m), 3.8-3.9 (1H, m), 6.82 (1H, d, J = 5.2 Hz), 7.0-7.15 (2H, m), 7.15-7.25 (1H, m), 7.46 (1H, dd, J = 8.3 Hz, 2.1 Hz), 7.54 (1H, d, J = 8.3 Hz), 7.65 (1H, d, J = 2.1 Hz), 7.7-7.8 (2H, m), 9.65 (1H, s) |
| 3 | | (CDCl₃) 1.6-1.75 (2H, m), 2.4-2.6 (2H, m), 3.7-3.9 (2H, m), 6.89 (1H, d, J = 5.8 Hz), 7.0-7.15 (2H, m), 7.15-7.25 (1H, m), 7.32 (1H, d, J = 5.8 Hz), 7.46 (1H, dd, J = 8.4 Hz, 2.1 Hz), 7.55 (1H, d, J = 8.4 Hz), 7.64 (1H, d, J = 2.1 Hz), 7.75-7.8 (1H, m), 9.54 (1H, brs) |
| 4 | | (CDCl₃) 1.6-1.8 (2H, m), 2.4-2.6 (2H, m), 3.65-3.8 (4H, m), 3.8-3.9 (1H, m), 7.0-7.15 (2H, m), 7.15-7.25 (1H, m), 7.49 (1H, dd, J = 8.4 Hz, 1.9 Hz), 7.55 (1H, d, J = 8.4 Hz), 7.59 (1H, d, J = 1.9 Hz), 7.75 (1H, d, J = 7.5 Hz), 7.91 (1H, s) |

TABLE 47-continued

| Ex No. | Strc | (Solv) ¹H-NMR δ ppm: |
|---|---|---|
| 5 | | (CDCl$_3$) 1.95-2.05 (2H, m), 2.75-2.85 (2H, m), 3.3-3.35 (2H, m), 4.48 (2H, s), 6.5 (1H, d, J = 8.4 Hz), 6.55-6.65 (1H, m), 6.81 (1H, d, J = 5.6 Hz), 6.9-7.0 (2H, m), 7.2-7.35 (3H, m), 7.51 (1H, d, J = 8.4 Hz), 9.94 (1H, brs) |
| 6 | | (CDCl$_3$) 1.38 (3H, t, J = 7.1 Hz), 1.6-1.75 (2H, m), 2.4-2.6 (2H, m), 3.7-3.85 (2H, m), 4.41 (2H, q, J = 7.1 Hz), 6.82 (1H, s), 7.0-7.15 (2H, m), 7.15-7.25 (1H, m), 7.47 (1H, dd, J = 8.5 Hz, 2.2 Hz), 7.53 (1H, d, J = 8.5 Hz), 7.6 (1H, d, J = 2.2 Hz), 7.7-7.8 (1H, m), 9.11 (1H, s) |
| 7 | | (CDCl$_3$) 1.2-1.35 (2H, m), 1.75-1.9 (2H, m), 2.4-2.55 (2H, m), 3.2-4.3 (2H, br), 6.87 (1H, d, J = 5.3 Hz), 7.1-7.2 (2H, m), 7.25-7.35 (2H, m), 7.63 (1H, d, J = 8.5 Hz), 7.69 (1H, dd, J = 8.5 Hz, 1.9 Hz), 7.78 (1H, d, J = 1.9 Hz), 9.5-10.2 (1H, br) |

TABLE 48

| Ex No. | Strc | (Solv) ¹H-NMR δ ppm: |
|---|---|---|
| 8 | | (CDCl$_3$) 3.2 (3H, s), 6.87 (1H, d, J = 5.4 Hz), 7.1-7.15 (2H, m), 7.2-7.35 (4H, m), 7.54 (1H, dd, J = 8.4 Hz, 2.0 Hz), 7.6 (1H, d, J = 2.0 Hz), 7.64 (1H, d, J = 8.4 Hz), 9.5-11.0 (1H, br) |
| 9 | | (CDCl$_3$) 0.9-1.8 (10H, m), 2.77 (3H, s), 3.7-3.8 (1H, m), 6.87 (1H, d, J = 5.7 Hz), 7.3 (1H, d, J = 5.7 Hz), 7.69 (1H, d, J = 8.1 Hz), 7.8-7.9 (2H, m), 9.5-10.5 (1H, br) |
| 10 | | (DMSO-d$_6$) 3.26 (3H, s), 7.19 (1H, d, J = 5.7 Hz), 7.22 (1H, d, J = 5.7 Hz), 7.25-7.3 (1H, m), 7.45-7.55 (1H, m), 7.62 (1H, dd, J = 8.5 Hz, 2.1 Hz), 7.8-7.9 (2H, m), 8.04 (1H, d, J = 2.1 Hz), 8.3-8.4 (1H, m), 12.54 (1H, s) |

TABLE 48-continued
| Ex No. | Strc | (Solv) ¹H-NMR δ ppm: |
|---|---|---|
| 11 | 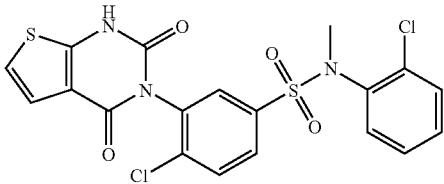 [SMILES: CN(c1ccccc1Cl)S(=O)(=O)c1ccc(Cl)c(-n2c(=O)[nH]c3sccc3c2=O)c1] | (DMSO-d$_6$) 3.16 (3H, s), 7.05 (1H, d, J = 7.8 Hz), 7.15-7.45 (4H, m), 7.5-7.6 (1H, m), 7.75-8.1 (3H, m), 12.55 (1H, s) |
| 12 | 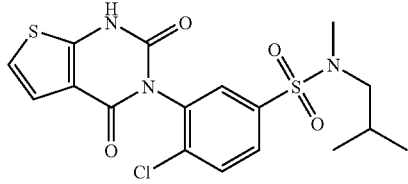 [SMILES: CC(C)CN(C)S(=O)(=O)c1ccc(Cl)c(-n2c(=O)[nH]c3sccc3c2=O)c1] | (DMSO-d$_6$) 0.8-0.9 (6H, m), 1.75-1.95 (1H, m), 2.6-2.8 (5H, m), 7.15-7.25 (2H, m), 7.8-7.95 (2H, m), 8.0-8.1 (1H, m), 12.53 (1H, s) |
| 13 | 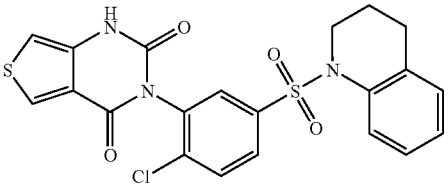 [SMILES: O=c1[nH]c2cscc2c(=O)n1-c1cc(S(=O)(=O)N2CCCc3ccccc32)ccc1Cl] | (DMSO-d$_6$) 1.6-1.75 (2H, m), 2.4-2.55 (2H, m), 3.7-3.85 (2H, m), 6.95 (1H, d, J = 3.1 Hz), 7.05-7.25 (3H, m), 7.52 (1H, dd, J = 8.5 Hz, 2.0 Hz), 7.56 (1H, d, J = 8.1 Hz), 7.78 (1H, d, J = 8.5 Hz), 8.04 (1H, d, J = 2.0 Hz), 8.52 (1H, d, J = 3.1 Hz), 11.53 (1H, s) |
| 14 | 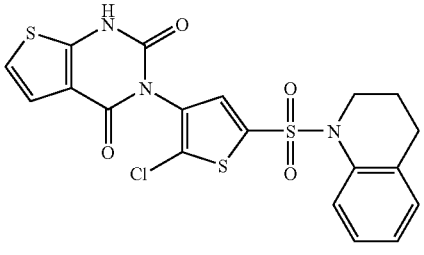 [SMILES: O=c1[nH]c2sccc2c(=O)n1-c1cc(S(=O)(=O)N2CCCc3ccccc32)sc1Cl] | (CDCl$_3$) 1.75-1.9 (2H, m), 2.55-2.7 (2H, m), 3.75-3.95 (2H, m), 6.9 (1H, d, J = 5.5 Hz), 7.05-7.25 (4H, m), 7.29 (1H, d, J = 5.5 Hz), 7.74 (1H, d, J = 8.2 Hz), 10.17 (1H, s) |
TABLE 49
| Ex No. | Strc | (Solv) ¹H-NMR δ ppm: |
|---|---|---|
| 15 | 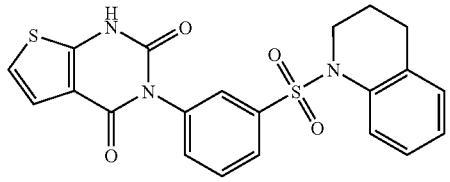 [SMILES: O=c1[nH]c2sccc2c(=O)n1-c1cccc(S(=O)(=O)N2CCCc3ccccc32)c1] | (DMSO-d$_6$) 1.6-1.7 (2H, m), 2.4-2.5 (2H, m), 3.7-3.8 (2H, m), 7.05-7.1 (2H, m), 7.1-7.25 (3H, m), 7.45-7.65 (4H, m), 7.74 (1H, d, J = 1.0 Hz), 12.37 (1H, s) |
| 16 | 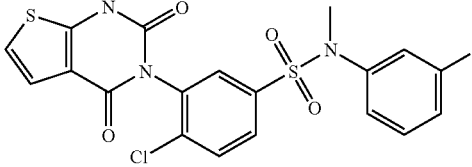 | (DMSO-d$_6$) 3.18 (3H, s), 7.0-7.1 (1H, m), 7.15-7.25 (3H, m), 7.35-7.4 (2H, m), 7.6 (1H, dd, J = 8.5 Hz, 2.3 Hz), 7.87 (1H, d, J = 8.5 Hz), 7.96 (1H, d, J = 2.3 Hz), 12.54 (1H, s) |
| 17 | 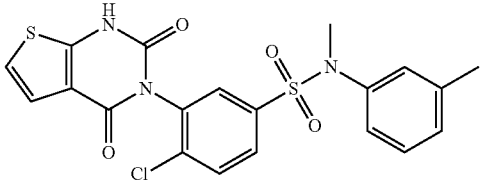 [SMILES: Cc1cccc(N(C)S(=O)(=O)c2ccc(Cl)c(-n3c(=O)[nH]c4sccc4c3=O)c2)c1] | (DMSO-d$_6$) 2.26 (3H, s), 3.15 (3H, s), 6.8-6.95 (2H, m), 7.05-7.25 (4H, m), 7.6 (1H, dd, J = 8.4 Hz, 2.3 Hz), 7.8-7.9 (2H, m), 12.54 (1H, s) |

TABLE 49-continued

| Ex No. | Strc | (Solv) ¹H-NMR δ ppm: |
|---|---|---|
| 18 | | (DMSO-d$_6$) 5.1 (2H, s), 7.14 (1H, dd, J = 9.0 Hz, 2.9 Hz), 7.18 (1H, d, J = 5.6 Hz), 7.22 (1H, d, J = 5.6 Hz), 7.25 (1H, d, J = 2.9 Hz), 7.3-7.5 (5H, m), 7.53 (1H, d, J = 9.0 Hz), 12.48 (1H, s) |
| 19 | | (DMSO-d$_6$) 1.85-2.0 (2H, m), 2.7-2.8 (2H, m), 3.3-3.4 (2H, m), 3.81 (3H, s), 4.5 (2H, s), 6.4-6.5 (2H, m), 6.85-6.95 (2H, m), 7.2 (1H, s), 7.31 (1H, dd, J = 8.2 Hz, 2.1 Hz), 7.4 (1H, d, J = 2.1 Hz), 7.56 (1H, d, J = 8.2 Hz), 11.61 (1H, s) |
| 20 | | (DMSO-d$_6$) 7.05-7.3 (7H, m), 7.75-7.9 (2H, m), 7.95-8.05 (1H, m), 10.48 (1H, s), 12.56 (1H, s) |
| 21 | | (DMSO-d$_6$) 7.0-7.3 (7H, m), 7.55-7.7 (2H, m), 7.75-7.85 (2H, m), 10.4 (1H, s), 12.4 (1H, s) |

TABLE 50

| Ex No. | Strc | (Solv) ¹H-NMR δ ppm: |
|---|---|---|
| 22 | | (DMSO-d$_6$) 1.6-1.7 (2H, m), 2.4-2.55 (2H, m), 3.7-3.8 (2H, m), 7.05-7.25 (3H, m), 7.39 (1H, s), 7.55 (1H, d, J = 8.2 Hz), 7.6 (1H, dd, J = 8.5 Hz, 2.4 Hz), 7.83 (1H, d, J = 8.5 Hz), 8.09 (1H, d, J = 2.4 Hz), 12.03 (1H, s), 14.23 (1H, s) |
| 23 | | (DMSO-d$_6$) 5.11 (2H, s), 7.19 (1H, dd, J = 9.0 Hz, 2.9 Hz), 7.3-7.45 (5H, m), 7.45-7.5 (2H, m), 7.57 (1H, d, J = 9.0 Hz), 12.04 (1H, s), 14.45 (1H, brs) |
| 24 | | (DMSO-d$_6$) 1.85-2.0 (2H, m), 2.7-2.8 (2H, m), 3.3-3.4 (2H, m), 4.52 (2H, s), 6.44 (1H, d, J = 8.2 Hz), 6.45-6.5 (1H, m), 6.85-6.95 (2H, m), 7.36 (1H, d, J = 8.2 Hz), 7.38 (1H, s), 7.48 (1H, d, J = 2.1 Hz), 7.61 (1H, d, J = 8.2 Hz), 12.0 (1H, s), 14.45 (1H, brs) |

TABLE 50-continued

| Ex No. | Strc | (Solv) $^1$H-NMR δ ppm: |
|---|---|---|
| 25 | | (DMSO-d$_6$) 2.33 (3H, s), 5.09 (2H, s), 7.15-7.3 (4H, m), 7.35 (1H, d, J = 2.7 Hz), 7.41 (1H, s), 7.43 (1H, d, J = 7.7 Hz), 7.58 (1H, d, J = 9.0 Hz), 12.04 (1H, s), 14.44 (1H, s) |
| 26 | | (DMSO-d$_6$) 2.32 (3H, s), 5.07 (2H, s), 7.1-7.35 (6H, m), 7.41 (1H, s), 7.57 (1H, d, J = 8.7 Hz), 12.04 (1H, s), 14.45 (1H, brs) |
| 27 | | (DMSO-d$_6$) 5.24 (2H, s), 7.2 (1H, dd, J = 8.8 Hz, 3.0 Hz), 7.35 (1H, d, J = 3.0 Hz), 7.41 (1H, s), 7.59 (1H, d, J = 8.8 Hz), 7.69 (2H, d, J = 8.2 Hz), 7.78 (2H, d, J = 8.2 Hz), 12.04 (1H, s), 14.43 (1H, s) |
| 28 | | (DMSO-d$_6$) 1.5-1.6 (3H, m), 5.45-5.55 (1H, m), 7.0-7.1 (1H, m), 7.23 (1H, dd, J = 6.1 Hz, 2.9 Hz), 7.25-7.5 (7H, m), 11.95-12.1 (1H, m), 14.42 (1H, s) |

TABLE 51

| Ex No. | Strc | (Solv) $^1$H-NMR δ ppm: |
|---|---|---|
| 29 | | (DMSO-d$_6$) 2.85-3.0 (4H, m), 7.15-7.35 (8H, m), 7.38 (1H, s), 7.41 (1H, t, J = 7.7 Hz), 11.92 (1H, s), 14.94 (1H, brs) |
| 30 | | (DMSO-d$_6$) 1.6-1.7 (2H, m), 2.4-2.55 (2H, m), 3.7-3.85 (2H, m), 7.0-7.2 (3H, m), 7.24 (1H, s), 7.56 (1H, d, J = 8.3 Hz), 7.59 (1H, dd, J = 8.5 Hz, 2.1 Hz), 7.81 (1H, d, J = 8.5 Hz), 8.05-8.15 (2H, m), 9.55 (1H, s), 11.81 (1H, s) |
| 31 | | (CDCl$_3$) 1.65-1.75 (2H, m), 2.4-2.6 (2H, m), 2.99 (3H, d, J = 4.7 Hz), 3.7-3.9 (2H, m), 6.91 (1H, s), 6.95-7.15 (2H, m), 7.15-7.25 (1H, m), 7.5-7.65 (3H, m), 7.7-7.8 (1H, m), 8.91 (1H, s), 10.05-10.15 (1H, m) |

TABLE 51-continued

| Ex No. | Strc | (Solv) $^1$H-NMR δ ppm: |
|---|---|---|
| 32 | | (CDCl$_3$) 1.55 (6H, s), 1.6-1.75 (2H, m), 2.4-2.55 (2H, m), 3.7-3.9 (2H, m), 6.04 (1H, s), 6.49 (1H, s), 7.0-7.15 (2H, m), 7.15-7.25 (2H, m), 7.5-7.55 (1H, m), 7.55-7.6 (2H, m), 7.76 (1H, d, J = 8.3 Hz), 8.41 (1H, s) |
| 33 | | (DMSO-d$_6$) 1.6-1.75 (2H, m), 2.45-2.55 (2H, m), 3.7-3.85 (2H, m), 4.95-5.05 (2H, m), 5.99 (1H, t, J = 5.5 Hz), 6.73 (1H, s), 7.05-7.15 (2H, m), 7.15-7.25 (1H, m), 7.5-7.6 (2H, m), 7.78 (1H, d, J = 8.5 Hz), 7.97 (1H, d, J = 2.3 Hz), 11.41 (1H, s) |
| 34 | | (DMSO-d$_6$) 1.6-1.75 (2H, m), 2.45-2.55 (2H, m), 3.7-3.8 (2H, m), 7.05-7.15 (2H, m), 7.15-7.25 (1H, m), 7.5-7.6 (3H, m), 7.82 (1H, d, J = 8.5 Hz), 8.09 (1H, d, J = 2.1 Hz), 10.5-10.55 (1H, m), 11.88 (1H, s) |

TABLE 52

| Ex No. | Strc | (Solv) $^1$H-NMR δ ppm: |
|---|---|---|
| 35 | | (DMSO-d$_6$) 1.64 (3H, d, J = 6.5 Hz), 3.8-3.9 (6H, m), 5.79 (1H, q, J = 6.5 Hz), 6.7-6.8 (1H, m), 6.85-6.95 (2H, m), 6.95-7.05 (1H, m), 7.15-7.25 (2H, m), 7.25-7.35 (1H, m), 11.63 (1H, s) |
| 36 | | (DMSO-d$_6$) 3.83 (3H, s), 3.85 (3H, s), 4.99 (2H, s), 6.85-7.0 (2H, m), 7.1-7.2 (2H, m), 7.21 (1H, s), 7.25-7.35 (1H, m), 7.4-7.5 (1H, m), 11.68 (1H, s) |
| 37 | | (DMSO-d$_6$) 3.75 (3H, s), 3.85 (3H, s), 4.99 (2H, s), 6.85-7.0 (2H, m), 7.1-7.2 (2H, m), 7.25-7.35 (1H, m), 7.4-7.5 (1H, m), 7.65 (1H, s), 12.64 (1H, s) |
| 38 | | (DMSO-d$_6$) 1.54 (3H, d, J = 6.3 Hz), 3.8-3.85 (3H, m), 5.46 (1H, q, J = 6.3 Hz), 6.9-7.0 (1H, m), 7.05-7.1 (1H, m), 7.15-7.45 (7H, m), 11.63 (1H, s) |

TABLE 52-continued

| Ex No. | Strc | (Solv) ¹H-NMR δ ppm: |
|---|---|---|
| 39 | | (DMSO-d₆) 1.7 (3H, d, J = 6.8 Hz), 3.8-3.85 (3H, m), 5.7-5.8 (1H, m), 6.9-7.0 (1H, m), 7.05-7.15 (3H, m), 7.15-7.3 (2H, m), 7.35-7.5 (1H, m), 11.63 (1H, s) |
| 40 | | (DMSO-d₆) 1.71 (3H, d, J = 6.6 Hz), 3.82 (3H, s), 5.95-6.05 (1H, m), 6.8-6.9 (1H, m), 7.0-7.05 (1H, m), 7.15-7.3 (2H, m), 7.3-7.4 (1H, m), 7.45-7.5 (2H, m), 11.63 (1H, s) |
| 41 | | (DMSO-d₆) 1.58 (3H, d, J = 6.3 Hz), 3.8-3.85 (3H, m), 5.66 (1H, q, J = 6.3 Hz), 6.9-7.0 (1H, m), 7.05-7.15 (1H, m), 7.15-7.3 (4H, m), 7.3-7.4 (1H, m), 7.45-7.55 (1H, m), 11.63 (1H, s) |
| 42 | | (DMSO-d₆) 1.69 (3H, d, J = 6.4 Hz), 3.7-3.75 (3H, m), 5.7-5.8 (1H, m), 6.9-7.0 (1H, m), 7.05-7.15 (3H, m), 7.2-7.3 (1H, m), 7.35-7.5 (1H, m), 7.6-7.65 (1H, m), 12.59 (1H, s) |

TABLE 53

| Ex No. | Strc | (Solv) ¹H-NMR δ ppm: |
|---|---|---|
| 43 | | (DMSO-d₆) 1.71 (3H, d, J = 6.6 Hz), 3.74 (3H, s), 5.95-6.05 (1H, m), 6.8-6.9 (1H, m), 6.95-7.05 (1H, m), 7.2-7.3 (1H, m), 7.3-7.4 (1H, m), 7.4-7.5 (2H, m), 7.6-7.65 (1H, m), 12.59 (1H, s) |
| 44 | | (DMSO-d₆) 1.64 (3H, d, J = 6.7 Hz), 3.7-3.8 (3H, m), 3.8-3.9 (3H, m), 5.75-5.85 (1H, m), 6.7-6.8 (1H, m), 6.85-6.95 (2H, m), 6.95-7.05 (1H, m), 7.15-7.25 (1H, m), 7.25-7.35 (1H, m), 7.63 (1H, s), 12.58 (1H, s) |
| 45 | | (DMSO-d₆) 1.51 (3H, d, J = 6.3 Hz), 3.8-3.9 (6H, m), 5.6-5.7 (1H, m), 6.8-6.9 (1H, m), 6.9-7.0 (1H, m), 7.0-7.1 (2H, m), 7.15-7.3 (3H, m), 7.3-7.4 (1H, m), 11.6 (1H, s) |

TABLE 53-continued

| Ex No. | Strc | (Solv) $^1$H-NMR δ ppm: |
|---|---|---|
| 46 | | (DMSO-d$_6$) 1.57 (3H, d, J = 6.3 Hz), 3.8-3.85 3H, m), 5.6-5.7 (1H, m), 6.8-6.9 (1H, m), 7.05-7.1 (1H, m), 7.15-7.3 (2H, m), 7.3-7.4 m), 7.45-7.5 (1H, m), 7.5-7.6 (1H, m), 11.61 (1H,s) |
| 47 | | (DMSO-d$_6$) 1.54 (3H, d, J = 6.2 Hz), 3.75-3.85 (3H, m), 5.45-5.55 (1H, m), 6.95-7.05 (1H, m), 7.05-7.15 (1H, m), 7.15-7.25 (2H, m), 7.3-7.45 (3H, m), 7.49 (1H, s), 11.61 (1H, s) |
| 48 | | (DMSO-d$_6$) 1.65 (3H, d, J = 6.5 Hz), 3.8-3.9 3H, m), 5.75-5.85 (1H, m), 6.7-6.8 (1H, m), 6.85-7.0 (2H, m), 7.05-7.1 (1H, m), 7.2-7.35 (2H, m), 7.37 (1H, d, J = 3.6 Hz), 12.01 (1H, s), 14.43 (1H, s) |
| 49 | | (DMSO-d$_6$) 3.85 (3H, s), 5.0 (2H, s), 6.88 (1H, t, J = 8.7 Hz), 6.95 (1H, d, J = 8.7 Hz), 7.15-7.25 (2H, m), 7.3-7.5 (3H, m), 12.06 (1H, s), 14.43 (1H, s) |
| 50 | | (DMSO-d$_6$) 3.85 (3H, s), 5.0 (2H, s), 6.88 (1H, t, J = 8.6 Hz), 6.95 (1H, d, J = 8.6 Hz), 7.1-7.2 (1H, m), 7.2-7.25 (1H, m), 7.3-7.4 (1H, m), 7.4-7.5 (1H, m), 7.94 (1H, s), 13.04 (1H, s), 13.93 (1H, s) |

TABLE 54

| Ex No. | Strc | (Solv) $^1$H-NMR δ ppm: |
|---|---|---|
| 51 | | (DMSO-d$_6$) 1.5-1.6 (3H, m), 5.4-5.5 (1H, m), 6.95-7.05 (1H, m), 7.1-7.2 (1H, m), 7.2-7.4 (5H, m), 7.4-7.45 (2H, m), 11.95-12.05 (1H, m), 14.42 (1H, s) |
| 52 | | (DMSO-d$_6$) 1.7 (3H, d, J = 6.6 Hz), 5.76 (1H, q, J = 6.6 Hz), 7.0-7.2 (4H, m), 7.25-7.35 (1H, m), 7.35-7.5 (2H, m), 11.95-12.05 (1H, m), 14.42 (1H, s) |

TABLE 54-continued

| Ex No. | Strc | (Solv) ¹H-NMR δ ppm: |
|---|---|---|
| 53 | | (DMSO-d₆) 1.65-1.75 (3H, m), 6.03 (1H, q, J = 6.6 Hz), 6.85-6.95 (1H, m), 7.05-7.15 (1H, m), 7.25-7.4 (3H, m), 7.4-7.5 (2H, m), 11.95-12.05 (1H, m), 14.4 (1H, s) |
| 54 | | (DMSO-d₆) 1.55-1.65 (3H, m), 5.65 (1H, q, J = 6.5 Hz), 7.0-7.05 (1H, m), 7.15-7.25 (3H, m), 7.25-7.4 (3H, m), 7.45-7.55 (1H, m), 11.95-12.05 (1H, m), 14.42 (1H, s) |
| 55 | | (DMSO-d₆) 1.65-1.75 (3H, m), 5.7-5.8 (1H, m), 6.95-7.2 (4H, m), 7.2-7.5 (2H, m), 7.93 (1H, d, J = 7.2 Hz), 12.98 (1H, s), 13.85-14.0 (1H, m) |
| 56 | | (DMSO-d₆) 1.72 (3H, d, J = 6.6 Hz), 6.0-6.1 (1H, m), 6.85-6.95 (1H, m), 7.05-7.1 (1H, m), 7.25-7.4 (2H, m), 7.45-7.5 (2H, m), 7.92 (1H, d, J = 11.1 Hz), 12.98 (1H, brs), 13.85-14.0 (1H, m) |
| 57 | | (DMSO-d₆) 1.65 (3H, d, J = 6.6 Hz), 3.8-3.9 (3H, m), 5.79 (1H, q, J = 6.6 Hz), 6.7-6.8 (1H, m), 6.85-6.95 (2H, m), 7.0-7.1 (1H, m), 7.2-7.35 (2H, m), 7.85-8.0 (1H, m), 12.98 (1H, brs), 13.85-14.05 (1H, m) |
| 58 | | (DMSO-d₆) 1.52 (3H, d, J = 6.3 Hz), 3.8-3.9 (3H, m), 5.64 (1H, q, J = 6.3 Hz), 6.85-7.0 (2H, m), 7.0-7.15 (2H, m), 7.2-7.4 (4H, m), 11.95-12.0 (1H, m), 14.41 (1H, s) |

TABLE 55

| Ex No. | Strc | (Solv) ¹H-NMR δ ppm: |
|---|---|---|
| 59 | | (DMSO-d₆) 1.45-1.65 (3H, m), 5.55-5.8 (1H, m), 6.8-7.7 (8H, m), 11.98 (1H, s), 14.39 (1H, s) |

TABLE 55-continued

| Ex No. | Stro | (Solv) ¹H-NMR δ ppm: |
|---|---|---|
| 60 | | (DMSO-d$_6$) 1.45-1.65 (3H, m), 5.4-5.6 (1H, m), 6.95-7.6 (8H, m), 11.99 (1H, s), 14.39 (1H, s) |
| 61 | | (DMSO-d$_6$) 1.56 (3H, s), 1.57 (3H, s), 3.82 (3H, s), 7.15-7.45 (8H, m), 7.8-7.9 (1H, m), 11.68 (1H, s) |
| 62 | | (DMSO-d$_6$) 1.5-1.6 (6H, m), 3.34 (3H, s), 3.82 (3H, s), 6.84 (1H, d, J = 8.2 Hz), 7.0-7.1 (1H, m), 7.1-7.3 (3H, m), 7.3-7.4 (1H, m), 7.5-7.6 (1H, m), 7.8-7.9 (1H, m), 11.63 (1H, s) |
| 63 | | (DMSO-d$_6$) 1.59 (3H, s), 1.6 (3H, s), 3.82 (3H, s), 7.05-7.15 (1H, m), 7.19 (1H, s), 7.2-7.4 (3H, m), 7.4-7.5 (1H, m), 7.65-7.75 (1H, m), 7.9-8.0 (1H, m), 11.7 (1H, s) |
| 64 | | (DMSO-d$_6$) 1.57 (3H, s), 1.58 (3H, s), 3.82 (3H, s), 7.06 (1H, d, J = 8.4 Hz), 7.1-7.25 (3H, m), 7.25-7.35 (1H, m), 7.35-7.45 (2H, m), 7.8-7.9 (1H, m), 11.68 (1H, s) |
| 65 | | (DMSO-d$_6$) 1.54 (6H, s), 3.31 (3H, s), 3.82 (3H, s), 6.8-6.9 (1H, m), 7.0-7.1 (1H, m), 7.15-7.25 (2H, m), 7.3-7.45 (2H, m), 7.8-7.9 (1H, m), 11.63 (1H, s) |
| 66 | | (DMSO-d$_6$) 1.55-1.6 (6H, m), 7.25-7.45 (8H, m), 7.9-8.0 (1H, m), 12.0 (1H, s), 14.29 (1H, s) |

TABLE 56

| Ex No. | Strc | (Solv) ¹H-NMR δ ppm: |
|---|---|---|
| 67 | | (DMSO-d$_6$) 1.55 (3H, s), 1.56 (3H, s), 3.33 (3H, s), 6.84 (1H, d, J = 8.2 Hz), 7.0-7.1 (1H, m), 7.15-7.3 (2H, m), 7.37 (1H, s), 7.4-7.5 (1H, m), 7.5-7.55 (1H, m), 7.9-7.95 (1H, m), 11.99 (1H, s), 14.35 (1H, s) |
| 68 | | (DMSO-d$_6$) 1.59 (3H, s), 1.62 (3H, s), 7.0-7.1 (1H, m), 7.25-7.4 (4H, m), 7.5-7.6 (1H, m), 7.65-7.75 (1H, m), 7.95-8.05 (1H, m), 12.01 (1H, s), 14.29 (1H, s) |
| 69 | | (DMSO-d$_6$) 1.58 (3H, s), 1.59 (3H, s), 7.0-7.25 (3H, m), 7.3-7.45 (3H, m), 7.45-7.55 (1H, m), 7.9-7.95 (1H, m), 12.02 (1H, s), 14.29 (1H, s) |
| 70 | | (DMSO-d$_6$) 1.54 (3H, s), 1.56 (3H, s), 3.31 (3H, s), 6.8-6.9 (1H, m), 7.0-7.1 (1H, m), 7.26 (1H, t, J = 9.2 Mz), 7.3-7.4 (2H, m), 7.5-7.6 (1H, m), 7.85-7.95 (1H, m), 11.99 (1H, s), 14.36 (1H, s) |
| 71 | | (DMSO-d$_6$) 1.55-1.6 (3H, m), 3.82 (3H, s), 4.6-4.7 (1H, m), 7.1-7.2 (2H, m), 7.2-7.45 (8H, m), 11.49 (1H, s) |
| 72 | | (DMSO-d$_6$) 1.36 (3H, d, J = 7.2 Hz), 3.82 (3H, s), 4.05-4.15 (1H, m), 7.15-7.65 (10H, m), 11.54 (1H, s) |
| 73 | | (DMSO-d$_6$) 1.56 (3H, d, J = 7.1 Hz), 3.83 (3H, s), 4.71 (1H, q, J = 7.1 Hz), 7.18 (1H, s), 7.2-7.35 (5H, m), 7.6-7.7 (3H, m), 7.75-7.8 (1H, m), 11.56 (1H, s) |

TABLE 56-continued

| Ex No. | Strc | (Solv) $^1$H-NMR δ ppm: |
|---|---|---|
| 74 | | (DMSO-d$_6$) 3.82 (3H, s), 4.44 (2H, s), 7.1-7.25 (2H, m), 7.3-7.4 (1H, m), 7.4-7.45 (3H, m), 7.45-7.55 (2H, m), 11.5 (1H, s) |

TABLE 57

| Ex No. | Strc | (Solv) $^1$H-NMR δ ppm: |
|---|---|---|
| 75 | | (DMSO-d$_6$) 1.64 (6H, s), 3.82 (3H, s), 7.05-7.25 (4H, m), 7.25-7.4 (4H, m), 7.4-7.5 (2H, m), 11.45 (1H, s) |
| 76 | | (DMSO-d$_6$) 1.57 (3H, d, J = 6.9 Hz), 3.74 (3H, s), 4.66 (1H, q, J = 6.9 Hz), 7.1-7.15 (1H, m), 7.2-7.45 (8H, m), 7.59 (1H, s), 12.44 (1H, s) |
| 77 | | (DMSO-d$_6$) 1.56 (3H, d, J = 6.8 Hz), 3.76 (3H, s), 4.65-4.75 (1H, m), 7.2-7.35 (5H, m), 7.6-7.75 (4H, m), 7.78 (1H, s), 12.52 (1H, s) |
| 78 | | (DMSO-d$_6$) 3.74 (3H, s), 4.44 (2H, s), 7.15-7.25 (1H, m), 7.3-7.55 (6H, m), 7.59 (1H, s), 12.45 (1H, s) |
| 79 | | (DMSO-d$_6$) 1.58 (3H, d, J = 6.9 Hz), 4.65 (1H, q, J = 6.9 Hz), 7.2-7.5 (10H, m), 11.93 (1H, s), 14.87 (1H, s) |
| 80 | | (DMSO-d$_6$) 1.39 (3H, d, J = 7.3 Hz), 4.05-4.15 (1H, m), 7.2-7.8 (10H, m), 11.95 (1H, s), 14.8 (1H, s) |

TABLE 57-continued

| Ex No. | Strc | (Solv) ¹H-NMR δ ppm: |
|---|---|---|
| 81 | | (DMSO-$d_6$) 1.59 (3H, d, J = 7.7 Hz), 4.72 (1H, q, J = 7.7 Hz), 7.2-7.35 (5H, m), 7.39 (1H, s), 7.65-7.9 (4H, m), 11.96 (1H, s), 14.73 (1H, s) |
| 82 | | (DMSO-$d_6$) 4.44 (2H, s), 7.25-7.45 (3H, m), 7.45-7.55 (5H, m), 11.93 (1H, s), 14.87 (1H, s) |

TABLE 58

| Ex No. | Strc | (Solv) ¹H-NMR δ ppm: |
|---|---|---|
| 83 | | (DMSO-$d_6$) 4.94 (2H, s), 7.35-7.55 (4H, m), 7.75-7.85 (3H, m), 7.95-8.0 (1H, m), 11.96 (1H, s), 14.75 (1H, s) |
| 84 | | (DMSO-$d_6$) 1.65 (6H, s), 7.1-7.5 (10H, m), 11.88 (1H, s), 14.84 (1H, s) |
| 85 | | (DMSO-$d_6$) 1.58 (3H, d, J = 7.0 Hz), 4.66 (1H, q, J = 7.0 Hz), 7.15-7.45 (9H, m), 8.0 (1H, s), 12.94 (1H, s), 14.43 (1H, s) |
| 86 | | (DMSO-$d_6$) 1.58 (3H, d, J = 7.0 Hz), 4.72 (1H, q, J = 7.0 Hz), 7.2-7.35 (5H, m), 7.65-7.8 (3H, m), 7.84 (1H, s), 7.98 (1H, s), 12.96 (1H, s), 14.26 (1H, s) |
| 87 | | (DMSO-$d_6$) 4.45 (2H, s), 7.25-7.3 (1H, m), 7.3-7.4 (1H, m), 7.45-7.55 (5H, m), 8.0 (1H, s), 12.94 (1H, s), 14.42 (1H, s) |

TABLE 58-continued

| Ex No. | Strc | (Solv) ¹H-NMR δ ppm: |
|---|---|---|
| 88 | | (DMSO-d₆) 4.94 (2H, s), 7.35-7.45 (1H, m), 7.45-7.55 (2H, m), 7.7-7.85 (3H, m), 7.95-8.0 (2H, m), 12.96 (1H, s), 14.3 (1H, s) |
| 89 | | (DMSO-d₆) 3.37 (3H, s), 3.83 (3H, s), 7.15-7.25 (5H, m), 7.25-7.35 (2H, m), 7.44 (1H, d, J = 8.1 Hz), 7.56 (1H, d, J = 1.9 Hz), 11.63 (1H, s) |
| 90 | | (DMSO-d₆) 3.37 (3H, s), 3.83 (3H, s), 7.15-7.35 (8H, m), 7.53 (1H, dd, J = 7.3 Hz, 1.9 Hz), 11.63 (1H, s) |

TABLE 59

| Ex No. | Strc | (Solv) ¹H-NMR δ ppm: |
|---|---|---|
| 91 | | (DMSO-d₆) 3.37 (3H, s), 3.82 (3H, s), 7.1-7.4 10H, m), 11.46 (1H, s) |
| 92 | | (DMSO-d₆) 3.37 (3H, s), 3.74 (3H, s), 7.1-7.4 (9H, m), 7.58 (1H, s), 12.42 (1H, s) |
| 93 | | (DMSO-d₆) 3.38 (3H, s), 7.15-7.4 (8H, m), 7.5-7.6 (1H, m), 11.96 (1H, s), 14.34 (1H, s) |
| 94 | | (DMSO-d₆) 3.37 (3H, s), 7.15-7.4 (7H, m), 7.44 (1H, d, J = 8.7 Hz), 7.72 (1H, s) |

TABLE 59-continued

| Ex No. | Strc | (Solv) ¹H-NMR δ ppm: |
|---|---|---|
| 95 | | (DMSO-d₆) 3.38 (3H, s), 7.15-7.25 (3H, m), 7.25-7.35 (3H, m), 7.38 (1H, s), 7.5 (1H, d, J = 7.5 Hz), 7.58 (1H, d, J = 1.9 Hz), 11.98 (1H, s), 14.33 (1H, s) |
| 96 | | (DMSO-d₆) 3.37 (3H, s), 7.15-7.4 (10H, m), 11.89 (1H, s), 14.81 (1H, s) |
| 97 | | (DMSO-d₆) 3.37 (3H, s), 7.15-7.4 (9H, m), 7.99 (1H, s), 12.9 (1H, s), 14.37 (1H, s) |
| 98 | | (DMSO-d₆) 3.75-3.85 (3H, m), 6.3-6.4 (1H, m), 7.05-7.15 (1H, m), 7.2 (1H, s), 7.32 (1H, dd, J = 7.6 Hz, 2.9 Hz), 7.45-7.55 (4H, m), 7.55-7.65 (2H, m), 11.66 (1H, s) |

TABLE 60

| Ex No. | Strc | Solv ¹H-NMR δ ppm: |
|---|---|---|
| 99 | | (DMSO-d₆) 3.75-3.95 (6H, m), 6.2-6.35 (1H, m), 6.9-7.0 (1H, m), 7.0-7.1 (1H, m), 7.17 (1H, d, J = 8.0 Hz), 7.21 (1H, s), 7.31 (1H, dd, J = 6.4 Hz, 3.0 Hz), 7.4-7.55 (3H, m), 11.64 (1H, s) |
| 100 | | (DMSO-d₆) 3.7-3.75 (3H, m), 3.85-3.95 (3H, m), 6.2-6.35 (1H, m), 6.9-7.0 (1H, m), 7.04 (1H, t, J = 7.6 Hz), 7.15-7.2 (1H, m), 7.25-7.35 (1H, m), 7.4-7.55 (3H, m), 7.64 (1H, s), 12.6 (1H, s) |
| 101 | | (DMSO-d₆) 6.3-6.4 (1H, m), 7.1-7.2 (1H, m), 7.35-7.4 (2H, m), 7.45-7.55 (3H, m), 7.55-7.65 (3H, m), 11.95-12.1 (1H, m), 14.32 (1H, s) |

TABLE 60-continued

| Ex No. | Strc | Solv ¹H-NMR δ ppm: |
|---|---|---|
| 102 | | (DMSO-d₆) 3.85-3.95 (3H, m), 6.25-6.35 (1H, m), 6.95-7.1 (2H, m), 7.15-7.2 (1H, m), 7.35-7.5 (4H, m), 7.56 (1H, d, J = 8.9 Hz), 12.0-12.1 (1H, m), 14.34 (1H, s) |
| 103 | | (DMSO-d₆) 3.85-3.95 (3H, m), 6.25-6.35 (1H, m), 6.95-7.1 (2H, m), 7.15-7.2 (1H, m), 7.3-7.4 (1H, m), 7.4-7.5 (2H, m), 7.55 (1H, d, J = 9.0 Hz), 7.92 (1H, d, J = 4.5 Hz), 13.0 (1H, brs), 13.8-13.95 (1H, m) |

TABLE 61

| Ex No. | Strc | (Solv) ¹H-NMR δ ppm: |
|---|---|---|
| 104 | | (CDCl3) 3.89 (3H, s), 6.84 (1H, d, J = 5.8 Hz), 7.05-7.1 (1H, m), 7.28 (1H, d, J = 5.8 Hz), 7.45-7.55 (1H, m), 7.59 (1H, d, J = 8.5 Hz), 7.65-7.75 (1H, m), 7.8-7.85 (1H, m), 7.85-8.0 (2H, m), 10.06 (1H, s), 10.75 (1H, s) |
| 105 | | (CDCl3) 1.6-1.75 (2H, m), 2.45-2.55 (2H, m), 3.45-3.6 (1H, m), 3.7-3.85 (2H, m), 6.45 (1H, d, J = 0.5 Hz), 7.01 (1H, d, J = 7.0 Hz), 7.05-7.25 (2H, m), 7.5-7.6 (3H, m), 7.76 (1H, d, J = 7.7 Hz), 10.68 (1H, s) |
| 106 | | (DMSO-d6) 3.74 (3H, s), 3.83 (3H, s), 4.15-4.2 (2H, m), 6.75-6.85 (1H, m), 7.21 (1H, s), 7.25-7.4 (2H, m), 7.4-7.5 (1H, m), 7.5-7.55 (1H, m), 11.65 (1H, s) |
| 107 | | (DMSO-d6) 3.77 (3H, s), 3.83 (3H, s), 4.15 (2H, s), 6.75-6.9 (2H, m), 7.15-7.55 (5H, m), 11.65 (1H, s) |
| 108 | | (CDCl3) 3.16 (3H, s), 6.88 (1H, d, J = 5.8 Hz), 7.0-7.1 (2H, m), 7.25-7.35 (3H, m), 7.5-7.6 (2H, m), 7.6-7.7 (1H, m), 9.5-11.0 (1H, br) |

TABLE 61-continued

| Ex No. | Strc | (Solv) ¹H-NMR δ ppm: |
|---|---|---|
| 109 | | (DMSO-d6) 7.1-7.25 (3H, m), 7.44 (1H, d, J = 8.5 Hz), 7.5-7.6 (1H, m), 7.87 (1H, d, J = 8.5 Hz), 7.9-8.0 (2H, m), 8.18 (1H, d, J = 2.2 Hz), 11.0-12.0 (1H, br), 12.52 (1H, s) |
| 110 | | (CDCl3) 3.22 (3H, s), 7.05-7.15 (3H, m), 7.25-7.35 (3H, m), 7.45-7.55 (1H, m), 7.71 (1H, s), 9.22 (1H, s), 14.14 (1H, s) |

TABLE 62

| Ex No. | Strc | (Solv) ¹H-NMR δ ppm: |
|---|---|---|
| 111 | | (CDCl3) 1.11 (3H, t, J = 7.1 Hz), 3.5-3.6 (1H, m), 3.65-3.8 (1H, m), 7.05-7.1 (2H, m), 7.13 (1H, s), 7.25-7.35 (3H, m), 7.55 (1H, d, J = 2.2 Hz), 7.7 (1H, d, J = 8.4 Hz), 7.77 (1H, dd, J = 8.4 Hz, 2.2 Hz), 9.22 (1H, s), 14.17 (1H, s) |
| 112 | | (CDCl3) 3.33 (3H, s), 7.1 (1H, s), 7.15-7.2 (1H, m), 7.57 (1H, d, J = 8.2 Hz), 7.6-7.75 (4H, m), 8.3-8.4 (1H, m), 9.05 (1H, s), 14.09 (1H, s) |
| 113 | | (DMSO-d6) 1.6-1.75 (2H, m), 2.45-2.55 (2H, m), 3.7-3.85 (2H, m), 6.9-7.0 (1H, m), 7.05-7.25 (3H, m), 7.5-7.6 (2H, m), 7.78 (1H, d, J = 8.5 Hz), 8.0-8.05 (1H, m), 8.5-8.55 (1H, m), 11.52 (1H, s) |
| 114 | | (DMSO-d6) 3.17 (3H, s), 7.05-7.15 (2H, m), 7.25-7.4 (3H, m), 7.63 (1H, dd, J = 8.6 Hz, 2.2 Hz), 7.85-7.95 (3H, m), 12.5-13.5 (1H, br), 13.79 (1H, s) |
| 115 | | (DMSO-d6) 3.26 (3H, s), 7.25-7.3 (1H, m), 7.45-7.55 (1H, m), 7.65-7.75 (1H, m), 7.8-7.95 (3H, m), 8.05-8.1 (1H, m), 8.3-8.4 (1H, m) |

TABLE 62-continued

| Ex No. | Strc | (Solv) ¹H-NMR δ ppm: |
|---|---|---|
| 116 | | (CDCl3) 3.17 (3H, s), 6.9-7.0 (1H, m), 7.13 (1H, s), 7.29 (1H, d, J = 2.5 Hz), 7.39 (1H, d, J = 8.4 Hz), 7.51 (1H, d, J = 1.2 Hz), 7.7-7.8 (2H, m), 9.12 (1H, s), 14.05 (1H, s) |
| 117 | | (CDCl3) 3.25 (3H, s), 6.75-6.9 (2H, m), 7.13 (1H, s), 7.2-7.3 (1H, m), 7.63 (1H, d, J = 2.1 Hz), 7.75 (1H, d, J = 8.6 Hz), 7.8-7.85 (1H, m), 9.03 (1H, s), 14.11 (1H, s) |

TABLE 63

| Ex No. | Strc | (Solv) ¹H-NMR δ ppm: |
|---|---|---|
| 118 | | (CDCl3) 3.22 (3H, s), 7.08 (1H, s), 7.15-7.25 (2H, m), 7.38 (1H, d, J = 1.7 Hz), 7.7-7.8 (2H, m), 8.55-8.65 (2H, m) |
| 119 | | (DMSO-d6) 3.23 (3H, s), 3.8 (3H, s), 6.9-6.95 (1H, m), 7.35-7.55 (3H, m), 7.7-7.85 (2H, m), 7.9-8.0 (2H, m), 12.03 (1H, s), 14.29 (1H, s) |
| 120 | | (DMSO-d6) 3.12 (3H, s), 3.73 (3H, s), 6.85-6.9 (2H, m), 6.95-7.0 (2H, m), 7.39 (1H, s), 7.68 (1H, dd, J = 8.4 Hz, 2.3 Hz), 7.85-7.95 (2H, m), 12.03 (1H, s), 14.3 (1H, s) |
| 121 | | (DMSO-d6) 3.51 (3H, s), 6.85-6.95 (2H, m), 7.15-7.25 (2H, m), 7.38 (1H, s), 7.7-7.8 (1H, m), 7.85-7.95 (1H, m), 7.95-8.0 (1H, m), 9.74 (1H, s), 12.02 (1H, s), 13.5-15.0 (1H, br) |
| 122 | | (DMSO-d6) 3.67 (3H, s), 6.6-6.75 (3H, m), 7.1-7.2 (1H, m), 7.38 (1H, s), 7.84 (1H, dd, J = 8.5 Hz, 2.2 Hz), 7.89 (1H, d, J = 8.5 Hz), 8.13 (1H, d, J = 2.2 Hz), 10.49 (1H, s), 12.04 (1H, s), 14.22 (1H, s) |

TABLE 63-continued

| Ex No. | Strc | (Solv) ¹H-NMR δ ppm: |
|---|---|---|
| 123 | | (DMSO-d6) 3.69 (3H, s), 6.83 (2H, d, J = 8.9 Hz), 6.99 (2H, d, J = 8.9 Hz), 7.38 (1H, s), 7.75 (1H, dd, J = 8.5 Hz, 2.0 Hz), 7.88 (1H, d, J = 8.5 Hz), 7.99 (1H, d, J = 2.0 Hz), 10.08 (1H, s), 12.03 (1H, s), 14.24 (1H, s) |
| 124 | | (DMSO-d6) 3.17 (3H, s), 3.47 (3H, s), 6.9-7.0 (2H, m), 7.15-7.2 (1H, m), 7.25-7.35 (1H, m), 7.39 (1H, s), 7.71 (1H, dd, J = 8.6 Hz, 2.2 Hz), 7.9 (1H, d, J = 8.6 Hz), 8.02 (1H, d, J = 2.2 Hz), 12.02 (1H, s), 14.31 (1H, s) |

TABLE 64

| Ex No. | Strc | (Solv) ¹H-NMR δ ppm: |
|---|---|---|
| 125 | | (DMSO-d6) 3.18 (3H, s), 3.69 (3H, s), 6.55-6.7 (2H, m), 6.8-6.9 (1H, m), 7.2-7.3 (1H, m), 7.35-7.4 (1H, m), 7.6-7.7 (1H, m), 7.85-8.05 (2H, m), 12.04 (1H, s), 14.26 (1H, s) |
| 126 | | (DMSO-d6) 3.18 (3H, s), 7.1-7.35 (3H, m), 7.35-7.45 (2H, m), 7.81 (1H, d, J = 2.3 Hz), 7.95 (1H, d, J = 8.5 Hz), 8.03 (1H, d, J = 2.3 Hz), 12.03 (1H, s), 14.29 (1H, s) |
| 127 | | (DMSO-d6) 3.19 (3H, s), 6.95-7.05 (2H, m), 7.1-7.2 (1H, m), 7.35-7.45 (2H, m), 7.7-7.75 (1H, m), 7.9-8.0 (2H, m), 12.04 (1H, s), 14.27 (1H, s) |
| 128 | | (DMSO-d6) 3.15 (3H, s), 7.05-7.25 (4H, m), 7.38 (1H, s), 7.69 (1H, dd, J = 8.5 Hz, 2.5 Hz), 7.9 (1H, d, J = 2.5 Hz), 7.93 (1H, d, J = 8.5 Hz), 12.05 (1H, s), 14.29 (1H, s) |
| 129 | | (DMSO-d6) 3.15 (3H, s), 7.1-7.15 (2H, m), 7.35-7.45 (3H, m), 7.7 (1H, dd, J = 8.6 Hz, 2.1 Hz), 7.9-7.95 (2H, m), 12.05 (1H, s), 14.28 (1H, s) |

TABLE 64-continued

| Ex No. | Strc | (Solv) $^1$H-NMR δ ppm: |
|---|---|---|
| 130 | | (DMSO-d6) 3.19 (3H, s), 7.05-7.1 (1H, m), 7.2-7.25 (1H, m), 7.35-7.45 (3H, m), 7.72 (1H, dd, J = 8.5 Hz, 2.1 Hz), 7.9-8.0 (2H, m), 12.06 (1H, s), 14.3 (1H, s) |
| 131 | | (DMSO-d6) 3.16 (3H, s), 7.0-7.1 (1H, m), 7.25-7.45 (3H, m), 7.55-7.6 (1H, m), 7.85-7.9 (1H, m), 7.97 (1H, d, J = 8.5 Hz), 8.1 (1H, s), 12.06 (1H, s), 14.31 (1H, s) |

TABLE 65

| Ex No. | Strc | (Solv) $^1$H-NMR δ ppm: |
|---|---|---|
| 132 | | (DMSO-d6) 3.13 (3H, s), 7.0-7.1 (1H, m), 7.3-7.4 (2H, m), 7.45-7.55 (2H, m), 7.86 (1H, dd, J = 8.5 Hz, 2.4 Hz), 7.98 (1H, d, J = 8.5 Hz), 8.02 (1H, d, J = 2.4 Hz), 12.03 (1H, s), 14.3 (1H, s) |
| 133 | | (DMSO-d6) 3.17 (3H, s), 7.2-7.3 (2H, m), 7.3-7.4 (3H, m), 7.71 (1H, dd, J = 8.5 Hz, 2.1 Hz), 7.9 (1H, d, J = 2.1 Hz), 7.93 (1H, d, J = 8.5 Hz), 12.0 (1H, s), 14.25 (1H, s) |
| 134 | | (DMSO-d6) 3.15 (3H, s), 7.06 (1H, d, J = 8.5 Hz), 7.35-7.45 (2H, m), 7.76 (1H, d, J = 2.4 Hz), 7.85-7.9 (1H, m), 7.97 (1H, d, J = 8.54 Hz), 8.07 (1H, d, J = 2.2 Hz), 12.03 (1H, s), 14.27 (1H, s) |
| 135 | | (DMSO-d6) 3.16 (3H, s), 7.05-7.1 (2H, m), 7.25-7.4 (4H, m), 7.55-7.65 (1H, m), 7.7-7.8 (3H, m), 11.95 (1H, s), 14.77 (1H, s) |
| 136 | | (DMSO-d6) 3.16 (3H, s), 7.05-7.1 (2H, m), 7.25-7.4 (3H, m), 7.55-7.65 (1H, m), 7.7-7.8 (3H, m), 7.98 (1H, s), 12.95 (1H, s), 14.31 (1H, s) |

TABLE 65-continued

| Ex No. | Strc | (Solv) ¹H-NMR δ ppm: |
|---|---|---|
| 137 | | (DMSO-d6) 3.16 (3H, s), 3.47 (3H, s), 6.85-7.0 (2H, m), 7.1-7.2 (1H, m), 7.25-7.35 (1H, m), 7.69 (1H, dd, J = 8.4 Hz, 2.1 Hz), 7.85-7.95 (2H, m), 7.99 (1H, d, J = 2.1 Hz), 12.5-13.5 (1H, br), 13.83 (1H, brs) |
| 138 | | (DMSO-d6) 3.17 (3H, s), 7.1-7.25 (2H, m), 7.25-7.35 (1H, m), 7.35-7.45 (2H, m), 7.65-7.75 (1H, m), 7.8-7.9 (1H, m), 8.02 (1H, dd, J = 6.6 Hz, 2.3 Hz), 12.03 (1H, s), 14.31 (1H, s) |

TABLE 66

| Ex No. | Strc | (Solv) ¹H-NMR δ ppm: |
|---|---|---|
| 139 | | (DMSO-d6) 3.16 (3H, s), 3.47 (3H, s), 6.9-7.0 (2H, m), 7.19 (1H, dd, J = 8.0 Hz, 1.5 Hz), 7.3-7.35 (1H, m), 7.37 (1H, s), 7.6-7.7 (1H, m), 7.7-7.8 (1H, m), 8.0 (1H, dd, J = 6.6 Hz, 2.5 Hz), 12.02 (1H, s), 14.32 (1H, s) |
| 140 | | (DMSO-d6) 1.6-1.7 (2H, m), 2.45-2.55 (5H, m), 3.7-3.8 (2H, m), 7.05-7.25 (3H, m), 7.56 (1H, d, J = 8.5 Hz), 7.6-7.65 (1H, m), 7.84 (1H, d, J = 8.5 Hz), 8.1 (1H, d, J = 2.4 Hz), 11.94 (1H, s), 14.22 (1H, s) |
| 141 | | (CD3OD) 3.36 (3H, s), 3.54 (3H, s), 4.01 (3H, s), 6.85-6.95 (2H, m), 7.15-7.35 (4H, m), 7.69 (1H, d, J = 8.4 Hz) |
| 142 | | (DMSO-d6) 3.3 (3H, s), 3.87 (3H, s), 7.15-7.4 (6H, m), 7.42 (1H, d, J = 11.7 Hz), 7.92 (1H, d, J = 8.3 Hz), 11.95 (1H, s), 14.39 (1H, s) |
| 143 | | (DMSO-d6) 3.17 (3H, s), 7.05-7.15 (2H, m), 7.25-7.4 (4H, m), 7.6-7.75 (2H, m), 7.9-8.0 (1H, m), 12.02 (1H, s), 14.29 (1H, s) |

TABLE 66-continued

| Ex No. | Strc | (Solv) ¹H-NMR δ ppm: |
|---|---|---|
| 144 | | (DMSO-d6) 4.42 (2H, s), 7.2-7.45 (6H, m), 7.86 (1H, d, J = 8.5 Hz), 8.2 (1H, dd, J = 8.5 Hz, 2.2 Hz), 8.29 (1H, d, J = 2.2 Hz), 12.06 (1H, brs), 14.32 (1H, brs) |
| 145 | | (DMSO-d6) 1.4-1.5 (3H, m), 4.9-5.0 (1H, m), 7.15-7.45 (6H, m), 7.7-7.8 (1H, m), 8.1-8.15 (1H, m), 8.2-8.3 (1H, m), 12.0-12.1 (1H, m), 14.2-14.35 (1H, m) |

TABLE 67

| Ex No. | Strc | (Solv) ¹H-NMR δ ppm: |
|---|---|---|
| 146 | | (DMSO-d6) 1.57 (6H, s), 7.25-7.45 (7H, m), 7.5-7.6 (1H, m), 7.9-8.0 (1H, m), 11.9-12.1 (1H, br), 14.2-14.4 (1H, br) |
| 147 | | (DMSO-d6) 1.55 (3H, s), 1.57 (3H, s), 3.33 (3H, s), 6.8-6.85 (1H, m), 7.0-7.1 (1H, m), 7.2-7.3 (1H, m), 7.3-7.5 (3H, m), 7.5-7.55 (1H, m), 7.94 (1H, d, J = 2.4 Hz), 12.0 (1H, s), 14.37 (1H, brs) |
| 148 | | (DMSO-d6) 1.6 (3H, s), 1.62 (3H, s), 7.0-7.15 (1H, m), 7.25-7.4 (3H, m), 7.47 (1H, dd, J = 8.7 Hz, 2.0 Hz), 7.57 (1H, d, J = 8.7 Hz), 7.65-7.75 (1H, m), 8.01 (1H, d, J = 2.0 Hz), 12.03 (1H, s), 14.3 (1H, brs) |
| 149 | | (DMSO-d6) 4.42 (2H, s), 7.2-7.35 (5H, m), 7.86 (1H, d, J = 8.5 Hz), 7.94 (1H, s), 8.15-8.3 (2H, m), 13.84 (1H, s) |
| 150 | | (DMSO-d6) 1.55 (6H, s), 7.25-7.55 (8H, m), 7.6-7.65 (1H, m), 11.99 (1H, s), 14.46 (1H, brs) |

TABLE 67-continued

| Ex No. | Strc | (Solv) ¹H-NMR δ ppm: |
|---|---|---|
| 151 | | (DMSO-d6) 1.49 (3H, s), 1.5 (3H, s), 3.66 (3H, s), 6.55-6.65 (1H, m), 6.75-6.85 (1H, m), 6.95-7.05 (1H, m), 7.25-7.5 (4H, m), 7.5-7.6 (1H, m), 11.99 (1H, s), 14.5 (1H, s) |
| 152 | | (DMSO-d6) 1.536 (3H, s), 1.543 (3H, s), 3.61 (3H, s), 6.75-6.85 (2H, m), 7.3-7.4 (3H, m), 7.45-7.6 (2H, m), 11.98 (1H, s), 14.5 (1H, s) |

TABLE 68

| Ex No. | Strc | (Solv) ¹H-NMR δ ppm: |
|---|---|---|
| 153 | | (DMSO-d6) 1.49 (3H, s), 1.5 (3H, s), 3.66 (3H, s), 6.55-6.65 (1H, m), 6.75-6.85 (1H, m), 6.95-7.05 (1H, m), 7.25-7.55 (4H, m), 7.94 (1H, s), 12.8-13.1 (1H, br), 14.01 (1H, s) |
| 154 | | (DMSO-d6) 5.15 (2H, s), 6.9-7.1 (3H, m), 7.25-7.35 (2H, m), 7.4 (1H, s), 7.55-7.65 (1H, m), 7.65-7.75 (2H, m), 12.05 (1H, s), 14.42 (1H, s) |
| 155 | | (DMSO-d6) 2.85-2.95 (4H, m), 7.1-7.6 (9H, m), 12.04 (1H, s), 14.46 (1H, s) |
| 156 | | (DMSO-d6) 2.8-3.0 (4H, m), 7.15-7.45 (9H, m), 12.03 (1H, s), 14.46 (1H, brs) |
| 157 | | (DMSO-d6) 2.8-2.9 (4H, m), 3.79 (3H, s), 6.8-6.9 (1H, m), 6.9-7.0 (1H, m), 7.1-7.25 (2H, m), 7.25-7.45 (4H, m), 12.02 (1H, s), 14.48 (1H, brs) |

TABLE 68-continued

| Ex No. | Strc | (Solv) ¹H-NMR δ ppm: |
|---|---|---|
| 158 | | (DMSO-d6) 2.85-3.0 (4H, m), 7.05-7.2 (2H, m), 7.2-7.45 (6H, m), 12.03 (1H, s), 14.46 (1H, brs) |
| 159 | | (DMSO-d6) 2.8-2.95 (4H, m), 3.72 (3H, s), 6.7-6.85 (3H, m), 7.15-7.25 (1H, m), 7.25-7.45 (4H, m), 11.95-12.1 (1H, br), 14.35-14.55 (1H, br) |

TABLE 69

| Ex No. | Strc | (Solv) ¹H-NMR δ ppm: |
|---|---|---|
| 160 | | (DMSO-d6) 2.75-2.95 (4H, m), 3.71 (3H, s), 6.8-6.9 (2H, m), 7.1-7.2 (2H, m), 7.25-7.45 (4H, m), 12.01 (1H, brs), 14.4-14.55 (1H, br) |
| 161 | | (DMSO-d6) 2.85-3.0 (4H, m), 6.95-7.05 (1H, m), 7.05-7.15 (2H, m), 7.25-7.45 (5H, m), 12.03 (1H, brs), 14.3-14.6 (1H, br) |
| 162 | | (DMSO-d6) 2.8-2.95 (4H, m), 7.05-7.15 (2H, m), 7.2-7.45 (6H, m), 12.03 (1H, brs), 14.3-14.6 (1H, br) |
| 163 | | (DMSO-d6) 2.28 (3H, s), 2.8-2.9 (4H, m), 7.05-7.25 (4H, m), 7.25-7.5 (4H, m), 12.04 (1H, brs), 14.47 (1H, brs) |
| 164 | | (DMSO-d6) 2.27 (3H, s), 2.8-2.95 (4H, m), 6.95-7.1 (3H, m), 7.1-7.2 (1H, m), 7.25-7.45 (4H, m), 12.03 (1H, brs), 14.47 (1H, brs) |

TABLE 69-continued

| Ex No. | Strc | (Solv) $^1$H-NMR δ ppm: |
|---|---|---|
| 165 | | (DMSO-d6) 2.25 (3H, s), 2.8-2.95 (4H, m), 7.05-7.15 (4H, m), 7.25-7.45 (4H, m), 12.03 (1H, brs), 14.35-14.6 (1H, br) |
| 166 | | (DMSO-d6) 1.23 (3H, s), 1.25 (3H, s), 2.85 (2H, s), 3.67 (3H, s), 6.7-6.8 (2H, m), 6.85-6.95 (1H, m), 7.1-7.2 (1H, m), 7.25-7.35 (1H, m), 7.35-7.45 (2H, m), 7.5-7.6 (1H, m), 12.0 (1H, s), 14.55 (1H, s) |

TABLE 70

| Ex No. | Strc | (Solv) $^1$H-NMR δ ppm: |
|---|---|---|
| 167 | | (DMSO-d6) 2.65-2.75 (2H, m), 2.8-2.9 (2H, m), 3.75 (6H, s), 6.55-6.7 (2H, m), 7.1-7.2 (1H, m), 7.25-7.45 (4H, m), 12.0 (1H, s), 14.48 (1H, brs) |
| 168 | | (DMSO-d6) 2.8-2.95 (4H, m), 3.77 (3H, s), 6.9-7.1 (3H, m), 7.25-7.45 (4H, m), 12.01 (1H, s), 14.46 (1H, brs) |
| 169 | | (DMSO-d6) 2.85-2.95 (4H, m), 3.75 (3H, s), 6.9-7.05 (1H, m), 7.05-7.2 (1H, m), 7.3-7.45 (4H, m), 12.01 (1H, s), 14.45 (1H, brs) |
| 170 | | (DMSO-d6) 2.75-2.85 (2H, m), 2.85-2.95 (2H, m), 3.77 (3H, s), 6.75-6.85 (1H, m), 7.15-7.35 (4H, m), 7.37 (1H, s), 11.99 (1H, s), 14.46 (1H, brs) |

TABLE 70-continued

| Ex No. | Strc | (Solv) ¹H-NMR δ ppm: |
|---|---|---|
| 171 | | (DMSO-d6) 2.75-2.9 (4H, m), 3.86 (3H, s), 7.08 (1H, d, J = 12.2 Hz), 7.15-7.35 (6H, m), 7.38 (1H, s), 11.97 (1H, s), 14.55 (1H, brs) |
| 172 | | (DMSO-d6) 4.28 (2H, s), 7.2-7.35 (3H, m), 7.35-7.5 (4H, m), 7.58 (1H, d, J = 8.5 Hz), 7.66 (1H, d, J = 2.2 Hz), 12.06 (1H, s), 14.41 (1H, s) |
| 173 | | (DMSO-d6) 4.29 (2H, s), 7.2-7.45 (6H, m), 7.57 (1H, d, J = 8.5 Hz), 7.64 (1H, d, J = 2.3 Hz), 7.94 (1H, s), 13.03 (1H, s), 13.94 (1H, s) |

TABLE 71

| Ex No. | Strc | (Solv) ¹H-NMR δ ppm: |
|---|---|---|
| 174 | | (DMSO-d6) 1.69 (6H, s), 7.0-7.2 (4H, m), 7.25-7.4 (5H, m), 11.89 (1H, s), 14.86 (1H, s) |
| 175 | | (DMSO-d6) 4.24 (2H, s), 7.2-7.5 (8H, m), 7.62 (1H, dd, J = 6.7 Hz, 2.2 Hz), 12.05 (1H, s), 14.41 (1H, s) |
| 176 | | (DMSO-d6) 1.65 (6H, s), 7.0-7.1 (1H, m), 7.1-7.45 (8H, m), 11.88 (1H, s), 14.83 (1H, s) |
| 177 | | (DMSO-d6) 2.8-2.9 (2H, m), 3.15-3.25 (2H, m), 7.15-7.55 (8H, m), 7.58 (1H, dd, J = 6.8 Hz, 2.3 Hz) |

TABLE 71-continued

| Ex No. | Strc | (Solv) ¹H-NMR δ ppm: |
|---|---|---|
| 178 | | (DMSO-d6) 4.21 (2H, s), 7.0-7.15 (2H, m), 7.3-7.45 (3H, m), 7.5-7.65 (2H, m), 12.0 (1H, s), 14.37 (1H, s) |
| 179 | | (DMSO-d6) 3.76 (3H, s), 4.15 (2H, s), 6.75-6.9 (2H, m), 7.25-7.35 (2H, m), 7.35-7.45 (1H, m), 7.45-7.6 (2H, m) |
| 180 | | (DMSO-d6) 4.27 (2H, s), 7.15-7.5 (10H, m), 11.93 (1H, s), 14.88 (1H, s) |

TABLE 72

| Ex No. | Strc | (Solv) ¹H-NMR δ ppm: |
|---|---|---|
| 181 | | (DMSO-d6) 1.65-1.7 (6H, m), 3.86 (3H, s) 6.75-6.85 (1H, m), 7.0-7.15 (3H, m), 7.2-7.3 (2H, m), 7.37 (1H, s), 7.42 (1H, dd, J = 6.9 Hz, 2.2 Hz), 11.98 (1H, s), 14.38 (1H, s) |
| 182 | | (DMSO-d6) 3.79 (3H, s), 4.16 (2H, s), 6.8-6.9 (1H, m), 6.95-7.05 (1H, m), 7.2-7.3 (2H, m), 7.3-7.5 (3H, m), 7.59 (1H, dd, J = 7.0 hz, 2.2 Hz), 12.02 (1H, s), 14.39 (1H, s) |
| 183 | | (DMSO-d6) 1.69 (6H, s), 7.0-7.35 (6H, m), 7.37 (1H, s), 7.46 (1H, dd, J = 6.7 Hz, 2.2 Hz), 11.98 (1H, s), 14.37 (1H, brs) |
| 184 | | (DMSO-d6) 4.24 (2H, s), 7.05-7.25 (2H, m), 7.25-7.45 (4H, m), 7.45-7.55 (1H, m), 7.63 (1H, dd, J = 6.8 Hz, 2.5 Hz), 12.03 (1H, s), 14.38 (1H, s) |

TABLE 72-continued
| Ex No. | Strc | (Solv) ¹H-NMR δ ppm: |
|---|---|---|
| 185 | 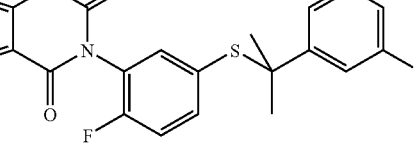 | (DMSO-d6) 4.25 (2H, s), 7.0-7.1 (1H, m), 7.15-7.2 (2H, m), 7.25-7.5 (4H, m), 7.62 (1H, dd, J = 6.7 Hz, 2.3 Hz), 12.03 (1H, s), 14.37 (1H, s) |
| 186 | 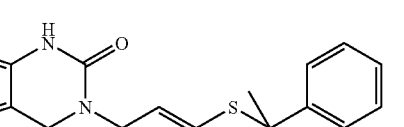 | (DMSO-d6) 4.4 (2H, s), 7.3-7.6 (6H, m), 7.65-7.75 (1H, m), 12.01 (1H, s), 14.37 (1H, s) |
| 187 | 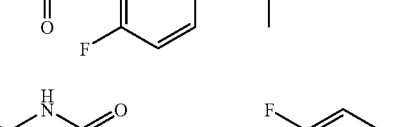 | (DMSO-d6) 1.75-1.8 (6H, m), 7.05-7.15 (1H, m), 7.15-7.3 (4H, m), 7.37 (1H, s), 7.4-7.5 (2H, m), 11.97 (1H, s), 14.37 (1H, s) |
TABLE 73
| Ex. No. | Strc | (Solv) ¹H-NMR δ ppm: |
|---|---|---|
| 188 | 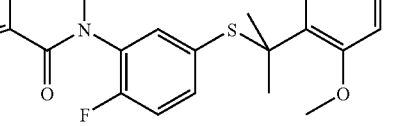 | (DMSO-d6) 1.65 (6H, s), 7.15-7.25 (1H, m), 7.25-7.45 (6H, m), 7.5-7.6 (1H, m), 12.0 (1H, s), 14.38 (1H, s) |
| 189 | | (DMSO-d6) 1.64 (6H, s), 7.15-7.35 (5H, m), 7.37 (1H, s), 7.4-7.45 (2H, m), 7.52 (1H, dd, J = 7.3 Hz, 2.3 Hz), 11.99 (1H, s), 14.37 (1H, brs) |
| 190 | | (DMSO-d6) 1.75-1.85 (6H, m), 3.77 (3H, s), 6.6-6.7 (1H, m), 6.85 (1H, d, J = 8.1 Hz), 7.05-7.15 (1H, m), 7.2-7.35 (2H, m), 7.37 (1H, s), 7.4-7.45 (1H, m), 11.97 (1H, s), 14.4 (1H, brs) |
| 191 | | (DMSO-d6) 1.65-1.7 (6H, m), 3.85 (3H, s), 6.75-6.8 (1H, m), 7.0-7.1 (2H, m), 7.1-7.2 (1H, m), 7.25-7.35 (1H, m), 7.37 (1H, s), 7.4 (1H, dd, J = 7.3 Hz, 2.2 hz), 11.98 (1H, s), 14.39 (1H, brs) |

TABLE 73-continued
| Ex. No. | Strc | (Solv) ¹H-NMR δ ppm: |
|---|---|---|
| 192 | 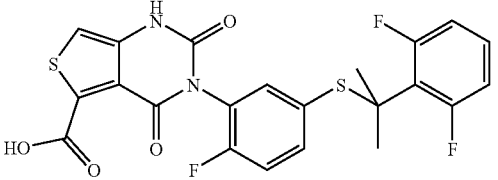 [SMILES: CC(C)(Sc1ccc(F)c(-n2c(=O)[nH]c3csc(C(=O)O)c3c2=O)c1)c1c(F)cccc1F] | (DMSO-d6) 1.81 (6H, s), 6.9-7.05 (2H, m), 7.1-7.2 (1H, m), 7.25-7.4 (3H, m), 7.45-7.5 (1H, m), 11.97 (1H, s), 14.38 (1H, brs) |
| 193 | 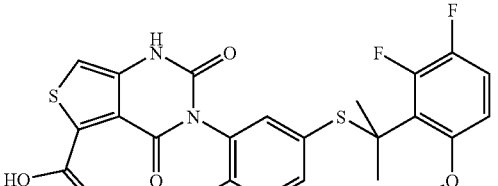 | (DMSO-d6) 1.8-1.85 (6H, m), 3.76 (3H, s), 6.75-6.85 (1H, m), 7.15-7.45 (5H, m), 11.98 (1H, s), 14.38 (1H, brs) |
| 194 | 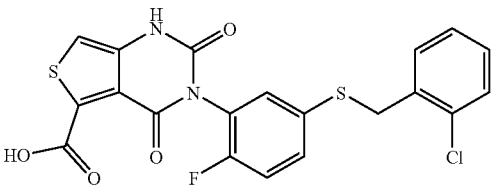 [SMILES: O=C(O)c1scc2[nH]c(=O)n(-c3cc(SCc4ccccc4Cl)ccc3F)c(=O)c12] | (DMSO-d6) 4.29 (2H, s), 7.2-7.35 (2H, m), 7.35-7.55 (5H, m), 7.6-7.7 (1H, m), 12.02 (1H, s), 14.38 (1H, brs) |
TABLE 74
| Ex. No. | Strc | (Solv) ¹H-NMR δ ppm: |
|---|---|---|
| 195 | 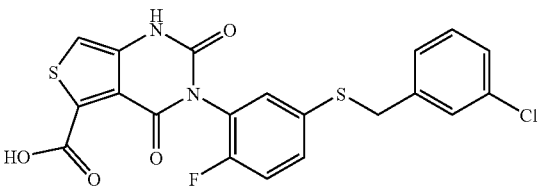 [SMILES: O=C(O)c1scc2[nH]c(=O)n(-c3cc(SCc4cccc(Cl)c4)ccc3F)c(=O)c12] | (DMSO-d6) 4.24 (2H, s), 7.25-7.5 (7H, m), 7.6-7.65 (1H, m), 12.03 (1H, s), 14.38 (1H, brs) |
| 196 | 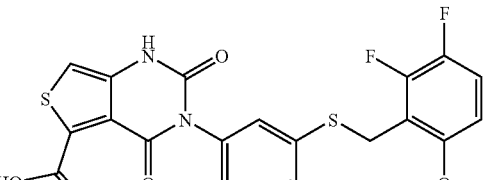 | (DMSO-d6) 3.73 (3H, s), 4.16 (2H, s), 6.75-6.85 (1H, m), 7.1-7.6 (5H, m) |
| 197 | 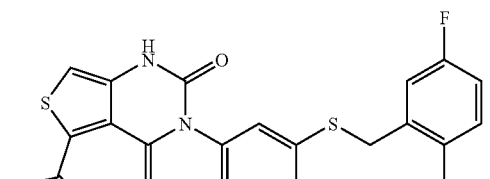 | (DMSO-d6) 3.77 (3H, s), 4.15 (2H, s), 6.95-7.15 (3H, m), 7.35-7.5 (3H, m), 7.6-7.65 (1H, m), 12.06 (1H, s), 14.41 (1H, s) |

TABLE 74-continued

| Ex. No. | Strc | (Solv) ¹H-NMR δ ppm: |
|---|---|---|
| 198 | | (DMSO-d6) 1.6-1.7 (6H, m), 7.0-7.1 (1H, m), 7.15-7.25 (3H, m), 7.3-7.4 (3H, m), 7.5-7.55 (1H, m), 12.01 (1H, s), 14.4 (1H, s) |
| 199 | | (DMSO-d6) 1.66 (3H, s), 1.67 (3H, s), 3.86 (3H, s), 7.0 (1H, d, J = 2.5 Hz), 7.06 (1H, d, J = 8.8 Hz), 7.1-7.2 (1H, m), 7.25-7.35 (2H, m), 7.38 (1H, s), 7.4-7.5 (1H, m), 12.01 (1H, s), 14.41 (1H, brs) |
| 200 | | (DMSO-d6) 1.75-1.9 (1H, m), 2.15-2.3 (1H, m), 2.4-2.65 (4H, m), 7.0-7.2 (4H, m), 7.2-7.35 (3H, m), 7.37 (1H, s), 7.45-7.5 (1H, m), 11.98 (1H, s), 14.41 (1H, brs) |
| 201 | | (DMSO-d6) 2.05-2.25 (4H, m), 3.5-3.65 (2H, m), 3.85-3.95 (2H, m), 6.85-6.95 (1H, m), 7.15-7.4 (8H, m), 11.98 (1H, s), 14.38 (1H, brs) |

TABLE 75

| Ex No. | Strc | (Solv) ¹H-NMR δ ppm: |
|---|---|---|
| 202 | | (DMSO-d6) 1.73 (6H, s), 7.3-7.4 (7H, m), 7.5-7.6 (1H, m), 7.95 (1H, dd, J = 6.7 Hz, 2.2 Hz), 12.01 (1H, s), 14.25 (1H, s) |
| 203 | | (DMSO-d6) 1.7 (6H, s), 6.89 (1H, s), 7.2-7.4 (6H, m), 7.5-7.7 (3H, m) |

TABLE 75-continued

| Ex No. | Strc | (Solv) ¹H-NMR δ ppm: |
|---|---|---|
| 204 | | (DMSO-d6) 4.77 (2H, s), 7.15-7.25 (2H, m), 7.25-7.35 (3H, m), 7.39 (1H, s), 7.87 (1H, dd, J = 8.6 Hz, 2.2 Hz), 7.95 (1H, d, J = 8.6 Hz), 8.09 (1H, d, J = 2.2 Hz), 12.08 (1H, s), 14.26 (1H, s) |
| 205 | | (DMSO-d6) 4.77 (2H, s), 7.15-7.25 (2H, m), 7.25-7.35 (3H, m), 7.8-8.0 (3H, m), 8.08 (1H, d, J = 2.3 Hz), 13.78 (1H, s) |
| 206 | | (DMSO-d6) 4.76 (2H, s), 7.05-7.15 (2H, m), 7.36 (1H, s), 7.4-7.55 (1H, m), 7.7-7.8 (1H, m), 7.95-8.1 (2H, m), 12.02 (1H, s), 14.26 (1H, s) |
| 207 | | (DMSO-d6) 1.89 (6H, s), 7.0-7.1 (2H, m), 7.36 (1H, s), 7.4-7.5 (1H, m), 7.6-7.7 (2H, m), 8.0-8.1 (1H, m), 12.0 (1H, s), 14.28 (1H, s) |
| 208 | | (DMSO-d6) 4.72 (2H, s), 7.15-7.25 (2H, m), 7.25-7.35 (3H, m), 7.39 (1H, s), 7.7-7.95 (4H, m), 11.97 (1H, s), 14.72 (1H, s) |

TABLE 76

| Ex No. | Strc | (Solv) ¹H-NMR δ ppm: |
|---|---|---|
| 209 | | (DMSO-d6) 1.86 (6H, s), 3.35 (3H, s), 6.83 (1H, d, J = 8.6 Hz), 6.9-7.0 (1H, m), 7.25-7.35 (2H, m), 7.37 (1H, s), 7.4-7.45 (1H, m), 7.5-7.6 (1H, m), 7.85-7.95 (1H, m), 12.0 (1H, s), 14.29 (1H, s) |
| 210 | | (DMSO-d6) 3.46 (3H, s), 4.63 (2H, s), 6.85-6.95 (2H, m), 7.2-7.35 (2H, m), 7.37 (1H, s), 7.6-7.75 (2H, m), 7.9-8.0 (1H, m), 12.02 (1H, s), 14.26 (1H, s) |

TABLE 76-continued

| Ex No. | Strc | (Solv) ¹H-NMR δ ppm: |
|---|---|---|
| 211 | | (DMSO-d6) 1.81 (6H, s), 7.05-7.2 (2H, m), 7.3-7.45 (3H, m), 7.5-7.65 (2H, m), 7.98 (1H, dd, J = 6.7 Hz, 2.3 Hz), 12.01 (1H, s), 14.27 (1H, s) |
| 212 | | (DMSO-d6) 4.81 (2H, s), 6.95-7.05 (2H, m), 7.1-7.2 (1H, m), 7.3-7.4 (2H, m), 7.7-7.75 (1H, m), 7.9-8.0 (1H, m), 8.04 (1H, dd, J = 6.8 Hz, 2.6 Hz), 12.05 (1H, s), 14.24 (1H, s) |
| 213 | | (DMSO-d6) 4.7-4.8 (2H, m), 7.1-7.3 (3H, m), 7.35-7.45 (2H, m), 7.65-7.75 (1H, m), 7.9-8.0 (1H, m), 8.05 (1H, dd, J = 6.8 Hz, 2.5 Hz), 12.03 (1H, s), 14.25 (1H, s) |
| 214 | | (DMSO-d6) 1.75-1.85 (6H, m), 7.05-7.2 (2H, m), 7.3-7.5 (4H, m), 7.6-7.8 (3H, m), 11.91 (1H, s), 14.72 (1H, s) |
| 215 | | (DMSO-d6) 4.74 (2H, s), 7.15-7.2 (2H, m), 7.25-7.35 (3H, m), 7.37 (1H, s), 7.65-7.75 (1H, m), 7.85-7.95 (1H, m), 8.07 (1H, dd, J = 6.6 Hz, 2.5 Hz), 12.04 (1H, s), 14.24 (1H, s) |

TABLE 77

| Ex No. | Strc | (Solv) ¹H-NMR δ ppm: |
|---|---|---|
| 216 | | (DMSO-d6) 1.72 (6H, s), 7.1-7.25 (3H, m), 7.3-7.45 (3H, m), 7.6-7.7 (1H, m), 7.7-7.8 (2H, m), 11.92 (1H, s), 14.7 (1H, s) |
| 217 | | (DMSO-d6) 2.85-2.95 (2H, m), 3.65-3.75 (2H, m), 7.15-7.3 (5H, m), 7.37 (1H, s), 7.7-7.8 (1H, m), 8.1-8.15 (1H, m), 8.27 (1H, dd, J = 6.6 Hz, 2.6 Hz), 12.05 (1H, s), 14.23 (1H, brs) |

TABLE 77-continued

| Ex No. | Strc | (Solv) ¹H-NMR δ ppm: |
|---|---|---|
| 218 | | (DMSO-d6) 3.47 (3H, s), 4.62 (2H, s), 6.75 (1H, d, J = 8.4 Hz), 6.8-6.9 (1H, m), 7.3-7.4 (2H, m), 7.65-7.75 (1H, m), 7.8-7.9 (1H, m), 7.95-8.05 (1H, m), 12.0 (1H, s), 14.27 (1H, brs) |
| 219 | | (DMSO-d6) 3.45 (3H, s), 4.68 (2H, s), 6.7-6.75 (1H, m), 7.35-7.45 (2H, m), 7.65-7.75 (1H, m), 7.85-8.0 (2H, m), 12.01 (1H, s), 14.25 (1H, brs) |
| 220 | | (DMSO-d6) 1.9-2.0 (6H, m), 3.38 (3H, s), 6.65-6.8 (2H, m), 7.3-7.4 (2H, m), 7.4-7.5 (1H, m), 7.55-7.6 (1H, m), 7.95-8.0 (1H, m), 12.0 (1H, s), 14.28 (1H, brs) |
| 221 | | (DMSO-d6) 1.85 (6H, s), 3.34 (3H, s), 6.84 (1H, dd, J = 9.1 Hz, 5.2 Hz), 7.1-7.25 (2H, m), 7.37 (1H, s), 7.4-7.45 (1H, m), 7.55-7.65 (1H, m), 7.9-8.0 (1H, m), 12.0 (1H, s), 14.29 (1H, brs) |
| 222 | | (DMSO-d6) 1.9-2.0 (6H, m), 3.36 (3H, s), 6.65-6.7 (1H, m), 7.35-7.45 (2H, m), 7.5-7.65 (2H, m), 7.95-8.0 (1H, m), 12.0 (1H, s), 14.28 (1H, brs) |

TABLE 78

| Ex No. | Strc | (Solv) ¹H-NMR δ ppm: |
|---|---|---|
| 223 | | (DMSO-d6) 4.85 (2H, s), 7.3-7.45 (5H, m), 7.65-7.75 (1H, m), 7.8-7.9 (1H, m), 8.05-8.1 (1H, m), 12.03 (1H, s), 14.25 (1H, brs) |
| 224 | | (DMSO-d6) 4.81 (2H, s), 7.05-7.15 (1H, m), 7.25-7.45 (4H, m), 7.7-7.8 (1H, m), 7.9-8.0 (1H, m), 8.05-8.1 (1H, m), 12.05 (1H, s), 14.24 (1H, brs) |

TABLE 78-continued

| Ex No. | Strc | (Solv) ¹H-NMR δ ppm: |
|---|---|---|
| 225 | | (DMSO-d6) 1.95 (6H, s), 7.25-7.45 (5H, m), 7.5-7.65 (2H, m), 8.03 (1H, dd, J = 6.8 Hz, 2.4 Hz), 12.0 (1H, s), 14.28 (1H, s) |
| 226 | | (DMSO-d6) 1.72 (6H, s), 7.3-7.5 (6H, m), 7.55-7.65 (1H, m), 8.01 (1H, dd, J = 6.7 Hz, 2.3 Hz), 12.02 (1H, s), 14.25 (1H, s) |
| 227 | | (DMSO-d6) 4.96 (2H, s), 7.35-7.45 (2H, m), 7.45-7.55 (2H, m), 7.65-7.75 (1H, m), 7.85-7.95 (1H, m), 8.15-8.2 (1H, m), 12.05 (1H, s), 14.28 (1H, s) |
| 228 | | (DMSO-d6) 3.43 (3H, s), 4.6-4.7 (2H, m), 6.85-6.9 (1H, m), 7.1-7.2 (2H, m), 7.37 (1H, s), 7.65-7.7 (1H, m), 7.75-7.85 (1H, m), 7.9-8.0 (1H, m), 12.04 (1H, s), 14.29 (1H, s) |
| 229 | | (DMSO-d6) 1.72 (3H, s), 1.73 (3H, s), 7.15-7.25 (3H, m), 7.35-7.45 (2H, m), 7.45-7.55 (1H, m), 7.6 (1H, t, J = 9.1 Hz), 7.9-8.0 (1H, m), 12.04 (1H, s), 14.28 (1H, brs) |

TABLE 79

| Ex No. | Strc | (Solv) ¹H-NMR δ ppm: |
|---|---|---|
| 230 | | (DMSO-d6) 1.86 (6H, s), 6.87 (1H, d, J = 8.8 Hz), 7.35-7.45 (4H, m), 7.55-7.65 (1H, m), 7.95-8.0 (1H, m), 12.03 (1H, s), 14.3 (1H, brs) |

TABLE 79-continued
| Ex No. | Strc | (Solv) ¹H-NMR δ ppm: |
|---|---|---|
| 231 | 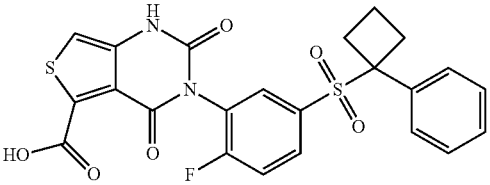 [SMILES: O=C(O)c1scc2[nH]c(=O)n(-c3cc(S(=O)(=O)C4(c5ccccc5)CCC4)ccc3F)c(=O)c12] | (DMSO-d6) 1.8-1.95 (1H, m), 2.0-2.15 (1H, m), 2.55-2.7 (2H, m), 3.0-3.15 (2H, m), 6.95-7.05 (2H, m), 7.2-7.35 (4H, m), 7.37 (1H, s), 7.45-7.55 (1H, m), 7.9-8.0 (1H, m), 12.0 (1H, s), 14.28 (1H, brs) |
| 232 | 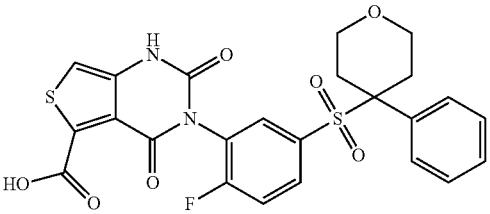 [SMILES: O=C(O)c1scc2[nH]c(=O)n(-c3cc(S(=O)(=O)C4(c5ccccc5)CCOCC4)ccc3F)c(=O)c12] | (DMSO-d6) 2.2-2.35 (2H, m), 3.05-3.2 (2H, m), 3.8-3.9 (2H, m), 7.2-7.4 (7H, m), 7.45-7.55 (1H, m), 7.8-7.9 (1H, m), 12.02 (1H, s), 14.25 (1H, brs) |
| 233 | 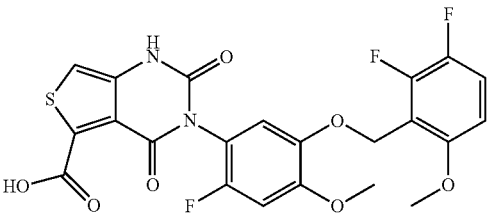 [SMILES: COc1cc(F)c(-n2c(=O)[nH]c3csc(C(=O)O)c3c2=O)cc1OCc1c(OC)ccc(F)c1F] | (DMSO-d6) 3.75-3.85 (6H, m), 4.96 (2H, s), 6.85-6.95 (1H, m), 7.13 (1H, d, J = 11.3 Hz), 7.26 (1H, d, J = 7.2 Hz), 7.39 (1H, s), 7.4-7.55 (1H, m), 12.0 (1H, s), 14.53 (1H, s) |
| 234 | 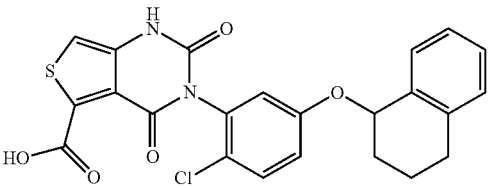 [SMILES: O=C(O)c1scc2[nH]c(=O)n(-c3cc(OC4CCCc5ccccc54)ccc3Cl)c(=O)c12] | (DMSO-d6) 1.7-2.1 (4H, m), 2.65-2.9 (2H, m), 5.45-5.5 (1H, m), 7.1-7.45 (7H, m), 7.57 (1H, d, J = 9.0 Hz), 12.0-12.1 (1H, m), 14.45 (1H, s) |
| 235 | 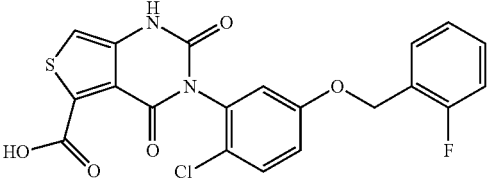 [SMILES: O=C(O)c1scc2[nH]c(=O)n(-c3cc(OCc4ccccc4F)ccc3Cl)c(=O)c12] | (DMSO-d6) 5.14 (2H, s), 7.15-7.5 (6H, m), 7.55-7.65 (2H, m), 12.05 (1H, s), 14.43 (1H, s) |
| 236 | 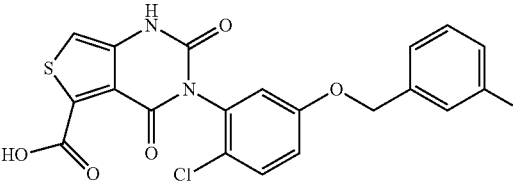 | (DMSO-d6) 5.14 (2H, s), 7.15-7.25 (2H, m), 7.25-7.5 (5H, m), 7.58 (1H, d, J = 9.1 Hz), 12.05 (1H, s), 14.43 (1H, s) |
TABLE 80
| Ex No. | Strc | (Solv) ¹H-NMR δ ppm: |
|---|---|---|
| 237 | 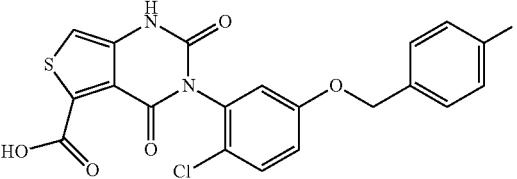 | (DMSO-d6) 5.09 (2H, s), 7.15-7.3 (3H, m), 7.32 (1H, d, J = 2.9 Hz), 7.41 (1H, s), 7.5-7.6 (3H, m), 12.04 (1H, s), 14.44 (1H, s) |

TABLE 80-continued

| Ex No. | Strc | (Solv) ¹H-NMR δ ppm: |
|---|---|---|
| 238 | | (DMSO-d6) 5.13 (2H, s), 7.19 (1H, dd, J = 9.0 Hz, 3.0 Hz), 7.3-7.5 (5H, m), 7.5-7.6 (2H, m), 12.05 (1H, s), 14.44 (1H, s) |
| 239 | | (DMSO-d6) 3.76 (3H, s), 5.08 (2H, s), 6.85-6.95 (1H, m), 7.0-7.05 (2H, m), 7.18 (1H, dd, J = 9.1 Hz, 3.1 Hz), 7.25-7.35 (2H, m), 7.41 (1H, s), 7.57 (1H, d, J = 9.1 Hz), 12.04 (1H, s), 14.44 (1H, s) |
| 240 | | (DMSO-d6) 1.5-1.6 (3H, m), 5.45-5.55 (1H, m), 7.0-7.1 (1H, m), 7.23 (1H, dd, J = 6.1 Hz, 2.9 Hz), 7.25-7.5 (7H, m), 11.95-12.1 (1H, m), 14.42 (1H, s) |
| 241 | | (DMSO-d6) 1.5-1.6 (3H, m), 5.45-5.55 (1H, m), 7.0-7.1 (1H, m), 7.23 (1H, dd, J = 6.1 Hz, 2.9 Hz), 7.25-7.5 (7H, m), 11.95-12.1 (1H, m), 14.42 (1H, s) |
| 242 | | (DMSO-d6) 3.82 (3H, s), 5.04 (2H, s), 6.95-7.0 (1H, m), 7.06 (1H, d, J = 7.9 Hz), 7.17 (1H, dd, J = 9.1 Hz, 2.9 Hz), 7.3-7.45 (4H, m), 7.56 (1H, d, J = 9.1 Hz), 12.04 (1H, s), 14.46 (1H, s) |
| 243 | | (DMSO-d6) 3.76 (3H, s), 5.02 (2H, s), 6.9-7.0 (2H, m), 7.15-7.2 (1H, m), 7.3 (1H, d, J = 3.3 Hz), 7.35-7.45 (3H, m), 7.56 (1H, d, J = 9.0 Hz), 12.04 (1H, s), 14.46 (1H, s) |

TABLE 81

| Ex No. | Strc | (Solv) ¹H-NMR δ ppm: |
|---|---|---|
| 244 | | (DMSO-d6) 5.18 (2H, s), 7.02 (1H, s), 7.16 (1H, dd, J = 9.0 Hz, 2.7 Hz), 7.25-7.4 (2H, m), 7.5-7.6 (2H, m), 7.8-7.9 (1H, m), 8.58 (1H, d, J = 4.5 Hz), 11.0-12.5 (1H, br) |

TABLE 81-continued

| Ex No. | Strc | (Solv) ¹H-NMR δ ppm: |
|---|---|---|
| 245 | | (DMSO-d6) 5.11 (2H, s), 7.15-7.2 (1H, m), 7.32 (1H, d, J = 2.9 Hz), 7.41 (1H, s), 7.45-7.55 (4H, m), 7.57 (1H, d, J = 8.6 Hz), 12.06 (1H, s), 14.43 (1H, s) |
| 246 | | (DMSO-d6) 5.16 (2H, s), 7.1-7.25 (2H, m), 7.31 (1H, d, J = 2.9 Hz), 7.4-7.5 (1H, m), 7.56 (1H, d, J = 9.0 Hz), 7.85-7.95 (1H, m), 8.5-8.6 (1H, m), 8.69 (1H, s), 11.0-13.0 (1H, br) |
| 247 | | (DMSO-d6) 2.1-2.25 (2H, m), 4.1-4.2 (1H, m), 4.25-4.35 (1H, m), 5.45-5.55 (1H, m), 6.8-6.95 (2H, m), 7.2-7.35 (3H, m), 7.35-7.45 (2H, m), 7.59 (1H, d, J = 8.7 Hz), 12.0-12.05 (1H, m), 14.42 (1H, s) |
| 248 | | (DMSO-d6) 5.2 (2H, s), 7.1-7.2 (2H, m), 7.3 (1H, d, J = 2.9 Hz), 7.4-7.5 (2H, m), 7.56 (1H, d, J = 8.8 Hz), 8.55-8.65 (2H, m), 11.0-13.0 (1H, br) |
| 249 | | (DMSO-d6) 1.6 (3H, d, J = 6.3 Hz), 5.65-5.75 (1H, m), 7.0-7.1 (1H, m), 7.15-7.3 (3H, m), 7.3-7.45 (2H, m), 7.45-7.55 (2H, m), 11.95-12.1 (1H, m), 14.42 (1H, s) |
| 250 | | (DMSO-d6) 1.5-1.6 (3H, m), 5.5-5.6 (1H, m), 7.0-7.15 (2H, m), 7.2-7.3 (3H, m), 7.35-7.55 (3H, m), 11.95-12.0 (1H, m), 14.41 (1H, s) |

TABLE 82

| Ex No. | Strc | (Solv) ¹H-NMR δ ppm: |
|---|---|---|
| 251 | | (DMSO-d6) 1.5-1.6 (3H, m), 5.45-5.6 (1H, m), 7.0-7.1 (1H, m), 7.15-7.25 (3H, m), 7.4 (1H, d, J = 4.1 Hz), 7.45-7.55 (3H, m), 11.95-12.05 (1H, m), 14.42 (1H, s) |

TABLE 82-continued

| Ex No. | Strc | (Solv) ¹H-NMR δ ppm: |
|---|---|---|
| 252 | | (DMSO-d6) 1.35-1.5 (1H, m), 1.65-2.05 (5H, m), 2.8-3.0 (2H, m), 5.45-5.6 (1H, m), 7.05-7.2 (4H, m), 7.25-7.35 (2H, m), 7.39 (1H, d, J = 3.8 Hz), 7.52 (1H, d, J = 8.8 Hz), 12.02 (1H, s), 14.43 (1H, s) |
| 253 | | (DMSO-d6) 1.73 (3H, d, J = 6.6 Hz), 6.07 (1H, q, J = 6.6 Hz), 6.89 (1H, dd, J = 9.0 Hz, 3.0 Hz), 7.15-7.2 (1H, m), 7.3-7.4 (2H, m), 7.45-7.55 (3H, m), 12.0 (1H, s), 14.4 (1H, s) |
| 254 | | (DMSO-d6) 1.53 (3H, d, J = 6.2 Hz), 5.68 (1H, q, J = 6.2 Hz), 6.85-7.0 (2H, m), 7.05 (1H, d, J = 8.4 Hz), 7.2 (1H, t, J = 3.2 Hz), 7.25-7.4 (3H, m), 7.47 (1H, d, J = 9.3 Hz), 12.01 (1H, s), 14.45 (1H, s) |
| 255 | | (DMSO-d6) 1.5-1.6 (3H, m), 3.7-3.75 (3H, m), 5.4-5.5 (1H, m), 6.8-6.9 (1H, m), 6.95-7.1 (3H, m), 7.2-7.3 (2H, m), 7.4 (1H, d, J = 3.4 Hz), 7.47 (1H, dd, J = 9.0 Hz, 1.6 Hz), 11.95-12.05 (1H, m), 14.43 (1H, s) |
| 256 | | (DMSO-d6) 1.5-1.6 (3H, m), 3.73 (3H, s), 5.4-5.5 (1H, m), 6.85-6.95 (2H, m), 7.0-7.05 (1H, m), 7.15-7.25 (1H, m), 7.3-7.5 (4H, m), 11.95-12.05 (1H, m), 14.44 (1H, s) |
| 257 | | (DMSO-d6) 0.93 (3H, t, J = 7.5 Hz), 1.9-2.05 (1H, m), 2.1-2.25 (1H, m), 5.55 (1H, t, J = 7.3 Hz), 6.95-7.25 (4H, m), 7.35-7.5 (2H, m), 7.52 (1H, d, J = 8.7 Hz), 11.95-12.05 (1H, m), 14.4 (1H, s) |

TABLE 83

| Ex No. | Strc | (Solv) ¹H-NMR δ ppm: |
|---|---|---|
| 258 | | (DMSO-d6) 0.93 (3H, t, J = 7.4 Hz), 1.9-2.05 (1H, m), 2.1-2.25 (1H, m), 5.5-5.6 (1H, m), 6.95-7.25 (4H, m), 7.35-7.5 (1H, m), 7.52 (1H, d, J = 9.2 Hz), 7.95 (1H, d, J = 6.7 Hz), 12.99 (1H, s), 13.8-14.0 (1H, m) |

TABLE 83-continued
| Ex No. | Strc | (Solv) ¹H-NMR δ ppm: |
|---|---|---|
| 259 | 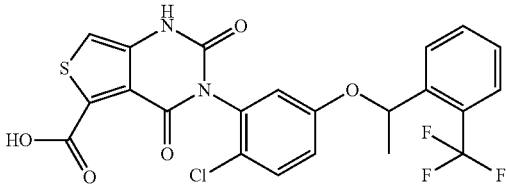 [SMILES: CC(Oc1ccc(Cl)c(-n2c(=O)[nH]c3csc(C(=O)O)c3c2=O)c1)c1ccccc1C(F)(F)F] | (DMSO-d6) 1.55-1.65 (3H, m), 5.65-5.8 (1H, m), 6.9-7.0 (1H, m), 7.2-7.3 (1H, m), 7.35-7.45 (1H, m), 7.45-7.6 (2H, m), 7.7-7.85 (3H, m), 12.03 (1H, s), 14.41 (1H, s) |
| 260 | 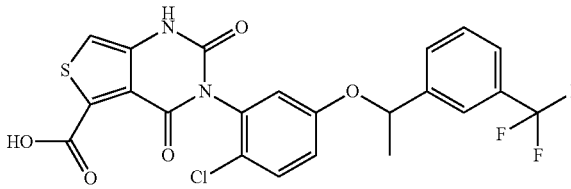 | (DMSO-d6) 1.55-1.65 (3H, m), 5.6-5.7 (1H, m), 7.05-7.15 (1H, m), 7.25-7.3 (1H, m), 7.4 (1H, d, J = 5.6 Hz), 7.45-7.55 (1H, m), 7.55-7.85 (4H, m), 11.95-12.1 (1H, m), 14.4 (1H, s) |
| 261 | 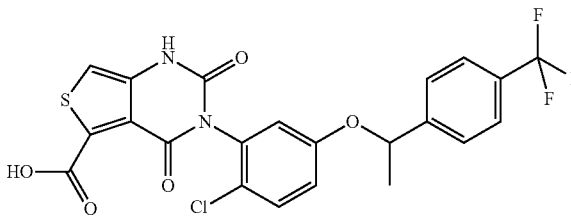 | (DMSO-d6) 1.55-1.65 (3H, m), 5.6-5.7 (1H, m), 7.0-7.1 (1H, m), 7.25 (1H, dd, J = 6.6 Hz, 3.0 Hz), 7.4 (1H, d, J = 5.3 Hz), 7.45-7.55 (1H, m), 7.6-7.7 (2H, m), 7.7-7.8 (2H, m), 11.95-12.1 (1H, m), 14.4 (1H, s) |
| 262 | 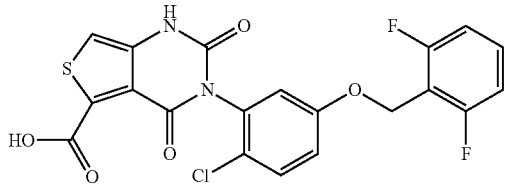 [SMILES: O=C(O)c1scc2[nH]c(=O)n(-c3cc(OCc4c(F)cccc4F)ccc3Cl)c(=O)c12] | (DMSO-d6) 5.13 (2H, s), 7.15-7.3 (3H, m), 7.34 (1H, d, J = 2.9 Hz), 7.4 (1H, s), 7.5-7.65 (2H, m), 12.03 (1H, s), 14.4 (1H, s) |
| 263 | 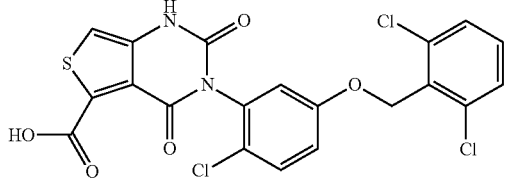 [SMILES: O=C(O)c1scc2[nH]c(=O)n(-c3cc(OCc4c(Cl)cccc4Cl)ccc3Cl)c(=O)c12] | (DMSO-d6) 5.24 (2H, s), 7.2-7.65 (7H, m), 12.02 (1H, s), 14.39 (1H, s) |
| 264 | 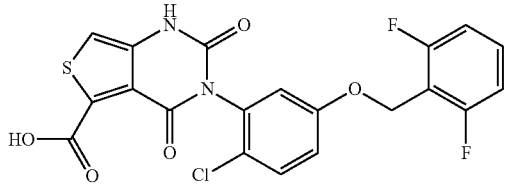 [SMILES: O=C(O)c1scc2[nH]c(=O)n(-c3cc(OCc4c(F)cccc4F)ccc3Cl)c(=O)c12] | (DMSO-d6) 5.12 (2H, s), 7.15-7.25 (3H, m), 7.32 (1H, d, J = 3.1 Hz), 7.5-7.65 (2H, m), 7.94 (1H, s), 12.8-13.2 (1H, br), 13.93 (1H, s) |
TABLE 84
| Ex No. | Strc | (Solv) ¹H-NMR δ ppm: |
|---|---|---|
| 265 | 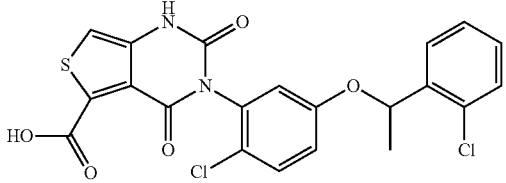 [SMILES: CC(Oc1ccc(Cl)c(-n2c(=O)[nH]c3csc(C(=O)O)c3c2=O)c1)c1ccccc1Cl] | (DMSO-d6) 1.59 (3H, d, J = 6.3 Hz), 5.71 (1H, q, J = 6.3 Hz), 6.85-6.95 (1H, m), 7.2-7.25 (1H, m), 7.3-7.45 (3H, m), 7.45-7.55 (3H, m), 11.95-12.05 (1H, m), 14.39 (1H, s) |

TABLE 84-continued

| Ex No. | Strc | (Solv) $^1$H-NMR δ ppm: |
| --- | --- | --- |
| 266 | | (DMSO-d6) 1.56 (3H, d, J = 6.2 Hz), 5.45-5.6 (1H, m), 7.0-7.1 (1H, m), 7.2-7.55 (7H, m), 11.95-12.05 (1H, m), 14.39 (1H, s) |
| 267 | | (DMSO-d6) 1.5-1.6 (3H, m), 5.45-5.6 (1H, m), 7.0-7.05 (1H, m), 7.22 (1H, dd, J = 8.9 Hz, 3.0 Hz), 7.35-7.5 (6H, m), 11.9-12.05 (1H, m), 14.39 (1H, s) |
| 268 | | (DMSO-d6) 1.9-2.15 (4H, m), 3.75-3.85 (1H, m), 4.1-4.25 (1H, m), 5.45-5.55 (1H, m), 6.95-7.45 (7H, m), 7.53 (1H, d, J = 8.9 Hz), 11.95-12.05 (1H, m), 14.42 (1H, s) |
| 269 | | (DMSO-d6) 0.91 (3H, t, J = 7.5 Hz), 1.75-2.0 (2H, m), 5.2-5.3 (1H, m), 6.95-7.05 (1H, m), 7.15-7.5 (8H, m), 11.95-12.05 (1H, m), 14.39 (1H, s) |
| 270 | | (DMSO-d6) 1.71 (3H, d, J = 6.5 Hz), 5.81 (1H, q, J = 6.5 Hz), 7.0-7.15 (3H, m), 7.2-7.25 (1H, m), 7.35-7.5 (2H, m), 7.53 (1H, d, J = 9.2 Hz), 11.95-12.05 (1H, m), 14.41 (1H, s) |
| 271 | | (DMSO-d6) 1.65-1.75 (6H, m), 6.64 (1H, dd, J = 8.7 Hz, 2.8 Hz), 7.07 (1H, d, J = 2.8 Hz), 7.25-7.5 (7H, m), 11.97 (1H, s), 14.42 (1H, s) |

TABLE 85

| Ex No. | Strc | (Solv) $^1$H-NMR δ ppm: |
| --- | --- | --- |
| 272 | | (DMSO-d6) 0.82 (3H, d, J = 6.4 Hz), 0.95-1.05 (3H, m), 2.05-2.15 (1H, m), 5.0-5.1 (1H, m), 6.95-7.05 (1H, m), 7.15-7.5 (8H, m), 11.95-12.05 (1H, m), 14.4 (1H, s) |

TABLE 85-continued

| Ex No. | Strc | (Solv) ¹H-NMR δ ppm: |
|---|---|---|
| 273 | | (DMSO-d6) 0.91 (3H, t, J = 7.4 Hz), 1.25-1.5 (2H, m), 1.7-1.8 (1H, m), 1.85-2.0 (1H, m), 5.3-5.35 (1H, m), 6.95-7.05 (1H, m), 7.15-7.5 (8H, m), 11.95-12.05 (1H, m), 14.41 (1H, brs) |
| 274 | | (DMSO-d6) 0.91 (3H, t, J = 7.4 Hz), 1.75-2.0 (2H, m), 5.25-5.35 (1H, m), 7.0-7.1 (1H, m), 7.2-7.25 (1H, m), 7.3-7.55 (6H, m), 11.95-12.05 (1H, m), 14.4 (1H, s) |
| 275 | | (DMSO-d6) 0.85 (3H, t, J = 7.1 Hz), 1.2-1.45 (4H, m), 1.7-1.85 (1H, m), 1.9-2.0 (1H, m), 5.25-5.35 (1H, m), 6.95-7.05 (1H, m), 7.15-7.5 (8H, m), 11.95-12.05 (1H, m), 14.41 (1H, s) |
| 276 | | (DMSO-d6) 3.05 (2H, t, J = 7.0 Hz), 4.19 (2H, t, J = 7.0 Hz), 7.05-7.15 (1H, m), 7.2-7.35 (6H, m), 7.4 (1H, s), 7.54 (1H, d, J = 9.2 Hz), 12.03 (1H, s), 14.45 (1H, s) |
| 277 | | (DMSO-d6) 3.09 (2H, t, J = 6.8 Hz), 4.19 (2H, t, J = 6.8 Hz), 7.05-7.35 (5H, m), 7.35-7.45 (2H, m), 7.54 (1H, d, J = 8.9 Hz), 12.03 (1H, s), 14.45 (1H, s) |
| 278 | | (DMSO-d6) 1.22 (3H, d, J = 6.0 Hz), 2.8-2.9 (1H, m), 2.95-3.05 (1H, m), 4.6-4.75 (1H, m), 7.09 (1H, dd, J = 9.0 Hz, 3.0 Hz), 7.15-7.35 (6H, m), 7.35-7.45 (1H, m), 7.52 (1H, d, J = 9.2 Hz), 12.02 (1H, s), 14.46 (1H, s) |

TABLE 86

| Ex No. | Strc | (Solv) ¹H-NMR δ ppm: |
|---|---|---|
| 279 | | (DMSO-d6) 0.93 (3H, t, J = 7.5 Hz), 1.8-2.05 (2H, m), 5.47 (1H, t, J = 6.1 Hz), 6.95-7.05 (1H, m), 7.15-7.25 (3H, m), 7.3-7.55 (4H, m), 11.95-12.05 (1H, m), 14.35-14.45 (1H, m) |

TABLE 86-continued

| Ex No. | Strc | (Solv) ¹H-NMR δ ppm: |
|---|---|---|
| 280 | | (DMSO-d6) 1.32 (3H, d, J = 6.9 Hz), 3.15-3.3 (1H, m), 4.0-4.15 (2H, m), 7.09 (1H, dd, J = 8.9 Hz, 3.1 Hz), 7.15-7.45 (7H, m), 7.52 (1H, d, J = 8.9 Hz), 12.02 (1H, s), 14.45 (1H, s) |
| 281 | | (DMSO-d6) 0.93 (3H, t, J = 7.5 Hz), 1.8-2.05 (2H, m), 5.48 (1H, t, J = 6.5 Hz), 6.95-7.05 (1H, m), 7.15-7.25 (3H, m), 7.3-7.4 (1H, m), 7.4-7.55 (2H, m), 7.94 (1H, d, J = 3.4 Hz), 12.98 (1H, s), 13.93 (1H, s) |
| 282 | | (DMSO-d6) 1.32 (3H, d, J = 6.9 Hz), 3.15-3.3 (1H, m), 4.0-4.15 (2H, m), 7.05-7.1 (1H, m), 7.15-7.4 (6H, m), 7.52 (1H, d, J = 9.0 Hz), 7.95 (1H, s), 13.0 (1H, s), 13.98 (1H, s) |
| 283 | | (DMSO-d6) 5.15 (2H, s), 7.15-7.3 (4H, m), 7.35 (1H, d, J = 2.8 Hz), 7.46 (1H, s), 7.59 (1H, d, J = 8.8 Hz), 12.19 (1H, s) |
| 284 | | (DMSO-d6) 5.14 (2H, s), 7.2-7.5 (6H, m), 7.6 (1H, d, J = 8.7 Hz), 12.11 (1H, s), 14.44 (1H, s) |
| 285 | | (DMSO-d6) 1.4 (6H, s), 4.01 (2H, s), 7.05-7.15 (1H, m), 7.15-7.25 (2H, m), 7.3-7.35 (2H, m), 7.39 (1H, s), 7.4-7.5 (2H, m), 7.52 (1H, d, J = 9.2 Hz), 12.0 (1H, s), 14.44 (1H, s) |

TABLE 87

| Ex No. | Strc | (Solv) ¹H-NMR δ ppm: |
|---|---|---|
| 286 | | (DMSO-d6) 1.52 (3H, d, J = 6.3 Hz), 3.67 (3H, s), 3.75-3.85 (3H, m), 5.65 (1H, q, J = 6.3 Hz), 6.8-7.0 (4H, m), 7.15-7.25 (1H, m), 7.39 (1H, d, J = 1.9 Hz), 7.48 (1H, d, J = 8.9 Hz), 11.99 (1H, s), 14.42 (1H, s) |

TABLE 87-continued

| Ex No. | Strc | (Solv) $^1$H-NMR δ ppm: |
|---|---|---|
| 287 | | (DMSO-d6) 1.55 (3H, d, J = 6.3 Hz), 3.31 (3H, s), 3.7-3.75 (3H, m), 5.35-5.45 (1H, m), 6.35-6.45 (1H, m), 6.5-6.6 (2H, m), 7.0-7.1 (1H, m), 7.2-7.3 (1H, m), 7.39 (1H, d, J = 2.0 Hz), 7.45-7.5 (1H, m), 11.95-12.05 (1H, m), 14.41 (1H, s) |
| 288 | | (DMSO-d6) 1.5-1.6 (3H, m), 3.81 (3H, s), 5.4-5.5 (1H, m), 7.0-7.3 (5H, m), 7.4 (1H, d, J = 3.9 Hz), 7.48 (1H, dd, J = 8.9 Hz, 1.6 Hz), 11.95-12.05 (1H, m), 14.41 (1H, s) |
| 289 | | (DMSO-d6) 1.58 (3H, d, J = 6.4 Hz), 3.75 (3H, s), 5.55-5.7 (1H, m), 6.75-6.9 (2H, m), 6.95-7.05 (1H, m), 7.15-7.55 (4H, m), 11.95-12.05 (1H, m), 14.42 (1H, s) |
| 290 | | (DMSO-d6) 1.75 (6H, s), 6.78 (1H, dd, J = 9.0 Hz, 3.0 Hz), 7.0-7.55 (7H, m), 11.91 (1H, brs), 14.0-14.8 (1H, br) |
| 291 | | (DMSO-d6) 0.8 (3H, t, J = 7.3 Hz), 1.65-1.7 (3H, m), 1.85-2.05 (2H, m), 6.55-6.65 (1H, m), 7.08 (1H, dd, J = 6.6 Hz, 3.0 Hz), 7.25-7.45 (7H, m), 11.97 (1H, s), 14.43 (1H, s) |
| 292 | | (DMSO-d6) 1.83 (6H, s), 6.69 (1H, dd, J = 9.1 Hz, 3.1 Hz), 7.06 (1H, d, J = 3.1 Hz), 7.3-7.5 (5H, m), 7.61 (1H, dd, J = 7.7 Hz, 1.8 Hz), 11.96 (1H, s), 14.42 (1H, s) |

TABLE 88

| Ex No. | Strc | (Solv) $^1$H-NMR δ ppm: |
|---|---|---|
| 293 | | (DMSO-d6) 5.15 (2H, s), 7.15-7.75 (7H, m), 12.03 (1H, s), 14.41 (1H, s) |

TABLE 88-continued

| Ex No. | Strc | (Solv) ¹H-NMR δ ppm: |
|---|---|---|
| 294 | | (DMSO-d6) 5.14 (2H, s), 7.23 (1H, dd, J = 8.8 Hz, 3.2 Hz), 7.3-7.45 (3H, m), 7.45-7.55 (1H, m), 7.59 (1H, d, J = 9.1 Hz), 7.65-7.7 (1H, m), 12.03 (1H, s), 14.41 (1H, s) |
| 295 | | (DMSO-d6) 1.56 (3H, d, J = 6.3 Hz), 5.45-5.55 (1H, m), 6.85-6.9 (1H, m), 6.95-7.05 (2H, m), 7.25-7.45 (7H, m), 11.9 (1H, s) |
| 296 | | (DMSO-d6) 1.56 (3H, d, J = 6.4 Hz), 5.5 (1H, q, J = 6.4 Hz), 6.85-6.9 (1H, m), 6.9-7.05 (2H, m), 7.25-7.4 (4H, m), 7.4-7.45 (2H, m), 7.99 (1H, s), 12.86 (1H, s), 14.43 (1H, s) |
| 297 | | (DMSO-d6) 1.52 (3H, d, J = 6.0 Hz), 3.84 (3H, s), 5.6-5.7 (1H, m), 6.85-7.55 (7H, m), 11.99 (1H, s), 14.42 (1H, s) |
| 298 | | (DMSO-d6) 1.52 (3H, d, J = 6.4 Hz), 3.85-3.9 (3H, m), 5.6-5.7 (1H, m), 6.75-6.8 (1H, m), 6.85-7.0 (2H, m), 7.15-7.25 (1H, m), 7.3-7.45 (2H, m), 7.48 (1H, d, J = 9.2 Hz), 12.0 (1H, s), 14.44 (1H, s) |
| 299 | | (DMSO-d6) 1.3-1.4 (3H, m), 1.54 (3H, d, J = 6.3 Hz), 4.05-4.2 (2H, m), 5.65-5.75 (1H, m), 6.85-7.0 (2H, m), 7.0-7.05 (1H, m), 7.15-7.35 (3H, m), 7.39 (1H, d, J = 4.2 Hz), 7.48 (1H, d, J = 9.1 Hz), 11.95-12.05 (1H, m), 14.42 (1H, s) |

TABLE 89

| Ex No. | Strc | (Solv) ¹H-NMR δ ppm: |
|---|---|---|
| 300 | | (DMSO-d6) 1.66 (3H, d, J = 6.6 Hz), 3.85-3.9 (3H, m), 5.8-5.9 (1H, m), 6.75-6.85 (1H, m), 6.85-7.0 (2H, m), 7.17 (1H, d, J = 2.6 Hz), 7.25-7.4 (2H, m), 7.48 (1H, d, J = 8.6 Hz), 12.0 (1H, s), 14.42 (1H, s) |

TABLE 89-continued

| Ex No. | Strc | (Solv) ¹H-NMR δ ppm: |
|---|---|---|
| 301 | | (DMSO-d6) 1.5-1.6 (3H, m), 1.95 (3H, s), 5.4-5.5 (1H, m), 6.85-6.95 (1H, m), 6.98 (1H, dd, J = 5.8 Hz, 2.6 Hz), 7.15-7.45 (7H, m), 11.85-11.95 (1H, m), 14.76 (1H, s) |
| 302 | | (DMSO-d6) 1.56 (3H, d, J = 6.3 Hz), 5.52 (1H, q, J = 6.3 Hz), 7.03 (1H, dd, J = 9.0 Hz, 3.0 Hz), 7.15-7.5 (7H, m), 7.9-8.0 (1H, m), 12.99 (1H, brs), 13.95 (1H, s) |
| 303 | | (DMSO-d6) 3.85 (3H, s), 5.03 (2H, s), 6.85-7.0 (2H, m), 7.21 (1H, dd, J = 8.9 Hz, 3.1 Hz), 7.32 (1H, d, J = 3.1 Hz), 7.4-7.5 (2H, m), 7.58 (1H, d, J = 8.9 Hz), 12.06 (1H, s), 14.43 (1H, s) |
| 304 | | (DMSO-d6) 1.73 (3H, d, J = 6.7 Hz), 6.0-6.1 (1H, m), 6.8-6.85 (1H, m), 6.9-7.0 (2H, m), 7.3-7.4 (3H, m), 7.45-7.5 (2H, m), 11.89 (1H, s), 14.86 (1H, s) |
| 305 | | (DMSO-d6) 1.73 (3H, d, J = 6.7 Hz), 6.05 (1H, q, J = 6.7 Hz), 6.8-7.0 (3H, m), 7.3-7.4 (2H, m), 7.45-7.5 (2H, m), 7.99 (1H, s), 12.92 (1H, s), 14.43 (1H, s) |
| 306 | | (DMSO-d6) 1.56 (3H, d, J = 5.7 Hz), 5.45-5.55(1H, m), 7.0-7.5 (8H, m), 11.95-12.05 (1H, m), 14.4 (1H, brs) |

TABLE 90

| Ex No. | Strc | (Solv) ¹H-NMR δ ppm: |
|---|---|---|
| 307 | | (DMSO-d6) 1.52 (3H, d, J = 6.2 Hz), 3.84 (3H, s), 5.55-5.65 (1H, m), 6.9-7.0 (1H, m), 7.0-7.15 (4H, m), 7.2-7.3 (1H, m), 7.35-7.4 (1H, m), 11.98 (1H, s), 14.4 (1H, s) |

TABLE 90-continued

| Ex No. | Strc | (Solv) $^1$H-NMR δ ppm: |
|---|---|---|
| 308 | | (DMSO-d6) 5.2-5.35 (2H, m), 7.25 (1H, dd, J = 9.1 Hz, 3.0 Hz), 7.38 (1H, d, J = 3.0 Hz), 7.41 (1H, s), 7.55-7.65 (2H, m), 7.75-7.8 (2H, m), 7.94 (1H, d, J = 7.7 Hz), 12.05 (1H, s), 14.43 (1H, s) |
| 309 | | (DMSO-d6) 3.26 (3H, s), 3.6-3.7 (2H, m), 4.1-4.2 (2H, m), 5.07 (2H, s), 6.95-7.0 (1H, m), 7.07 (1H, d, J = 8.0 Hz), 7.15-7.2 (1H, m), 7.3-7.4 (2H, m), 7.4-7.45 (2H, m), 7.55 (1H, d, J = 9.3 Hz), 12.04 (1H, s), 14.46 (1H, s) |
| 310 | | (DMSO-d6) 3.83 (3H, s), 5.0-5.1 (2H, m), 6.9-6.95 (1H, m), 7.15-7.25 (2H, m), 7.3-7.4 (2H, m), 7.45-7.55 (1H, m), 12.02 (1H, s), 14.4 (1H, s) |
| 311 | | (DMSO-d6) 1.66 (3H, d, J = 6.5 Hz), 3.8-3.9 (3H, m), 5.75-5.85 (1H, m), 6.8-7.0 (2H, m), 7.05-7.15 (1H, m), 7.2-7.4 (3H, m), 11.95-12.05 (1H, m), 14.39 (1H, s) |
| 312 | | (DMSO-d6) 2.48 (3H, s), 5.09 (2H, s), 7.15-7.25 (2H, m), 7.34 (1H, d, J = 2.9 Hz), 7.35-7.45 (3H, m), 7.49 (1H, d, J = 7.2 Hz), 7.58 (1H, d, J = 9.0 Hz), 12.04 (1H, s), 14.45 (1H, s) |
| 313 | | (DMSO-d6) 5.1 (2H, s), 6.95-7.0 (1H, m), 7.05-7.15 (2H, m), 7.3-7.5 (7H, m), 11.88 (1H, s), 14.89 (1H, s) |

TABLE 91

| Ex No. | Strc | (Solv) $^1$H-NMR δ ppm: |
|---|---|---|
| 314 | | (DMSO-d6) 5.14 (2H, s), 7.2-7.3 (3H, m), 7.35-7.45 (2H, m), 7.55-7.65 (1H, m), 12.02 (1H, s), 14.38 (1H, s) |

| Ex No. | Strc | (Solv) ¹H-NMR δ ppm: |
|---|---|---|
| 315 | | (DMSO-d6) 5.08 (2H, s), 7.15-7.25 (1H, m), 7.25-7.3 (1H, m), 7.35-7.4 (2H, m), 7.55-7.7 (1H, m), 7.7-7.8 (1H, m), 12.0 (1H, s), 14.4 (1H, s) |
| 316 | | (DMSO-d6) 5.2 (2H, s), 7.2-7.3 (2H, m), 7.35-7.45 (2H, m), 7.95-8.05 (1H, m), 12.02 (1H, s), 14.38 (1H, s) |
| 317 | | (DMSO-d6) 3.82 (3H, s), 5.02 (2H, s), 6.95-7.0 (1H, m), 7.06 (1H, d, J = 8.2 Hz), 7.1-7.2 (1H, m), 7.24 (1H, dd, J = 6.0 Hz, 3.2 Hz), 7.3-7.45 (4H, m), 12.01 (1H, s), 14.44 (1H, s) |
| 318 | | (DMSO-d6) 1.31 (3H, t, J = 6.9 Hz), 4.09 (2H, q, J = 6.9 Hz), 5.03 (2H, s), 6.9-7.0 (1H, m), 7.04 (1H, d, J = 8.2 Hz), 7.1-7.2 (1H, m), 7.2-7.25 (1H, m), 7.3-7.45 (4H, m), 12.01 (1H, s), 14.43 (1H, s) |
| 319 | | (DMSO-d6) 5.08 (2H, s), 7.05-7.5 (7H, m), 7.55-7.65 (1H, m), 12.01 (1H, s), 14.42 (1H, s) |
| 320 | | (DMSO-d6) 2.34 (6H, s), 5.03 (2H, s), 7.0-7.45 (7H, m), 12.0 (1H, s), 14.4 (1H, s) |

TABLE 92

| Ex No. | Strc | (Solv) ¹H-NMR δ ppm: |
|---|---|---|
| 321 | | (DMSO-d6) 5.17 (2H, s), 7.2-7.3 (2H, m), 7.35-7.45 (2H, m), 7.74 (1H, d, J = 8.2 Hz), 7.9-8.0 (1H, m), 12.02 (1H, s), 14.38 (1H, s) |
| 322 | | (DMSO-d6) 2.2-2.3 (3H, m), 5.05-5.15 (2H, m), 7.2-7.3 (2H, m), 7.32 (1H, d, J = 8.6 Hz), 7.35-7.45 (3H, m), 12.02 (1H, s), 14.39 (1H, s) |
| 323 | | (DMSO-d6) 3.85-3.95 (3H, m), 5.07 (2H, s), 7.1-7.4 (7H, m), 12.01 (1H, s), 14.42 (1H, s) |
| 324 | | (DMSO-d6) 5.18 (2H, s), 7.15-7.25 (1H, m), 7.25-7.35 (1H, m), 7.35-7.5 (3H, m), 7.55-7.7 (2H, m), 12.01 (1H, s), 14.41 (1H, s) |
| 325 | | (DMSO-d6) 3.81 (3H, s), 5.02 (2H, s), 7.0-7.1 (1H, m), 7.1-7.2 (2H, m), 7.2-7.4 (4H, m), 12.01 (1H, s), 14.42 (1H, s) |
| 326 | | (DMSO-d6) 3.75 (3H, s), 5.08 (2H, s), 6.9-7.0 (1H, m), 7.1-7.25 (3H, m), 7.27 (1H, dd, J = 6.1 Hz, 3.2 Hz), 7.3-7.4 (2H, m), 12.02 (1H, s), 14.41 (1H, s) |
| 327 | | (DMSO-d6) 5.14 (2H, s), 7.15-7.35 (3H, m), 7.35-7.45 (2H, m), 7.7-7.8 (1H, m), 12.02 (1H, s), 14.39 (1H, s) |

TABLE 93

| Ex No. | Strc | (Solv) ¹H-NMR δ ppm: |
|---|---|---|
| 328 | | (DMSO-d6) 3.83 (3H, s), 5.01 (2H, s), 7.09 (1H, d, J = 8.8 Hz), 7.15-7.2 (1H, m), 7.25-7.35 (1H, m), 7.3-7.45 (3H, m), 7.48 (1H, d, J = 2.6 Hz), 12.02 (1H, s), 14.43 (1H, s) |
| 329 | | (DMSO-d6) 5.12 (2H, s), 7.15-7.25 (1H, m), 7.27 (1H, dd, J = 6.0 Hz, 3.2 Hz), 7.3-7.4 (2H, m), 7.4-7.5 (2H, m), 7.5-7.6 (1H, m), 7.7 (1H, dd, J = 7.4 Hz, 1.6 Hz), 12.01 (1H, s), 14.41 (1H, s) |
| 330 | | (DMSO-d6) 3.85 (3H, s), 5.1 (2H, s), 7.2-7.35 (2H, m), 7.35-7.45 (3H, m), 7.63 (1H, d, J = 8.7 Hz), 12.01 (1H, s), 14.38 (1H, s) |
| 331 | | (DMSO-d6) 5.21 (2H, s), 7.2-7.35 (2H, m), 7.35-7.45 (2H, m), 7.53 (1H, t, J = 9.2 Hz), 7.8-7.9 (1H, m), 8.02 (1H, d, J = 6.1 Hz), 12.02 (1H, s), 14.4 (1H, s) |
| 332 | | (DMSO-d6) 5.21 (2H, s), 7.15-7.25 (1H, m), 7.3 (1H, dd, J = 5.8 Hz, 3.0 Hz), 7.35-7.5 (3H, m), 7.65-7.75 (1H, m), 7.89 (1H, dd, J = 8.7 Hz, 5.4 Hz), 12.01 (1H, s), 14.4 (1H, s) |
| 333 | | (DMSO-d6) 2.24 (3H, s), 5.08 (2H, s), 7.05-7.15 (1H, m), 7.15-7.3 (2H, m), 7.35-7.45 (3H, m), 12.02 (1H, s), 14.4 (1H, s) |
| 334 | | (DMSO-d6) 2.13 (3H, s), 3.82 (3H, s), 5.0 (2H, s), 6.85-6.95 (1H, m), 7.25 (1H, d, J = 10.0 Hz), 7.32 (1H, d, J = 6.4 Hz), 7.39 (1H, s), 7.4-7.55 (1H, m), 12.01 (1H, s), 14.47 (1H, s) |

TABLE 94

| Ex No. | Strc | (Solv) ¹H-NMR δ ppm: |
|---|---|---|
| 335 | | (DMSO-d6) 2.12 (3H, s), 3.84 (3H, s), 4.96 (2H, s), 6.8-7.0 (2H, m), 7.24 (1H, d, J = 10.2 Hz), 7.32 (1H, d, J = 6.3 Hz), 7.35-7.5 (2H, m), 12.04 (1H, s), 14.48 (1H, s) |
| 336 | | (DMSO-d6) 2.36 (3H, s), 5.1-5.15 (2H, m), 7.2-7.3 (3H, m), 7.35-7.45 (2H, m), 7.5 (1H, dd, J = 8.7 Hz, 6.2 Hz), 12.03 (1H, s), 14.4 (1H, s) |
| 337 | | (DMSO-d6) 3.86 (3H, s), 5.04 (2H, s), 7.0 (1H, d, J = 9.3 Hz), 7.15-7.25 (2H, m), 7.3-7.4 (2H, m), 7.55-7.65 (1H, m), 12.03 (1H, s), 14.41 (1H, s) |
| 338 | | (DMSO-d6) 2.3 (3H, s), 5.06 (2H, s), 7.1-7.45 (7H, m), 12.03 (1H, s), 14.43 (1H, s) |
| 339 | | (DMSO-d6) 3.88 (3H, s), 5.13 (2H, s), 7.15-7.25 (3H, m), 7.27 (1H, dd, J = 6.0 Hz, 3.2 Hz), 7.3-7.4 (3H, m), 12.02 (1H, s), 14.42 (1H, s) |
| 340 | | (DMSO-d6) 3.85 (3H, s), 5.11 (2H, s), 7.05-7.3 (5H, m), 7.3-7.4 (2H, m), 12.02 (1H, s), 14.42 (1H, s) |
| 341 | | (DMSO-d6) 1.1 (3H, t, J = 7.5 Hz), 2.45-2.6 (2H, m), 3.82 (3H, s), 5.0 (2H, s), 6.9-6.95 (1H, m), 7.23 (1H, d, J = 10.3 Hz), 7.34 (1H, d, J = 6.3 Hz), 7.39 (1H, s), 7.4-7.55 (1H, m), 12.03 (1H, s), 14.47 (1H, s) |

TABLE 95
| Ex No. | Strc | (Solv) ¹H-NMR δ ppm: |
|---|---|---|
| 342 | 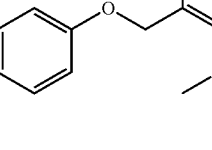 | (DMSO-d6) 3.84 (3H, s), 5.1 (2H, s), 7.13 (1H, dd, J = 9.2 Hz, 4.0 Hz), 7.15-7.3 (2H, m), 7.3-7.4 (2H, m), 7.45-7.55 (1H, m), 12.03 (1H, s) |
| 343 | 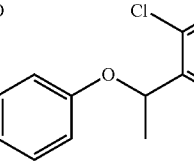 | (DMSO-d6) 1.73 (3H, d, J = 6.7 Hz), 2.5-2.55 (3H, m), 6.07 (1H, q, J = 6.7 Hz), 6.85-6.95 (1H, m), 7.15-7.2 (1H, m), 7.3-7.4 (1H, m), 7.45-7.55 (3H, m), 11.89 (1H, s), 14.37 (1H, s) |
| 344 | 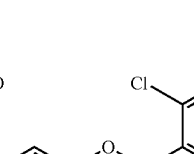 | (DMSO-d6) 3.86 (3H, s), 5.12 (2H, s), 7.1-7.3 (3H, m), 7.3-7.4 (2H, m), 7.69 (1H, d, J = 8.7 Hz), 12.03 (1H, s), 14.41 (1H, s) |
| 345 | 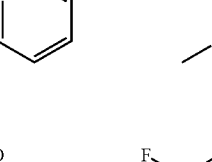 | (DMSO-d6) 2.15-2.2 (3H, m), 3.81 (3H, s), 5.0 (2H, s), 6.84 (1H, d, J = 8.5 Hz), 7.15-7.25 (2H, m), 7.25-7.4 (3H, m), 12.03 (1H, s), 14.42 (1H, s) |
| 346 | 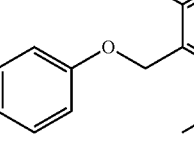 | (DMSO-d6) 5.08 (2H, s), 7.1-7.5 (9H, m), 12.01 (1H, s), 14.42 (1H, s) |
| 347 | 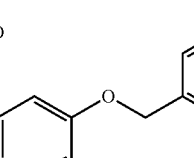 | (DMSO-d6) 1.1 (3H, t, J = 7.5 Hz), 2.45-2.55 (2H, m), 3.84 (3H, s), 4.97 (2H, s), 6.85-7.0 (2H, m), 7.22 (1H, d, J = 10.2 Hz), 7.33 (1H, d, J = 6.4 Hz), 7.35-7.5 (2H, m), 12.02 (1H, s), 14.47 (1H, brs) |
| 348 | 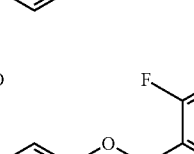 | (DMSO-d6) 5.11 (2H, s), 7.1-7.3 (2H, m), 7.3-7.45 (2H, m), 7.5-7.65 (3H, m), 12.0 (1H, brs), 14.41 (1H, brs) |

TABLE 96

| Ex No. | Strc | (Solv) ¹H-NMR δ ppm: |
|---|---|---|
| 349 | | (DMSO-d6) 2.33 (3H, s), 3.78 (3H, s), 5.04 (2H, s), 6.8-6.95 (2H, m), 7.1-7.3 (3H, m), 7.3-7.4 (2H, m), 12.01 (1H, s), 14.42 (1H, brs) |
| 350 | | (DMSO-d6) 1.19 (3H, t, J = 7.5 Hz), 2.68 (2H, q, J = 7.5 Hz), 5.07 (2H, s), 7.15-7.4 (7H, m), 7.4-7.5 (1H, m), 12.0 (1H, brs), 14.3-14.55 (1H, br) |
| 351 | | (DMSO-d6) 3.84 (3H, s), 5.09 (2H, s), 7.2-7.25 (1H, m), 7.25-7.35 (1H, m), 7.35-7.45 (2H, m), 7.58 (1H, d, J = 2.7 Hz), 7.68 (1H, d, J = 2.7 Hz), 12.01 (1H, brs), 14.41 (1H, brs) |
| 352 | | (DMSO-d6) 5.25 (2H, s), 7.2-7.35 (2H, m), 7.35-7.45 (2H, m), 7.95-8.05 (1H, m), 8.1-8.2 (1H, m), 12.01 (1H, brs), 14.4 (1H, brs) |
| 353 | | (DMSO-d6) 1.19 (3H, t, J = 7.6 Hz), 2.62 (2H, q, J = 7.6 Hz), 5.05 (2H, s), 7.1-7.4 (8H, m), 12.01 (1H, brs), 14.43 (1H, brs) |
| 354 | | (DMSO-d6) 3.3 (3H, s), 4.53 (2H, s), 5.13 (2H, s), 7.1-7.3 (2H, m), 7.3-7.45 (5H, m), 7.45-7.55 (1H, m), 12.01 (1H, brs), 14.42 (1H, brs) |
| 355 | | (DMSO-d6) 3.29 (3H, s), 4.43 (2H, s), 5.09 (2H, s), 7.1-7.2 (1H, m), 7.2-7.45 (7H, m), 12.01 (1H, brs), 14.42 (1H, brs) |

TABLE 97
| Ex No. | Strc | (Solv) ¹H-NMR δ ppm: |
|---|---|---|
| 356 | 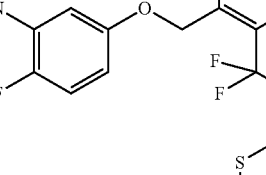 | (DMSO-d6) 5.19 (2H, s), 7.15-7.25 (1H, m), 7.25-7.3 (1H, m), 7.35-7.45 (2H, m), 7.92 (1H, t, J = 8.0 Hz), 8.21 (2H, d, J = 28.0 Hz), 12.01 (1H, s), 14.38 (1H, brs) |
| 357 | 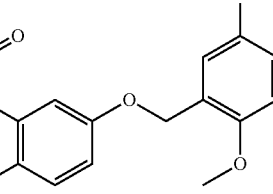 | (DMSO-d6) 2.25 (3H, s), 2.44 (3H, s), 3.7 (3H, s), 5.02 (2H, s), 7.1-7.25 (3H, m), 7.25-7.3 (1H, m), 7.3-7.4 (2H, m), 12.01 (1H, brs), 14.3-14.55 (1H, br) |
| 358 | 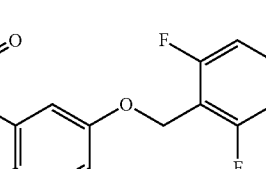 | (DMSO-d6) 3.85 (3H, s), 5.09 (2H, s), 7.05-7.35 (4H, m), 7.35-7.45 (2H, m), 12.02 (1H, brs), 14.39 (1H, brs) |
| 359 | 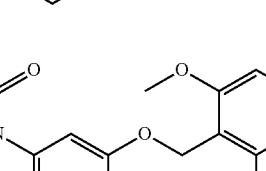 | (DMSO-d6) 3.89 (3H, s), 5.07 (2H, s), 7.15-7.3 (2H, m), 7.3-7.5 (4H, m), 7.6-7.7 (1H, m), 12.01 (1H, s), 14.4 (1H, brs) |
| 360 | 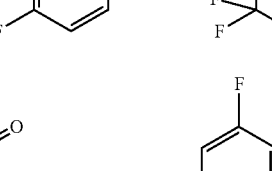 | (DMSO-d6) 5.18 (2H, s), 7.2-7.45 (5H, m), 7.5-7.65 (1H, m), 12.02 (1H, s), 14.4 (1H, brs) |
| 361 | 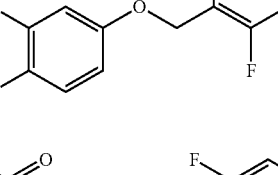 | (DMSO-d6) 5.14 (2H, s), 7.15-7.3 (2H, m), 7.3-7.45 (2H, m), 7.6-7.8 (3H, m), 12.02 (1H, s), 14.39 (1H, s) |
| 362 | 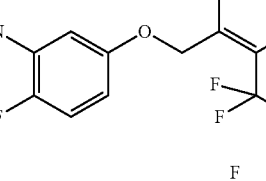 | (DMSO-d6) 3.82 (3H, s), 5.1 (2H, s), 7.15-7.45 (5H, m), 7.45-7.55 (1H, m), 12.01 (1H, s), 14.4 (1H, s) |

TABLE 98

| Ex No. | Strc | (Solv) ¹H-NMR δ ppm: |
|---|---|---|
| 363 | | (DMSO-d6) 2.27 (3H, s), 3.71 (3H, s), 5.05 (2H, s), 7.05-7.25 (3H, m), 7.25-7.3 (1H, m), 7.3-7.4 (2H, m), 12.02 (1H, s), 14.42 (1H, brs) |
| 364 | | (DMSO-d6) 3.76 (3H, s), 3.85 (3H, s), 5.03 (2H, s), 7.05-7.3 (4H, m), 7.3-7.4 (2H, m), 12.02 (1H, brs), 14.42 (1H, brs) |
| 365 | | (DMSO-d6) 3.8-3.9 (3H, m), 5.08 (2H, s), 7.15-7.25 (2H, m), 7.25-7.45 (4H, m), 12.02 (1H, brs), 14.41 (1H, brs) |
| 366 | | (DMSO-d6) 3.79 (3H, s), 3.83 (3H, s), 4.92 (2H, s), 6.8-7.0 (2H, m), 7.11 (1H, d, J = 11.2 Hz), 7.27 (1H, d, J = 27.6 Hz), 7.38 (1H, s), 7.4-7.5 (1H, m), 11.99 (1H, brs), 14.55 (1H, brs) |
| 367 | | (DMSO-d6) 3.23 (3H, s), 3.55-3.65 (2H, m), 4.1-4.2 (2H, m), 5.09 (2H, s), 6.9-7.0 (1H, m), 7.15-7.3 (2H, m), 7.3-7.4 (2H, m), 7.4-7.5 (1H, m), 12.03 (1H, brs), 14.42 (1H, brs) |
| 368 | | (DMSO-d6) 1.02 (3H, t, J = 6.9 Hz), 3.43 (2H, q, J = 6.9 Hz), 3.6-3.7 (2H, m), 4.1-4.2 (2H, m), 5.08 (2H, s), 6.9-7.0 (1H, m), 7.15-7.25 (2H, m), 7.3-7.4 (2H, m), 7.4-7.5 (1H, m), 12.02 (1H, s), 14.42 (1H, brs) |
| 369 | | (DMSO-d6) 3.71 (3H, s), 3.77 (3H, s), 4.99 (2H, s), 6.85-6.95 (1H, m), 6.95-7.05 (2H, m), 7.1-7.2 (1H, m), 7.2-7.3 (1H, m), 7.3-7.4 (2H, m), 12.01 (1H, s), 14.44 (1H, brs) |

TABLE 99

| Ex No. | Strc | (Solv) $^1$H-NMR δ ppm: |
|---|---|---|
| 370 | | (DMSO-d6) 2.25 (3H, s), 3.78 (3H, s), 4.98 (2H, s), 6.94 (1H, d, J = 7.9 Hz), 7.1-7.2 (2H, m), 7.2-7.3 (2H, m), 7.3-7.4 (2H, m), 12.01 (1H, brs), 14.45 (1H, brs) |
| 371 | | (DMSO-d6) 1.85-1.95 (2H, m), 3.16 (3H, s), 3.39 (2H, t, J = 6.2 Hz), 4.08 (2H, t, J = 6.2 Hz), 5.06 (2H, s), 6.85-6.95 (1H, m), 7.15-7.3 (2H, m), 7.3-7.5 (3H, m), 12.03 (1H, s), 14.42 (1H, brs) |
| 372 | | (DMSO-d6) 3.78 (3H, s), 3.85 (3H, s), 4.94 (2H, s), 7.0-7.1 (1H, m), 7.1-7.2 (2H, m), 7.2-7.35 (2H, m), 7.36 (1H, s), 11.96 (1H, brs), 14.56 (1H, brs) |
| 373 | | (DMSO-d6) 1.36 (3H, t, J = 6.9 Hz), 3.78 (3H, s), 4.13 (2H, q, J = 6.9 Hz), 4.96 (2H, s), 7.0-7.1 (1H, m), 7.1-7.2 (2H, m), 7.2-7.35 (2H, m), 7.37 (1H, s), 11.97 (1H, brs), 14.56 (1H, brs) |
| 374 | | (DMSO-d6) 1.3 (3H, t, J = 7.0 Hz), 3.82 (3H, s), 4.08 (2H, q, J = 27.0 Hz), 4.94 (2H, s), 6.8-7.0 (2H, m), 7.1 (1H, d, J = 11.6 Hz), 7.26 (1H, d, J = 7.6 Hz), 7.35-7.5 (2H, m), 11.99 (1H, s), 14.55 (1H, brs) |
| 375 | | (DMSO-d6) 1.31 (3H, t, J = 7.0 Hz), 3.79 (3H, s), 4.09 (2H, q, J = 7.0 Hz), 4.95-5.05 (2H, m), 6.85-6.95 (1H, m), 7.12 (1H, d, J = 11.7 Hz), 7.23 (1H, d, J = 7.3 Hz), 7.38 (1H, s), 7.4-7.5 (1H, m), 11.99 (1H, s), 14.54 (1H, brs) |
| 376 | | (DMSO-d6) 3.83 (3H, s), 5.18 (2H, s), 6.9-7.0 (1H, m), 7.38 (1H, s), 7.45-7.6 (1H, m), 7.7-7.85 (1H, m), 8.0-8.1 (1H, m), 12.08 (1H, s), 14.16 (1H, brs) |

TABLE 100
| Ex No. | Strc | (Solv) $^1$H-NMR δ ppm: |
|---|---|---|
| 377 | 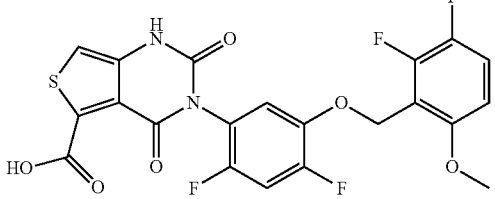 | (DMSO-d6) 3.81 (3H, s), 5.07 (2H, s), 6.9-6.95 (1H, m), 7.39 (1H, s), 7.45-7.55 (1H, m), 7.55-7.65 (2H, m), 12.06 (1H, s), 14.37 (1H, brs) |
| 378 | 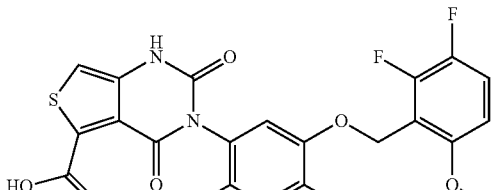 | (DMSO-d6) 3.82 (3H, s), 5.08 (2H, s), 6.9-7.0 (1H, m), 7.39 (1H, s), 7.45-7.6 (1H, m), 7.61 (1H, d, J = 6.7 Hz), 7.73 (1H, d, J = 9.1 Hz), 12.07 (1H, s), 14.33 (1H, brs) |
| 379 | 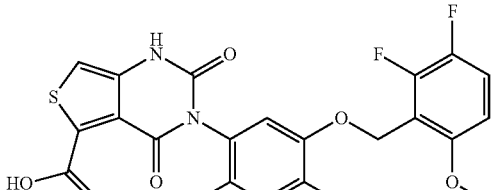 | (DMSO-d6) 3.82 (3H, s), 5.07 (2H, s), 6.9-7.0 (1H, m), 7.39 (1H, s), 7.45-7.55 (1H, m), 7.58 (1H, d, J = 6.5 Hz), 7.84 (1H, d, J = 8.8 Hz), 12.07 (1H, s), 14.33 (1H, s) |
| 380 | 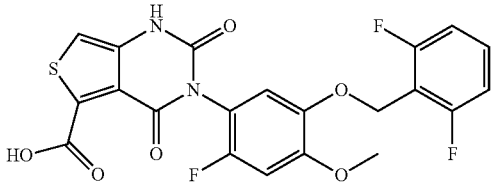 [SMILES: COc1cc(F)c(-n2c(=O)[nH]c3csc(C(=O)O)c3c2=O)cc1OCc1c(F)cccc1F] | (DMSO-d6) 3.81 (3H, s), 5.0 (2H, s), 7.1-7.25 (3H, m), 7.29 (1H, d, J = 7.4 Hz), 7.39 (1H, s), 7.45-7.6 (1H, m), 12.01 (1H, s), 14.54 (1H, s) |
| 381 | 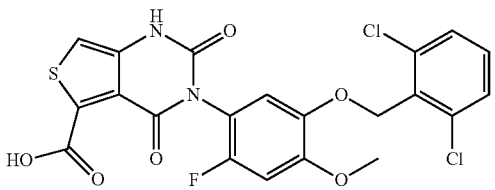 [SMILES: COc1cc(F)c(-n2c(=O)[nH]c3csc(C(=O)O)c3c2=O)cc1OCc1c(Cl)cccc1Cl] | (DMSO-d6) 3.82 (3H, s), 5.13 (2H, s), 7.15 (1H, d, J = 11.4 Hz), 7.33 (1H, d, J = 7.3 Hz), 7.39 (1H, s), 7.45-7.6 (3H, m), 12.01 (1H, s), 14.54 (1H, s) |
| 382 | 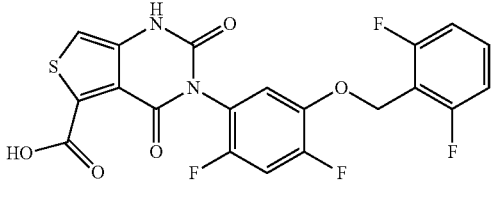 [SMILES: O=C(O)c1scc2[nH]c(=O)n(-c3cc(OCc4c(F)cccc4F)c(F)cc3F)c(=O)c12] | (DMSO-d6) 5.12 (2H, s), 7.15-7.25 (2H, m), 7.39 (1H, s), 7.5-7.7 (3H, m), 12.06 (1H, s), 14.36 (1H, brs) |
| 383 | 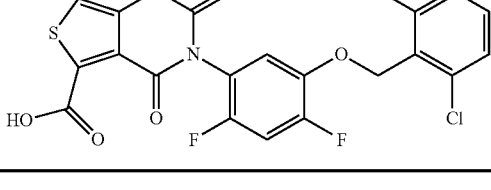 | (DMSO-d6) 5.24 (2H, s), 7.39 (1H, s), 7.45-7.55 (1H, m), 7.55-7.75 (4H, m), 12.06 (1H, s), 14.36 (1H, brs) |

TABLE 101

| Ex No. | Strc | (Solv) ¹H-NMR δ ppm: |
|---|---|---|
| 384 | | (DMSO-d6) 3.78 (3H, s), 3.81 (3H, s), 4.96 (2H, s), 6.85-7.0 (2H, m), 7.07 (1H, d, J = 8.4 Hz), 7.18 (1H, d, J = 2.4 Hz), 7.37 (1H, s), 7.4-7.55 (1H, m), 11.87 (1H, s), 14.97 (1H, s) |
| 385 | | (DMSO-d6) 3.2 (3H, s), 3.5-3.6 (2H, m), 3.81 (3H, s), 4.05-4.15 (2H, m), 5.01 (2H, s); 6.85-6.95 (1H, m), 7.13 (1H, d, J = 11.2 Hz), 7.23 (1H, d, J = 7.0 Hz), 7.39 (1H, s), 7.4-7.5 (1H, m), 11.99 (1H, s), 14.52 (1H, s) |
| 386 | | (DMSO-d6) 1.0 (3H, t, J = 7.0 Hz), 3.4 (2H, q, J = 7.0 Hz), 3.55-3.65 (2H, m), 3.81 (3H, s), 4.05-4.15 (2H, m), 5.0 (2H, s), 6.85-6.95 (1H, m), 7.13 (1H, d, J = 11.4 Hz), 7.23 (1H, d, J = 7.7 Hz), 7.38 (1H, s), 7.4-7.5 (1H, m), 11.99 (1H, s), 14.53 (1H, brs) |
| 387 | | (DMSO-d6) 3.19 (3H, s), 3.5-3.65 (2H, m), 4.05-4.2 (2H, m), 5.13 (2H, s), 6.9-7.0 (1H, m), 7.38 (1H, s), 7.4-7.65 (3H, m), 12.03 (1H, s), 14.34 (1H, brs) |
| 388 | | (DMSO-d6) 0.99 (3H, t, J = 7.0 Hz), 3.4 (2H, q, J = 7.0 Hz), 3.55-3.7 (2H, m), 4.05-4.2 (2H, m), 5.11 (2H, s), 6.9-7.0 (1H, m), 7.38 (1H, s), 7.4-7.65 (3H, m), 12.03 (1H, s), 14.35 (1H, brs) |
| 389 | | (DMSO-d6) 1.75-1.9 (1H, m), 1.9-2.05 (1H, m), 2.5-2.7 (4H, m), 6.55-6.6 (1H, m), 6.9-6.95 (1H, m), 7.1-7.2 (1H, m), 7.25-7.45 (4H, m), 7.45-7.55 (2H, m), 11.96 (1H, s), 14.41 (1H, s) |
| 390 | | (DMSO-d6) 3.82 (3H, s), 5.08 (2H, s), 6.9-7.0 (1H, m), 7.0-7.1 (1H, m), 7.3-7.4 (2H, m), 7.4-7.55 (2H, m), 11.91 (1H, brs), 14.82 (1 H, brs) |

TABLE 102

| Ex No. | Strc | (Solv) ¹H-NMR δ ppm: |
|---|---|---|
| 391 | | (DMSO-d6) 1.8-1.95 (1H, m), 2.25-2.4 (1H, m), 2.6-2.8 (4H, m), 3.6 (3H, s), 6.65-6.75 (1H, m), 7.05-7.15 (1H, m), 7.25-7.35 (2H, m), 7.35-7.5 (1H, m), 11.7-12.2 (1H, br), 14.1-14.8 (1H, br) |
| 392 | | (DMSO-d6) 3.78 (3H, s), 3.81 (3H, s), 4.9-5.1 (4H, m), 5.95 (1H, t, J = 5.6 Hz), 6.71 (1H, s), 6.85-6.95 (1H, m), 7.05 (1H, d, J = 11.2 Hz), 7.17 (1H, d, J = 7.4 Hz), 7.4-7.55 (1H, m), 11.32 (1H, s) |
| 393 | | (DMSO-d6) 3.8 (3H, s), 3.81 (3H, s), 4.95 (2H, s), 6.85-6.95 (1H, m), 7.1 (1H, d, J = 11.5 Hz), 7.2-7.3 (2H, m), 7.4-7.55 (1H, m), 8.05-8.15 (1H, m), 9.65-9.75 (1H, m), 11.77 (1H, s) |
| 394 | | (DMSO-d6) 1.58 (3H, d, J = 6.4 Hz), 5.65-5.75 (1H, m), 6.85-6.9 (1H, m), 7.2-7.25 (2H, m), 7.3-7.45 (2H, m), 7.45-7.55 (3H, m), 8.05-8.15 (1H, m), 9.6-9.7 (1H, m), 11.7-11.8 (1H, m) |
| 395 | | (DMSO-d6) 5.16 (2H, s), 7.19 (1H, dd, J = 8.9 Hz, 3.2 Hz), 7.24 (1H, s), 7.35-7.45 (3H, m), 7.5-7.7 (3H, m), 8.11 (1H, d, J = 2.1 Hz), 9.65-9.7 (1H, m), 11.8 (1H, s) |
| 396 | | (DMSO-d6) 3.6-3.75 (2H, m), 4.04 (2H, t, J = 4.9 Hz), 4.8-4.95 (1H, m), 5.13 (2H, s), 6.9-6.95 (1H, m), 7.15-7.3 (2H, m), 7.3-7.4 (2H, m), 7.4-7.5 (1H, m), 12.01 (1H, s), 14.4 (1H, brs) |
| 397 | | (DMSO-d6) 1.75-1.9 (2H, m), 3.45-3.55 (2H, m), 4.1 (2H, t, J = 6.2 Hz), 4.9-5.0 (1H, m), 5.06 (2H, s), 6.85-6.95 (1H, m), 7.15-7.25 (2H, m), 7.3-7.4 (2H, m), 7.4-7.5 (1H, m), 12.02 (1H, s), 14.4 (1H, brs) |

TABLE 103

| Ex No. | Strc | (Solv) ¹H-NMR δ ppm: |
|---|---|---|
| 398 | | (DMSO-d6) 3.55-3.65 (1H, m), 3.7-3.8 (1H, m), 5.15-5.25 (1H, m), 5.25-5.35 (1H, m), 7.0-7.05 (1H, m), 7.2-7.5 (8H, m), 11.95-12.05 (1H, m), 14.42 (1H, s) |
| 399 | | (DMSO-d6) 4.61 (2H, s), 5.16 (2H, s), 5.21 (1H, brs), 7.15-7.5 (7H, m), 7.57 (1H, d, J = 8.6 Hz), 12.0 (1H, s) |
| 400 | | (DMSO-d6) 4.51 (2H, d, J = 5.2 Hz), 5.1 (2H, s), 5.22 (1H, t, J = 5.2 Hz), 7.15-7.2 (1H, m), 7.25-7.45 (6H, m), 7.57 (1H, d, J = 8.6 Hz), 12.03 (1H, s), 14.44 (1H, s) |
| 401 | | (DMSO-d6) 4.61 (2H, s), 5.15 (2H, s), 7.15-7.5 (6H, m), 7.57 (1H, d, J = 9.2 Hz), 7.95 (1H, s), 13.95 (1H, s) |
| 402 | | (DMSO-d6) 3.55-3.65 (1H, m), 3.7-3.8 (1H, m), 5.0-5.4 (2H, m), 7.0-7.1 (1H, m), 7.15-7.5 (7H, m), 7.95 (1H, d, J = 5.9 Hz), 12.98 (1H, brs), 13.95 (1H, s) |
| 403 | | (DMSO-d6) 1.55 (3H, d, J = 6.3 Hz), 3.6-3.8 (2H, m), 3.95-4.15 (2H, m), 4.85-4.95 (1H, m), 5.75-5.9 (1H, m), 6.9-7.05 (3H, m), 7.15-7.5 (5H, m), 11.95-12.05 (1H, m), 14.43 (1H, s) |
| 404 | | (DMSO-d6) 1.55 (3H, d, J = 6.3 Hz), 3.6-3.8 (2H, m), 3.95-4.15 (2H, m), 4.8-5.0 (1H, br), 5.75-5.85 (1H, m), 6.9-7.05 (3H, m), 7.15-7.35 (3H, m), 7.43 (1H, d, J = 8.9 Hz), 7.9-8.0 (1H, m), 12.8-13.2 (1H, br), 13.99 (1H, s) |

TABLE 104

| Ex No. | Strc | (Solv) ¹H-NMR δ ppm: |
|---|---|---|
| 405 | | (DMSO-d6) 1.57 (3H, d, J = 6.2 Hz), 4.55-4.65 (1H, m), 4.65-4.75 (1H, m), 5.3-5.35 (1H, m), 5.7-5.8 (1H, m), 6.95-7.05 (1H, m), 7.2-7.5 (7H, m), 11.95-12.05 (1H, m), 14.42 (1H, s) |
| 406 | | (DMSO-d6) 3.65-3.75 (2H, m), 4.0-4.1 (2H, m), 4.87 (1H, brs), 5.12 (2H, s), 6.95-7.0 (1H, m), 7.05 (1H, d, J = 8.1 Hz), 7.19 (1H, dd, J = 9.0 Hz, 3.0 Hz), 7.25-7.45 (4H, m), 7.56 (1H, d, J = 9.0 Hz), 12.04 (1H, s), 14.46 (1H, s) |
| 407 | | (DMSO-d6) 1.54 (3H, d, J = 6.3 Hz), 1.85-1.95 (2H, m), 3.55-3.65 (2H, m), 4.05-4.2 (2H, m), 4.54 (1H, brs), 5.65-5.75 (1H, m), 6.85-7.0 (2H, m), 7.0-7.1 (1H, m), 7.15-7.2 (1H, m), 7.2-7.35 (2H, m), 7.4 (1H, d, J = 4.6 Hz), 7.47 (1H, d, J = 9.0 Hz), 11.95-12.05 (1H, m), 14.42 (1H, s) |
| 408 | | (DMSO-d6) 1.66 (3H, d, J = 6.4 Hz), 1.85-1.95 (2H, m), 3.5-3.6 (2H, m), 4.05-4.2 (2H, m), 5.75-5.85 (1H, m), 6.7-7.1 (4H, m), 7.2-7.4 (3H, 7), 11.95-12.05 (1H, m), 14.35-14.45 (1H, m) |
| 409 | | (DMSO-d6) 1.66 (3H, d, J = 6.6 Hz), 3.55-3.8 (2H, m), 3.85-4.0 (1H, m), 4.05-4.2 (1H, m), 4.9-5.05 (1H, m), 5.9-6.0 (1H, m), 6.7-6.9 (2H, m), 7.0-7.4 (5H, m), 11.95-12.05 (1H, m), 14.44 (1H, s) |
| 410 | | (DMSO-d6) 1.66 (3H, d, J = 6.4 Hz), 1.8-1.95 (2H, m), 3.5-3.6 (2H, m), 4.0-4.2 (2H, m), 5.8 (1H, q, J = 6.4 Hz), 6.7-6.8 (1H, m), 6.8-7.0 (2H, m), 7.0-7.05 (1H, m), 7.2-7.35 (2H, m), 7.9-7.95 (1H, m), 13.93 (1H, s) |
| 411 | | (DMSO-d6) 1.85-2.0 (1H, m), 2.2-2.35 (1H, m), 2.65-2.85 (4H, m), 6.75-6.85 (1H, m), 7.0-7.1 (3H, m), 7.24 (1H, t, J = 9.3 Hz), 7.3-7.45 (2H, m), 11.97 (1H, brs), 13.5-15.0 (1H, br) |

TABLE 105

| Ex No. | Strc | (Solv) ¹H-NMR δ ppm: |
|---|---|---|
| 412 | | (DMSO-d6) 1.820 (3H, s), 1.823 (3H, s), 6.75-6.8 (1H, m), 6.95-7.1 (3H, m), 7.15-7.25 (1H, m), 7.3-7.45 (2H, m), 11.96 (1H, brs), 14.43 (1H, brs) |
| 413 | | (DMSO-d6) 3.79 (3H, s), 5.05-5.2 (2H, m), 6.8-6.9 (1H, m), 7.05-7.2 (1H, m), 7.37 (1H, s), 7.5-7.6 (1H, m), 7.65-7.75 (1H, m), 12.02 (1H, s), 14.35 (1H, s) |
| 414 | | (DMSO-d6) 3.79 (3H, s), 3.85 (3H, s), 5.0-5.1 (2H, m), 6.8-6.9 (1H, m), 7.05-7.2 (2H, m), 7.38 (1H, s), 7.51 (1H, d, J = 8.5 Hz), 11.98 (1H, s), 14.54 (1H, brs) |
| 415 | | (DMSO-d6) 3.27 (3H, s), 3.6-3.7 (2H, m), 4.1-4.2 (2H, m), 5.13 (2H, s), 6.85-6.95 (1H, m), 7.05-7.2 (1H, m), 7.39 (1H, s), 7.4-7.5 (1H, m), 7.6-7.7 (2H, m), 12.05 (1H, s), 14.42 (1H, s) |
| 416 | | (DMSO-d6) 1.05 (3H, t, J = 7.1 Hz), 3.46 (2H, q, J = 7.1 Hz), 3.65-3.75 (2H, m), 4.1-4.2 (2H, m), 5.14 (2H, s), 6.85-6.95 (1H, m), 7.05-7.2 (1H, m), 7.38 (1H, s), 7.4-7.5 (1H, m), 7.55-7.7 (2H, m), 12.05 (1H, s), 14.41 (1H, s) |
| 417 | | (DMSO-d6) 1.27 (3H, t, J = 7.1 Hz), 3.68 (2H, t, J = 4.8 Hz), 4.05 (2H, t, J = 4.8 Hz), 4.3 (2H, q, J = 7.1 Hz), 5.12 (2H, s), 6.85-6.95 (1H, m), 7.1-7.25 (3H, m), 7.25-7.35 (1H, m), 7.4-7.5 (1H, m), 11.63 (1H, s) |

TABLE 106

| Ex No. | Strc | (Solv) ¹H-NMR δ ppm: |
|---|---|---|
| 418 | | (DMSO-d6) 1.13 (3H, t, J = 7.0 Hz), 1.27 (3H, t, J = 7.1 Hz), 4.03 (2H, q, J = 7.0 Hz), 4.25-4.35 (4H, m), 4.35-4.45 (2H, m), 5.07 (2H, s), 6.9-7.0 (1H, m), 7.1-7.2 (3H, m), 7.25-7.35 (1H, m), 7.4-7.55 (1H, m), 11.63 (1H, s) |
| 419 | | (DMSO-d6) 1.04 (9H, s), 1.27 (3H, t, J = 7.1 Hz), 4.2-4.35 (6H, m), 5.05 (2H, s), 6.9-7.05 (1H, m), 7.05-7.2 (3H, m), 7.25-7.35 (1H, m), 7.4-7.55 (1H, m), 11.63 (1H, s) |
| 420 | | (DMSO-d6) 2.7-2.75 (3H, m), 3.71 (3H, s), 4.1-4.25 (2H, m), 6.95-7.15 (4H, m), 7.38 (1H, s), 7.41 (1H, d, J = 8.6 Hz), 11.95 (1H, s), 14.57 (1H, brs) |
| 421 | | (DMSO-d6) 2.73 (3H, s), 3.74 (3H, s), 4.15-4.25 (2H, m), 7.08 (1H, d, J = 12.4 Hz), 7.15-7.2 (1H, m), 7.36 (1H, s), 7.4-7.45 (2H, m), 7.56 (1H, d, J = 8.7 Hz), 11.96 (1H, brs), 14.61 (1H, brs) |
| 422 | | (DMSO-d6) 2.68 (3H, s), 3.81 (3H, s), 4.15 (2H, s), 6.7-6.85 (2H, m), 7.0-7.1 (1H, m), 7.3-7.4 (2H, m), 7.45-7.55 (2H, m), 11.98 (1H, s), 14.45 (1H, s) |
| 423 | | (DMSO-d6) 2.75 (3H, s), 4.22 (2H, s), 6.95-7.15 (3H, m), 7.35-7.45 (2H, m), 7.45-7.5 (2H, m), 12.02 (1H, s) |

TABLE 107

| Ex No. | Strc | (Solv) $^1$H-NMR δ ppm: |
|---|---|---|
| 424 | | (DMSO-d6) 2.72 (3H, s), 4.3 (2H, s), 7.15-7.25 (1H, m), 7.35-7.5 (4H, m), 7.55-7.65 (2H, m), 12.03 (1H, s) |
| 425 | | (DMSO-d6) 2.7-2.75 (3H, m), 3.23 (3H, s), 3.6-3.7 (2H, m), 4.05-4.1 (2H, m), 4.22 (2H, s), 6.7-6.8 (1H, m), 7.0-7.1 (1H, m), 7.3-7.4 (2H, m), 7.45-7.55 (2H, m), 12.03 (1H, s), 14.46 (1H, brs) |
| 426 | | (DMSO-d6) 2.7-2.75 (3H, m), 3.79 (3H, s), 4.2 (2H, s), 6.7-6.8 (1H, m), 7.0-7.15 (1H, m), 7.3-7.4 (2H, m), 7.45-7.55 (2H, m), 12.02 (1H, s), 14.47 (1H, brs) |
| 427 | | (DMSO-d6) 3.7-3.8 (2H, m), 4.04 (2H, t, J = 4.6 Hz), 4.85-4.95 (1H, m), 5.17 (2H, s), 6.85-6.95 (1H, m), 7.05-7.15 (1H, m), 7.39 (1H, s), 7.4-7.5 (1H, m), 7.6-7.7 (2H, m), 12.05 (1H, s), 14.44 (1H, s) |
| 428 | | (DMSO-d6) 2.7-2.75 (3H, m), 3.7-3.8 (6H, m), 4.1-4.2 (2H, m), 6.7-6.75 (1H, m), 6.95-7.1 (2H, m), 7.37 (1H, s), 7.41 (1H, d, J = 8.8 Hz), 11.95 (1H, s), 14.57 (1H, s) |

Test Example 1

1) Cloning and Construction of the Vector Expressing Human GnRH Receptor1 (GnRHR1)

Using cDNA deprived from human pituitary (BECTON DICKINSON) as a template, the DNA fragment coding 45 to 1115 bp of human GnRHR1 (Accession No. L03380), which was reported by Kakar et al., was amplified by PCR method and inserted into the multi-cloning site of pcDNA3.1(+) (Invitrogen). The DNA sequence inserted was perfectly matched to the previously reported sequence.

2) Preparation of HEK293 (Human Embryonic Kidney) Cells Expressing Human GnRH Receptor1

The expression vector introduced human GnRHR1 gene was transfected into cultured HEK293 cells (medium : MEM, 10% FCS, containing antibiotics, non-essential amino acids and pyruvic acid) by means of lipofection with the use of Lipofectamine2000 (Invitrogen). After transfection, the cells were cultured for 2 days, and used for examinations.

3) Assay of GnRH Antagonizing Effect

Antagonizing effect of compounds for human GnRHR1 was evaluated by change of calcium levels in GnRH-stimulated cells. After removing the culture medium of HEK293 cells transiently expressing human GnRHR1, cells were washed with 200 μL piper well of the washing buffer (Hank's Balanced Salt Solutions, 20 mM N-2-hydroxyethylpiperazine-N'-2-ethanesulfonic acid, 1.3 mM calcium chloride, 0.5 mM magnesium chloride, 0.4 mM magnesium sulfate). One hundred μL of the $Ca^{2+}$ sensitive dye solution (FLIPR Calcium Assay Kit (Molecular Devices)) was added to the well, and the cells were incubated for 1 hour at 37° C., 5% $CO_2$.

Then, intracellular calcium levels were determined under the following condition by using FLEX STATION (Molecular Devices). In the equipment, which was warmed to 37° C., 50 µL of test compound diluted with the measurement buffer (the washing buffer with 0.1% Albumin bovine serum) was added to the well. After 1 minute, 50 µL of 5 nM GnRH was added to the well. The drug concentration, at which 50% GnRH-stimulated intracellular calcium flux was inhibited ($IC_{50}$ value), was calculated using logit plot (Table 108).

TABLE 108

| Example No. | $IC_{50}$ (nM) |
|---|---|
| 2 | 199 |
| 3 | 80 |
| 17 | 101 |
| 22 | 2 |
| 25 | 85 |
| 31 | 272 |
| 48 | 29 |
| 95 | 19 |
| 146 | 10 |
| 191 | 17 |
| 202 | 20 |
| 233 | 15 |
| 367 | 15 |
| 414 | 42 |
| 420 | 29 |
| Control compound 1 | 61 |
| Control compound 2 | 3 |

Test Example 2

Assay for Oral Absorbability

1) Preparation of the Samples for Measurement of the Drug Concentration After Intravenous Injection to the Tail Vein As experimental animal, overnight fasted SD rats (Charles River, male, 7 weeks of age, 170-210 g) were used. One mg of a test compound was dissolved by adding 0.2 mL of N,N-dimethylacetoamide, 0.798 mL of saline and 0.002 mL of 2N NaOH, and then 1.0 mg/mL solution was prepared. The body weights of rats were measured, and the solution of the test compound was injected intravenously to the tail vein of unanesthetized rats at the dose of 1 mL/kg (1 mg/kg). The intravenous injection to the tail vein was performed with 26 G injection needle and 1 mL syringe. The sampling times for collection of blood were 2, 15, 60, 120, 240 and 360 minutes after the intravenous injection to the tail vein. The blood was centrifuged, and the plasma was used as the sample for measurement of the drug concentration in blood.

2) Preparation of the Samples for Measurement of the Drug Concentration After Oral Administration As experimental animal, overnight fasted SD rats (Charles River, male, 7 weeks of age, 170-210 g) were used. Three mg of a test compound was dissolved by adding 0.2 mL of N,N-dimethylacetoamide, 9.794 mL of 0.5% aqueous sodium methylcellulose solution and 0.006 mL of 2N NaOH, and then 0.3 mg/mL solution was prepared. The body weights of rats were measured, and the solution of the test compound was administered orally at the dose of 10 mL/kg (3 mg/kg). The oral administration was performed with gastric tube for rat and 2.5 mL syringe. The sampling times for collection of blood were 15, 30, 60, 120, 240 and 360 minutes after the oral administration. The blood was centrifuged, and the plasma was used as the sample for measurement of the drug concentration in blood.

3) Measurement of the Drug Concentration

To 0.025 mL of the plasma obtained in 1) and 2) described above, 0.1 mL of an adequate internal standard material was added according to the usual method, and then deproteinization was performed by adding 0.875 mL of acetonitrile. After centrifugation, 0.005 mL of the supernatant was injected into LC-MS/MS. The drug concentration in plasma was measured by LC-MS/MS method under the conditions as follows. To 0.05 mL of the blank plasma were added the internal standard material and various test compounds adequately according to the usual method, similar operating described above was done, and then the standard curves were prepared.

LC
    Instrument: Agilent1100
    Column: Cadenza C18 3 µM 4.6×50 mm
    Mobile phase: 10 mM aqueous ammonium acetate solution (pH 4.5) (A)/acetonitrile (B) (Time and ratio of (A)/(B) are shown in Table 109.)
    Column temperature: 40° C.
    Flow rate: 0.5 mL/min
MS/MS
    Instrument: API-4000
    Ionization method: ESI (Turbo Ion Spray)

TABLE 109

| Time (min) | A (%) | B (%) |
|---|---|---|
| 0.0 | 90 | 10 |
| 3.0 | 90 | 10 |
| 4.0 | 10 | 90 |
| 7.0 | 10 | 90 |
| 7.1 | 90 | 10 |
| 12.0 | 90 | 10 |

Each area under the plasma drug concentration-time curve by intravenous injection to the tail vein and oral administration of the test compound was estimated with WinNonlin Professional by Pharsight Corporation from the plasma drug concentration at each time obtained from the above mentioned method, and then the bioavailability (%) was calculated based on the following formula.

Bioavailability (%)={[(Area under the plasma drug concentration-time curve by oral administration)/3]/(area under the plasma drug concentration -time curve by intravenous injection to the tail vein)}×100

In the oral administration, the maximum plasma drug concentration ($C_{max}$), bioavailability and the plasma drug concentration at 360 minutes after administration ($C_{360}$) are shown in Tables 110 to 112.

TABLE 110

| Test compound | Cmax (ng/mL) |
|---|---|
| Example 22 | 342 |
| Example 48 | 14460 |
| Example 95 | 322 |
| Example 146 | 17917 |
| Example 191 | 13504 |
| Example 202 | 1308 |
| Example 233 | 24959 |
| Example 271 | 17582 |
| Example 367 | 14120 |

TABLE 110-continued

| Test compound | Cmax (ng/mL) |
| --- | --- |
| Example 414 | 25560 |
| Example 420 | 15169 |
| Control compound 1 | <10 |
| Control compound 2 | 10 |

TABLE 111

| Test compound | Bioavailability (%) |
| --- | --- |
| Example 22 | 11 |
| Example 48 | 65 |
| Control compound 1 | <1 |
| Control compound 2 | <1 |

TABLE 112

| Test compound | $C_{360}$ |
| --- | --- |
| Example 146 | A |
| Example 202 | B |
| Example 233 | A |
| Example 271 | A |
| Example 367 | A |
| Example 414 | A |
| Example 420 | B |
| Control compound 1 | <10 |
| Control compound 2 | <10 |

A: >1000 ng/mL
B: 300 ng/mL to 1000 ng/mL

In Tables 110 to 112, Control compound 1 is the sulfonamide compound of Example 6 (4) described in the above Patent reference 2, and Control compound 2 is the sulfonamide compound of Example 31 described in the above Patent reference 2.

As shown above, a fused heterocyclic derivative of the present invention is more superior in blood kinetics such as availability and sustainability by oral administration than the Control compounds. For example, the fused heterocyclic derivatives of Examples 48, 146, 191, 202, 233, 271, 367, 414 and 420 exert more excellent availability than the compound of Example 22 having a sulfonamide group and the compound of Example 95 having an amide group, and thus, is more preferable as a pharmaceutical composition for oral administration. In addition, the fused heterocyclic derivatives of Examples 146, 202, 233, 271, 367, 414 and 420, more preferably Examples 146, 233, 271, 367 and 414, maintain their blood concentrations 6 hours after the oral administrations and more superior in sustainability than the Control compounds. Therefore, the fused heterocyclic derivatives of the present invention can be used as a long-acting preparation substantially without a sustained-release base such as hydroxyalkylcellulose, alkylcellulose or the like.

INDUSTRIAL APPLICABILITY

A fused heterocyclic derivative (I) of the present invention or a prodrug thereof, or a pharmaceutically acceptable salt thereof, or a hydrate or solvate thereof has an excellent GnRH antagonistic activity, and thus, can be used as an agent for the prevention or treatment of sex hormone-dependent diseases by controlling the effect of gonadotropin releasing hormone and controlling the production and secretion of gonadotropin and sex hormones. Therefore, the present invention can provide an agent for the prevention or treatment of benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostatic cancer, uterine cancer, ovary cancer, breast cancer or pituitary tumor, a reproduction regulator, a contraceptive, an ovulation inducing agent or an agent for the prevention of post-operative recurrence of sex hormone-dependent cancers and the like.

The invention claimed is:

1. A fused heterocyclic derivative of the general formula (I):

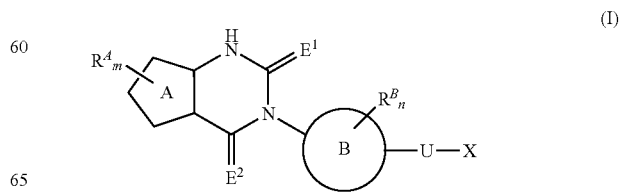

wherein ring A is a thiophene ring;

$R^A$ is a halogen atom, a cyano group, a nitro group, an optionally substituted lower alkyl group, an optionally substituted lower alkenyl group, an optionally substituted lower alkynyl group, a hydroxyiminomethyl group, an optionally substituted (lower alkyl)sulfonyl group, an optionally substituted (lower alkyl)sulfinyl group, a tetrazolyl group, $OW^1$, $SW^1$, $COW^1$, $COOW^1$, $NHCOW^1$, $NHCONW^2W^3$, $NW^2W^3$, $CONW^2W^3$ or $SO_2NW^2W^3$ in which $W^1$ to $W^3$ independently are a hydrogen atom or an optionally substituted lower alkyl group, or $W^2$ and $W^3$ may bind together with the neighboring nitrogen atom to form an optionally substituted cyclic amino group;

m is an integer number of 0 to 3;

ring B is aryl or a monocyclic heteroaryl group;

$R^B$ is a halogen atom, a cyano group, an optionally substituted lower alkyl group, $OW^4$, $COW^4$, $COOW^4$ or $CONW^5W^6$ in which $W^4$ to $W^6$ independently are a hydrogen atom or an optionally substituted lower alkyl group, or $W^5$ and $W^6$ may bind together with the neighboring nitrogen atom to form an optionally substituted cyclic amino group;

n is an integer number of 0 to 2;

$E^1$ is an oxygen atom;

$E^2$ is an oxygen atom;

U is a single bond;

X is a group of —S—L—Y, —O—L—Y, —CO—L—Y, or —SO$_2$—L—Y in which L is an optionally substituted lower alkylene group;

Y is a group of Z or —NW$^7$W$^8$ wherein W$^7$ and W$^8$ independently are a hydrogen atom, an optionally substituted lower alkyl group or Z with the proviso that W$^7$ and W$^8$ are not hydrogen atoms at the same time, or W$^7$ and W$^8$ may bind together with the neighboring nitrogen atom to form an optionally substituted cyclic amino group;

Z is an optionally fused and optionally substituted cycloalkyl group, an optionally fused and optionally substituted heterocycloalkyl group, an optionally fused and optionally substituted aryl group or an optionally fused and optionally substituted heteroaryl group;

or a pharmaceutically acceptable salt thereof.

2. A fused heterocyclic derivative as claimed in claim 1, wherein the ring A is a thiophene ring of the formula:

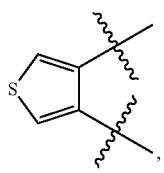 [SMILES: *c1cscc1*]

or a pharmaceutically acceptable salt thereof.

3. A fused heterocyclic derivative as claimed in claim 1, wherein $R^A$ is a halogen atom, an optionally substituted lower alkyl group, $COOW^1$ or $CONW^2W^3$ in which $W^1$ to $W^3$ independently are a hydrogen atom or an optionally substituted lower alkyl group, or $W^2$ and $W^3$ may bind together with the neighboring nitrogen atom to form an optionally substituted cyclic amino group, or a pharmaceutically acceptable salt thereof.

4. A fused heterocyclic derivative as claimed in claim 3, wherein $R^A$ is (1) a lower alkyl group substituted by any group selected from the group consisting of a hydroxyl group, a carboxy group and a carbamoyl group; (2) a carboxy group; or (3) a carbamoyl group, or a pharmaceutically acceptable salt thereof.

5. A fused heterocyclic derivative as claimed in claim 1, wherein m is 0 or 1, or a pharmaceutically acceptable salt thereof.

6. A fused heterocyclic derivative as claimed in claim 5, wherein m is 1 and ring A is a thiophene ring in which $R^A$ binds to the position of ring A at the position shown by the following general formula:

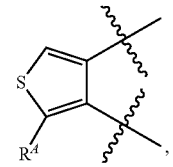

or a pharmaceutically acceptable salt thereof.

7. A fused heterocyclic derivative as claimed in claim 1, wherein ring B is a benzene ring, a thiophene ring or a pyridine ring, or a pharmaceutically acceptable salt thereof.

8. A fused heterocyclic derivative as claimed in claim 7, wherein ring B is any of rings of any of the formulae:

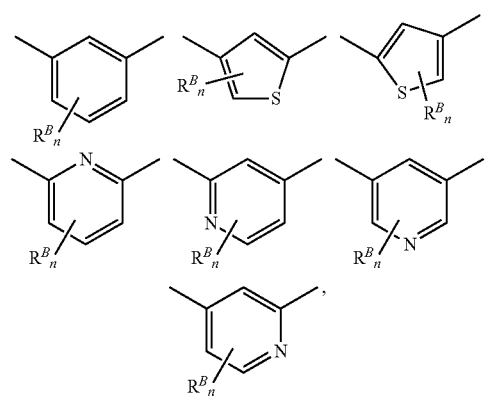

or a pharmaceutically acceptable salt thereof.

9. A fused heterocyclic derivative as claimed in claim 8, wherein n is 1 and ring B is any of rings in which $R^B$ binds to the position of ring B at the position shown by any of the following formulae:

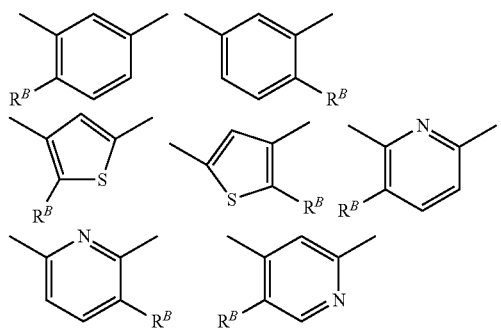

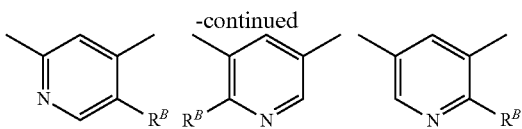

in the formulae, $R^B$ is a halogen atom, a cyano group, an optionally substituted lower alkyl group, $OW^4$, $COW^4$, $COOW^4$ or $CONW^5W^6$ in which $W^4$ to $W^6$ independently are a hydrogen atom or an optionally substituted lower alkyl group, or $W^5$ and $W^6$ may bind together with the neighboring nitrogen atom to form an optionally substituted cyclic amino group;
or a pharmaceutically acceptable salt thereof.

10. A fused heterocyclic derivative as claimed in claim 8, wherein ring B is any of rings of any of the formulae:

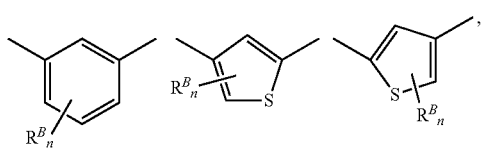

or a pharmaceutically acceptable salt thereof.

11. A fused heterocyclic derivative as claimed in claim 1, wherein $R^B$ is a halogen atom, an optionally substituted lower alkyl group, $OW^4$ in which $W^4$ is a hydrogen atom or an optionally substituted lower alkyl group, or a cyano group, or a pharmaceutically acceptable salt thereof.

12. A fused heterocyclic derivative as claimed in claim 11, wherein $R^B$ is a halogen atom, or a lower alkyl group which may be substituted by a halogen atom, or $OW^4$ in which $W^4$ is a hydrogen atom or an optionally substituted lower alkyl group, or a pharmaceutically acceptable salt thereof.

13. A fused heterocyclic derivative as claimed in claim 12, wherein $R^B$ is a fluorine atom, a chlorine atom or $OW^4$ in which $W^4$ is a lower alkyl group, or a pharmaceutically acceptable salt thereof.

14. A fused heterocyclic derivative as claimed in claim 1, wherein L is a $C_{1-3}$ alkylene group, or a pharmaceutically acceptable salt thereof.

15. A fused heterocyclic derivative as claimed in claim 1, wherein Z is an optionally fused and optionally substituted aryl group, or a pharmaceutically acceptable salt thereof.

16. A pharmaceutical composition comprising as an active ingredient a fused heterocyclic derivative as claimed in claim 1, or a pharmaceutically acceptable salt thereof.

17. A pharmaceutical composition as claimed in claim 16, which is a gonadotropin releasing hormone antagonist.

18. A pharmaceutical composition as claimed in claim 16, wherein the composition is an oral formulation.

19. A pharmaceutical composition as claimed in claim 16, which comprises a combination with at least one drug selected from the group consisting of a gonadotropin releasing hormone agonist, a chemotherapeutic agent, a peptidic gonadotropin releasing hormone antagonist, a 5α-reductase inhibitor, an α-adrenoceptor inhibitor, an aromatase inhibitor, an adrenal androgen production inhibitor and a hormonotherapeutic agent.

20. A pharmaceutical composition as claimed in claim 19, wherein the gonadotropin releasing hormone agonist is selected from the group consisting of leuprorelin acetate, gonadorelin, buserelin, triptorelin, goserelin, nafarelin, histrelin, deslorelin, meterelin and lecirelin.

21. A pharmaceutical composition as claimed in claim 19, wherein the chemotherapeutic agent is selected from the group consisting of ifosfamide, adriamycin, peplomycin, cisplatin, cyclophosphamide, 5-FU, UFT, methotrexate, mitomycin C, mitoxantrone, paclitaxel and dotaxel.

22. A pharmaceutical composition as claimed in claim 19, wherein the peptidic gonadotropin releasing hormone antagonist is selected from the group consisting of cetrorelix, ganirelix, abarelix, ozarelix, iturelix, degarelix and teverelix.

23. A pharmaceutical composition as claimed in claim 19, wherein the 5α-reductase inhibitor is selected from the group consisting of finasteride and dutasteride.

24. A pharmaceutical composition as claimed in claim 19, wherein the α-adrenoceptor inhibitor is selected from the group consisting of tamsulosin, silodosin and urapidil.

25. A pharmaceutical composition as claimed in claim 19, wherein the aromatase inhibitor is selected from the group consisting of fadrozole, letrozole, anastrozole and formestane.

26. A pharmaceutical composition as claimed in claim 19, wherein the adrenal androgen production inhibitor is liarozole.

27. A pharmaceutical composition as claimed in claim 19, wherein the hormonotherapeutic agent is selected from the group consisting of an antiestrogenic agent, a progestational agent, an androgenic agent, an estrogeninc agent and an antiandrogenic agent.

28. A fused heterocyclic derivative as claimed in claim 8, wherein n is 2 and ring B is any of rings in which $R^B$ binds to the position of ring B at the position shown by any of the following formulae:

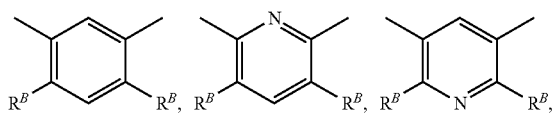

wherein $R^B$ can be the same or different from each other; or a pharmaceutically acceptable salt thereof.

29. 5-Carboxy-3-{2-fluoro-5-[1-(2-fluoro-6-methoxyphenyl)-ethoxy]phenyl}thieno[3,4-d]pyrimidine-2,4(1H,3H)-dione, or a pharmaceutically acceptable salt thereof.

30. 5-Carboxy-3-[2-fluoro-5-(2,3-difluoro-6-methoxybenzyloxy)-4-methoxyphenyl]thieno[3,4-d]pyrimidine-2,4(1H,3H)-dione, or a pharmaceutically acceptable salt thereof.

31. 5-Carboxy-3-[2-chloro-5-(1-methyl-1-phenylethoxy)phenyl]-thieno[3,4-d]pyrimidine-2,4(1H,3H)-dione, or a pharmaceutically acceptable salt thereof.

32. 5-Carboxy-3-{2-fluoro-5-[2,3-difluoro-6-(2-methoxyethoxy)-benzyloxy]phenyl}thieno[3,4-d]pyrimidine-2,4(1H,3H)-dione, or a pharmaceutically acceptable salt thereof.

* * * * *